(12) United States Patent
Yang et al.

(10) Patent No.: US 11,611,045 B2
(45) Date of Patent: Mar. 21, 2023

(54) ORGANIC COMPOUND, ELECTRONIC COMPONENT CONTAINING ORGANIC COMPOUND, AND ELECTRONIC DEVICE

(71) Applicant: Shaanxi Lighte Optoelectronics Material Co., Ltd., Xi'an (CN)

(72) Inventors: Min Yang, Xi'an (CN); Tiantian Ma, Xi'an (CN); Peng Nan, Xi'an (CN)

(73) Assignee: SHAANXI LIGHTE OPTOELECTRONICS MATERIAL CO., LTD., Shaanxi (CN)

( * ) Notice: Subject to any disclaimer, the term of this patent is extended or adjusted under 35 U.S.C. 154(b) by 0 days.

(21) Appl. No.: 17/623,356

(22) PCT Filed: Oct. 16, 2020

(86) PCT No.: PCT/CN2020/121667
§ 371 (c)(1),
(2) Date: Dec. 28, 2021

(87) PCT Pub. No.: WO2021/129072
PCT Pub. Date: Jul. 1, 2021

(65) Prior Publication Data
US 2022/0223796 A1    Jul. 14, 2022

(30) Foreign Application Priority Data
Dec. 26, 2019  (CN) .......................... 201911370729.7

(51) Int. Cl.
*H01L 51/00* (2006.01)
*C07D 213/06* (2006.01)
(Continued)

(52) U.S. Cl.
CPC ........ *H01L 51/0067* (2013.01); *C07D 213/06* (2013.01); *C07D 239/26* (2013.01);
(Continued)

(58) Field of Classification Search
CPC ............. H01L 51/0067; H01L 51/0052; H01L 51/0056; H01L 51/0058; H01L 51/0073; H01L 51/007
See application file for complete search history.

(56) References Cited

U.S. PATENT DOCUMENTS

2016/0329502 A1    11/2016    Dyatkin et al.

FOREIGN PATENT DOCUMENTS

| CN | 110128279 A | 8/2019 |
| CN | 110615759 A | 12/2019 |
| CN | 111018797 A | 4/2020 |
| CN | 111646983 A | 9/2020 |
| CN | 111825518 A | 10/2020 |
| KR | 20130115855 A | 10/2013 |

(Continued)

OTHER PUBLICATIONS

English translation of the WIPO Publication WO-2021128764-A1. (Year: 2022).*
English translation of the WIPO Publication WO-2021057550-A1. (Year: 2022).*
International Search Report from corresponding International Application No. PCT/CN2020/121667, dated Dec. 30, 2020, 5 pages.

*Primary Examiner* — Joseph R Kosack
*Assistant Examiner* — Sagar Patel
(74) *Attorney, Agent, or Firm* — Tucker Ellis LLP

(57) ABSTRACT

The present disclosure relates to the technical field of organic photoelectric materials, in particular to an organic compound, an electronic component containing the organic compound, and an electronic device. The compound has a structure as shown by chemical formula 1', wherein one of $R_1$ to $R_4$ is aa, and the other three are selected from substituents such as an alkyl, halogen and cyano; one of $R_5$ to $R_8$ is bb, and the other three are selected from substituents such as an alkyl, halogen and cyano; Y and $Y_1$ are each independently cc; and L and $L_1$ are a single bond, aryl, heteroaryl, etc. By using the organic compound of the present disclosure in an organic component, the driving voltage, luminous efficiency and lifespan of the organic component can be improved.

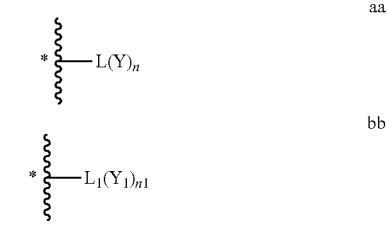

aa

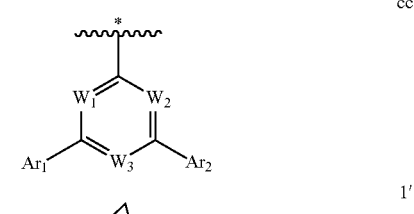
bb

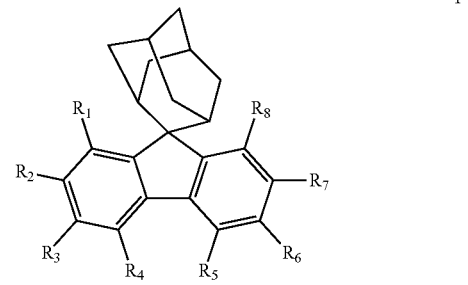
cc

1'

13 Claims, 1 Drawing Sheet

(51) Int. Cl.
  *C07D 239/26*   (2006.01)
  *C07D 251/24*   (2006.01)
  *C07D 405/14*   (2006.01)
  *C07D 409/14*   (2006.01)
  *H01L 51/50*    (2006.01)
  *C09K 11/06*   (2006.01)

(52) U.S. Cl.
  CPC ......... *C07D 251/24* (2013.01); *C07D 405/14* (2013.01); *C07D 409/14* (2013.01); *C09K 11/06* (2013.01); *H01L 51/0056* (2013.01); *H01L 51/0058* (2013.01); *H01L 51/0073* (2013.01); *H01L 51/0074* (2013.01); *C09K 2211/1018* (2013.01); *H01L 51/5072* (2013.01)

(56) References Cited

FOREIGN PATENT DOCUMENTS

| | | | |
|---|---|---|---|
| KR | 20140079306 A | 6/2014 | |
| KR | 20160060572 A | 5/2016 | |
| WO | 2020046049 A | 3/2020 | |
| WO | WO-2021057550 A1 * | 4/2021 | ........... C07D 213/22 |
| WO | WO-2021128764 A1 * | 7/2021 | ........... C07D 213/16 |

\* cited by examiner

ORGANIC COMPOUND, ELECTRONIC COMPONENT CONTAINING ORGANIC COMPOUND, AND ELECTRONIC DEVICE

CROSS REFERENCE TO RELATED APPLICATIONS

The present application claims the priority to Chinese patent application No. CN 201911370729.7 filed on Dec. 26, 2019, which is incorporated herein by reference in its entirety.

TECHNICAL FIELD

The present application relates to an organic compound, an electronic component containing the organic compound, and an electronic device.

BACKGROUND

At present, organic electroluminescent devices have become a research focus in the field of flat panel display. Compared with liquid crystal displays, plasma displays and the like, organic electroluminescent devices have the advantages of wide angle of view, fast response, low driving voltage, high luminous efficiency, easy implementation of ultra thinness and lightweight and the like.

A common organic electroluminescent device usually comprises an anode, a cathode and an organic compound layer arranged between the two electrodes. When voltage is applied between the two electrodes, holes and electrons are injected from the anode and cathode each transported in the organic compound layer; the holes and electrons form excitons after they meet, and the excitons emit light by a radiative transition from an excited state to a ground state.

A considerable variety of organic electroluminescent materials have been developed successively in recent years, comprising poly-phenylene vinylene, poly-p-phenylene, polythiophene, polyfluorene and their derivatives and the like. There are still problems in the current organic electroluminescent devices, such as driving voltage rise, lower luminous efficiency and lifespan shortening when driven at high temperature. It is expected to develop new organic electroluminescent materials to obtain organic electroluminescent devices that can still maintain good performance when driven at high temperature.

SUMMARY

In order to solve the above problems, the present disclosure provides an organic compound, an electronic component and an electronic device containing the organic compound, by using the organic compound, the electronic component with improved driving voltage, luminous efficiency and lifespan can be obtained when driven at high temperature.

The present disclosure relates to an organic compound represented by formula 1' as follows:

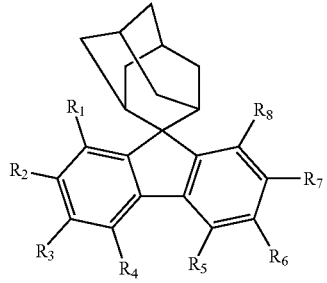

Formula 1' wherein, one of $R_1$ to $R_4$ is

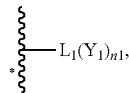

and the other three are each independently hydrogen, deuterium, fluorine, chlorine, bromine, cyano, C1-C10 alkyl, C1-C10 haloalkyl, C6-C20 aryl, C3-C20 heteroaryl, C6-C18 aryloxy, C6-C18 arylthio, C3-C12 alkylsilyl or C3-C10 cycloalkyl;

one of $R_5$ to $R_8$ is

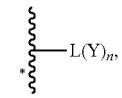

and the other three are each independently hydrogen, deuterium, fluorine, chlorine, bromine, cyano, C1-C10 alkyl, C1-C10 haloalkyl, C6-C20 aryl, C3-C20 heteroaryl, C6-C18 aryloxy, C6-C18 arylthio, C3-C12 alkylsilyl or C3-C10 cycloalkyl;

wherein each of Y and $Y_1$ is independently

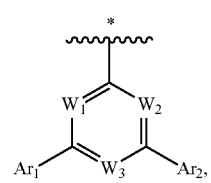

each of n and $n_1$ is independently 0, 1, 2 or 3, and $n+n_1 \geq 2$;

$W_1$ is $C(R^{w1})$ or N, $W_2$ is $C(R_{w2})$ or N, $W_3$ is $C(R^{w3})$ or N, and at least one of $W_1$, $W_2$ and $W_3$ is N;

$R^{w1}$, $R^{w2}$ and $R^{w3}$ are the same as or different from each other, and are each independently hydrogen, deuterium, fluorine, chlorine, bromine, cyano, C1-C10 alkyl, C1-C10 haloalkyl, C6-C20 aryl, C3-C20 heteroaryl, C6-C18 aryloxy, C6-C18 arylthio, C3-C12 alkylsilyl or C3-C10 cycloalkyl;

$Ar_1$ and $Ar_2$ are the same as or different from each other, and are each independently selected from the group consisting of hydrogen, deuterium, substituted or unsubstituted C6-C30 aryl, substituted or unsubstituted C3-C30 heteroaryl, substituted or unsubstituted C7-C30 arylalkyl and substituted or unsubstituted C3-C30 heteroarylalkyl;

L and $L_1$ are the same as or different from each other, and are each independently selected from the group consisting of a single bond, hydrogen, deuterium, substituted or unsubstituted C6-C30 arylene and substituted or unsubstituted C3-C30 heteroarylene;

the substituents in $Ar_1$, $Ar_2$, L and $L_1$ are the same as or different from each other, and are each independently selected from the group consisting of deuterium, a halogen group, cyano, alkyl, haloalkyl, aryl, heteroaryl, aryloxy, arylthio, alkylsilyl, alkylamino, arylamino and cycloalkyl.

Optionally, in the organic compound represented by formula 1', L and $L_1$ are the same as or different from each other, and are each independently selected from a single bond, substituted or unsubstituted arylene with 6-20 ring-forming carbon atoms, and substituted or unsubstituted heteroarylene with 3 to 18 ring-forming carbon atoms.

Optionally, in the organic compound represented by formula 1', the substituents in L and $L_1$ are the same as or different from each other, and are each independently selected from the group consisting of deuterium, fluorine, chlorine, bromine, cyano, C1-C6 alkyl, C1-C6 haloalkyl, C6-C12 aryl, C3-C12 heteroaryl, C6-C18 aryloxy, C6-C18 arylthio, C3-C12 alkylsilyl and C3-C10 cycloalkyl.

According to one aspect, the present disclosure relates to an organic compound represented by formula 1 as follows:

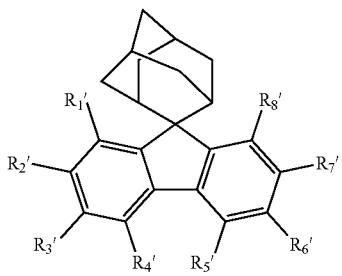

Formula 1 wherein, one of $R_1'$ to $R_4'$ is

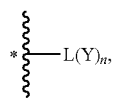

and the other three are each independently hydrogen, deuterium, fluorine, chlorine, bromine, cyano, C1-C10 alkyl, C1-C10 haloalkyl, C6-C20 aryl, C3-C20 heteroaryl, C6-C18 aryloxy, C6-C18 arylthio, C3-C12 alkylsilyl or C3-C10 cycloalkyl;

one of $R_5'$ to $R_8'$ is

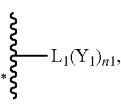

and the other three are each independently hydrogen, deuterium, fluorine, chlorine, bromine, cyano, C1-C10 alkyl, C1-C10 haloalkyl, C6-C20 aryl, C3-C20 heteroaryl, C6-C18 aryloxy, C6-C18 arylthio, C3-C12 alkylsilyl or C3-C10 cycloalkyl;

$n_1$ is 0, and n is 2;

Y is selected from the following structure:

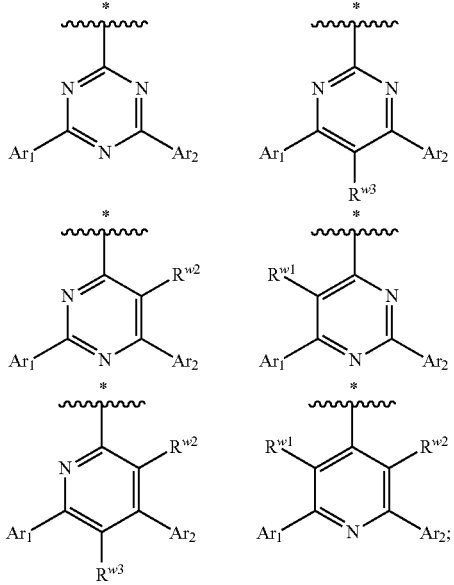

$Ar_1$ and $Ar_2$ are the same as or different from each other, and are each independently selected from the group consisting of hydrogen, substituted or unsubstituted C6-C30 aryl, substituted or unsubstituted C3-C30 heteroaryl, substituted or unsubstituted C7-C30 arylalkyl and substituted or unsubstituted C3-C30 heteroarylalkyl;

$L_1$ is hydrogen or deuterium;

L is selected from the group consisting of a single bond, substituted or unsubstituted C6-C30 arylene and substituted or unsubstituted C3-C30 heteroarylene;

the substituents in $Ar_1$, $Ar_2$, $L_1$ and L are each independently selected from the group consisting of deuterium, a halogen group, cyano, C1-C12 alkyl, C1-C12 haloalkyl, C6-C20 aryl, C3-C20 heteroaryl, C6-C18 aryloxy, C6-C18 arylthio, C3-C12 alkylsilyl and C3-C10 cycloalkyl;

$R^{w1}$, $R^{w2}$ and $R^{w3}$ are the same as or different from each other, and independently hydrogen, deuterium, fluorine, chlorine, bromine, cyano, C1-C6 alkyl, C1-C6 haloalkyl, C6-C20 aryl, C3-C20 heteroaryl, C3-C12 alkylsilyl or C3-C10 cycloalkyl.

Optionally, in the organic compound represented by formula 1, L is selected from substituted or unsubstituted arylene with 6 to 20 ring-forming carbon atoms, or substituted or unsubstituted heteroarylene with 3-18 ring-forming carbon atoms; the substituents in L are selected from the group consisting of deuterium, fluorine, chlorine, bromine, cyano, C1-C6 alkyl, C1-C6 haloalkyl, C6-C12 aryl, C3-C12 heteroaryl, C6-C18 aryloxy, C6-C18 arylthio, C3-C12 alkylsilyl and C3-C10 cycloalkyl.

Optionally, in the organic compound represented by formula 1, one of $R_1'$ to $R_4'$ is

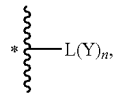

and the other three are each independently hydrogen, deuterium, fluorine, chlorine, bromine, cyano, C1-C6 alkyl, C1-C6 haloalkyl, C6-C15 aryl, C3-C12 heteroaryl or C3-C6 cycloalkyl; $R_5'$ to $R_8'$ are each independently hydrogen, deuterium, fluorine, chlorine, bromine, cyano, C1-C6 alkyl, C1-C6 haloalkyl, C6-C15 aryl, C3-C12 heteroaryl or C3-C6 cycloalkyl.

According to another aspect, the present disclosure also relates to an organic compound represented by formula 2 as follows:

Formula 2

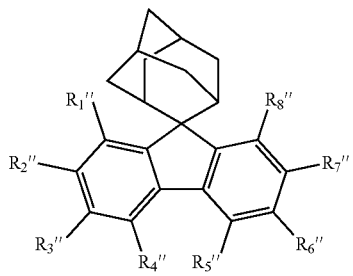

wherein, one of $R_1''$ to $R_4''$ is

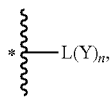

and the other three are each independently hydrogen, deuterium, fluorine, chlorine, bromine, cyano, C1-C10 alkyl, C1-C10 haloalkyl, C6-C20 aryl, C3-C20 heteroaryl, C6-C18 aryloxy, C6-C18 arylthio, C3-C12 alkylsilyl or C3-C10 cycloalkyl;

one of $R_5''$ to $R_8''$ is

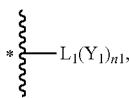

and the other three are each independently hydrogen, deuterium, fluorine, chlorine, bromine, cyano, C1-C10 alkyl, C1-C10 haloalkyl, C6-C20 aryl, C3-C20 heteroaryl, C6-C18 aryloxy, C6-C18 arylthio, C3-C12 alkylsilyl or C3-C10 cycloalkyl;

both $n_1$ and n are 1;

Y and $Y_1$ are each independently selected from:

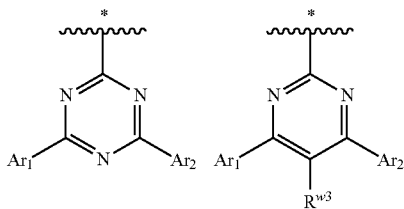

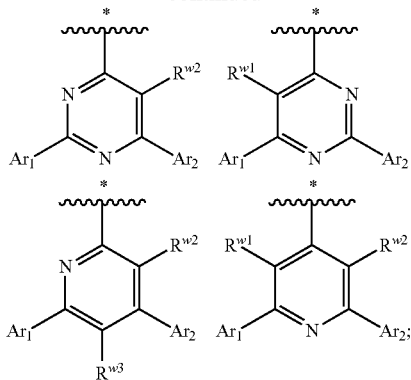

$Ar_1$ and $Ar_2$ are the same as or different from each other, and are each independently selected from the group consisting of hydrogen, substituted or unsubstituted C6-C30 aryl, substituted or unsubstituted C3-C30 heteroaryl, substituted or unsubstituted C7-C30 arylalkyl and substituted or unsubstituted C3-C30 heteroarylalkyl;

L and $L_1$ are the same as or different from each other, and are each independently selected from the group consisting of a single bond, substituted or unsubstituted C6-C30 arylene and substituted or unsubstituted C3-C30 heteroarylene;

the substituents in $Ar_1$, $Ar_2$, L and $L_1$ are the same as or different from each other, and are each independently selected from the group consisting of deuterium, a halogen group, cyano, C1-C12 alkyl, C1-C12 haloalkyl, C6-C20 aryl, C3-C20 heteroaryl, C6-C18 aryloxy, C6-C18 arylthio, C3-C12 alkylsilyl and C3-C10 cycloalkyl;

$R^{w1}$, $R^{w2}$ and $R^{w3}$ are the same as or different from each other, and are each independently hydrogen, deuterium, fluorine, chlorine, bromine, cyano, C1-C6 alkyl, C1-C6 haloalkyl, C6-C20 aryl, C3-C20 heteroaryl, C3-C12 alkylsilyl or C3-C10 cycloalkyl.

Optionally, in the organic compound represented by formulas 1' and 2, L and $L_1$ are the same as or different from each other, and are each independently selected from a single bond, substituted or unsubstituted arylene with 6 to 20 ring-forming carbon atoms, and substituted or unsubstituted heteroarylene with 3 to 18 ring-forming carbon atoms.

Optionally, in the organic compound represented by formula 2, the substituents in L and $L_1$ are the same as or different from each other, and are each independently selected from the group consisting of deuterium, fluorine, chlorine, bromine, cyano, C1-C6 alkyl, C1-C6 haloalkyl, C6-C12 aryl, C3-C12 heteroaryl, C6-C18 aryloxy, C6-C18 arylthio, C3-C12 alkylsilyl and C3-C10 cycloalkyl.

Optionally, in the organic compound represented by formula 2, one of $R_1''$ to $R_4''$ is

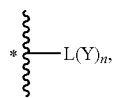

and the other three are each independently hydrogen, deuterium, fluorine, chlorine, bromine, cyano, C1-C6 alkyl, C1-C6 haloalkyl, C6-C15 aryl, C3-C12 heteroaryl or C3-C6 cycloalkyl; one of $R_5''$ to $R_8''$ is

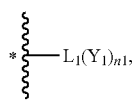

and the other three are hydrogen, deuterium, fluorine, chlorine, bromine, cyano, C1-C6 alkyl, C1-C6 haloalkyl, C6-C15 aryl, C3-C12 heteroaryl or C3-C6 cycloalkyl.

Optionally, in the organic compound of the present disclosure, the substituents in $Ar_1$ and $Ar_2$ are the same as or different from each other, and are each independently selected from the group consisting of deuterium, fluorine, chlorine, bromine, cyano, C1-C12 alkyl, C1-C12 haloalkyl, C6-C20 aryl, C3-C20 heteroaryl, C6-C18 aryloxy, C6-C18 arylthio, C3-C12 alkylsilyl and C3-C10 cycloalkyl.

According to another aspect, the present disclosure also relates to an electronic component, comprising an anode, a cathode and one or more functional layers arranged between the anode and cathode, wherein one or more layers in the functional layer contain the organic compound in the present disclosure.

According to another aspect, the present disclosure also relates to an electronic device, comprising the electronic component in the present disclosure.

The organic compound according to the present disclosure contains an adamantyl-fluorenyl group in its structure, wherein the adamantane-fluorenyl group has appropriate molecular weight and steric hindrance effect, which can effectively increase the glass transition temperature of the material, the adamantyl screwed on the fluorenyl has a large space volume and high rigidity, and therefore, it can reduce the interactive force between large planar-conjugated structures and π-π stacking between molecules and adjust the degree of stacking between molecules, and then the nitrogen-containing compound is not easy to crystallize or aggregate during film formation and can have more stable amorphous state, so that the material can have a better lifespan in the device. Adamantyl-fluorenyl can enhance the hole mobility of the organic light-emitting layer, help to promote the transport balance of holes and electrons in the organic light-emitting layer, improve the luminous efficiency of the organic electroluminescent device, and reduce the driving voltage of the organic electroluminescent device. Further, by introducing heteroaryl as an electron injection and transport group based on the adamantyl-fluorenyl group, the present disclosure makes the material have electron-rich characteristics, enhances the polarity of the whole molecule, which is more beneficial to the directional arrangement of material molecules, thus enhancing the injection and transport of electrons and improve the efficiency of the device. The improvement in the hole mobility of the nitrogen-containing compound of the present disclosure can also increase the recombination rate of electrons and holes in the organic light-emitting layer, and reduce or avoid the transport of electrons through the organic light-emitting layer to the hole transport layer, thus effectively protecting the hole transport layer material against the impact of electrons and improving the lifespan of the organic electroluminescent device.

According to the present disclosure, an electronic component with improved driving voltage, luminous efficiency and lifespan can be obtained when driven at high temperature by using the organic compound in the electronic component.

REFERENCE NUMERALS

Figure 1:
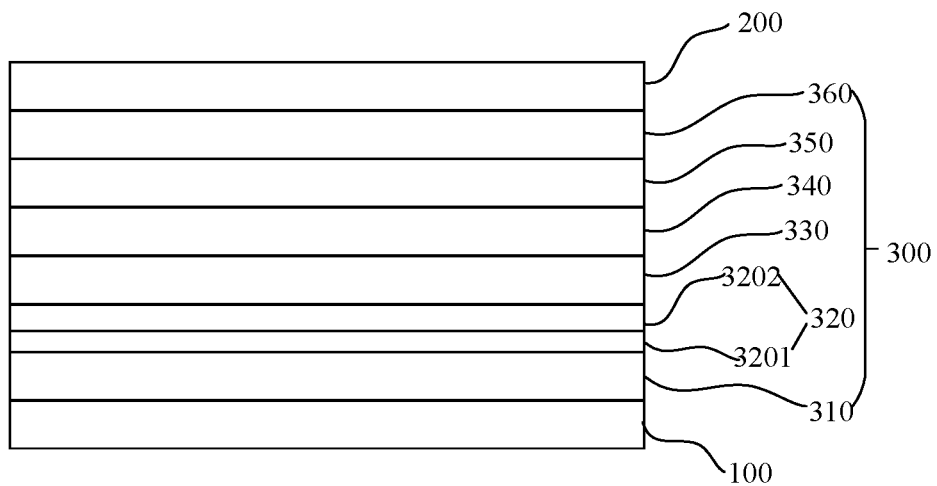
FIG. 1 shows an organic electroluminescent device containing the organic compound of the present disclosure as an embodiment of the present disclosure.

100: Anode, 200: Cathode, 300: Functional layer, 400: Electronic device, 310: Hole injection layer, 320: Hole transport layer, 330: Electron blocking layer, 340: Light-emitting layer, 350: Electron transport layer, 360: Electron injection layer, 370: Photoelectric conversion layer, 3201: First hole transport layer, 3202: Second hole transport layer DETAILED DESCRIPTION OF THE EMBODIMENTS A more detailed description of the present disclosure will be given hereinafter.

In the disclosure, the term "optional" or "optionally" means that an event or environment described later may but does not have to happen, and this description includes occasions where the event or environment happens or does not happen. For example, "heterocyclic group optionally substituted by an alkyl" means that the alkyl may but does not have to exist, and this description includes the scenario that a heterocyclic group is substituted by alkyl and the scenario that the heterocyclic group is not substituted by alkyl. In another example, "optionally, $R^{v2}$ and $R^{v3}$ connected to the same atom are connected to each other to form a saturated or unsaturated 5- to 10-membered aliphatic ring" means that $R^{v2}$ and $R^{v3}$ connected to the same atom may but do not have to form a ring, comprising the scenario that $R^{v2}$ and $R^{v3}$ are connected to each other to form a saturated or unsaturated 5- to 10-membered aliphatic ring, and the scenario that $R^{v2}$ and $R^{v3}$ exist independently of each other.

As a way of description used herein, " . . . are each independently" is interchangeable with "each . . . is independently selected from . . . " and " . . . are independently . . . ", all of which shall be understood in a broad sense, which can indicate that the specific options do not affect each other, and can also indicate that the specific options expressed between the same symbols in the same group do not affect each other.

For example

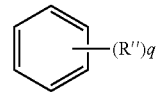

Formula Q-1

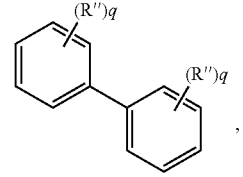

Formula Q-2 wherein each q is independently 0, 1, 2 or 3, and each R" is independently selected from hydrogen, fluorine, and chlorine" means that: formula Q-1 indicates that there are q substituents R" on a benzene ring, the R"s may be the same or different, and the options of each R" do not affect each other; formula Q-2 indicates that there are q substituents R" on each benzene ring of biphenyl, the number q of R" substituents on two benzene rings may be the same or different, the R" may be the same or different, and the options of each R" do not affect each other.

In the disclosure, "alkyl" refers to a saturated linear or branched monovalent hydrocarbyl group, wherein the alkyl can be optionally substituted by one or more substituents described herein. Unless otherwise specified, the alkyl herein contains 1 to 20 carbon atoms. In some embodiments, the alkyl in the present disclosure contains 1 to 10 carbon atoms; in other embodiments, the alkyl in the present disclosure contains 1 to 6 carbon atoms; in some more embodiments, the alkyl in the present disclosure contains 1 to 4 carbon atoms; in other embodiments, the alkyl in the present disclosure contains 1 to 3 carbon atoms. Examples of the alkyl in the present disclosure include, but are not limited to: methyl (Me, —$CH_3$), ethyl (Et, —$CH_2CH_3$), n-propyl (n-Pr, —$CH_2CH_2CH_3$), isopropyl (i-Pr, —CH($CH_3$)$_2$), n-butyl (n-Bu, —$CH_2CH_2CH_2CH$) and the like.

The "aryl" herein refers to a monocyclic structure formed by a plurality of carbon atoms, or a bicyclic or polycyclic system formed by a plurality of carbon atoms, wherein at least one aromatic ring system is contained, each ring system can contain a ring consisting of 3 to 7 atoms, that is, the aryl is either monocyclic aryl or polycyclic aryl. In other words, the aryl may be a monocyclic aryl, a polycyclic aryl, two or more monocyclic aryls conjugated by carbon-carbon bonds, a monocyclic aryl or polycyclic aryl conjugated by carbon-carbon bonds, and two or more polycyclic aryls conjugated by carbon-carbon bonds. That is, two or more aromatic groups conjugated by carbon-carbon bonds can also be regarded as the aryl of the disclosure. For example, biphenyl, terphenyl, etc. are aryls herein. In some embodiments of the present disclosure, the carbon number in the aryl of the present disclosure is 6 to 30; in other embodiments of the present disclosure, the carbon number in the aryl of the present disclosure is 6 to 18; in some more embodiments of the present disclosure, the carbon number in the aryl of the present disclosure is 6 to 12; in other embodiments of the present disclosure, the carbon number in the aryl of the present disclosure is 6 to 20; in other embodiments of the present disclosure, the carbon number in the aryl of the present disclosure is 6 to 14, and in other embodiments of the present disclosure, the carbon number in the aryl of the present disclosure is 6 to 15. Examples as the aryl of the present disclosure may include, but are not limited to, phenyl, naphthyl, fluorenyl, anthracyl, phenanthryl, biphenyl, terphenyl, quaterphenyl, quinquephenyl, benzo [9,10] phenanthryl, pyrenyl, benzofluoranthene, chrysenyl, perylenyl and the like.

A ring system formed by n atoms is called a n-membered ring herein, for example, phenyl is a 6-membered aryl; a 6- to 10-membered aromatic ring refers to a benzene ring, naphthalene ring, indene ring and the like.

There may be one or more connection points connected with other parts of the molecule on the "aryl" herein. The definition of "aryl" also applies to "arylene".

The substituted aryl herein means that one or more hydrogen atoms in the aryl are substituted by other groups, for example, at least one hydrogen atom on the aryl is substituted by a deuterium atom, fluorine, chlorine, bromine, CN, azyl, alkyl, haloalkyl, cycloalkyl, aryloxy, arylthio, alkylsilyl, alkylamino, arylamino, boryl, phosphino, aryl, heteroaryl or other groups.

It is understood that "substituted C6-C30 aryl" refers to substituted aryl with 6 to 30 carbon atoms, which means that the total number of carbon atoms on the aryl and substituent thereon is 6 to 30.

The "heteroaryl" herein is a monocyclic, bicyclic and polycyclic system, wherein at least one ring system is aromatic, at least one aromatic ring system contains one or more heteroatoms selected from B, O, N, P, Si, Se and S, wherein each ring system is a ring consisting of 5 to 7 atoms, and one or more connection points are connected with other parts of the molecule. The number of carbon atoms of heteroaryl herein may be 3 to 30, 3 to 18, or 3 to 12. The heteroaryl may be monocyclic or polycyclic heteroaryl, in other words, the heteroaryl is either a single aromatic ring system or a plurality of aromatic ring systems conjugated by carbon-carbon bonds, and any aromatic ring system is an aromatic monocycle or an aromatic fused ring. Exemplarily, the heteroaryl may include, but is not limited to, thienyl, furyl, pyrrolyl, imidazolyl, thiazolyl, oxazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridopyrimidyl, pyridopyrazinyl, pyrazinopyrazinyl, isoquinolinyl, indolyl, carbazolyl, N-arylcarbazolyl, N-heteroarylcarbazolyl, N-alkylcarbazolyl, benzoxazolyl, benzimidazolyl, benzothiazolyl, benzocarbazolyl, benzothiophenyl, dibenzothienyl, thiophenothiophenyl, benzofuranyl, phenanthrolinyl, isoxazolyl, thiadiazolyl, benzothiazolyl, phenothiazinyl, dibenzosilyl, dibenzofuranyl, phenyl substituted dibenzofuryl, phenyl substituted dibenzothienyl and the like. Wherein thienyl, furyl, phenanthrolinyl and the like are heteroaryls of a single aromatic ring system, and N-arylcarbazolyl (N-phenylcarbazolyl), N-heteroarylcarbazolyl, phenyl substituted dibenzofuranyl, dibenzofuranyl substituted phenyl and the like are heteroaryls of a plurality of aromatic ring systems conjugated by carbon-carbon bonds.

The number of carbon atoms in heteroaryl herein may be 3, 5, 8, 9, 12, 13, 15, 18, 20 or 30.

The "substituted heteroaryl" herein means that one or more hydrogen atoms in the heteroaryl are substituted by other groups, for example, at least one hydrogen atom in the heteroaryl is substituted by a deuterium atom, fluorine, chlorine, bromine, CN, azyl, alkyl, haloalkyl, cycloalkyl, aryloxy, arylthio, alkylsilyl, alkylamino, arylamino, boryl, phosphino, aryl, heteroaryl or other groups.

It is understood that there may be one bond, two bonds or more bonds connected with other parts in the molecule on the "heteroaryl". The definition of "heteroaryl" also applies to "heteroarylene".

It is understood that "substituted C3-C30 aryl" refers to a substituted heteroaryl with 3 to 30 carbon atoms, which means that the total number of carbon atoms on the heteroaryl and substituent thereon is 3 to 30.

The "aryl with the ring-forming carbon atom number of 6 to 20" herein means that the number of carbon atoms on an aromatic ring in the aryl is 6 to 20, and the number of carbon atoms in a substituent on the aryl is not included. In some embodiments of the present disclosure, the number of ring-forming carbon atoms in the aryl of the present disclosure is 6 to 30; in other embodiments of the present disclosure, the number of ring-forming carbon atoms in the aryl of the present disclosure is 6 to 20; in some more embodiments of the present disclosure, the number of ring-forming carbon atoms in the aryl of the present disclosure is, but is not limited to, 6 to 12. Exemplarily, fluorenyl belongs to an aryl with 13 ring-forming carbon atoms, and 9,9-dimethylfluorenyl belongs to an aryl with 15 substituted carbon atoms.

The "heteroaryl with the ring-forming carbon atom number of 3 to 18" herein means that the number of carbon atoms on a heteroaromatic ring in the heteroaryl is 3 to 18, and the number of carbon atoms in a substituent on the heteroaryl is not included. In some embodiments of the disclosure, the number of carbon atoms on the heteroaryl is 3 to 18; in other embodiments of the disclosure, the number of carbon atoms on the heteroaryl is 3 to 12; in other embodiments of the disclosure, the number of carbon atoms on the heteroaryl is 3 to 8, and in other embodiments, the number of carbon atoms on the heteroaryl is 5 to 12; in other embodiments, the number of carbon atoms on the heteroaryl is 5 to 18; but it is not limited thereto.

For example,

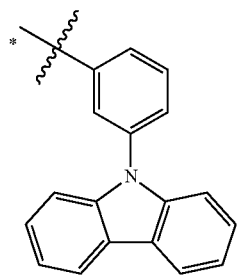

the group is a carbazolyl substituted phenyl, which belongs to not only a substituted aryl with 6 ring-forming carbon atoms but also a substituted C18 aryl;

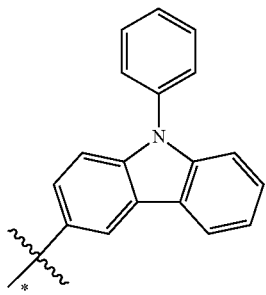 [SMILES: *c1ccc2c(c1)c1ccccc1n2-c1ccccc1]

the group is a phenyl substituted carbazolyl, which belongs to not only a substituted C18 heteroaryl but also a substituted heteroaryl with 12 ring-forming carbon atoms.

It is understood that the "substituted C7-C30 aralkyl" refers to substituted aralkyl with 7 to 30 carbon atoms, which means that the total number of carbon atoms on the aralkyl and substituent thereon is 7 to 30; the "substituted C3-C30 heteroarylalkyl" refers to substituted heteroarylalkyl with 3 to 30 carbon atoms, which means that the total number of carbon atoms on the heteroarylalkyl and substituent thereon is 3 to 30.

Non-orientating connection bond herein refers to single bond

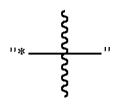

protruding from a ring system, which means that one end of the connection bond can be connected to any site in the ring system penetrated by the bond, and the other end is connected to the rest of a compound molecule. For example, as shown in the following formula (X), the naphthyl represented by formula (X) is connected with other sites of the molecule through two non-orientating connection bonds penetrating double rings, and what it means includes any possible connection mode represented by formula (X-1) to formula (X-10).

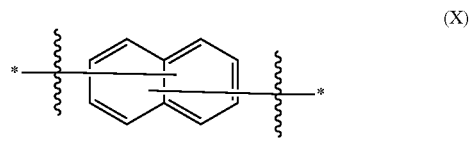
(X)

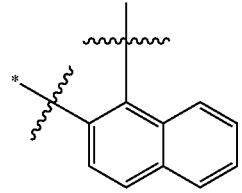
(X-1)

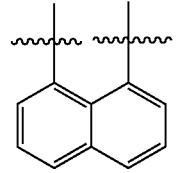
(X-2)

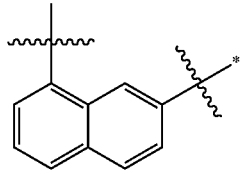
(X-3)

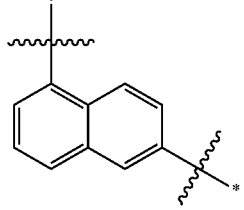
(X-4)

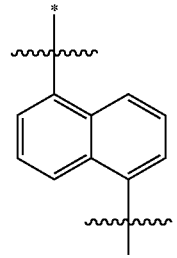
(X-5)

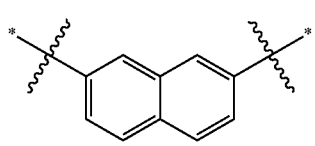
(X-6)

-continued (X-7)
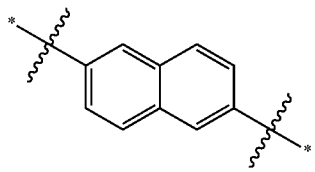

Formula (X-8)
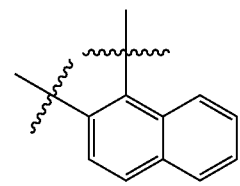

Formula (X-9)
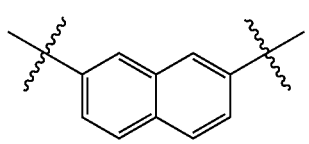

Formula (X-10)
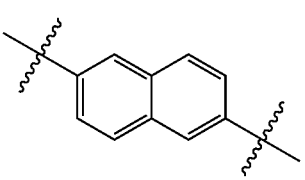

For example, as shown in the following formula (X'), the phenanthryl represented by formula (X') is connected with other sites of the molecule through a non-orientating connection bond protruding from a benzene ring at one side, and what it means includes any possible connection mode represented by formula (X'-1) to formula (X'-4).

(X')
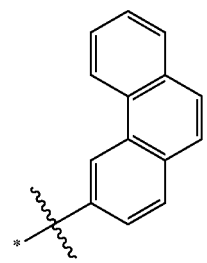

(X'-1)
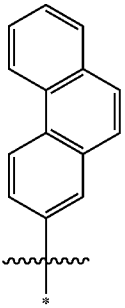

-continued (X'-2)
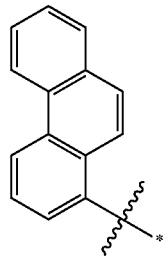

(X'-3)
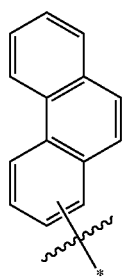

(X'-4)
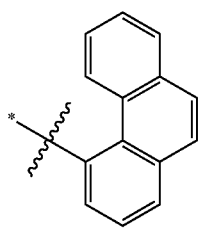

Non-orientating substituent herein refers to a substituent connected by a single bond protruding from the center of a ring system, which means that the substituent can be connected in any possible site in the ring system. For example, as shown in the following formula (Y), the substituent R group represented by formula (Y) is connected with a quinoline ring through a non-orientating connection bond, and what it means includes any possible connection mode represented by formula (Y-1) to formula (Y-7).

(Y)
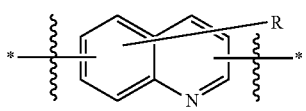

(Y-1)
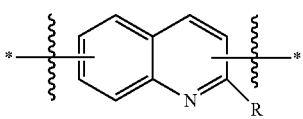

(Y-2)
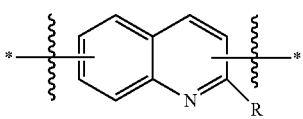

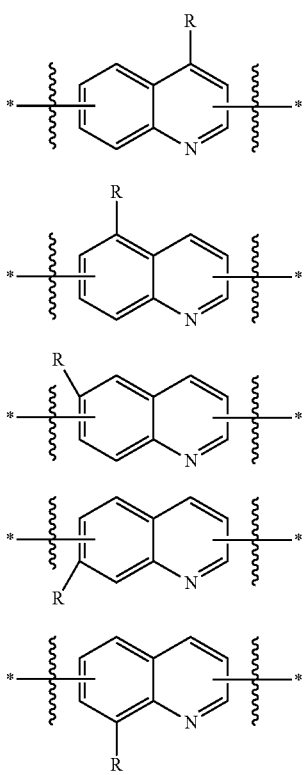

(Y-3)

(Y-4)

(Y-5)

(Y-6)

(Y-7)

The present disclosure provides an organic compound represented by formula 1', an electronic component containing the organic compound, and an electronic device.

The

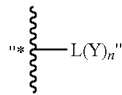

in the formula herein means that n sites on L are bound with Y.

The

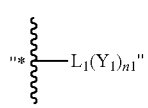

in the formula herein means that $n_1$ sites on $L_1$ are bound with Y.

A substituent in L herein refers to the substituent at a site other than those bound with Y in L.

A substituent in $L_1$ herein refers to the substituent at a site other than those bound with $Y_1$ in $L_1$.

The

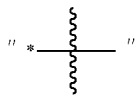 [SMILES: **]

herein refers to the site bound with other substituents or binding sites.

In the disclosure, the term "substituted or unsubstituted" refers to no substituent or being substituted by one or more substituents. The substituents include, but are not limited to, deuterium, halogen groups (fluorine, chlorine, bromine), cyano, alkyl, alkenyl, alkynyl, haloalkyl, aryl, heteroaryl, aryloxy, arylthio, alkylsilyl, alkylamino, arylamino, cycloalkyl and heterocyclyl.

Halogen groups as substituents herein may include fluorine, chlorine, bromine or iodine.

The alkyl as a substituent herein may be a linear or branched C1-30 alkyl, optionally C1-C10 alkyl, and more optionally C1-C6 alkyl. Specific examples of C1-C30 alkyl include, but are not limited to, methyl, ethyl, n-propyl, isopropyl, n-butyl, isobutyl, tert-butyl, sec-butyl, I-methylbutyl, 1-ethyl-butyl, pentyl, n-pentyl, isopentyl, neopentyl, tertpentyl, hexyl, n-hexyl, 2-methylpentyl, 2-ethylbutyl, heptyl, n-heptyl, octyl, n-octyl, tertoctyl, n-nonyl, decyl and the like.

The aryl as a substituent herein is C6-C30 aryl, optionally C6-C20 aryl. Specific examples of C6-C30 aryl include, but are not limited to, phenyl, naphthyl, biphenyl, fluorenyl, phenanthryl, dimethylfluorenyl, anthracyl and the like.

The heteroaryl as a substituent herein is C3-C30 heteroaryl, optionally C3-C20 heteroaryl. Specific examples of C3-C30 heteroaryl include, but are not limited to, pyridyl, pyrimidinyl, triazinyl, indolyl, quinolyl, carbazolyl, benzimidazolyl, benzothiazolyl, dibenzothienyl, benzofuranyl, dibenzofuranyl, carbazolyl, N-phenylcarbazolyl and the like.

The cycloalkyl as a substituent herein is C3-C30 cycloalkyl, optionally C3-C10 cycloalkyl, and more optionally C3-C5 cycloalkyl. Specific examples of C3-C10 cycloalkyl include cyclopropyl, cyclobutyl, cyclopentyl, cyclohexyl, cycloheptyl, cyclooctyl, cyclononyl and cyclodecyl, and cycloalkyls include, but are not limited to, fused cycloalkyl and spiro cycloalkyl and the like.

The C3-C12 alkylsilyl as a substituent herein refers to a silyl substituted by alkyl, for example, but not limited to, C3-C9 alkylsilyl, specifically for example, but not limited to, trimethylsilyl, triethylsilyl and the like.

The "aralkyl" herein refers to alkyl substituted by aryl, and the aryl in the aralkyl may be additionally substituted by halogen, alkyl, alkoxyl, haloalkyl and the like.

The "heteroarylalkyl" herein refers to alkyl substituted by heteroaryl, and the heteroaryl in the heteroarylalkyl may be additionally substituted by halogen, alkyl, alkoxyl, haloalkyl and the like.

According to an embodiment of the present disclosure, in the organic compound as shown by formula 1' of the present disclosure, one of $R_1$ to $R_4$ is

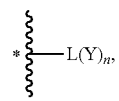

and the other three are each independently hydrogen, deuterium, fluorine, chlorine, bromine, cyano, methyl, ethyl, isopropyl, tert-butyl, phenyl, naphthyl, dimethylfluorenyl, pyridyl, pyrimidinyl, quinolyl, dibenzofuranyl or dibenzothienyl; one of $R_5$ to $R_8$ is

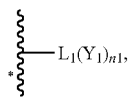

and the other three are each independently hydrogen, deuterium, fluorine, chlorine, bromine, cyano, methyl, ethyl, isopropyl, tert-butyl, phenyl, naphthyl, dimethylfluorenyl, pyridyl, pyrimidinyl, quinolyl, dibenzofuranyl or dibenzothienyl.

According to an embodiment of the present disclosure, in the organic compound of the present disclosure, $Ar_1$ and $Ar_2$ are the same as or different from each other, and are each independently selected from the group consisting of hydrogen, substituted or unsubstituted C6-C25 aryl and substituted or unsubstituted C3-C20 heteroaryl; the substituents in $Ar_1$ and $Ar_2$ are selected from the group consisting of deuterium, fluorine, chlorine, bromine, cyano, C1-C12 alkyl, C1-C12 haloalkyl, C6-C20 aryl, C3-C20 heteroaryl, C6-C18 aryloxy, C6-C18 arylthio, C3-C12 alkylsilyl and C3-C10 cycloalkyl.

According to an embodiment of the present disclosure, in the organic compound of the present disclosure, $Ar_1$ and $Ar_2$ are the same as or different from each other, and are each independently selected from the group consisting of hydrogen, substituted or unsubstituted C6-C18 aryl, and substituted or unsubstituted C4-C18 heteroaryl.

According to an embodiment of the present disclosure, in the organic compound of the present disclosure, the substituents in $Ar_1$ and $Ar_2$ are selected from the group consisting of deuterium, fluorine, chlorine, bromine, cyano, C1-C4 alkyl, C1-C4 haloalkyl, phenyl, biphenyl, naphthyl, phenanthrenyl, anthracyl, pyridyl, dibenzothienyl, dibenzofuranyl, carbazolyl and quinolyl.

According to an embodiment of the present disclosure, in the organic compound of the present disclosure, $Ar_1$ and $Ar_2$ are the same as or different from each other, and are each independently selected from the group consisting of hydrogen, substituted or unsubstituted aryl with 6 to 14 ring-forming carbon atoms and substituted or unsubstituted heteroaryl with 4 to 12 ring-forming carbon atoms.

According to an embodiment of the present disclosure, in the organic compound of the present disclosure, $Ar_1$ and $Ar_2$ are the same as or different from each other, and are each independently selected from the group consisting of hydrogen, substituted or unsubstituted phenyl, substituted or unsubstituted naphthyl, substituted or unsubstituted biphenyl, substituted or unsubstituted anthracyl, substituted or unsubstituted phenanthrenyl, substituted or unsubstituted fluorenyl, substituted or unsubstituted dibenzofuranyl, substituted or unsubstituted dibenzothienyl, substituted or unsubstituted carbazolyl, substituted or unsubstituted N-phenylcarbazolyl, substituted or unsubstituted pyridyl, substituted or unsubstituted quinolyl, substituted or unsubstituted pyrimidyl; the substituents in $Ar_1$ and $Ar_2$ are the same or different, and are each independently selected from the group consisting of deuterium, fluorine, chlorine, bromine, cyano, methyl, ethyl, isopropyl, tert-butyl, trifluoromethyl, phenyl, naphthyl, phenanthrenyl, anthracyl, pyridyl, dibenzothienyl, dibenzofuranyl, carbazolyl and quinolyl.

According to an embodiment of the present disclosure, in the organic compound of the present disclosure, $Ar_1$ and $Ar_2$ are the same as or different from each other, and are each independently hydrogen, deuterium, a substituted or unsubstituted group as follows:

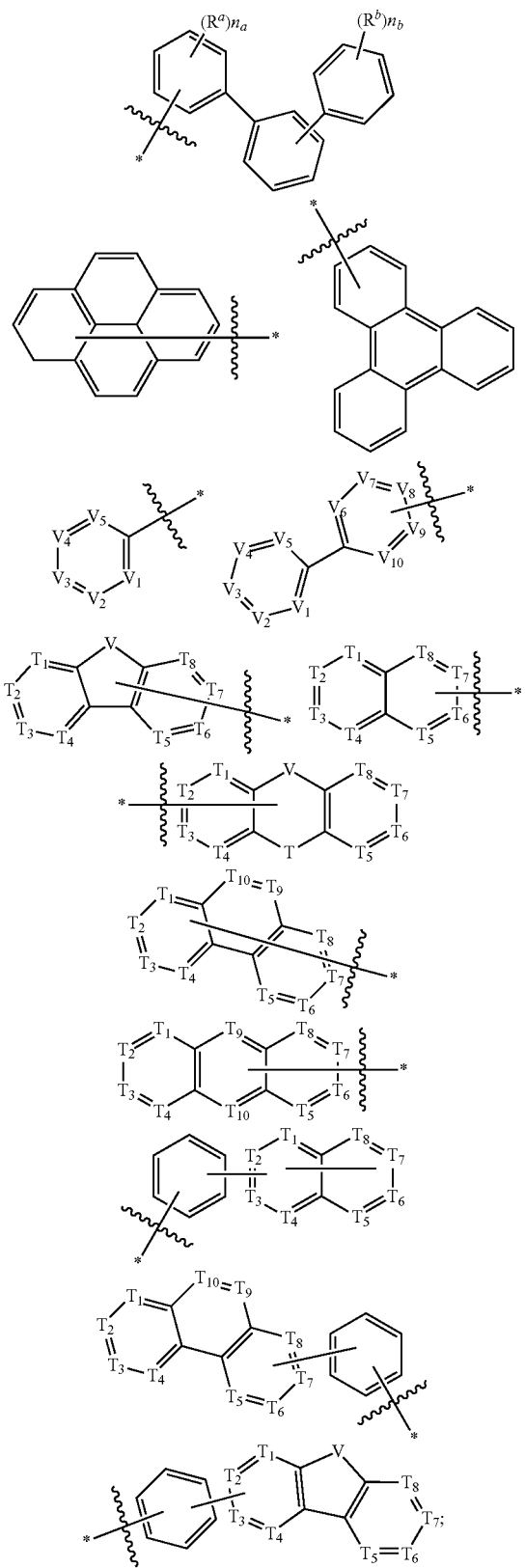

in the above group, $n_a$ is 1, 2, 3 or 4, and when two or more $R^a$ are contained in one group, the $R^a$ are the same as or different from each other; when $n_b$ is 1, 2, 3, 4 or 5, and when two or more $R^b$ are contained in one group, the $R^b$ are the same as or different from each other;

$V_1$ to $V_{10}$ are each independently selected from $C(R^v)$ and N, and when two or more $R^v$ are contained in one group, any two $R^v$ are the same as or different from each other;

each V is independently selected from the group consisting of O, S, Se, $N(R^{v1})$, $C(R^{v2}R^{v3})$ and $Si(R^{v2}R^{v3})$;

T is selected from O, S or $N(R^{v1})$;

$T_1$ to $T_{10}$ are each independently selected from $C(R^t)$ and N, and when two or more $R^t$ are contained in one group, any two $R^t$ are the same as or different from each other;

$R^a$, $R^b$, $R^t$, $R^v$, $R^{v2}$ and $R^{v3}$ are each independently hydrogen, deuterium, fluorine, chlorine, bromine, cyano, C1-C6 alkyl, C1-C6 haloalkyl. C1-C6 alkoxyl, C3-C12 alkylsilyl, C6-C12 aryl, C3-C12 heteroaryl and C3-C10 cycloalkyl;

each $R^{v1}$ is independently selected from the group consisting of hydrogen, deuterium, C1-C6 alkyl, C1-C6 haloalkyl, C6-C12 aryl, C3-C12 heteroaryl and C3-C10 cycloalkyl, and the $R^{v1}$ are the same as or different from each other when two $R^{v1}$ exist in the same group. Alternatively, optionally, two adjacent $R^{v1}$ together with the carbon atoms to which they are connected form an aromatic ring with 6 to 10 ring-forming atoms or a heteroaromatic ring with 5 to 12 ring-forming atoms (this means that two adjacent R herein may be connected together with the atom to which they are connected to form an aromatic ring or heteroaromatic ring, or the two $R^v$ may exist independently without affecting each other).

Optionally, $R^{v2}$ and $R^{v3}$ connected to the same atom are mutually connected to form a saturated or unsaturated 5- to 10-membered aliphatic ring (this means that $R^{v2}$ and $R^{v3}$ connected to the same atom herein together with the atom to which they are connected form a saturated or unsaturated 5- to 10-membered aliphatic ring, or exist independently without affecting each other).

According to an embodiment of the present disclosure, in the organic compound of the present disclosure, $Ar_1$ and $Ar_2$ are the same as or different from each other, and are each independently hydrogen, deuterium, or a substituted or unsubstituted group as follows:

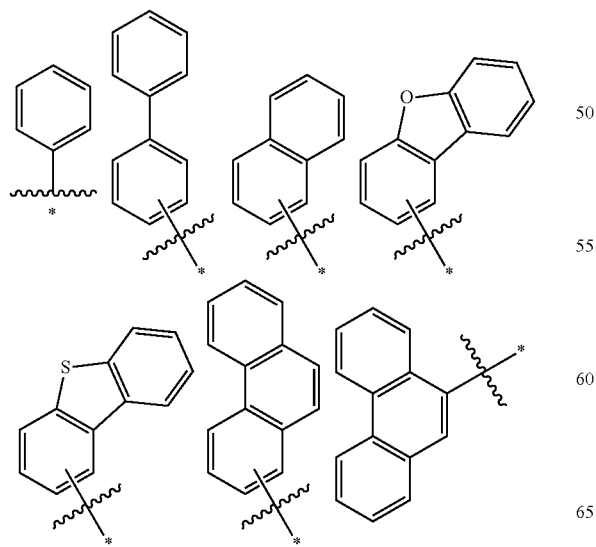

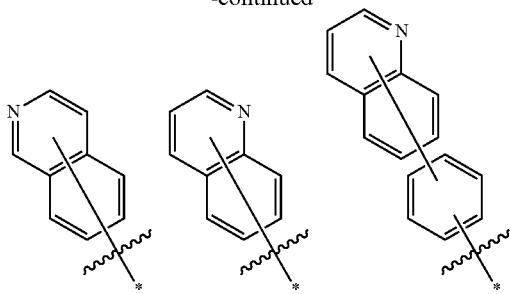

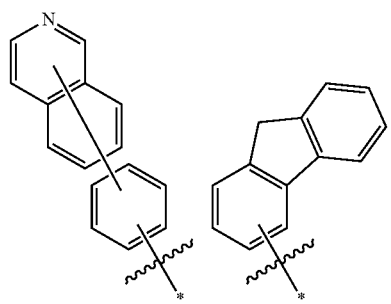

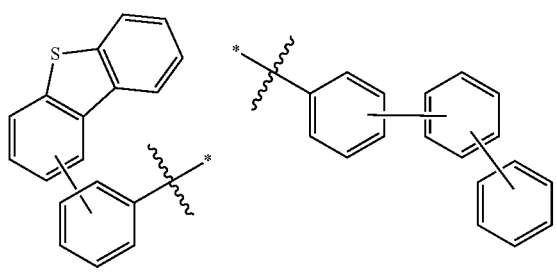

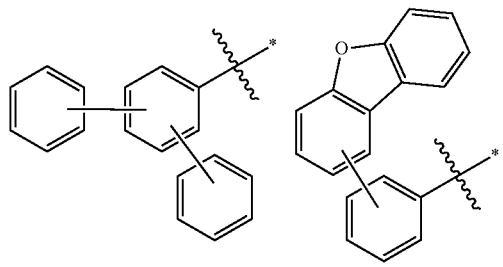

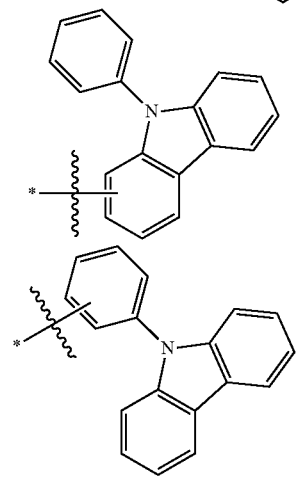

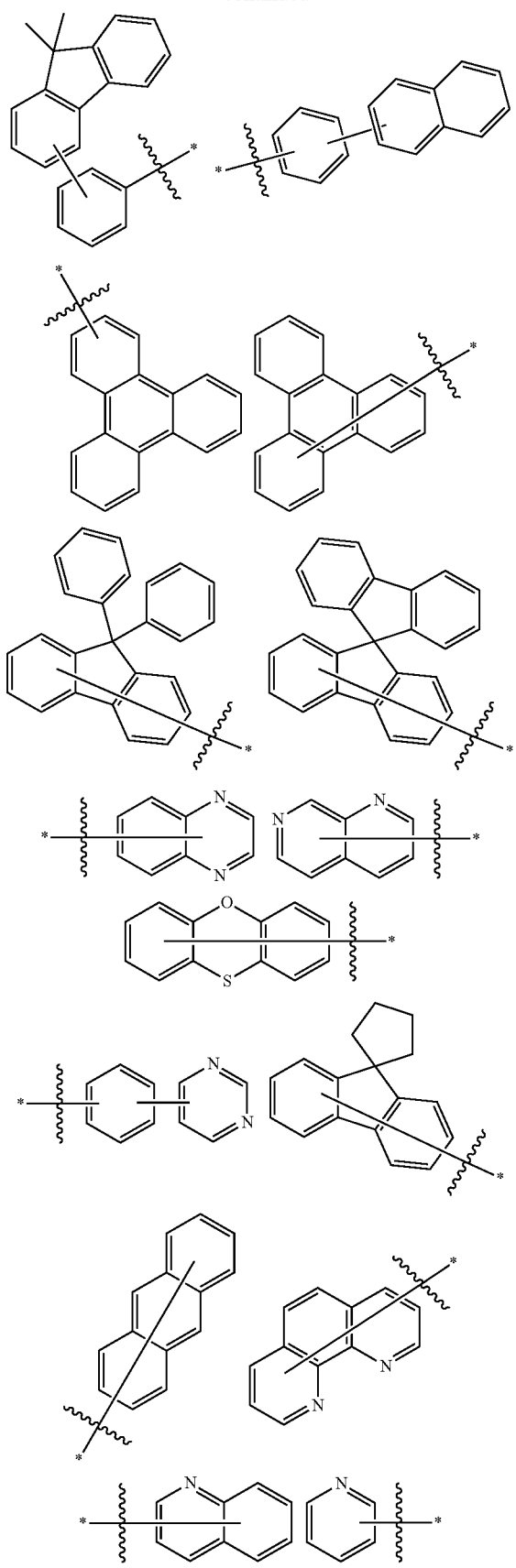
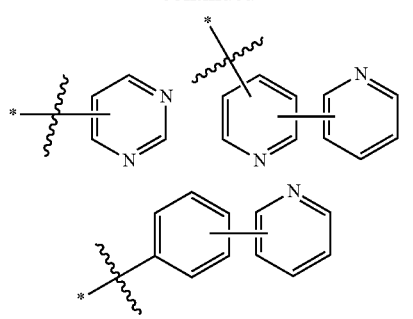

the above groups are optionally substituted by 0, 1, 2, 3, 4 or 5 substituents selected from deuterium, fluorine, chlorine, cyano, C1-C4 alkyl, C1-C4 alkoxyl, C1-C4 haloalkyl, C3-C9 alkylsilyl, C3-C10 cycloalkyl, C6-C12 aryl and C3-C12 heteroaryl.

According to an embodiment of the present disclosure, in the organic compound of the present disclosure, $Ar_1$ and $Ar_2$ are the same as or different from each other, and are each independently hydrogen, or a substituted or unsubstituted group as follows:

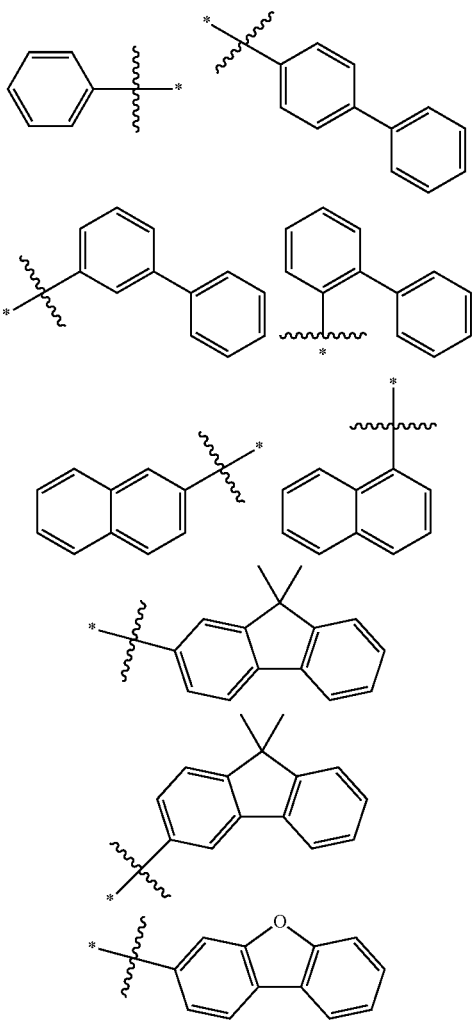

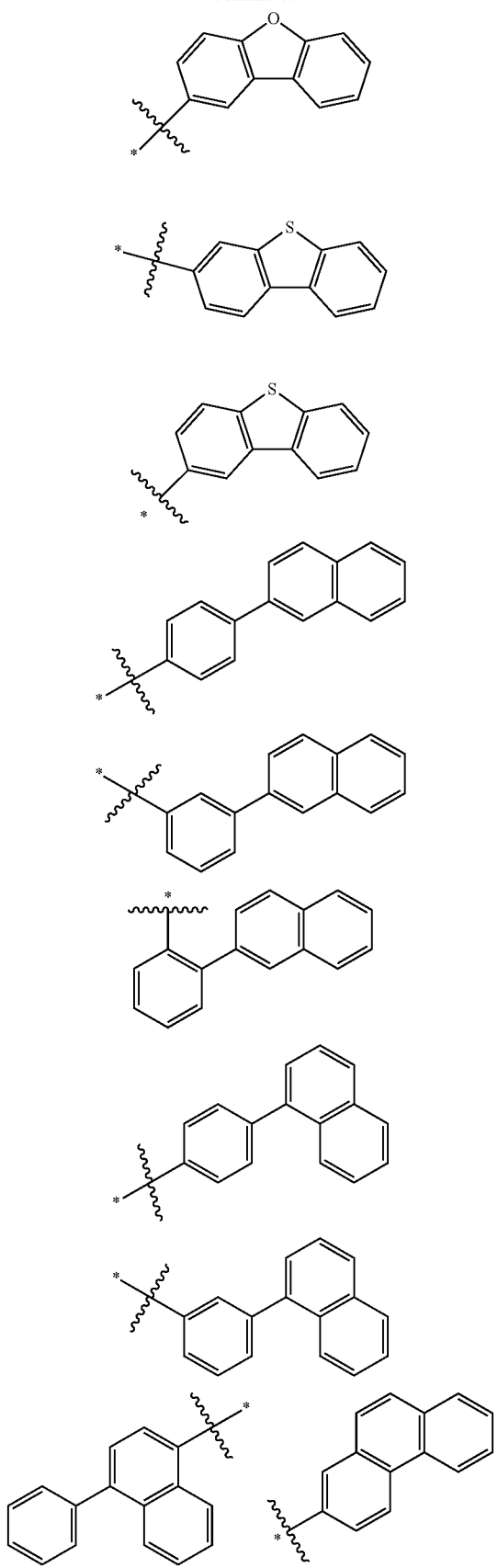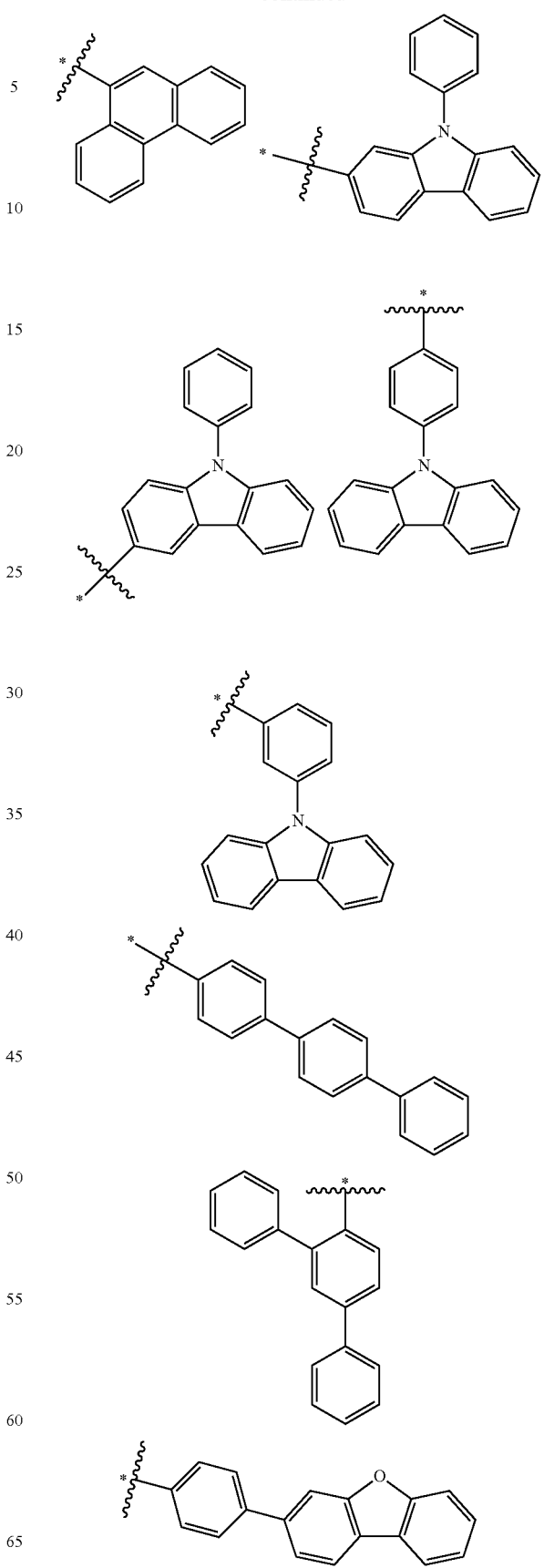

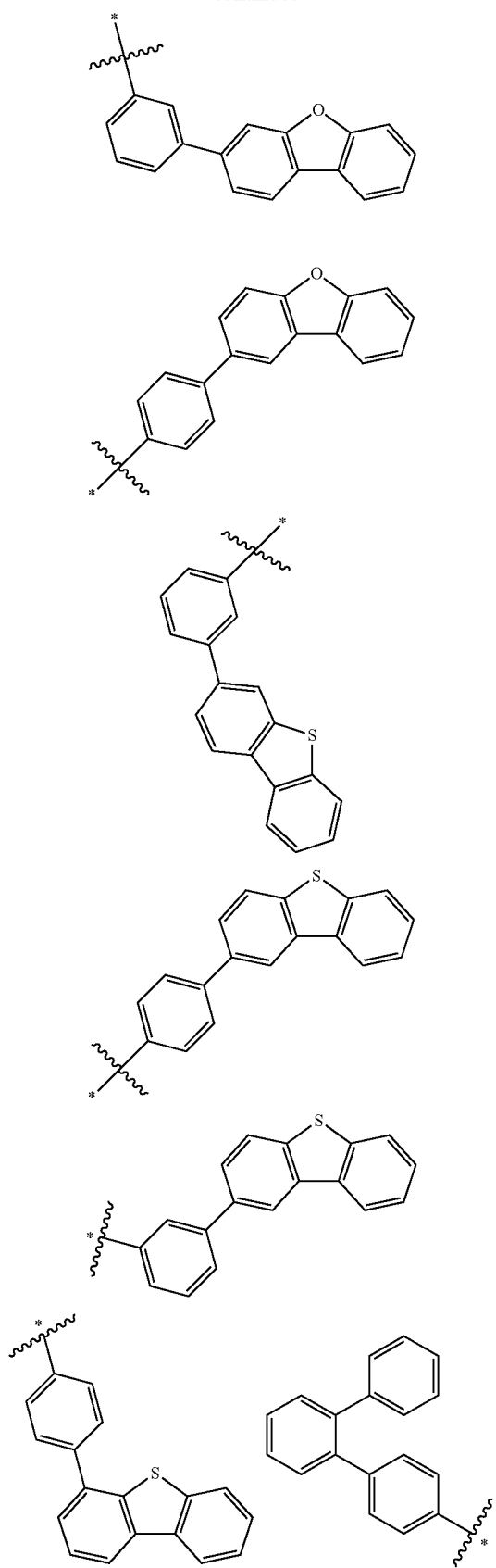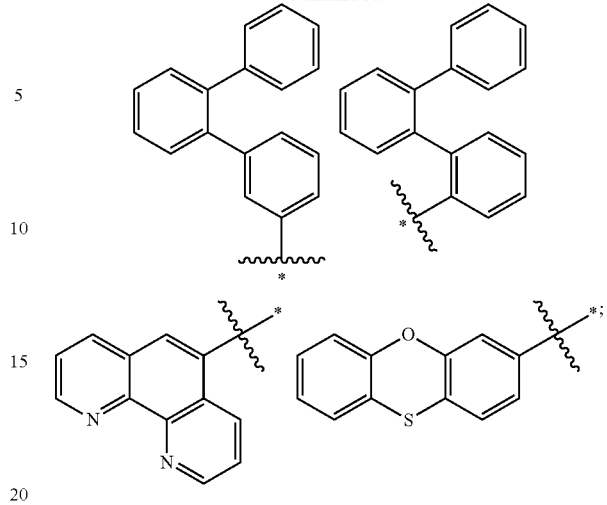

the above groups are optionally substituted by 0, 1, 2 or 3 substituents selected from deuterium, fluorine, chlorine, bromine, cyano, C1-C4 alkyl, C1-C3 haloalkyl, phenyl, naphthyl, dimethylfluorenyl and C3-C10 cycloalkyl.

According to an embodiment of the present disclosure, in the organic compound of the present disclosure, $Ar_1$ and $Ar_2$ are the same as or different from each other, and are each independently hydrogen, phenyl, diphenyl or naphthyl.

According to an embodiment of the present disclosure, in the organic compound of the present disclosure, one of $R_1$ to $R_4$ is

and all the other three are hydrogen; one of $R_5$ to $R_8$ is

and all the other three are hydrogen.

According to an embodiment of the present disclosure, in the organic compound represented by formula 1' or 1, L is selected from the group consisting of substituted or unsubstituted aryl with 6 to 20 ring-forming carbon atoms and substituted or unsubstituted heteroaryl with 3 to 18 ring-forming carbon atoms; the substituents in L are selected from the group consisting of deuterium, fluorine, chlorine, bromine, cyano, C1-C6 alkyl, C1-C6 haloalkyl, C6-C12 aryl, C3-C12 heteroaryl, C6-C18 aryloxy, C6-C18 arylthio, C3-C12 alkylsilyl and C3-C10 cycloalkyl.

According to an embodiment of the present disclosure, in the organic compound represented by formula 1' or 1, L is selected from the groups as follows: substituted or unsubstituted phenylene, substituted or unsubstituted biphenylene, substituted or unsubstituted terphenylene, substituted or unsubstituted quinquephenylene, and substituted or unsubstituted dinaphthylphenylene.

According to an embodiment of the present disclosure, in the organic compound represented by formula 1' or 1, L is selected from the groups as follows: substituted or unsubstituted quaterphenylene, substituted or unsubstituted naphthylene, substituted or unsubstituted naphthyl-phenylene, substituted or unsubstituted fluorenylene, substituted or unsubstituted phenanthrylene, and substituted or unsubstituted anthrylene.

According to an embodiment of the present disclosure, in the organic compound represented by formula 1' or 1, L is substituted or unsubstituted monocyclic C3-C5 heteroaryl.

According to an embodiment of the present disclosure, in the organic compound represented by formula 1' or 1, L is selected from the groups as follows: substituted or unsubstituted triazinylene, substituted or unsubstituted pyrimidylene, substituted or unsubstituted pyridinylene, substituted or unsubstituted pyrazinylene, substituted or unsubstituted pyrrolylene, substituted or unsubstituted thienylene, substituted or unsubstituted dibenzofuranylene, and substituted or unsubstituted phenyl-dibenzothienylene.

According to an embodiment of the present disclosure, in the organic compound represented by formula 1' or 1, L is selected from the groups as follows: substituted or unsubstituted dibenzothienylene, substituted or unsubstituted dibenzofuranylene, substituted or unsubstituted carbazolylene, substituted or unsubstituted dibenzocylosilylene, and substituted or unsubstituted quinolylene.

According to an embodiment of the present disclosure, in the organic compound represented by formula 1' or 1, L is selected from the groups as follows: phenyldibenzofuranylene, phenyldibenzothienylene, N-phenylcarbazolylene, substituted or unsubstituted phenanthrolinylene, substituted or unsubstituted phenothiazinylene, and substituted or unsubstituted phenoxazinylene.

According to an embodiment of the present disclosure, in the organic compound represented by formula 1' or 1, L is selected from the group consisting of deuterium, fluorine, chlorine, bromine, cyano, C1-C4 alkyl, C1-C3 haloalkyl, phenyl, naphthyl, fluorenyl, C3-C12 heteroaryl, C3-C12 alkylsilyl and C3-C10 cycloalkyl.

According to an embodiment of the present disclosure, in the organic compound represented by formula 1' or 1, L is selected from the groups as follows:

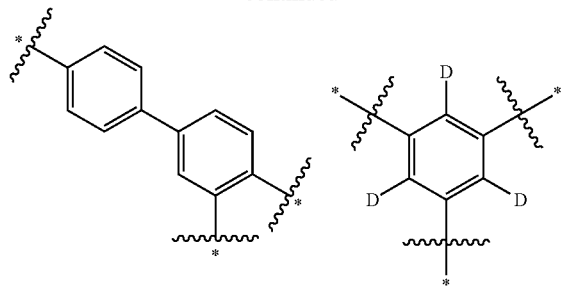

-continued

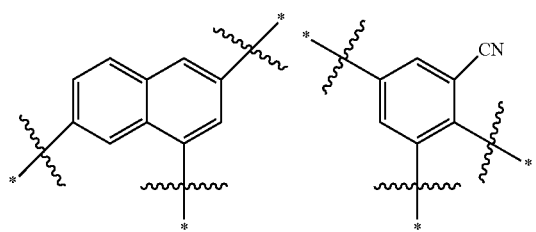

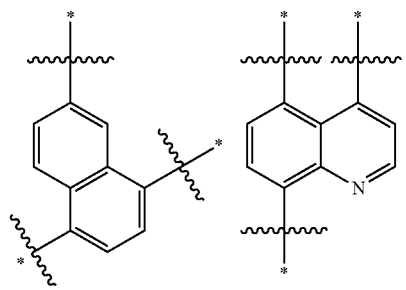

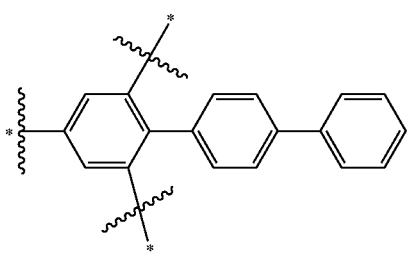

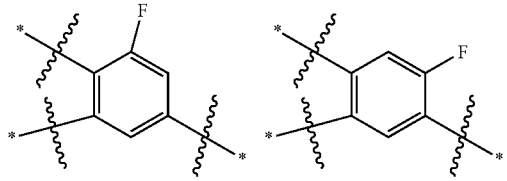

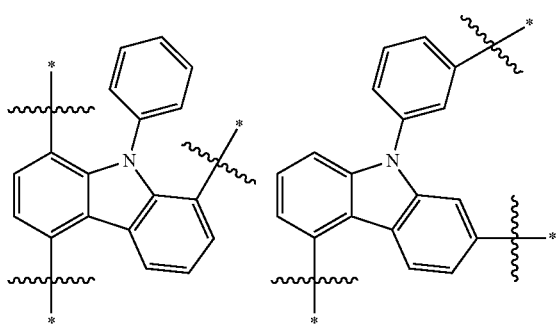

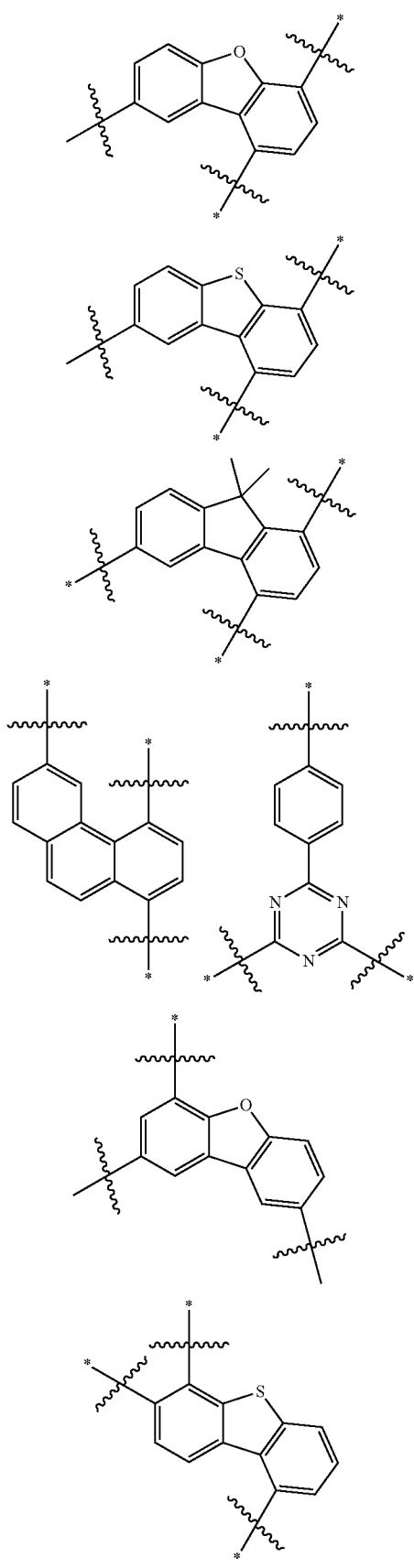
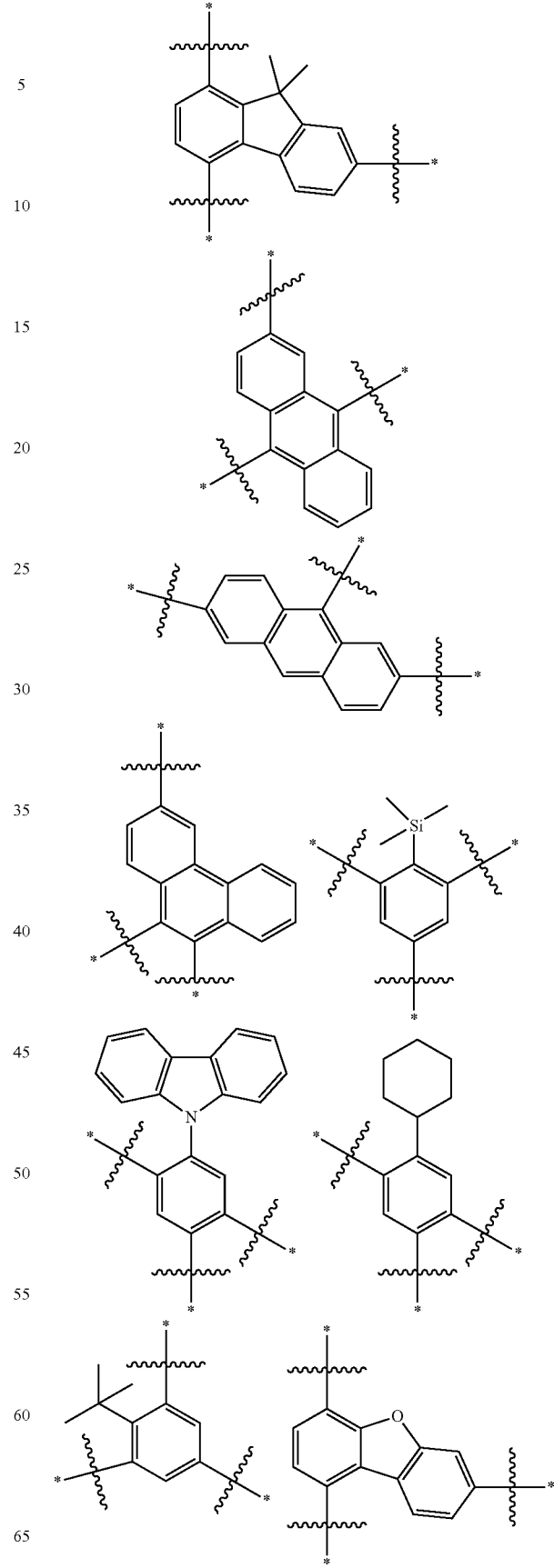

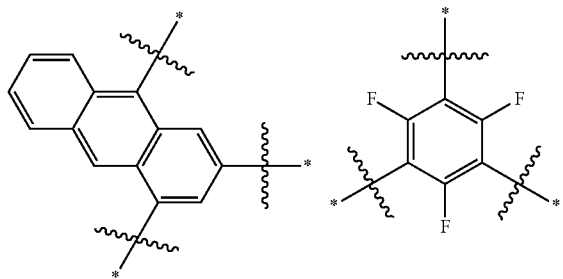

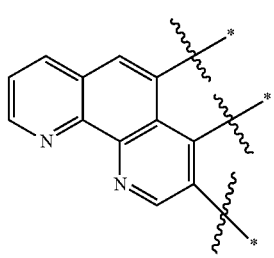

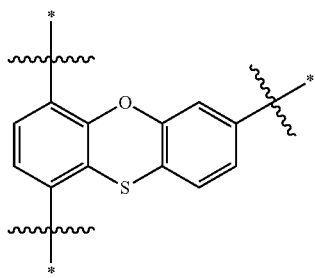

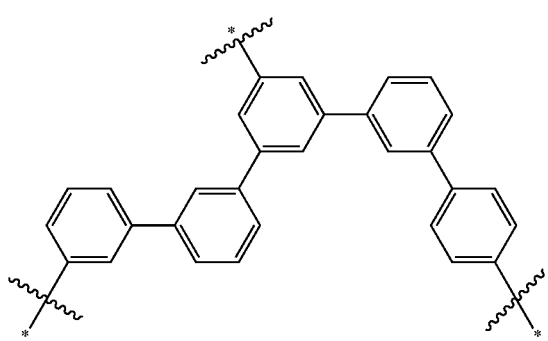

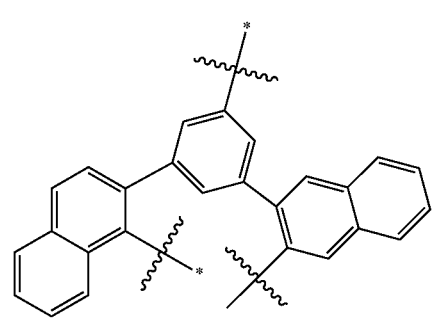

According to an embodiment of the present disclosure, in the organic compound represented by formula 1' or 1, the substituent on L is selected from the group consisting of deuterium, nuorine, cyano, methyl, isopropyl, tert-butyl, trifluoromethyl, phenyl, biphenyl, cyclohexyl and trimethylsilyl.

According to an embodiment of the present disclosure, in the organic compound represented by formula 1, one of $R_1'$ to $R_4'$ is

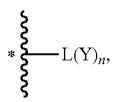

and the other three are each independently hydrogen, deuterium, fluorine, chlorine, bromine, cyano, C1-C4 alkyl, phenyl, naphthyl, dimethylfluorenyl, pyridyl, quinolyl, dibenzofuranyl or dibenzothienyl; one of $R_5'$ to $R_8'$ is

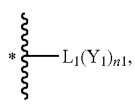

and the other three are each independently hydrogen, deuterium, fluorine, chlorine, bromine, cyano, methyl, ethyl, isopropyl or tert-butyl; Y is

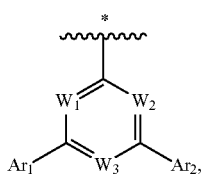

$W_1$, $W_2$ and $W_3$ are each independently N; $Ar_1$ and $Ar_2$ are each independently hydrogen, deuterium, substituted or unsubstituted aryl with 6 to 20 ring-forming carbon atoms (such as phenyl, naphthyl, diphenyl, terphenyl, phenyl-naphthyl, naphthyl-phenyl, fluorenyl, dimethylfluorenyl and the like), wherein substituents in $Ar_1$ and $Ar_2$ are selected from deuterium, halogen group, cyano, C1-C4 alkyl and phenyl;

L is substituted or unsubstituted arylene with 6 to 30 ring-forming carbon atoms (such as phenylene, naphthylene, diphenylene, terphenylene, benzonaphthylene, fluorenylene, quaterphenylene, quinquephenylene and the like) or substituted or unsubstituted heteroarylene with 3 to 18 ring-forming carbon atoms (for example, nitrogen-containing heteroarylene such as pyridylene, pyrimidylene, triazinylene and the like), wherein the substituent in L is selected from deuterium, a halogen group, cyano, C1-C4 alkyl and phenyl; $L_1$ is hydrogen or deuterium.

According to an embodiment of the present disclosure, in the organic compound represented by formula 1, one of $R_1'$ to $R_4'$ is

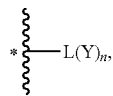

and the other three are each independently hydrogen, deuterium, fluorine, chlorine, bromine or cyano; one of $R_5'$ to $R_8'$ is

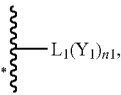

and the other three are each independently hydrogen, deuterium, fluorine, chlorine, bromine or cyano; Y is

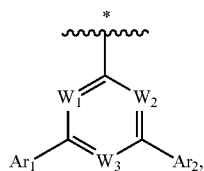

$W_1$ and $W_2$ are each independently N, $W_3$ is $C(R^{w3})$, wherein $R^{w3}$ is hydrogen, deuterium, fluorine, chlorine, bromine or cyano; $Ar_1$ and $Ar_2$ are each independently hydrogen, deuterium, substituted or unsubstituted aryl with 6 to 20 ring-forming carbon atoms (such as phenyl, naphthyl, diphenyl, terphenyl, benzonaphthyl, fluorenyl and the like), wherein substituents in $Ar_1$ and $Ar_2$ are selected from deuterium, a halogen group, cyano and C1-C4 alkyl; L is substituted or unsubstituted arylene with 6 to 30 ring-forming carbon atoms (such as phenylene, naphthylene, diphenylene, terphenylene, benzonaphthylene, fluorenylene, quaterphenylene, quinquephenylene and the like) or substituted or unsubstituted heteroarylene with 3 to 18 ring-forming carbon atoms (for example, nitrogen-containing heteroaryl with 3 to 5 ring-forming carbon atoms such as pyridyl, pyrimidyl, triazinyl and the like), wherein the substituent in L is selected from deuterium, a halogen group, C1-C4 alkyl, cyano and phenyl; $L_1$ is hydrogen or deuterium.

According to an embodiment of the present disclosure, in the organic compound represented by formula 1, one of $R_1'$ to $R_4'$ is

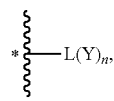

and the other three are each independently hydrogen, deuterium, fluorine, chlorine, bromine, cyano, methyl, ethyl, isopropyl, tert-butyl, phenyl, naphthyl, dimethylfluorenyl, pyridyl, quinolyl, dibenzofuranyl, dibenzothienyl; one of $R_5'$ to $R_8'$ is

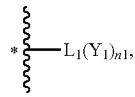

and the other three are each independently hydrogen, deuterium, fluorine, chlorine, bromine or cyano; Y is

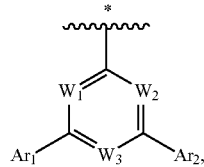

$W_1$ is N, $W_2$ and $W_3$ are each independently $C(R^{w2})$ and $C(R^{w3})$, wherein $R^{w2}$ and $R^{w3}$; are each independently hydrogen, deuterium, fluorine, chlorine, bromine or cyano; $Ar_1$ and $Ar_2$ are each independently hydrogen, deuterium, substituted or unsubstituted aryl with 6 to 20 ring-forming carbon atoms (such as phenyl, naphthyl, diphenyl, terphenyl, benzonaphthyl, fluorenyl and the like), wherein substituents in $Ar_1$ and $Ar_2$ are selected from deuterium, a halogen group, cyano and C1-C4 alkyl; L is substituted or unsubstituted arylene with 6 to 30 ring-forming carbon atoms (such as phenylene, naphthylene, diphenylene, triphenylene, benzonaphthylene, fluorenylene, tetradiphenylene, pentadiphenylene and the like), or substituted or unsubstituted heteroarylene with 3 to 18 ring-forming carbon atoms (for example, nitrogen-containing heteroaryl with 3 to 5 ring-forming carbon atoms such as pyridyl, pyrimidyl, triazinyl and the like), wherein the substituents in L are selected from deuteriunm, a halogen group, cyano, C1-C4 alkyl and phenyl; $L_1$ is hydrogen or deuterium.

According to an embodiment of the present disclosure, wherein the organic compound represented by formula 1 is selected from any one as follows:

Compound 1
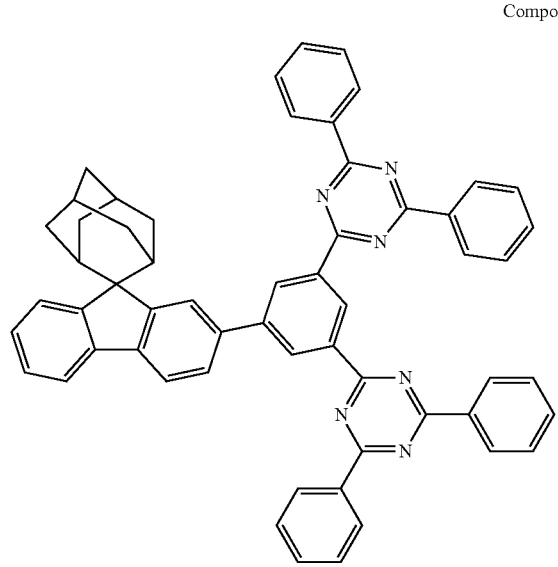
Compound 2
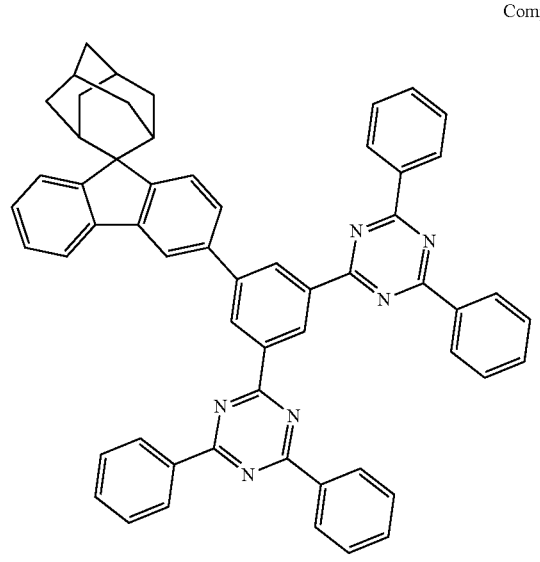
Compound 3
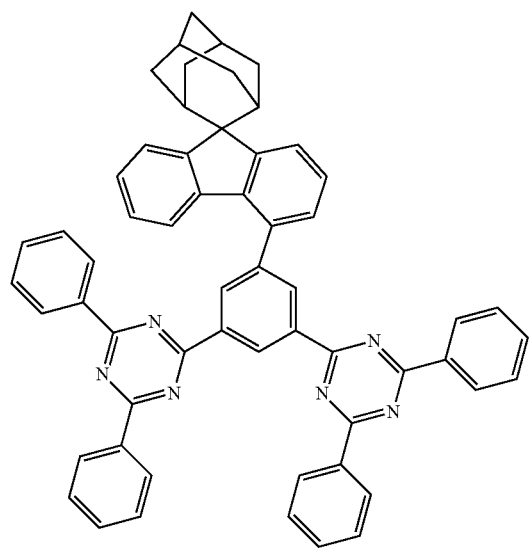
Compound 4
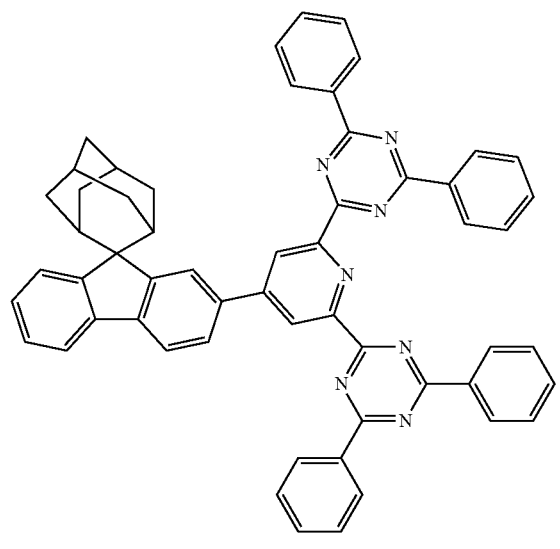
Compound 5
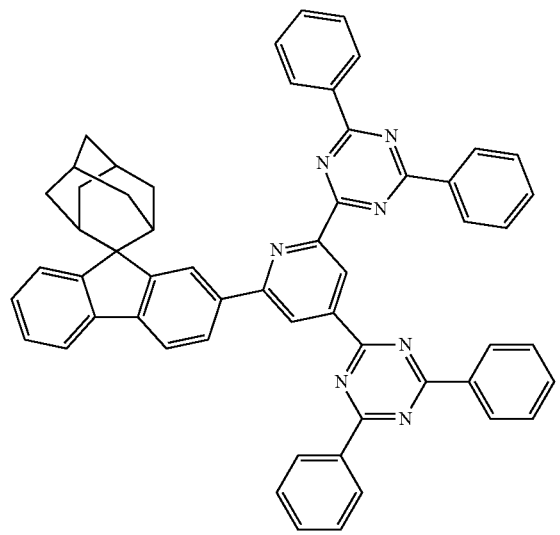
Compound 6
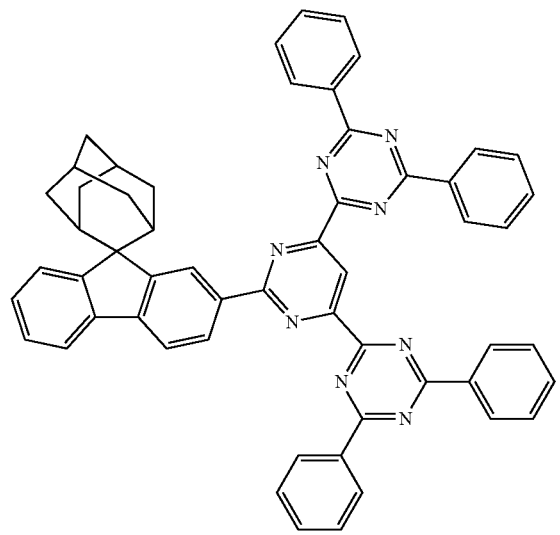

Compound 7
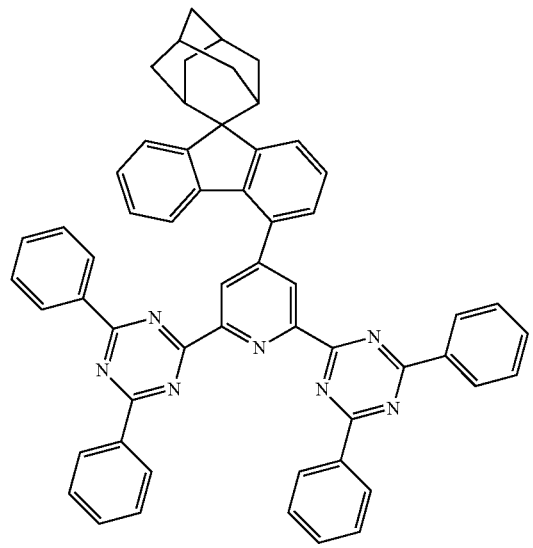
Compound 8
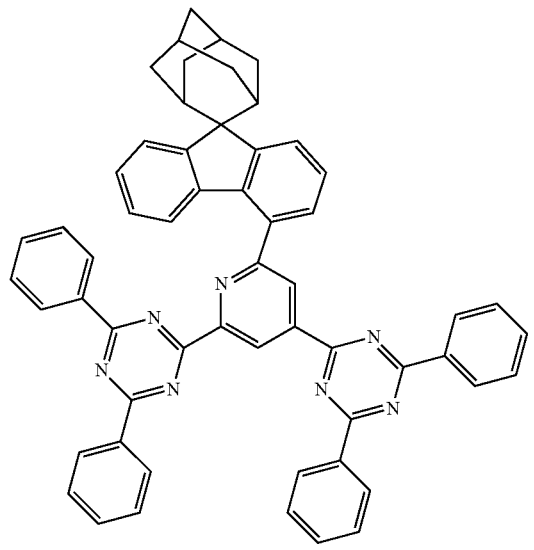
Compound 9
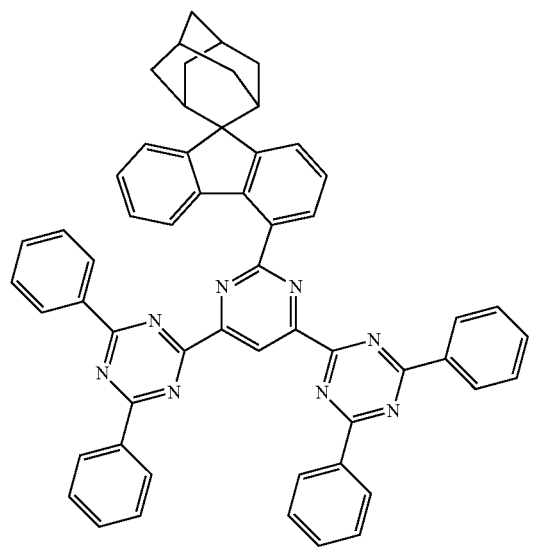
Compound 10
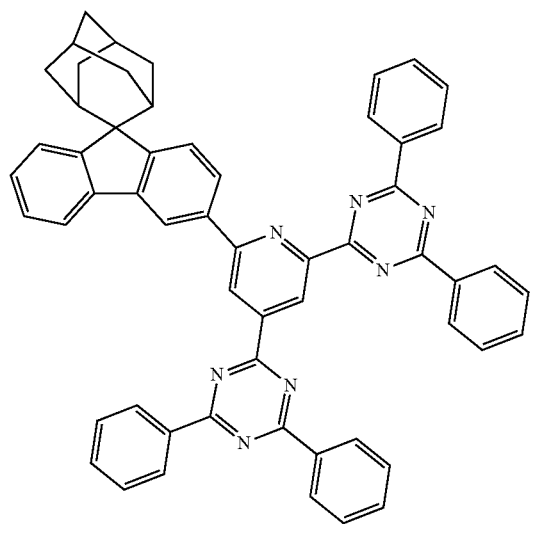

-continued
Compound 11
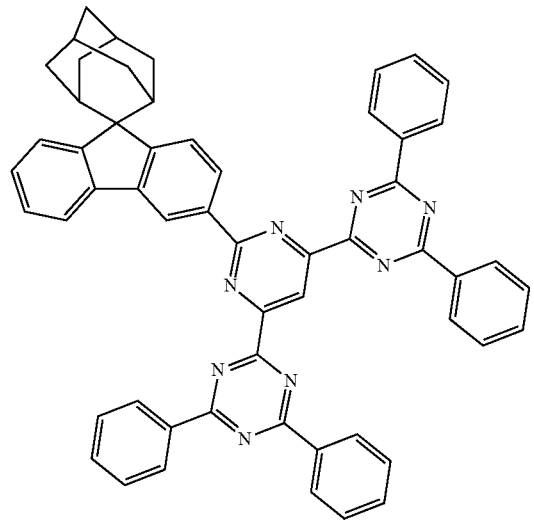
Compound 12
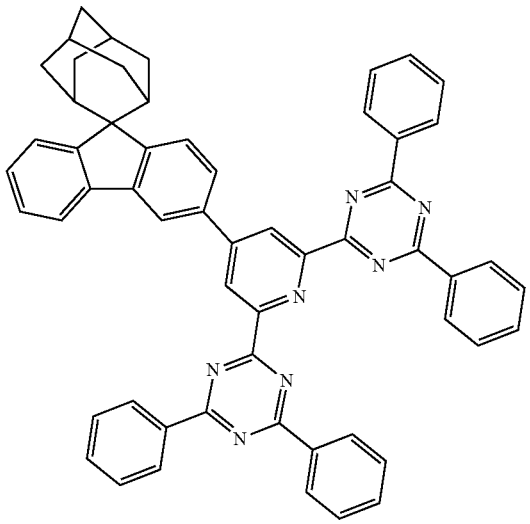
Compound 13
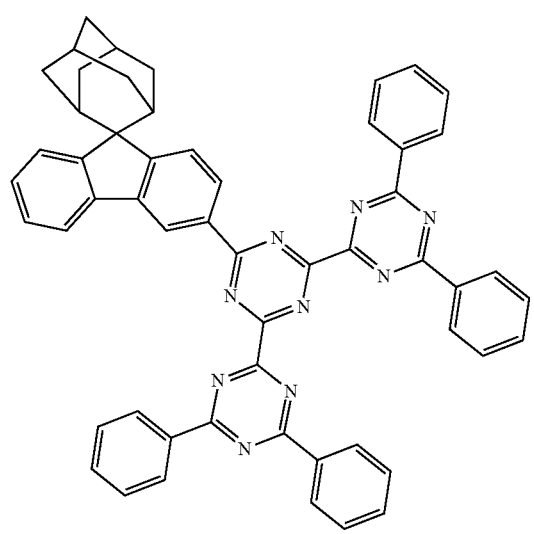
Compound 14
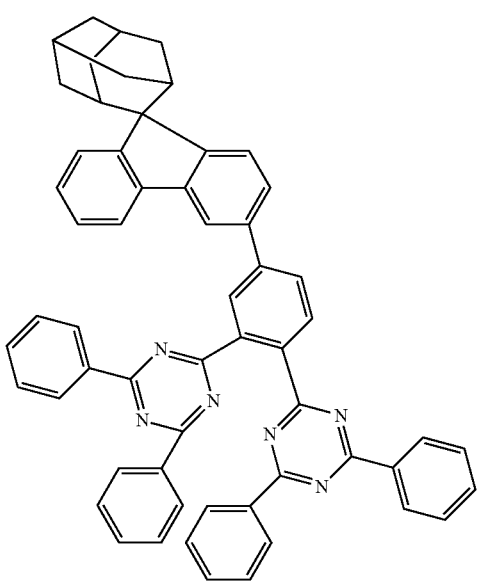
Compound A
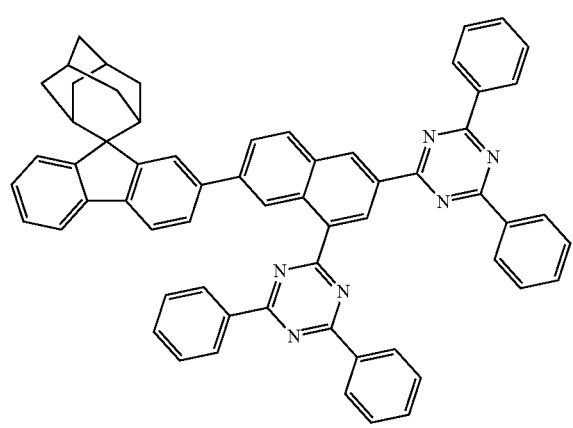
Compound B
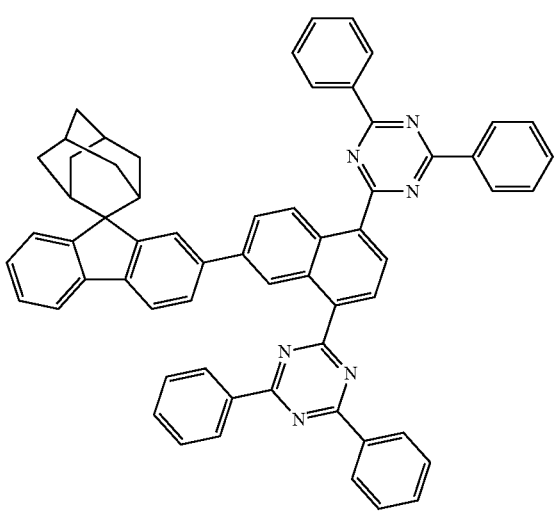

Compound C
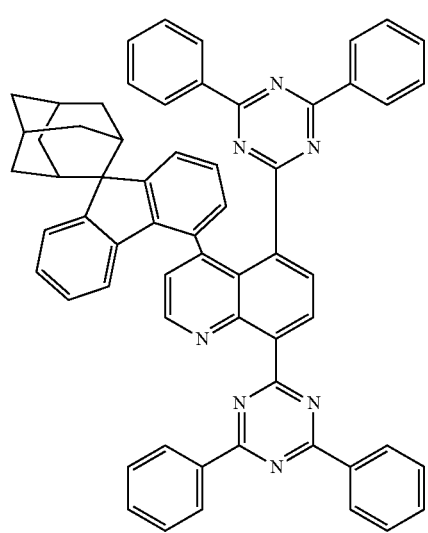
Compound D
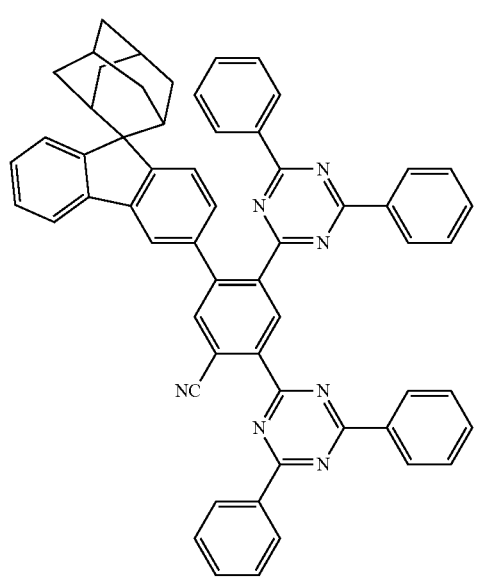
Compound E
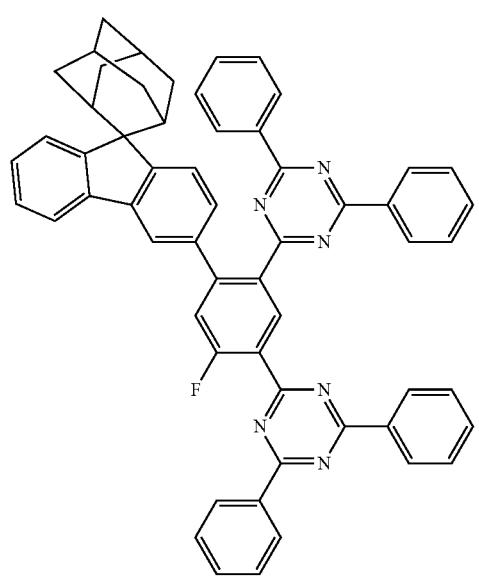
Compound F
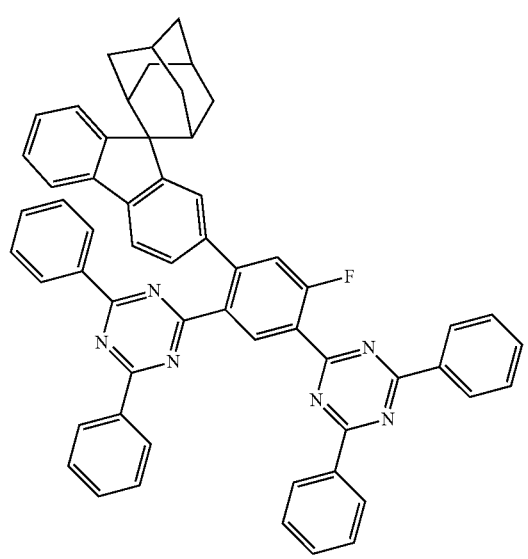

-continued
Compound G
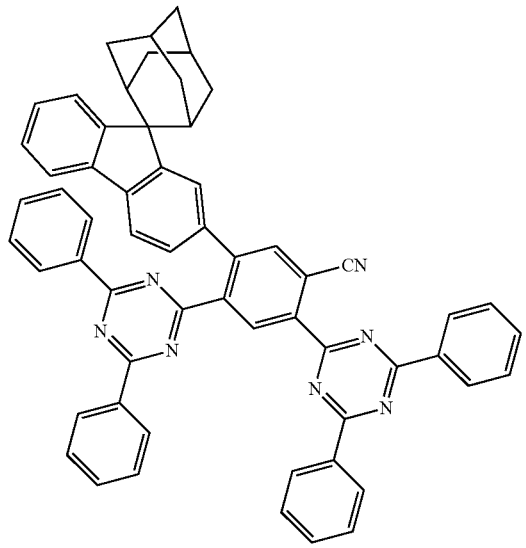
Compound H
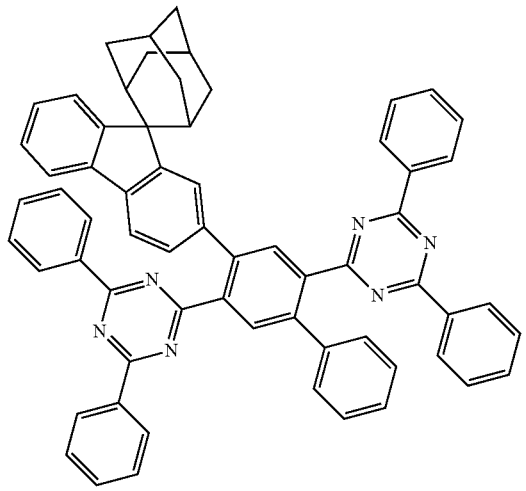
Compound I
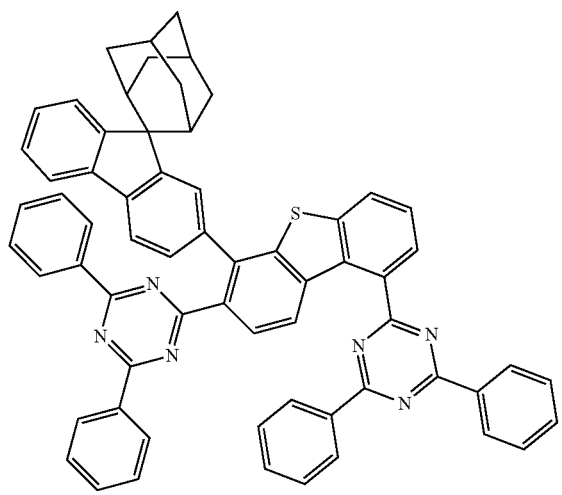
Compound J
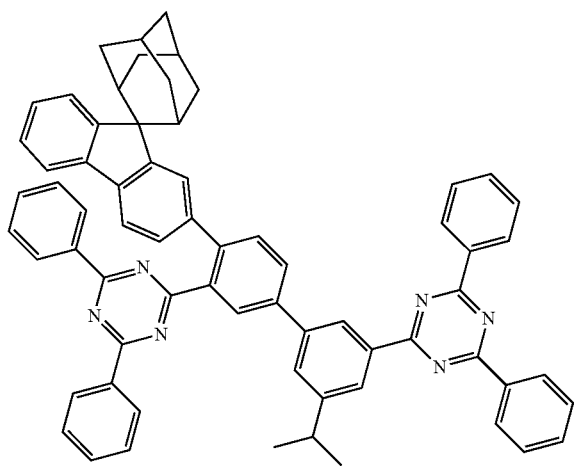
Compound K
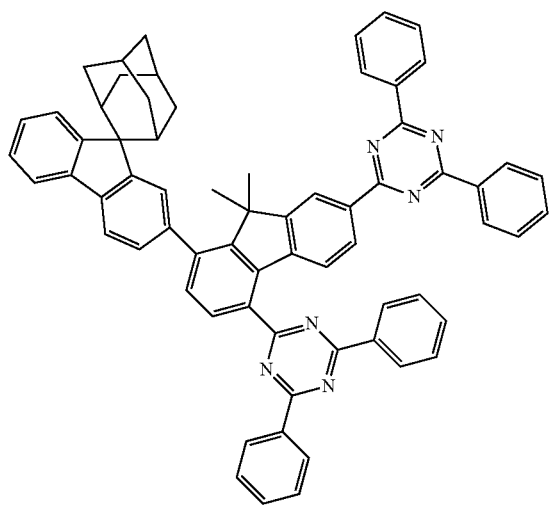
Compound L
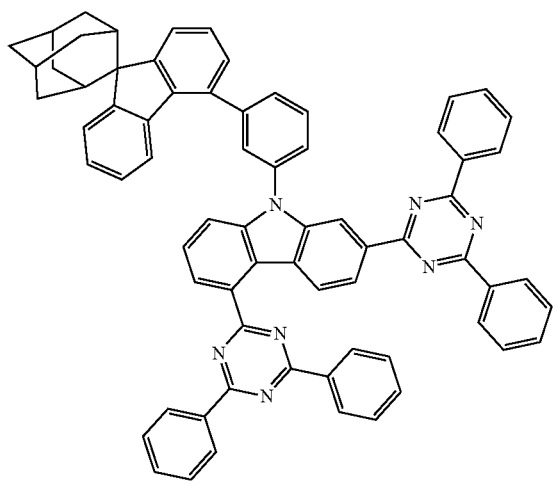

Compound M
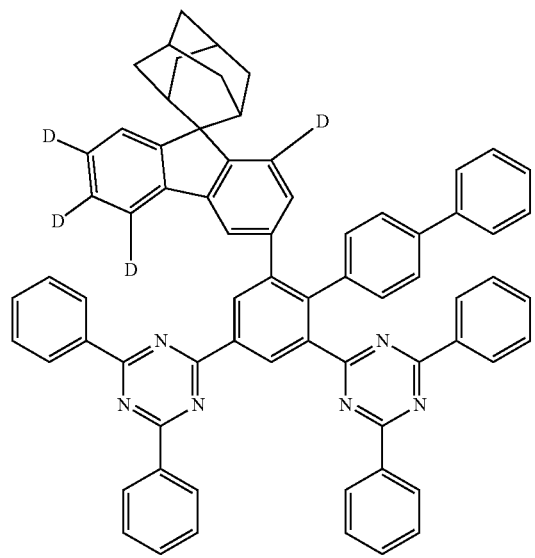
Compound M-1
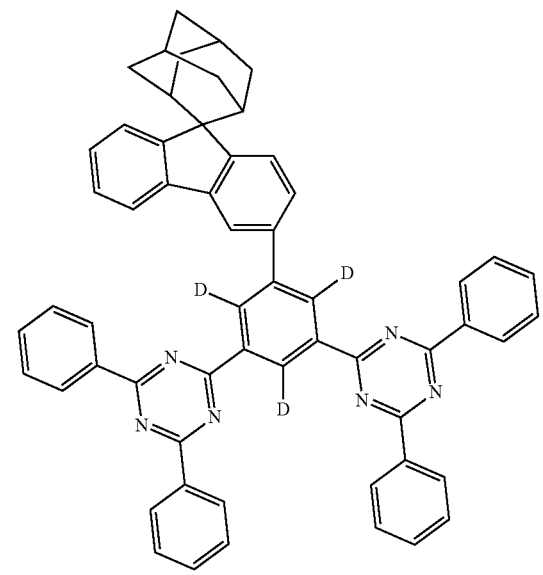
Compound M-2
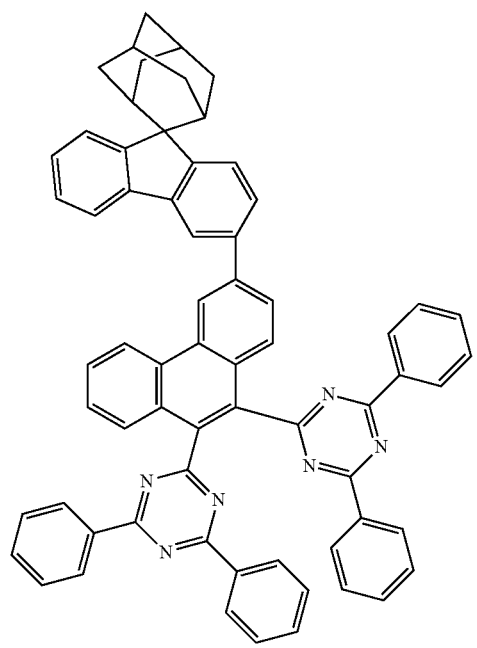
Compound M-3
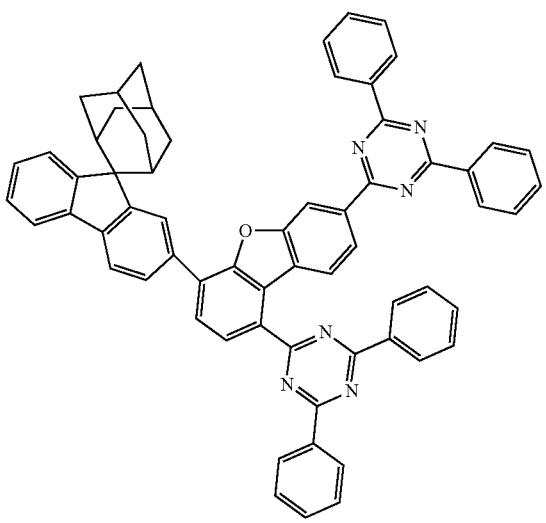

Compound M-4
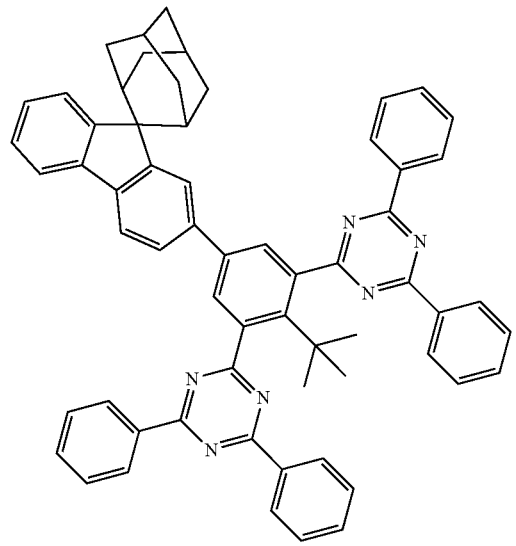
Compound M-5
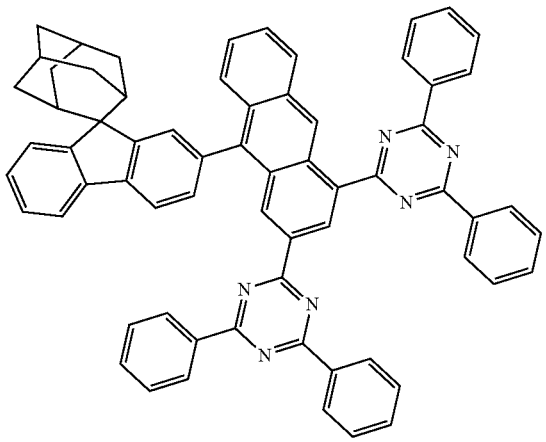
Compound M-6
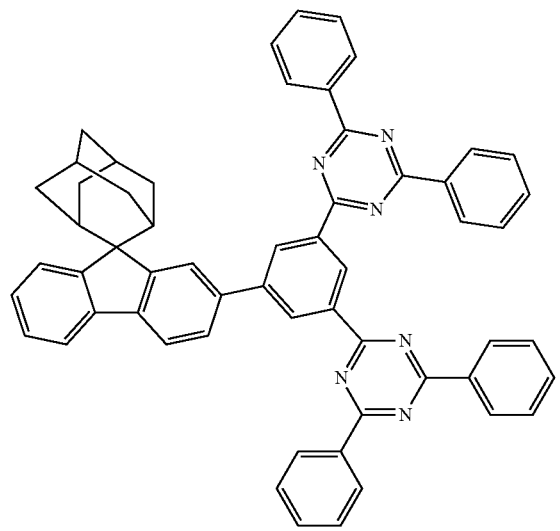
Compound M-7
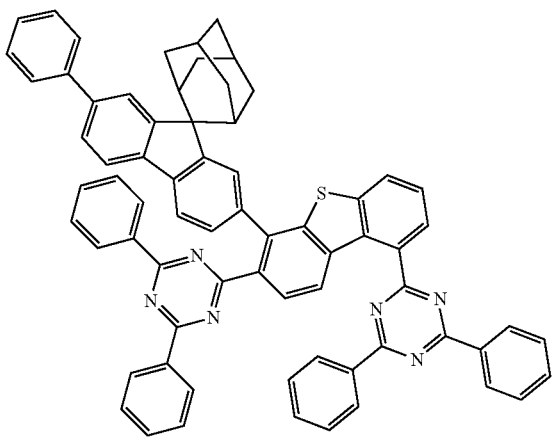

Compound M-8
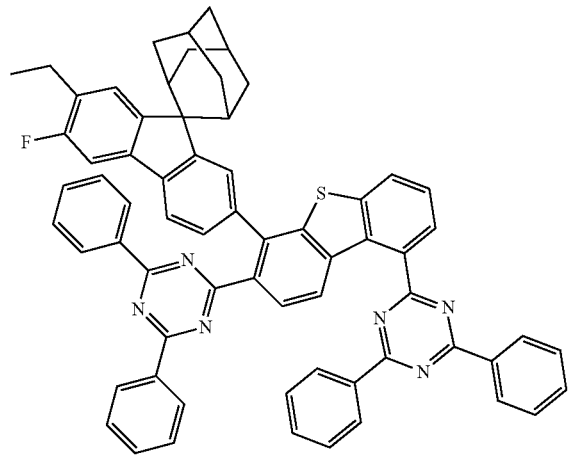
Compound M-9
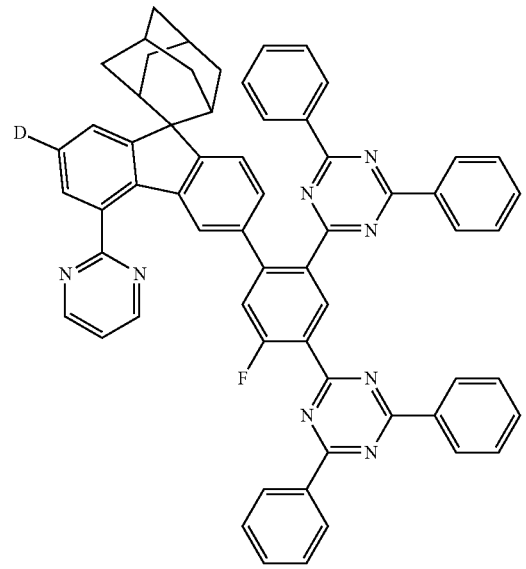
Compound M-10
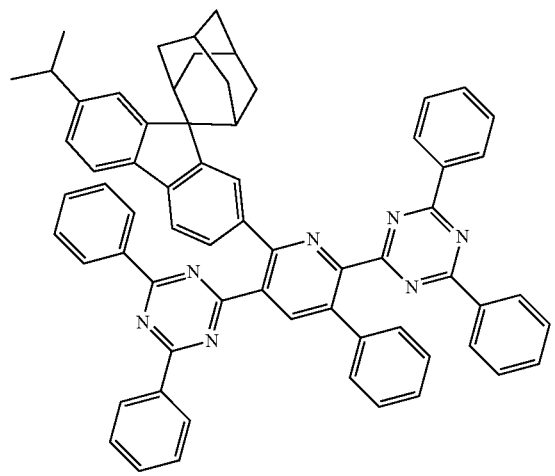
Compound M-11
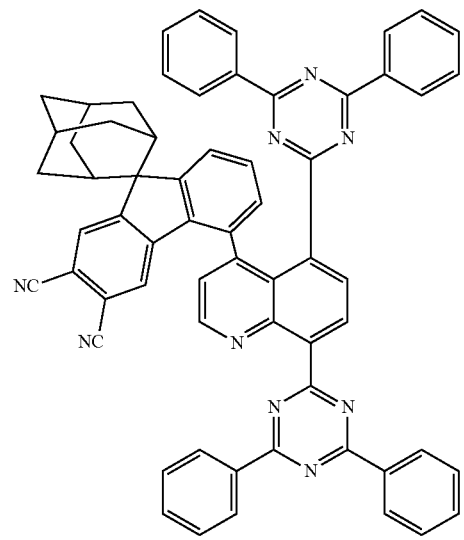

Compound M-12
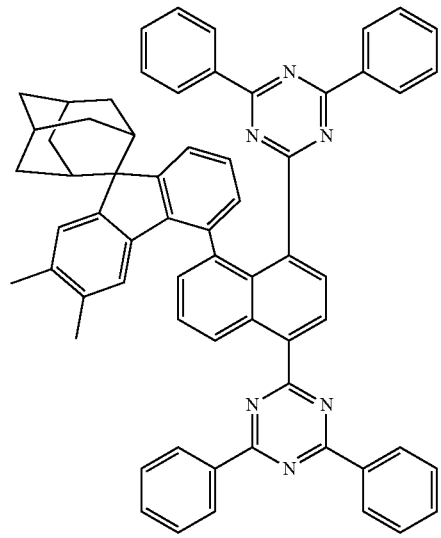
Compound M-13
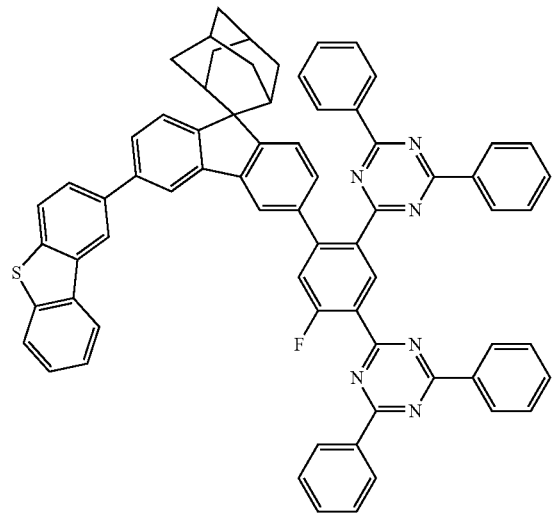
Compound M-14
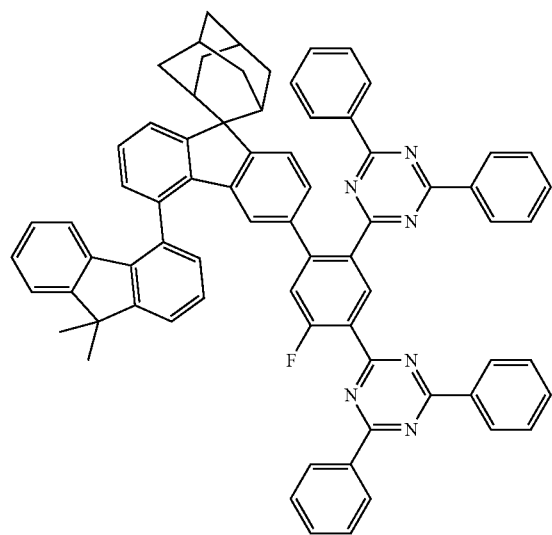
Compound M-15
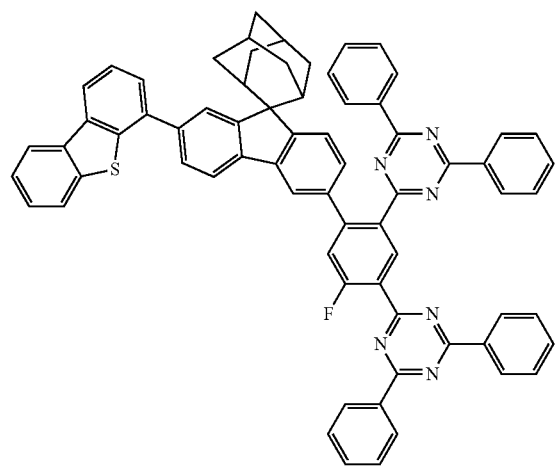

-continued
Compound M-16
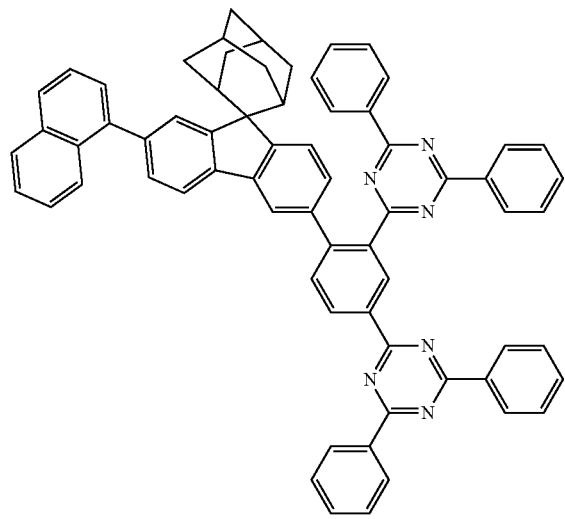
Compound M-17
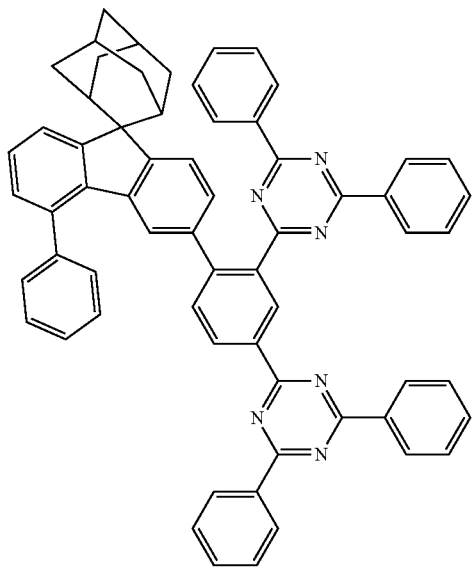
Compound M-18
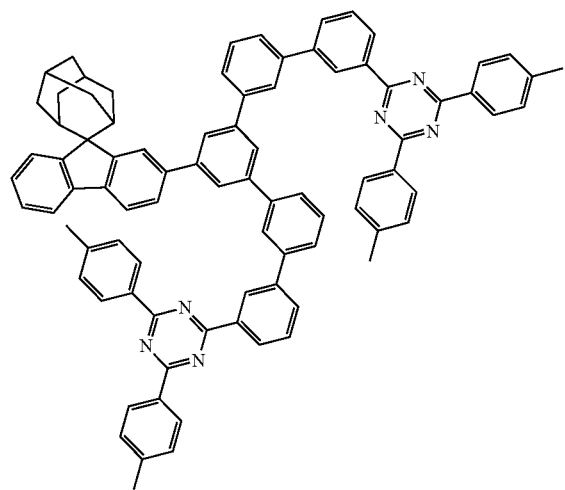
Compound M-19
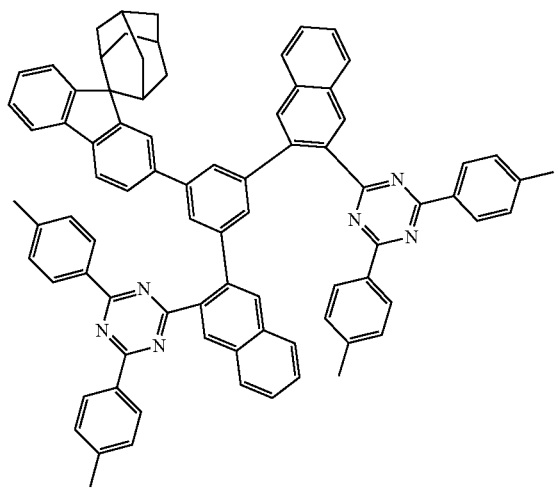
Compound M-20
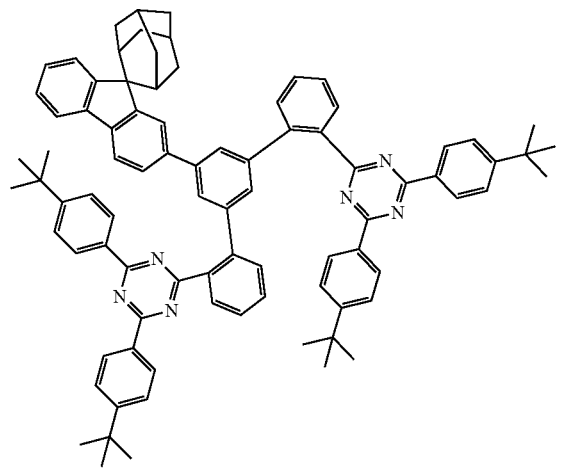
Compound M-21
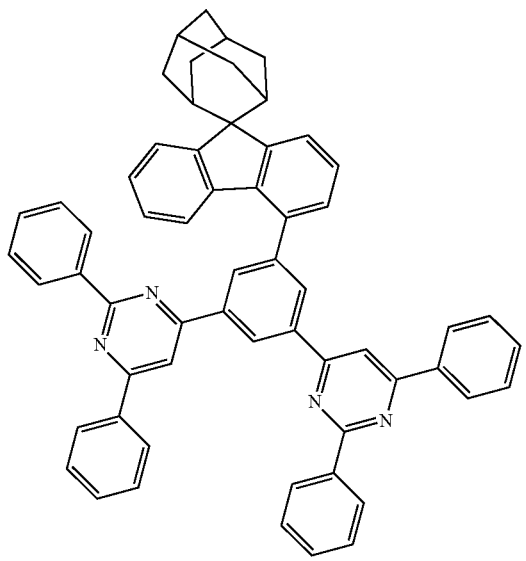

-continued
Compound M-22
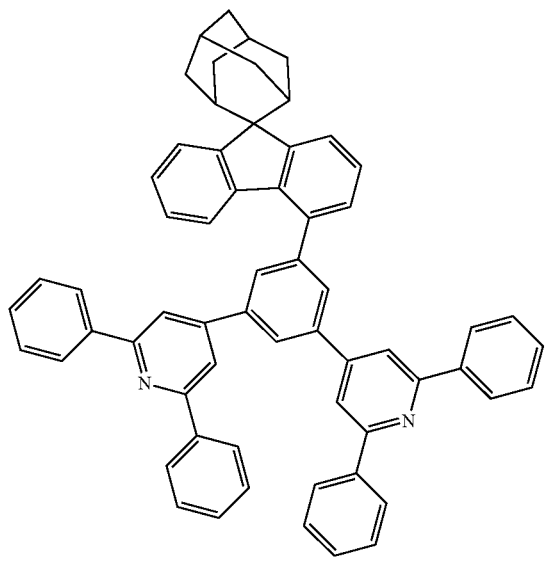
Compound M-23
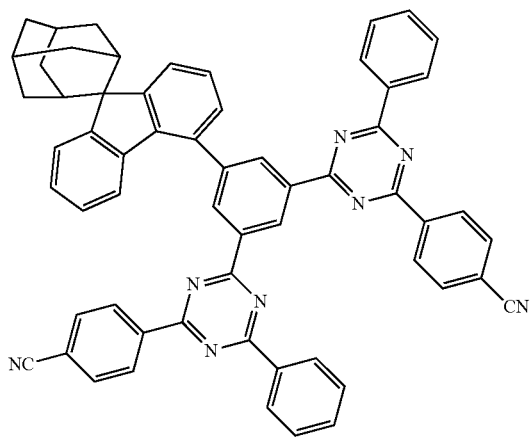
Compound M-24
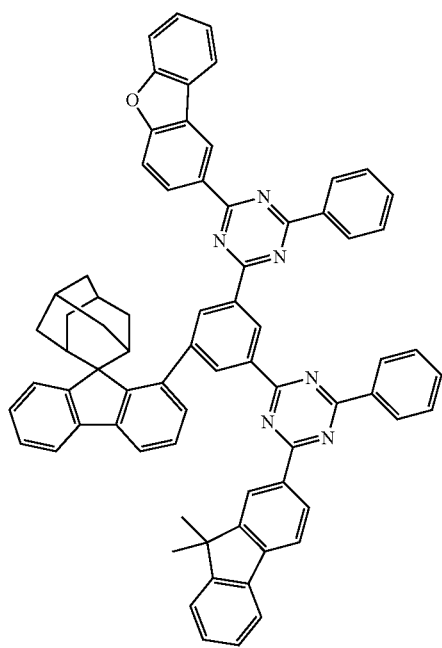

-continued
Compound M-25
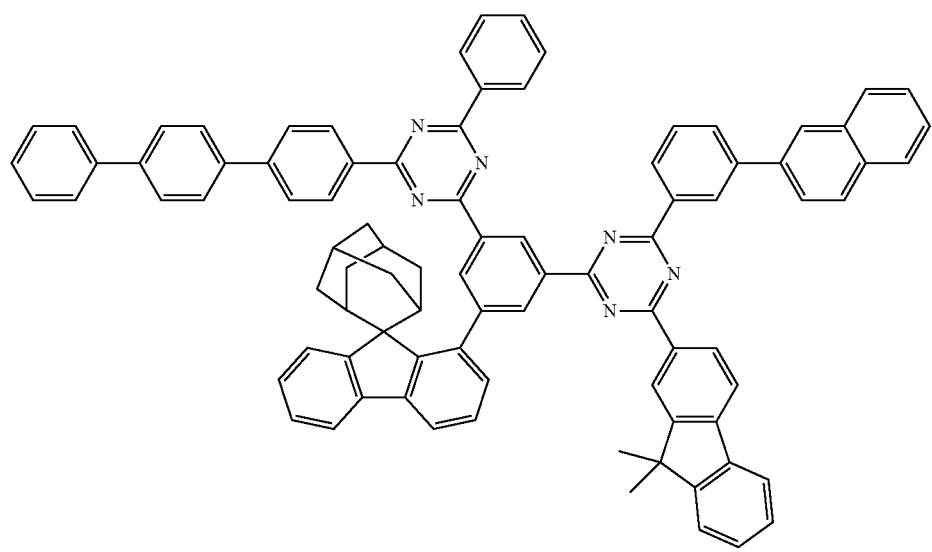
Compound M-26
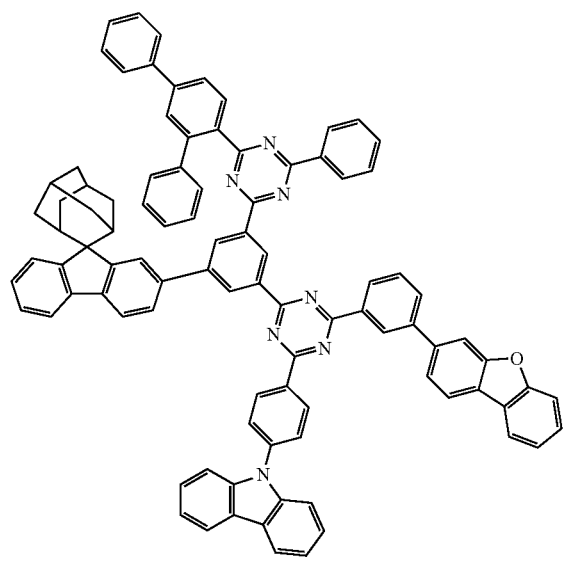
Compound M-27
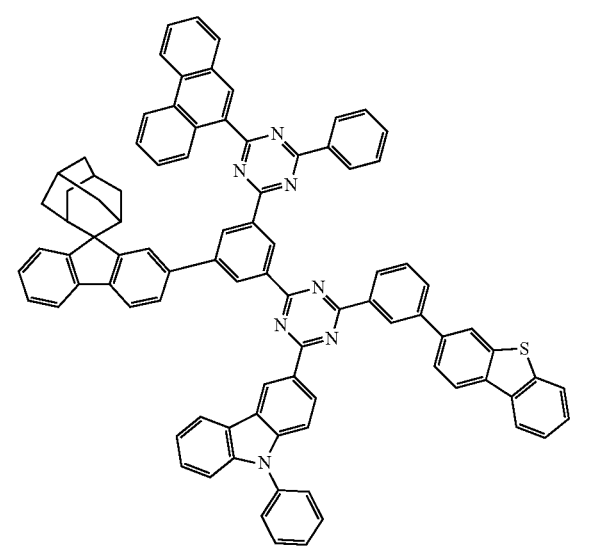
Compound M-28
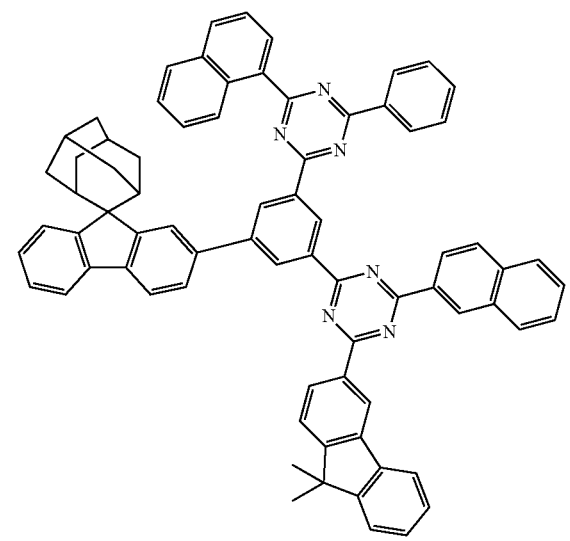
Compound M-29

Compound M-30

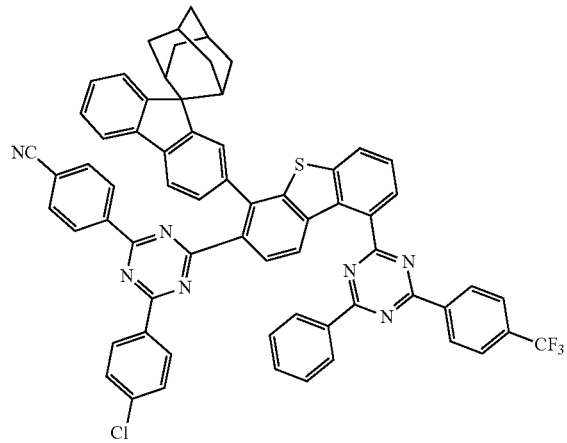

Compound M-31

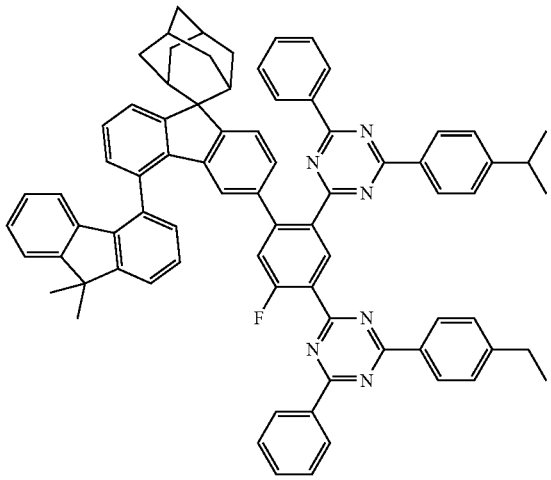

According to an embodiment of the present disclosure, in the organic compound represented by formula 1' 2, L and $L_1$ are the same as or different from each other, and are each independently selected from a single bond, substituted or unsubstituted arylene with 6 to 20 ring-forming carbon atoms, and substituted or unsubstituted heteroarylene with 3 to 18 ring-forming carbon atoms.

According to an embodiment of the present disclosure, in the organic compound represented by formula 1' or 2, L and $L_1$ are the same as or different from each other, and are each independently a single bond, or a substituted or unsubstituted group as follows:

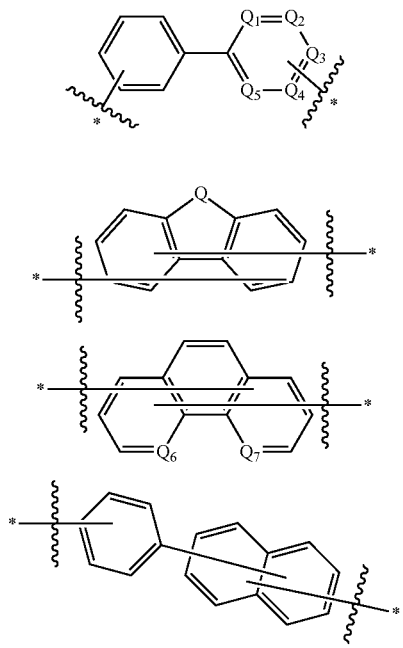

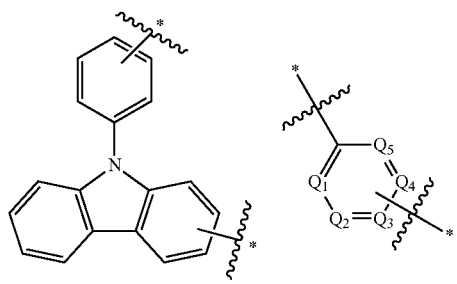

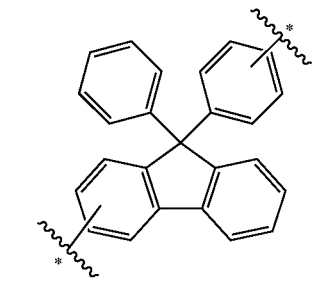

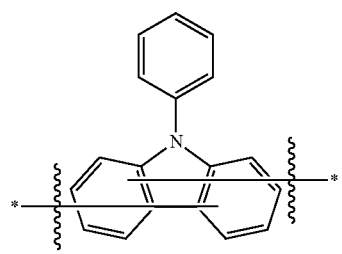

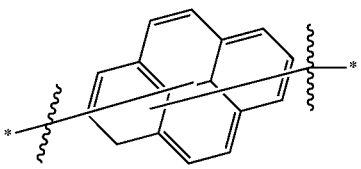

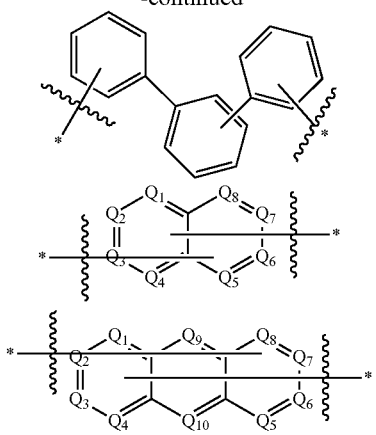

in the above groups, Q is selected from the group consisting of O, S, Se, C(R$^{Q1}$R$^{Q2}$), N(R$^{Q3}$) and Q$_1$ to Q$_{10}$ are each independently selected from C(R$^Q$) and N, and when two or more are contained in one group, any two R$^Q$ are the same as or different from each other;

R$^Q$, R$^{Q1}$ and R$^{Q2}$ are each independently from hydrogen, deuterium, fluorine, chlorine, bromine, cyano, C1-C6 alkyl, C1-C6 haloalkyl, C6-C12 aryl, C3-C12 heteroaryl, C6-C18 aryloxy, C6-C18 arylthio, C3-C12 alkylsilyl and C3-C10 cycloalkyl; alternatively;

optionally, R$^{Q1}$ and R$^{Q2}$ connected to the same atom are mutually connected to form a saturated or unsaturated 5- to 10-membered aliphatic ring (this means that R$^{Q1}$ and R$^{Q2}$ connected to the same atom herein can be mutually connected to form a saturated or unsaturated 5- to 10-membered aliphatic ring, or exist independently without affecting each other).

R$^{Q3}$ is independently selected from the group consisting of hydrogen, deuterium, C1-C6 alkyl, C1-C6 haloalkyl, C6-C12 aryl, C3-C12 heteroaryl and C3-C10 cycloalkyl;

the above groups are optionally substituted by 0, 1, 2 or 3 substituents selected from deuterium, fluorine, chlorine, cyano, C1-C6 alkyl, C1-C4 alkoxyl, C1-C4 haloalkyl, C3-C9 alkylsilyl, C3-C10 cycloalkyl, C6-C12 aryl and C3-C12 heteroaryl.

According to an embodiment of the present disclosure, in the organic compound represented by formula 1' or 2, L and L$_1$ are the same as or different from each other, and are each independently a single bond, or selected from the group consisting of groups as follows: substituted or unsubstituted phenylene, substituted or unsubstituted biphenylene, substituted or unsubstituted terphenylene, substituted or unsubstituted quaterphenylene, substituted or unsubstituted quinquephenylene, substituted or unsubstituted naphthylene, substituted or unsubstituted fluorenylene, substituted or unsubstituted phenanthrylene, substituted or unsubstituted anthrylene, substituted or unsubstituted triazinylene, substituted or unsubstituted pyrimidylene, substituted or unsubstituted pyridinylene, substituted or unsubstituted pyrazylene, substituted or unsubstituted pyrrolylene, substituted or unsubstituted thienylene, substituted or unsubstituted dibenzothienylene, substituted or unsubstituted dibenzofuranylene, substituted or unsubstituted phenyl-dibenzothienylene, substituted or unsubstituted phenyl-dibenzofuranylene, substituted or unsubstituted phenyl-carbazolylene, substituted or unsubstituted dibenzocylosilylene, substituted or unsubstituted quinolylene, substituted or unsubstituted phenanthrolinylene, substituted or unsubstituted phenothiazinylene, and substituted or unsubstituted phenoxazinylene;

the substituents in L and L$_1$ are the same as or different from each other, and are each independently selected from the group consisting of deuterium, fluorine, chlorine, bromine, cyano, C1-C4 alkyl, C1-C3 haloalkyl, phenyl, naphthyl, fluorenyl, C3-C12 heteroaryl, C6-C18 aryloxy, C6-C18 arylthio, C3-C12 alkylsilyl and C3-C10 cycloalkyl.

According to an embodiment of the present disclosure, in the organic compound represented by formula 1' or 2, L and L$_1$ are the same as or different from each other, and are each independently selected from a single bond, or substituted or unsubstituted groups as follows:

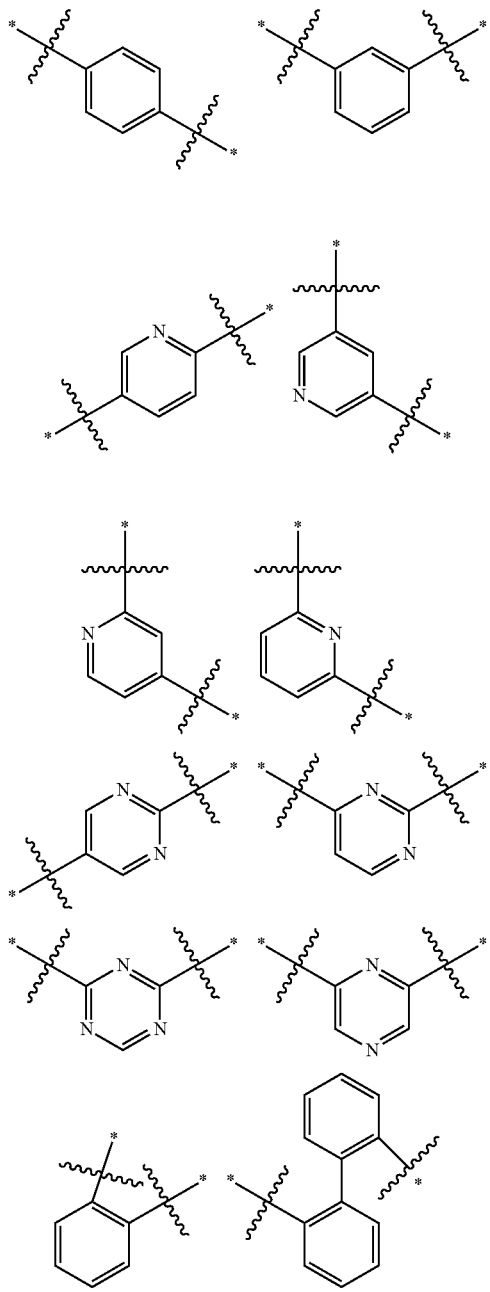

-continued
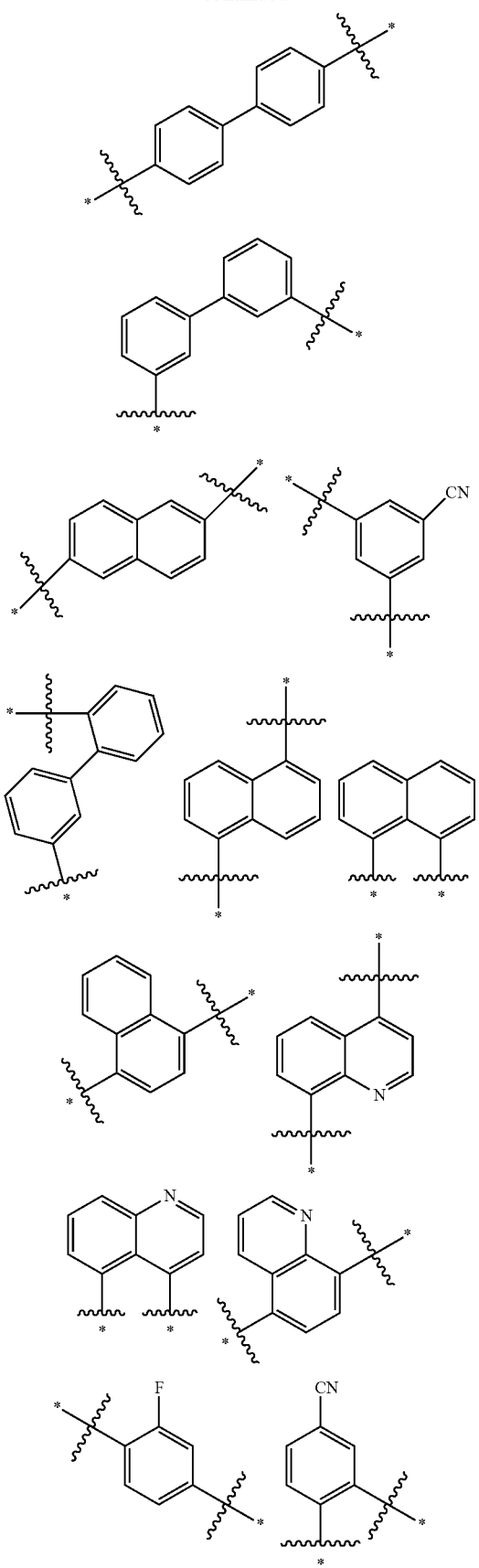
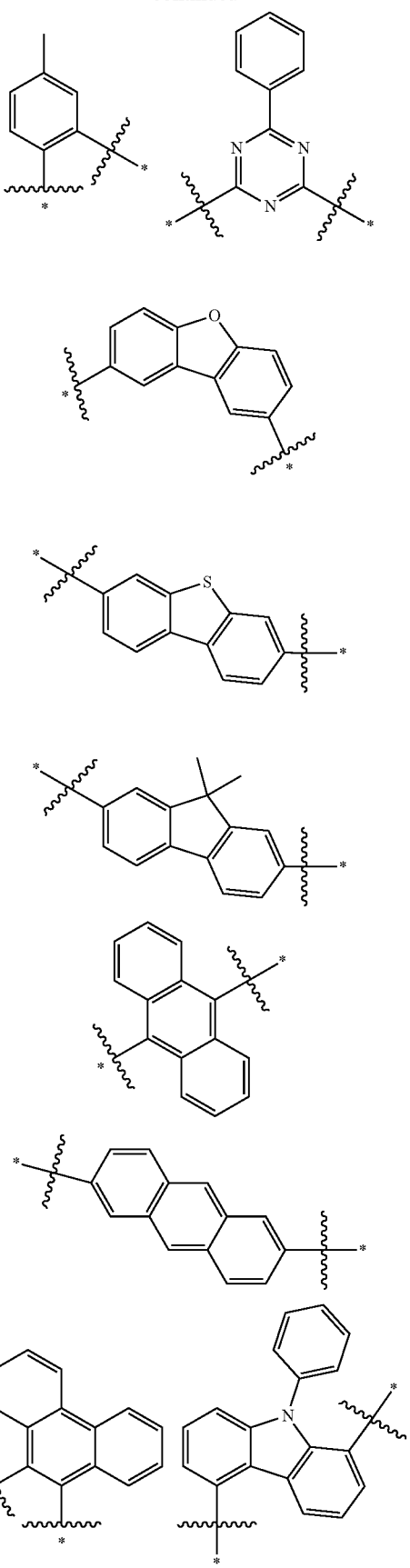

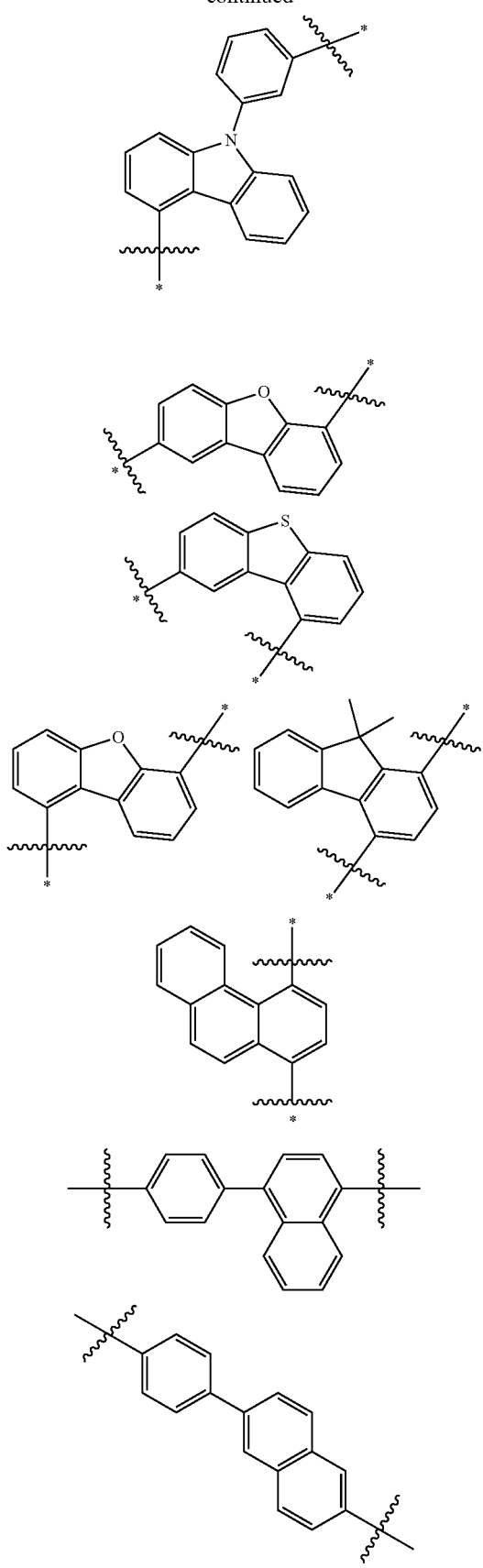
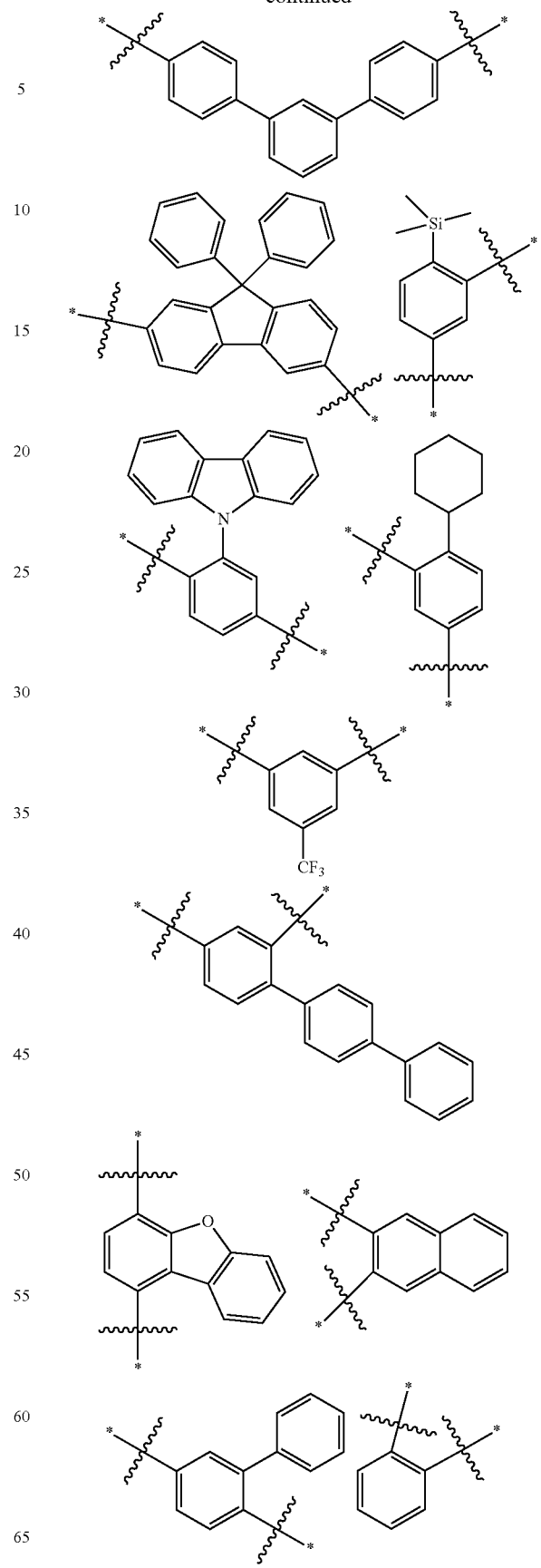

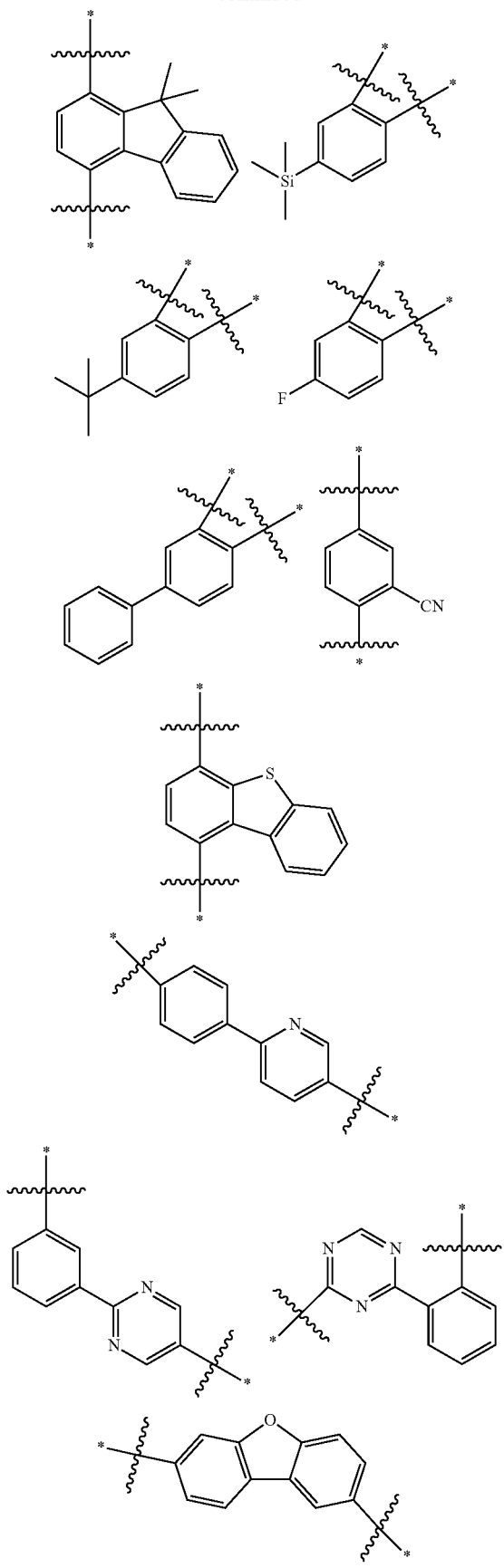
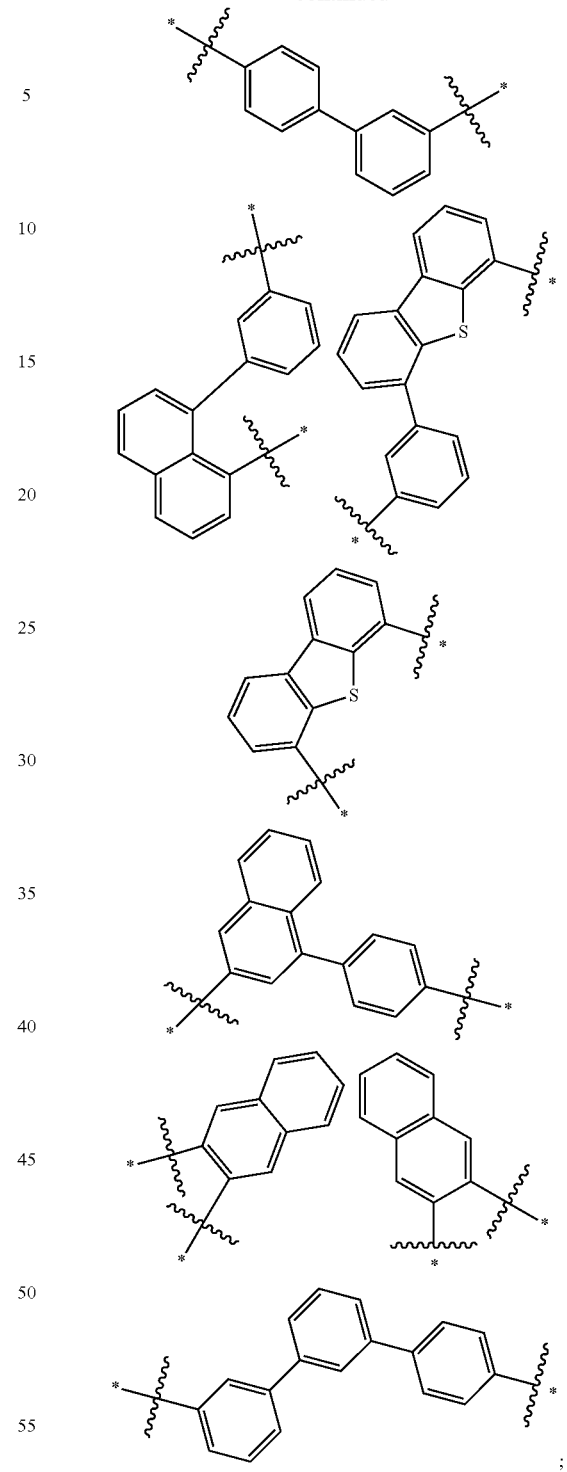

the above groups are optionally substituted by 0, 1, 2 or 3 substituents selected from deuterium, fluorine, chlorine, cyano, methyl, ethyl, isopropyl, tert-butyl, methoxy, ethoxy, isopropoxy, propoxy cyclopentyl, cyclohexyl, trifluoromethyl and trimethylsilyl.

According to an embodiment of the present disclosure, in the organic compound represented by formula 2, one of $R_1''$ to $R_4''$ is

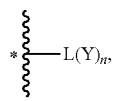

and the other three are each independently hydrogen, deuterium, fluorine, chlorine, bromine or cyano; one of $R_5''$ to $R_8''$ is

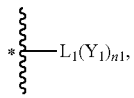

and the other three are each independently hydrogen, deuterium, fluorine, chlorine, bromine or cyano; $W_1$, $W_2$ and $W_3$ are each independently N; $Ar_1$ and $Ar_2$ are each independently hydrogen, deuterium, substituted or unsubstituted aryl with 6 to 20 ring-forming carbon atoms (such as phenyl, naphthyl, diphenyl, terphenyl, benzonaphthyl, fluorenyl and the like) or substituted or unsubstituted heteroaryl with 3 to 18 ring-forming carbon atoms (such as oxygen-containing heteroaryl, nitrogen-containing heteroaryl, sulfur-containing heteroaryl and the like), wherein substituents in $Ar_1$ and $Ar_2$ are selected from deuterium, a halogen group and cyano; L and $L_1$ are each independently a single bond, substituted or unsubstituted arylene with 6 to 30 ring-forming carbon atoms (such as phenylene, naphthylene, diphenylene, terphenylene, benzonaphthylene, fluorenylene, quaterphenylene, quinquephenylene and the like) or substituted or unsubstituted heteroarylene with 3 to 18 ring-forming carbon atoms (for example, oxygen-containing heteroarylene such as dibenzofuranylene; nitrogen-containing heteroarylene such as pyrimidylene, pyridylene and triazinylene; sulfur-containing heteroarylene such as dibenzothienylene and the like), wherein substituents in L and $L_1$ are selected from deuterium, halogen group and cyano.

According to an embodiment of the present disclosure, in the organic compound represented by formula 2, one of $R_1''$ to $R_4''$ is

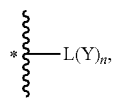

the other three are each independently hydrogen, deuterium, fluorine, chlorine, bromine and cyano; one of $R_5''$ to $R_8''$ is

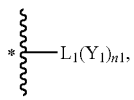

and the other three are each independently hydrogen, deuterium, fluorine, chlorine, bromine or cyano; $W_1$ and $W_2$ are each independently N, $W_3$ is $C(R^{w3})$, wherein $R^{w3}$ is hydrogen, deuterium, fluorine, chlorine, bromine or cyano; $Ar_1$ and $Ar_2$ are each independently hydrogen, deuterium, substituted or unsubstituted aryl with 6 to 20 ring-forming carbon atoms (such as phenyl, naphthyl, diphenyl, terphenyl, benzonaphthyl, fluorenyl and the like) or substituted or unsubstituted heteroaryl with 3 to 18 ring-forming carbon atoms (such as oxygen-containing heteroaryl, nitrogen-containing heteroaryl, sulfur-containing heteroaryl and the like), wherein substituents in $Ar_1$ and $Ar_2$ are selected from deuterium, a halogen group and cyano; L and $L_1$ are each independently a single bond, substituted or unsubstituted arylene with 6 to 30 ring-forming carbon atoms (such as phenylene, naphthylene, diphenylene, terphenylene, benzonaphthylene, fluorenylene, quaterphenylene, quinquephenylene and the like), or substituted or unsubstituted heteroarylene with 3 to 18 ring-forming carbon atoms (for example, oxygen-containing heteroarylene such as dibenzofuranylene; nitrogen-containing heteroarylene such as pyrimidylene, pyridylene and triazinylene; sulfur-containing heteroarylene such as dibenzothienylene and the like), wherein substituents in L and $L_1$ are selected from deuterium, halogen group and cyano.

According to an embodiment of the present disclosure, in the organic compound represented by formula 2, one of $R_1''$ to $R_4''$ is

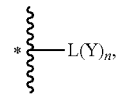

and the other three are each independently hydrogen, deuterium, fluorine, chlorine, bromine or cyano; one of $R_5''$ to $R_8''$ is

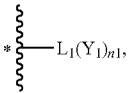

and the other three are each independently hydrogen, deuterium, fluorine, chlorine, bromine or cyano; $W_1$ is N, $W_2$ and $W_3$ are each independently $C(R^{w2})$ and $C(R^{w3})$, wherein $R^{w2}$ and $R^{w3}$ are each independently hydrogen, deuterium, fluorine, chlorine, bromine or cyano; $Ar_1$ and $Ar_2$ are each independently hydrogen, deuterium, substituted or unsubstituted aryl with 6 to 20 ring-forming carbon atoms (such as phenyl, naphthyl, diphenyl, terphenyl, benzonaphthyl, fluorenyl and the like), or substituted or unsubstituted heteroaryl with 3 to 18 ring-forming carbon atoms (for example oxygen-containing heteroaryl such as dibenzofuran; nitrogen-containing heteroaryl such as pyrimidyl, pyridyl and triazinyl; sulfur-containing heteroaryl such as dibenzothienyl and the like), wherein substituents in $Ar_1$ and $Ar_2$ are selected from deuterium, a halogen group and cyano; L and $L_1$ are each independently a single bond, substituted or unsubstituted arylene with 6 to 30 ring-forming carbon atoms (such as phenylene, naphthylene, diphenylene, terphenylene, benzonaphthylene, fluorenylene, quaterphenylene, quinquephenylene and the like), or substituted or unsubstituted heteroarylene with 3 to 18 ring-forming carbon atoms (for example, oxygen-containing heteroarylene such as dibenzofuranylene; nitrogen-containing heteroarylene such as pyrimidylene, pyridylene and triazinylene; sulfur-containing heteroarylene such as dibenzothienylene and the like), wherein substituents in L and $L_1$ are selected from deuterium, a halogen group and cyano.

According to an embodiment of the present disclosure, in the organic compound represented by formula 2, L and $L_1$ are each independently a single bond.

According to an embodiment of the present disclosure, in the organic compound represented by formula 2, one of L and $L_1$ is a single bond, and the other is selected from the groups as follows: substituted or unsubstituted C6-C30 arylene, substituted or unsubstituted C3-C30 heteroarylene, substituted or unsubstituted C7-C30 aralkylene, substituted or unsubstituted C3-C30 heteroaralkylene.

According to an embodiment of the present disclosure, in the organic compound represented by formula 2, one of L and $L_1$ is a single bond, and the other is substituted or unsubstituted C6-C20 arylene.

According to an embodiment of the present disclosure, in the organic compound represented by formula 2, one of L and $L_1$ is a single bond, and the other is selected from the groups as follows: substituted or unsubstituted phenylene, substituted or unsubstituted biphenylene, substituted or unsubstituted terphenylene, substituted or unsubstituted naphthylene, substituted or unsubstituted fluorenylene, substituted or unsubstituted phenanthrylene, and substituted or unsubstituted anthrylene.

According to an embodiment of the present disclosure, in the organic compound represented by formula 2, one of L and $L_1$ is a single bond, and the other is substituted or unsubstituted phenylene.

According to an embodiment of the present disclosure, in the organic compound represented by formula 2, one of L and $L_1$ is a single bond, and the other is substituted or unsubstituted C3-C20 heteroarylene.

According to an embodiment of the present disclosure, in the organic compound represented by formula 2, one of L and $L_1$ is a single bond, and the other is selected from the groups as follows: substituted or unsubstituted triazinylene, substituted or unsubstituted pyrimidylene, substituted or unsubstituted pyridinylene, substituted or unsubstituted pyrazinylene, substituted or unsubstituted pyrrolylene, substituted or unsubstituted thienylene, substituted or unsubstituted dibenzothienylene, substituted or unsubstituted dibenzofuranylene, substituted or unsubstituted carbazolylene, and substituted or unsubstituted quinolylene.

According to an embodiment of the present disclosure, in the organic compound represented by formula 2, one of L and $L_1$ is substituted or unsubstituted C6-C20 arylene, and the other is substituted or unsubstituted monocyclic C3-C12 heteroarylene.

According to an embodiment of the present disclosure, in the organic compound represented by formula 2, one of L and $L_1$ is selected from the groups as follows: substituted or unsubstituted phenylene, substituted or unsubstituted biphenylene, substituted or unsubstituted terphenylene, substituted or unsubstituted quaterphenylene, substituted or unsubstituted quinquephenylene, substituted or unsubstituted naphthylene, substituted or unsubstituted fluorenylene, substituted or unsubstituted phenanthrylene, substituted or unsubstituted anthrylene, and the other is selected from the groups as follows: substituted or unsubstituted triazinylene, substituted or unsubstituted pyrimidylene, substituted or unsubstituted pyridinylene, substituted or unsubstituted pyrazinylene, substituted or unsubstituted dibenzofuranylene, substituted or unsubstituted dibenzothienylene, substituted or unsubstituted carbazolylene, and substituted or unsubstituted quinolylene.

According to an embodiment of the present disclosure, in the organic compound represented by formula 2, one of L and $L_1$ is substituted or unsubstituted phenylene, and the other is substituted or unsubstituted pyridinylene.

According to an embodiment of the present disclosure, in the organic compound represented by formula 2, L and $L_1$ are the same as or different from each other, and are each independently substituted or unsubstituted C6-C20 arylene.

According to an embodiment of the present disclosure, in the organic compound represented by formula 2, L and $L_1$ are the same as or different from each other, and are each independently selected from the groups as follows: substituted or unsubstituted phenylene, substituted or unsubstituted biphenylene, substituted or unsubstituted terphenylene, substituted or unsubstituted quaterphenylene, substituted or unsubstituted quinquephenylene, substituted or unsubstituted naphthylene, substituted or unsubstituted fluorenylene, substituted or unsubstituted phenanthrylene, substituted or unsubstituted anthrylene.

According to an embodiment of the present disclosure, in the organic compound represented by formula 2, L and $L_1$ are the same, which are both substituted or unsubstituted phenylene.

According to an embodiment of the present disclosure, in the organic compound represented by formula 2, L and $L_1$ are the same as or different from each other, and are each independently substituted or unsubstituted C3-C20 heteroarylene.

According to an embodiment of the present disclosure, in the organic compound represented by chemical formula 2, L and $L_1$ are the same as or different from each other, and are each independently selected from the groups as follows: substituted or unsubstituted triazinylene, substituted or unsubstituted pyrimidylene, substituted or unsubstituted pyridinylene, substituted or unsubstituted pyrazinylene, substituted or unsubstituted pyrrolylene, substituted or unsubstituted thienylene, substituted or unsubstituted dibenzofuranylene, substituted or unsubstituted dibenzothienylene, substituted or unsubstituted carbazolylene, and substituted or unsubstituted quinolylene.

According to an embodiment of the present disclosure, in the organic compound represented by formula 2, the substituents on L and $L_1$ are selected from the group consisting of deuterium, fluorine, cyano, methyl, isopropyl, tert-butyl, trifluoromethyl, phenyl, biphenyl, cyclohexyl and trimethylsilyl.

According to an embodiment of the present disclosure, in the organic compound represented by formula 2, one of $R_1''$ to $R_4''$ is

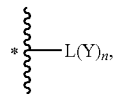

and the other three are each independently hydrogen; one of $R_5''$ to $R_8''$ is

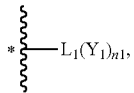

and the other three are each independently hydrogen; $W_1$, $W_2$ and $W_3$ are each independently N; L and $L_1$ are each independently a single bond; $Ar_1$ and $Ar_2$ are each independently hydrogen, deuterium, substituted or unsubstituted phenyl, substituted or unsubstituted diphenyl, substituted or unsubstituted naphthyl and substituted or unsubstituted dibenzofuranyl, wherein the substituents in $Ar_1$ and $Ar_2$ are selected from deuterium, a halogen group, cyano, methyl, ethyl, isopropyl, tert-butyl, trimethylsilyl and trifluoromethyl.

According to an embodiment of the present disclosure, in the organic compound represented by formula 2, one of $R_1''$ to $R_4''$ is

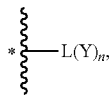

and the other three are each independently hydrogen; one of $R_5''$ to $R_8''$ is

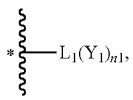

and the other three are each independently hydrogen; $W_1$, $W_2$ and $W_3$ are each independently N; one of L and $L_1$ is a single bond, and the other is selected from the groups as follows: substituted or unsubstituted C6-C30 arylene, substituted or unsubstituted C3-C30 heteroarylene; $Ar_1$ and $Ar_2$ are each independently hydrogen, deuterium, substituted or unsubstituted phenyl, substituted or unsubstituted naphthyl and substituted or unsubstituted dibenzofuranyl, wherein the substituents in the above groups are selected from deuterium, a halogen group, cyano, methyl, ethyl, isopropyl, tert-butyl, trimethylsilyl and trifluoromethyl.

According to an embodiment of the present disclosure, in the organic compound represented by formula 2, one of $R_1''$ to $R_4''$ is

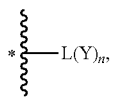

and the other three are each independently hydrogen; one of $R_5''$ to $R_8''$ is

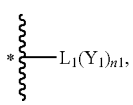

and the other three are each independently hydrogen; $W_1$, $W_2$ and $W_3$ are each independently N; one of L and $L_1$ is a single bond, and the other is substituted or unsubstituted C6-C20 arylene; $Ar_1$ and $Ar_2$ are each independently hydrogen, deuterium, substituted or unsubstituted phenyl, substituted or unsubstituted naphthyl and substituted or unsubstituted dibenzofuranyl, wherein the substituents in the above groups are selected from deuterium, a halogen group, cyano, methyl, ethyl, isopropyl, tert-butyl, trimethylsilyl and trifluoromethyl.

According to an embodiment of the present disclosure, in the organic compound represented by formula 2, one of $R_1''$ to $R_4''$ is

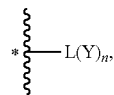

and the other three are each independently hydrogen; one of $R_5''$ to $R_8''$ is

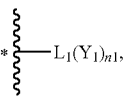

and the other three are each independently hydrogen; $W_1$, $W_2$ and $W_3$ are each independently N; one of L and $L_1$ is a single bond, and the other is selected from the groups as follows: substituted or unsubstituted phenylene, substituted or unsubstituted biphenylene, substituted or unsubstituted terphenylene, substituted or unsubstituted naphthylene, substituted or unsubstituted fluorenylene, substituted or unsubstituted phenanthrylene, and substituted or unsubstituted anthrylene; $Ar_1$ and $Ar_2$ are each independently hydrogen, deuterium, substituted or unsubstituted phenyl, substituted or unsubstituted naphthyl and substituted or unsubstituted dibenzofuranyl, wherein the substituents in the above groups are selected from deuterium, a halogen group, cyano, methyl, ethyl, isopropyl, tert-butyl, trimethylsilyl and trifluoromethyl.

According to an embodiment of the present disclosure, in the organic compound represented by formula 2, one of $R_1''$ to $R_4''$ is

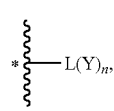

and the other three are each independently hydrogen; one of $R_5''$ to $R_8''$ is

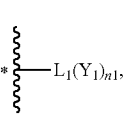

and the other three are each independently hydrogen; $W_1$, $W_2$ and $W_3$ are each independently N; one of L and $L_1$ is a single bond, and the other is substituted or unsubstituted phenylene; $Ar_1$ and $Ar_2$ are each independently hydrogen, deuterium, substituted or unsubstituted phenyl, substituted or unsubstituted naphthyl and substituted or unsubstituted dibenzofuranyl, wherein the substituents in the above groups are selected from deuterium, a halogen group, cyano, methyl, ethyl, isopropyl, tert-butyl, trimethylsilyl and trifluoromethyl.

According to an embodiment of the present disclosure, in the organic compound represented by formula 2, one of $R_1''$ to $R_4''$ is

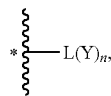

and the other three are each independently hydrogen; one of $R_5''$ to $R_8''$ is

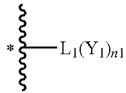

and the other three are each independently hydrogen; $W_1$, $W_2$ and $W_3$ are each independently N; one of L and $L_1$ is a single bond, and the other is substituted or unsubstituted C3-C20 heteroarylene; $Ar_1$ and $Ar_2$ are each independently hydrogen, deuterium, substituted or unsubstituted phenyl, substituted or unsubstituted naphthyl and substituted or unsubstituted dibenzofuranyl, wherein the substituents in the above groups are selected from deuterium, a halogen group, cyano, methyl, ethyl, isopropyl, tert-butyl, trimethylsilyl and trifluoromethyl.

According to an embodiment of the present disclosure, in the organic compound represented by formula 2, one of $R_1''$ to $R_4''$ is

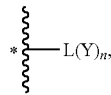

and the other three are each independently hydrogen; one of $R_5''$ to $R_8''$ is

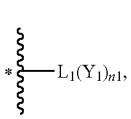

and the other three are each independently hydrogen; $W_1$, $W_2$ and $W_3$ are each independently N; one of L and $L_1$ is a single bond, and the other is selected from the groups as follows: substituted or unsubstituted triazinylene, substituted or unsubstituted pyrimidylene, substituted or unsubstituted pyridinylene, substituted or unsubstituted pyrazinylene, substituted or unsubstituted pyrrolylene, substituted or unsubstituted thienylene, substituted or unsubstituted dibenzofuranylene, substituted or unsubstituted dibenzothienylene, substituted or unsubstituted carbazolylene, and substituted or unsubstituted quinolylene; $Ar_1$ and $Ar_2$ are each independently hydrogen, deuterium, substituted or unsubstituted phenyl, substituted or unsubstituted naphthyl and substituted or unsubstituted dibenzofuranyl, wherein the substituents in the above groups are selected from deuterium, a halogen group, cyano, methyl, ethyl, isopropyl, tert-butyl, trimethylsilyl and trifluoromethyl.

According to an embodiment of the present disclosure, in the organic compound represented by formula 2, one of $R_1''$ to $R_4''$ is

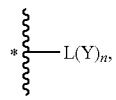

and the other three are each independently hydrogen; one of $R_5''$ to $R_8''$ is

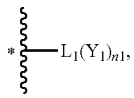

and the other three are each independently hydrogen; $W_1$, $W_2$ and $W_3$ are each independently N; one of L and $L_1$ is substituted or unsubstituted C6-C20 arylene, and the other is substituted or unsubstituted monocyclic C3-C12 heteroarylene; $Ar_1$ and $Ar_2$ are each independently hydrogen, deuterium, substituted or unsubstituted phenyl, substituted or unsubstituted naphthyl and substituted or unsubstituted dibenzofuranyl, wherein the substituents in the above groups are selected from deuterium, a halogen group, cyano, methyl, ethyl, isopropyl, tert-butyl, trimethylsilyl and trifluoromethyl.

According to an embodiment of the present disclosure, in the organic compound represented by formula 2, one of $R_1''$ to $R_4''$ is

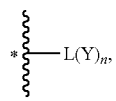

and the other three are each independently hydrogen; one of $R_5''$ to $R_8''$ is

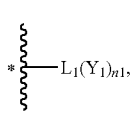

and the other three are each independently hydrogen; $W_1$, $W_2$ and $W_3$ are each independently N; one of L and $L_1$ is selected from the groups as follows: substituted or unsubstituted phenylene, substituted or unsubstituted biphenylene, substituted or unsubstituted terphenylene, substituted or unsubstituted quaterphenylene, substituted or unsubstituted quinquephenylene, substituted or unsubstituted naphthylene, substituted or unsubstituted fluorenylene, substituted or unsubstituted phenanthrylene and substituted or unsubstituted anthrylene, and the other is selected from the groups as follows: substituted or unsubstituted triazinylene, substituted or unsubstituted pyrimidylene, substituted or unsubstituted pyridinylene, substituted or unsubstituted pyrazinylene, substituted or unsubstituted dibenzofuranylene, substituted or unsubstituted dibenzothienylene, substituted or unsubstituted carbazolylene, and substituted or unsubstituted quinolylene; $Ar_1$ and $Ar_2$ are each independently hydrogen, deuterium, substituted or unsubstituted phenyl, substituted or unsubstituted naphthyl and substituted or unsubstituted dibenzofuranyl, wherein the substituents in the above groups are selected from deuterium, a halogen group, cyano, methyl, ethyl, isopropyl, tert-butyl, trimethylsilyl and trifluoromethyl.

According to an embodiment of the present disclosure, in the organic compound represented by formula 2, one of $R_1"$ to $R_4"$ is

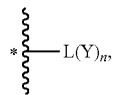

and the other three are each independently hydrogen; one of $R_5"$ to $R_8"$ is

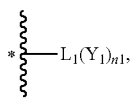

and the other three are each independently hydrogen; $W_1$, $W_2$ and $W_3$ are each independently N; one of L and $L_1$ is substituted or unsubstituted phenylene, and the other is substituted or unsubstituted pyridinylene; $Ar_1$ and $Ar_2$ are each independently hydrogen, deuterium, substituted or unsubstituted phenyl, substituted or unsubstituted naphthyl and substituted or unsubstituted dibenzofuranyl, wherein the substituents in the above groups are selected from deuterium, a halogen group, cyano, methyl, ethyl, isopropyl, tert-butyl, trimethylsilyl and trifluoromethyl.

According to an embodiment of the present disclosure, in the organic compound represented by formula 2, one of $R_1"$ to $R_4"$ is

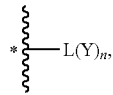

and the other three are each independently hydrogen; one of $R_5"$ to $R_8"$ is

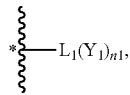

and the other three are each independently hydrogen; $W_1$, $W_2$ and $W_3$ are each independently N; L and $L_1$ are the same as or different from each other, and are each independently substituted or unsubstituted C6-C20 arylene; $Ar_1$ and $Ar_2$ are each independently hydrogen, deuterium, substituted or unsubstituted phenyl, substituted or unsubstituted naphthyl, or substituted or unsubstituted dibenzofuranyl, wherein the substituents in the above groups are selected from deuterium, a halogen group, cyano, methyl, ethyl, isopropyl, tert-butyl, trimethylsilyl and trifluoromethyl.

According to an embodiment of the present disclosure, in the organic compound represented by formula 2, one of $R_1"$ to $R_4"$ is

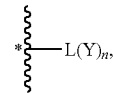

and the other three are each independently hydrogen; one of $R_5"$ to $R_8"$ is

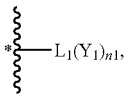

and the other three are each independently hydrogen; $W_1$, $W_2$ and $W_3$ are each independently N; L and $L_1$ are the same as or different from each other, and are each independently selected from the groups as follows: substituted or unsubstituted phenylene, substituted or unsubstituted biphenylene, substituted or unsubstituted terphenylene, substituted or unsubstituted naphthylene, substituted or unsubstituted fluorenylene, substituted or unsubstituted phenanthrylene and substituted or unsubstituted anthrylene; $Ar_1$ and $Ar_2$ are each independently hydrogen, deuterium, substituted or unsubstituted phenyl, substituted or unsubstituted naphthyl and substituted or unsubstituted dibenzofuranyl, wherein the substituents in the above groups are selected from deuterium, a halogen group, cyano, methyl, ethyl, isopropyl, tert-butyl, trimethylsilyl and trifluoromethyl.

According to an embodiment of the present disclosure, in the organic compound represented by formula 2, one of $R_1"$ to $R_4"$ is

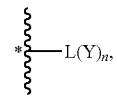

and the other three are each independently hydrogen; one of $R_5"$ to $R_8"$ is

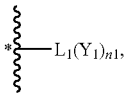

and the other three are each independently hydrogen; $W_1$, $W_2$ and $W_3$ are each independently N; L and $L_1$ are the same, and both substituted or unsubstituted phenylene; An and $Ar_2$ are each independently hydrogen, deuterium, substituted or unsubstituted phenyl, substituted or unsubstituted naphthyl and substituted or unsubstituted dibenzofuranyl, wherein the substituents in the above groups are selected from deuterium, a halogen group, cyano, methyl, ethyl, isopropyl, tert-butyl, trimethylsilyl and trifluoromethyl.

According to an embodiment of the present disclosure, in the organic compound represented by formula 2, one of $R_1"$ to $R_4"$ is

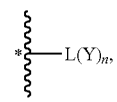

and the other three are each independently hydrogen; one of R$_5$" to R$_8$" is

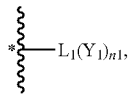

and the other three are each independently hydrogen; W$_1$, W$_2$ and W$_3$ are each independently N; L and L$_1$ are the same as or different from each other, and are each independently substituted or unsubstituted C3-C20 heteroarylene; Ar$_1$ and Ar$_2$ are each independently hydrogen, deuterium, substituted or unsubstituted phenyl, substituted or unsubstituted naphthyl, or substituted or unsubstituted dibenzofuranylene, wherein the substituents in the above groups are selected from deuterium, a halogen group, cyano, methyl, ethyl, isopropyl, tert-butyl, trimethylsilyl and trifluoromethyl.

According to an embodiment of the present disclosure, in the organic compound represented by formula 2, one of R$_1$" to R$_4$" is

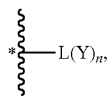

and the other three are each independently hydrogen; one of R$_5$" to R$_8$" is

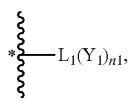

and the other three are each independently hydrogen; W$_1$, W$_2$ and W$_3$ are each independently N; L and L$_1$ are the same as or different from each other, and are each independently selected from the groups as follows: substituted or unsubstituted triazinylene, substituted or unsubstituted pyrimidylene, substituted or unsubstituted pyridinylene, substituted or unsubstituted pyrazinylene, substituted or unsubstituted pyrrolylene, substituted or unsubstituted thienylene, substituted or unsubstituted dibenzofuranylene, substituted or unsubstituted dibenzothienylene, substituted or unsubstituted phenyl-dibenzothienylene, substituted or unsubstituted phenyl-dibenzofuranylene, substituted or unsubstituted phenyl-carbazolylene, and substituted or unsubstituted quinolylene: Ar$_1$ and Ar$_2$ are each independently hydrogen, deuterium, substituted or unsubstituted phenyl, substituted or unsubstituted naphthyl, or substituted or unsubstituted dibenzofuranylene, wherein the substituents in the above groups are selected from deuterium, a halogen group, cyano, methyl, ethyl, isopropyl, tert-butyl, trimethylsilyl and trifluoromethyl.

According to an embodiment of the present disclosure, in the organic compound represented by formulas 1', 1 and 2, the substituents in L and L$_1$ are the same as or different from each other, and are each independently selected from the group consisting of deuterium, fluorine, chlorine, bromine, cyano, C1-C4 alkyl, C1-C3 haloalkyl, phenyl, naphthyl, fluorenyl, dimethylfluorenyl, dibenzothienyl, dibenzofuranyl, pyridyl, quinolyl, C6-C18 aryloxy, C6-C18 arylthio, trimethylsilyl and C3-C10 cycloalkyl.

According to an embodiment of the present disclosure, in the organic compound represented by formulas 1', 1 and 2, the substituents in L and L$_1$ are the same as or different from each other, and are each independently selected from the group consisting of deuterium, fluorine, chlorine, bromine, cyano, methyl, ethyl, isopropyl, tert-butyl, trifluoromethyl, phenyl, naphthyl, fluorenyl, dimethylfluorenyl, dibenzothienyl, dibenzofuranyl, pyridyl, quinolyl, trimethylsilyl, cyclopentyl and cyclohexyl.

According to an embodiment of the present disclosure, wherein the organic compound represented by formula 2 is selected from any one as follows:

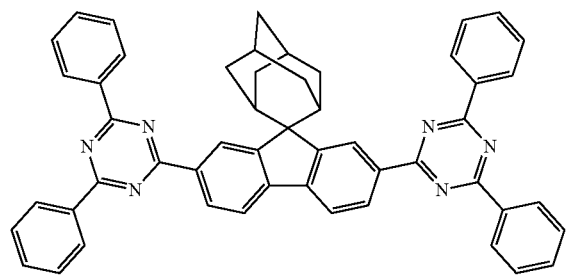

Compound 15

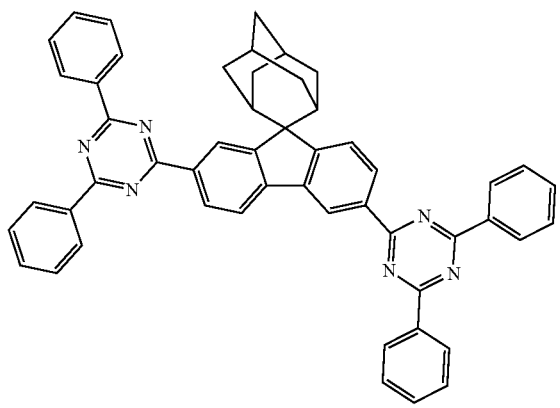

Compound 16

-continued
Compound 17
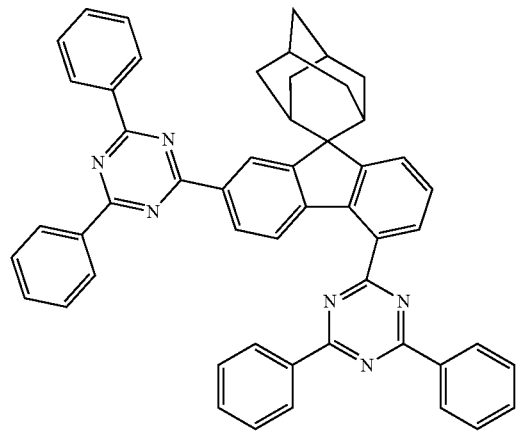
Compound 18
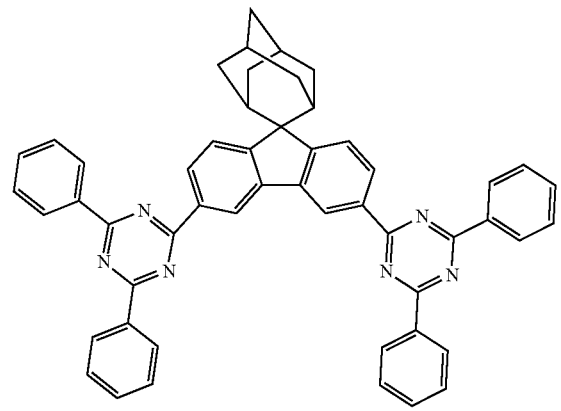
Compound 19
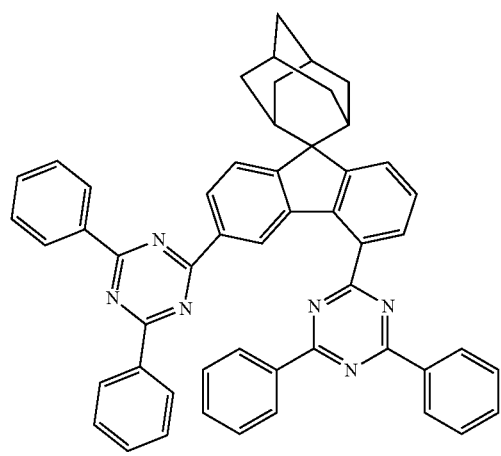
Compound 20
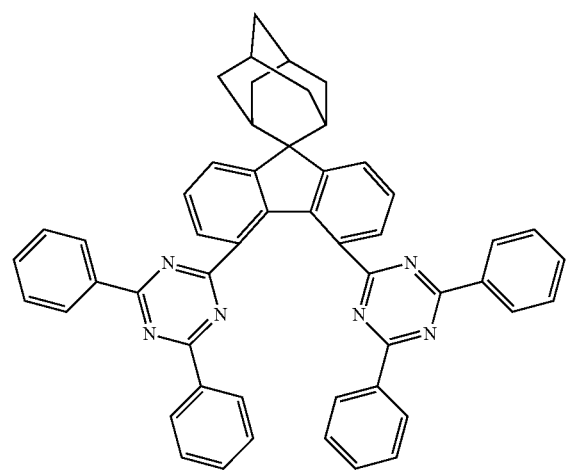
Compound 21
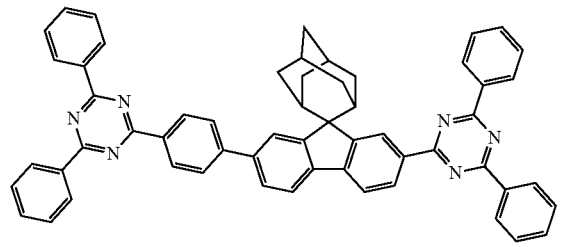
Compound 22
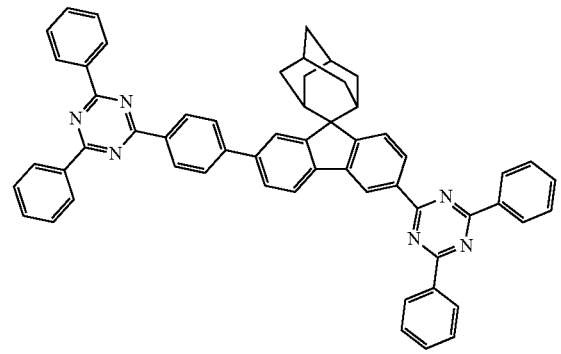

-continued
Compound 23
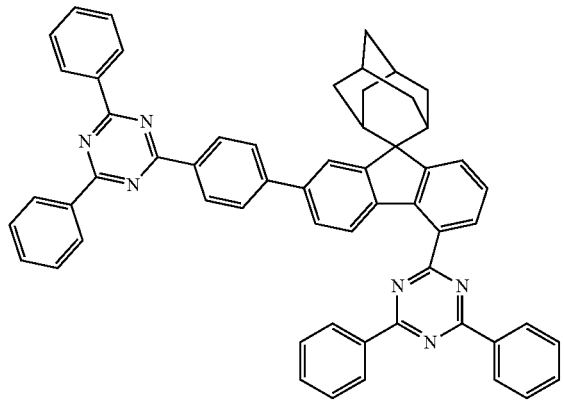
Compound 24
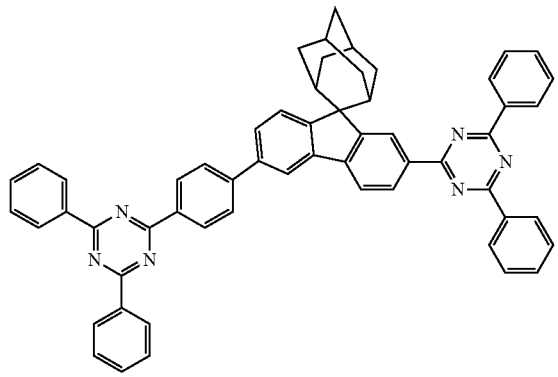
Compound 25
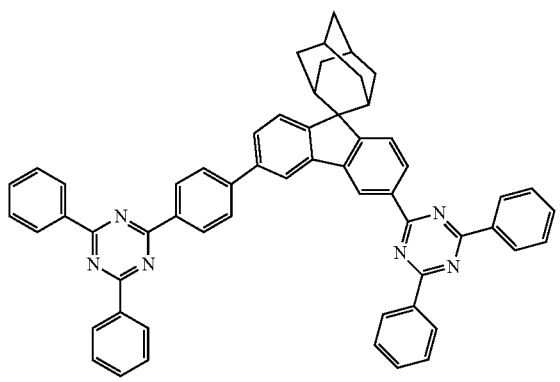
Compound 26
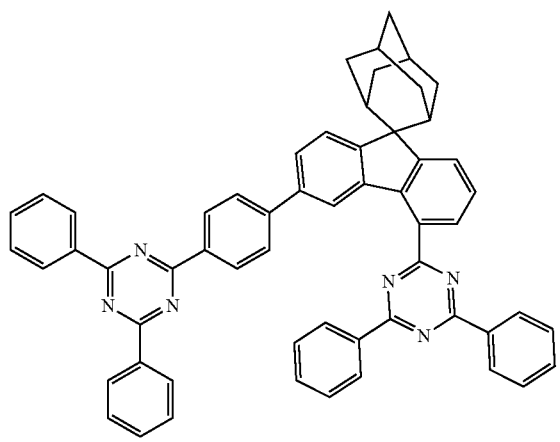
Compound 27
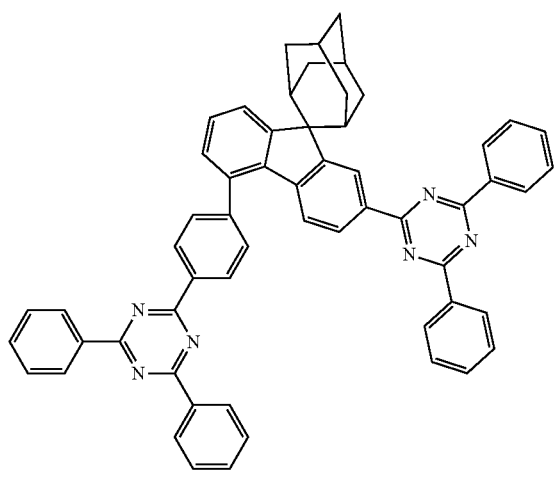
Compound 28
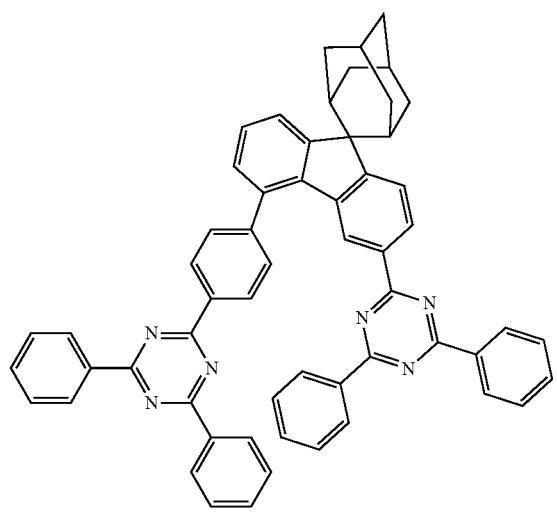

Compound 29
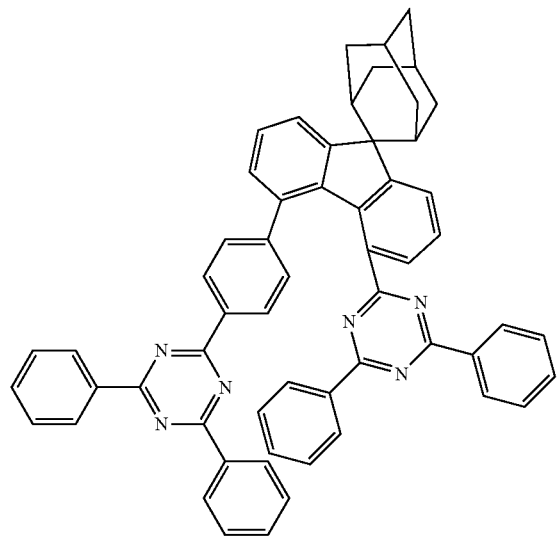
Compound 30
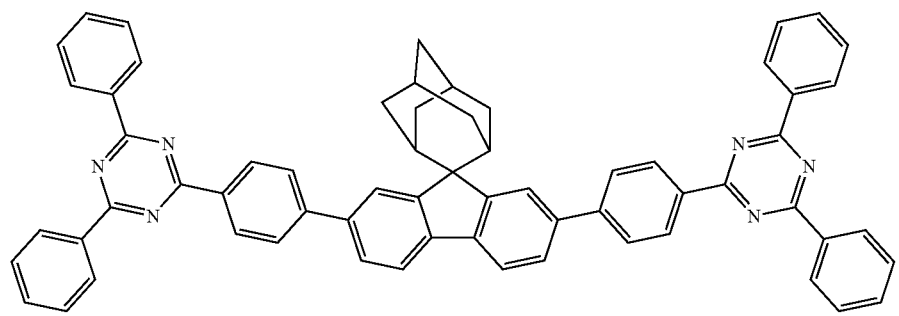
Compound 31
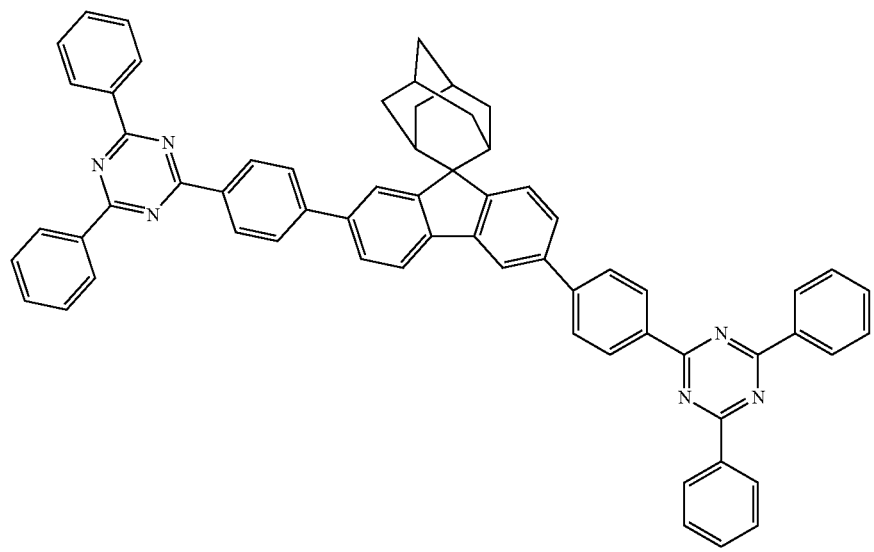

-continued
Compound 32
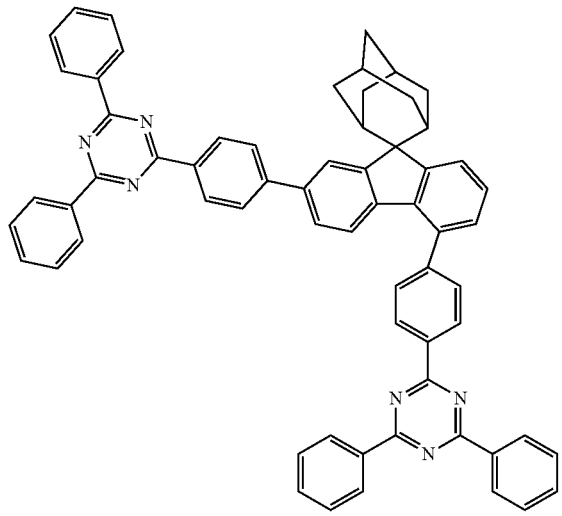
Compound 33
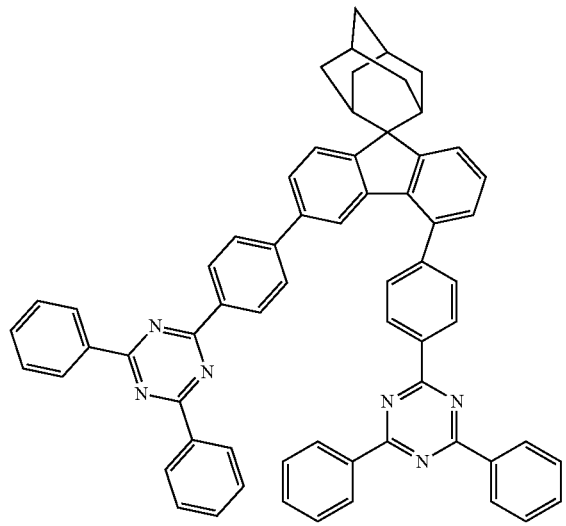
Compound 34
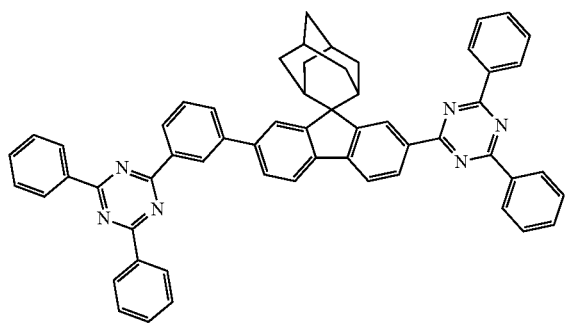
Compound 35
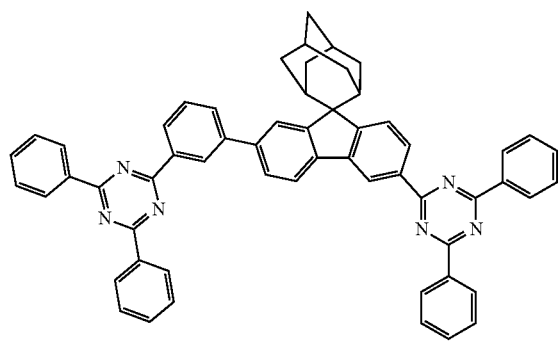
Compound 36
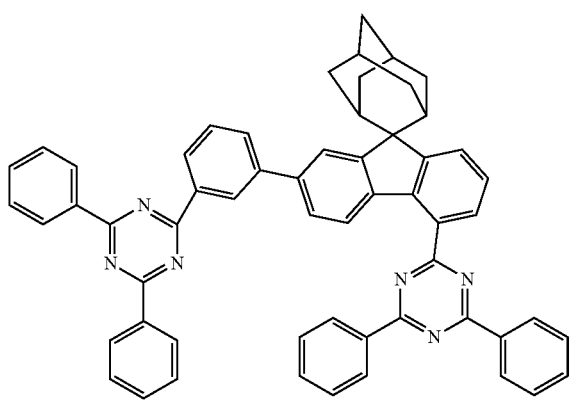
Compound 37
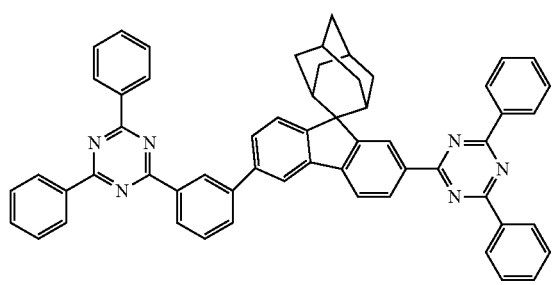

-continued
Compound 38
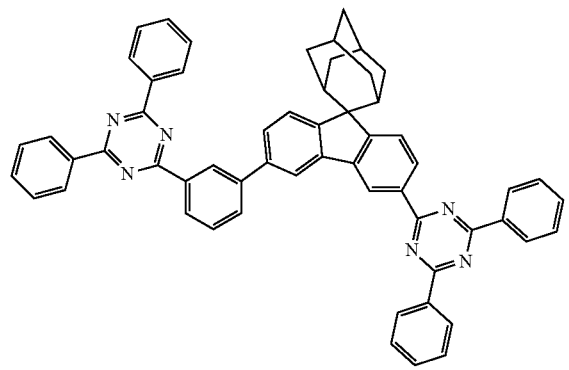
Compound 39
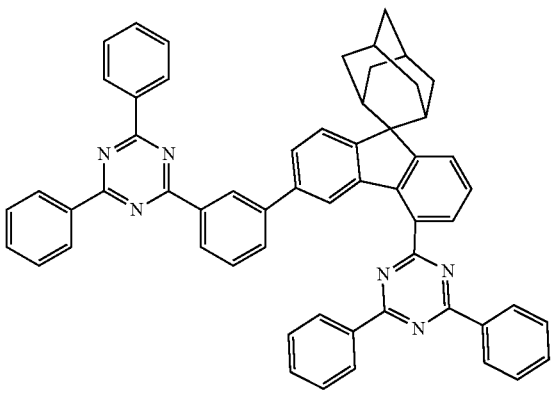
Compound 40
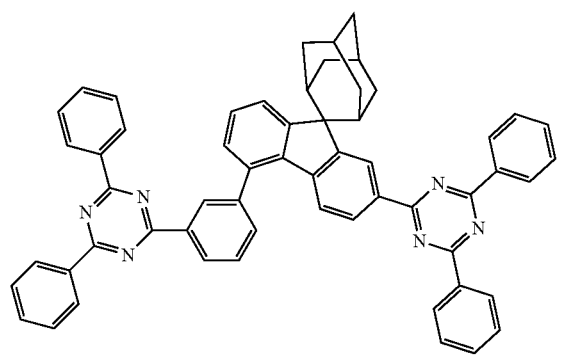
Compound 41
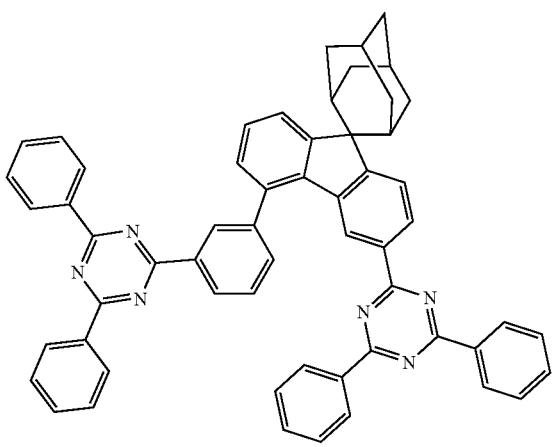
Compound 42
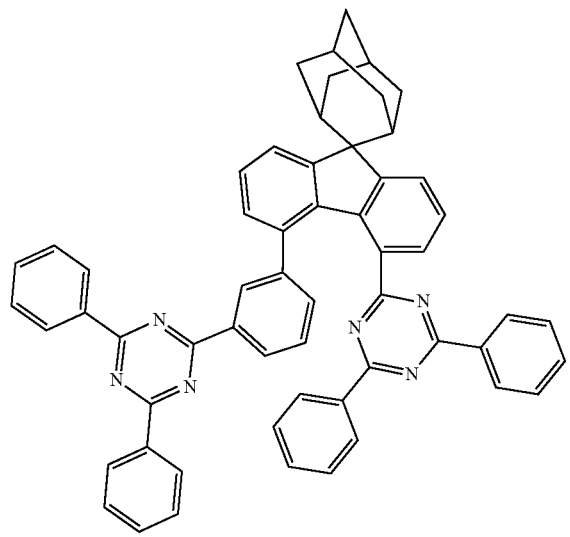

Compound 43
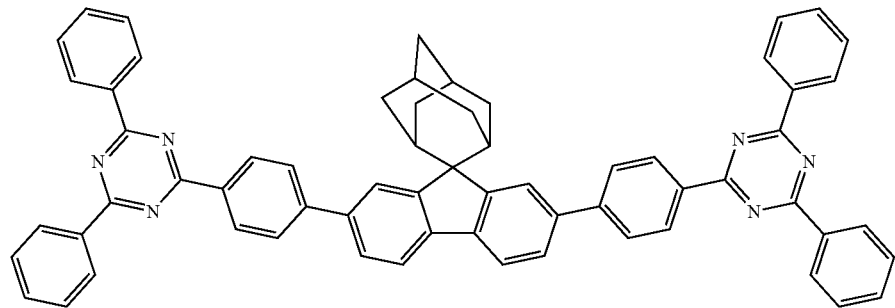
Compound 44
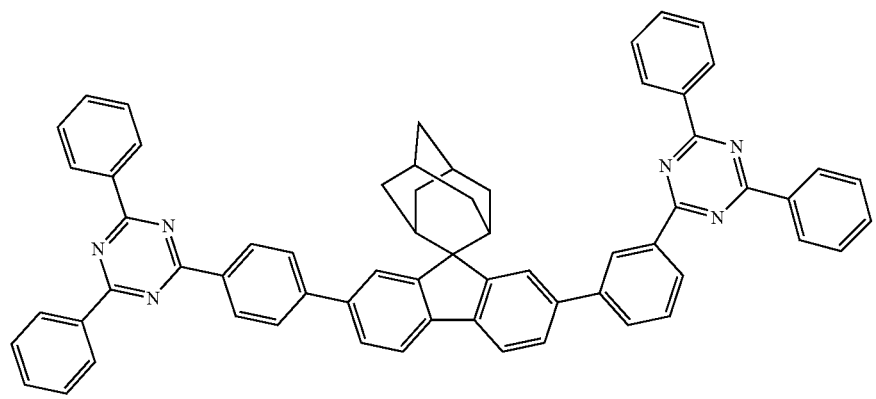
Compound 45
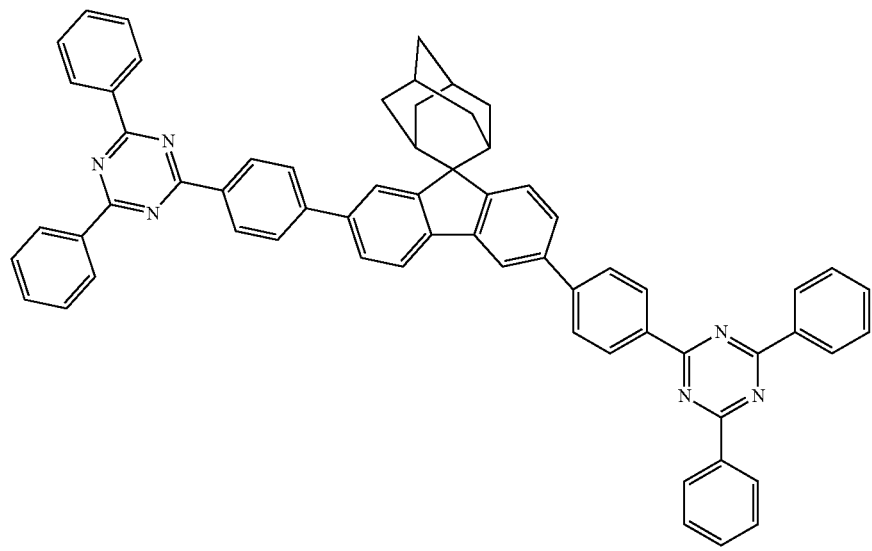

-continued
Compound 46
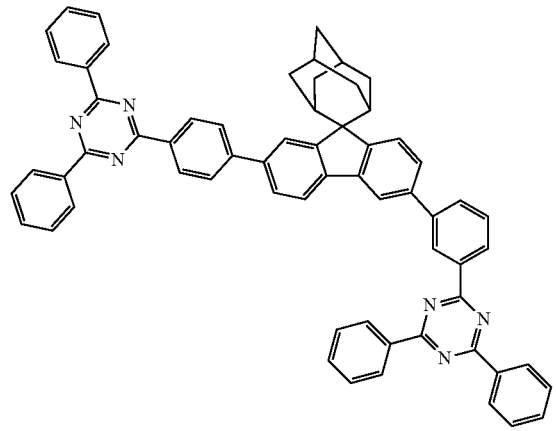
Compound 47
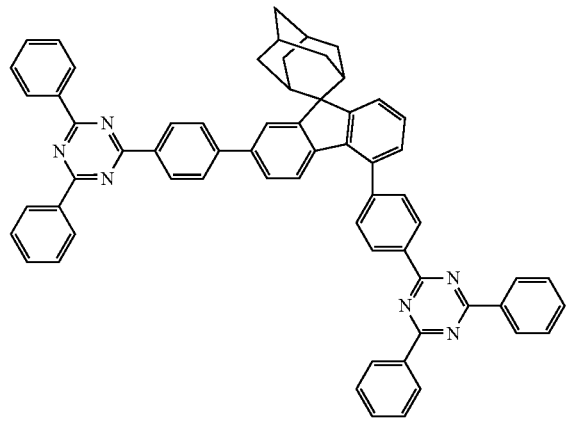
Compound 48
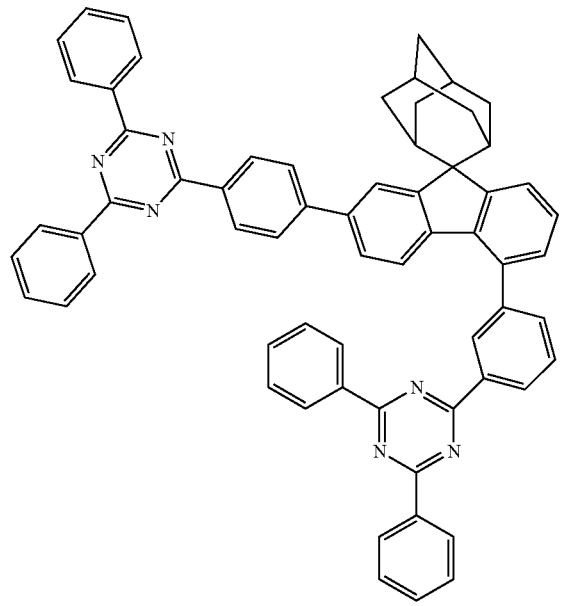
Compound 49
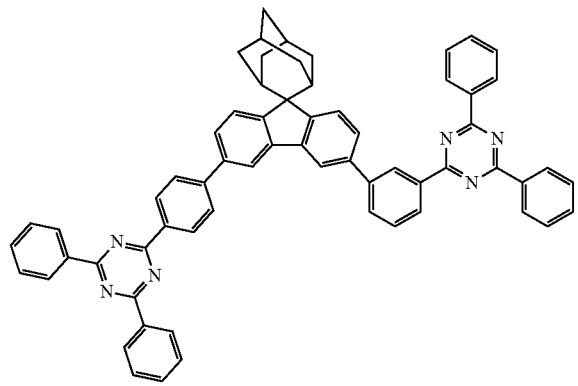
Compound 50
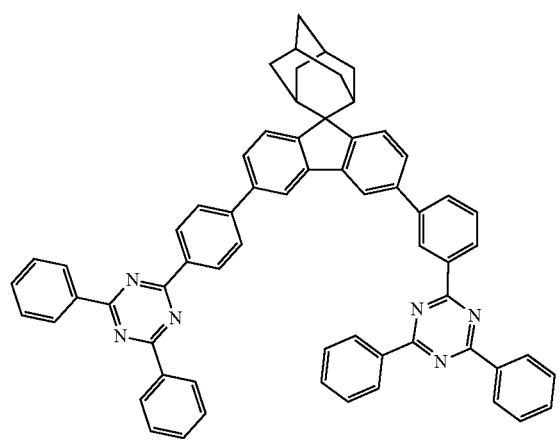
Compound 51
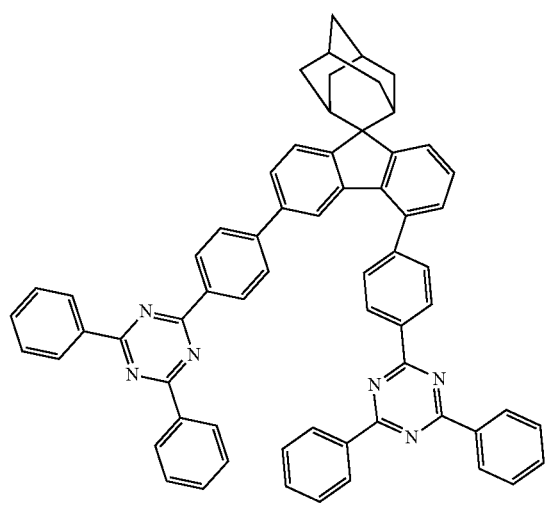

-continued
Compound 52
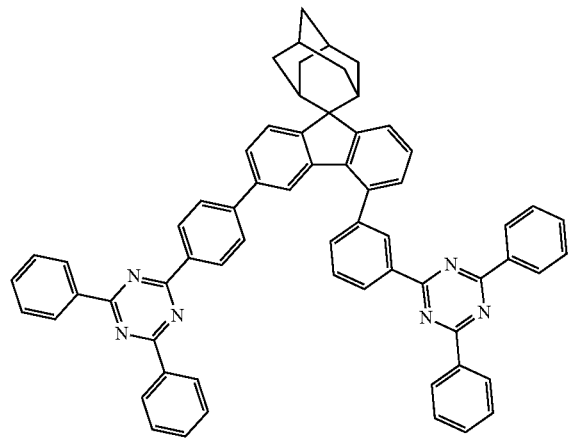
Compound 53
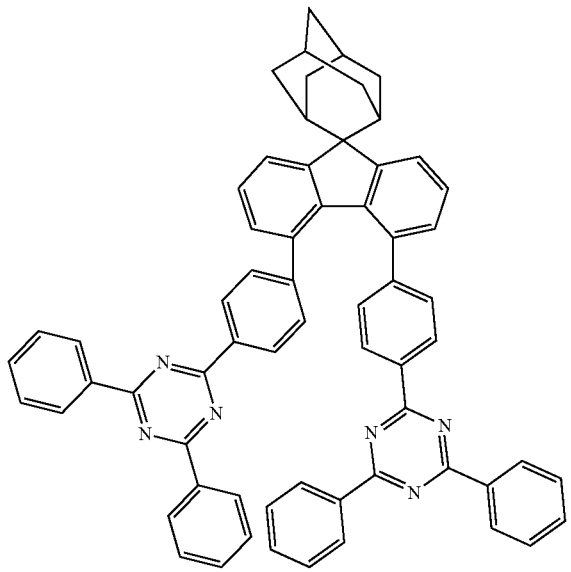
Compound 54
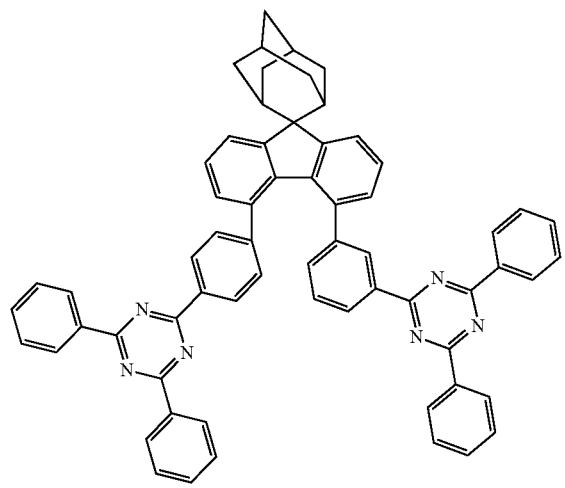
Compound 55
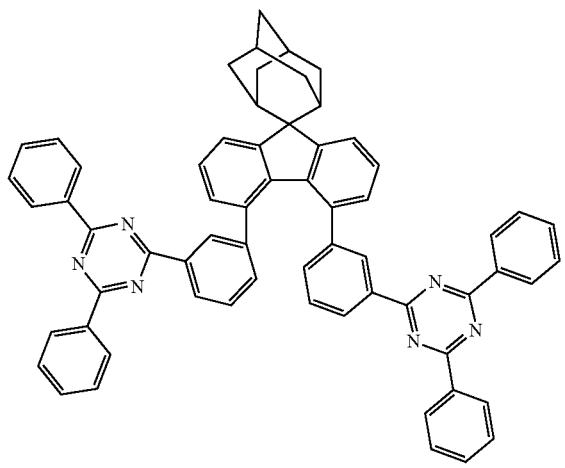
Compound 56
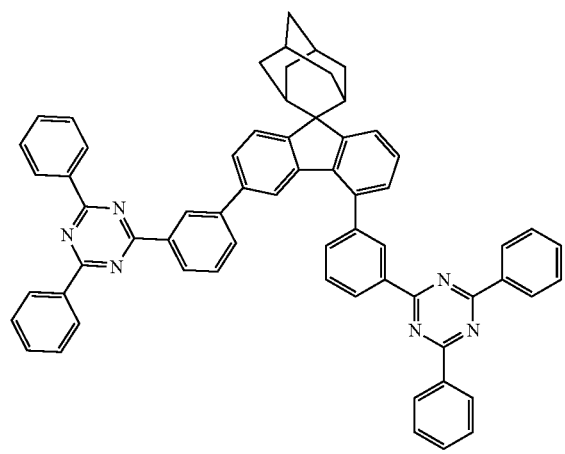
Compound 57
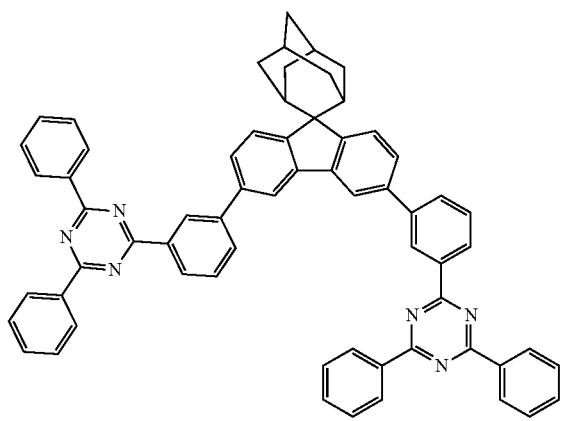

Compound 58
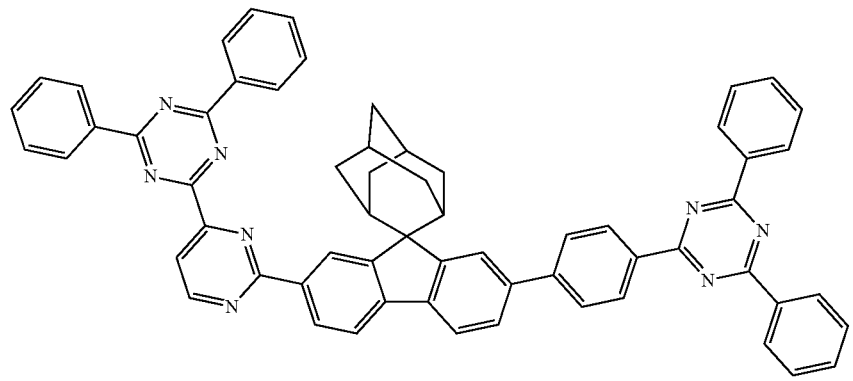
Compound 59
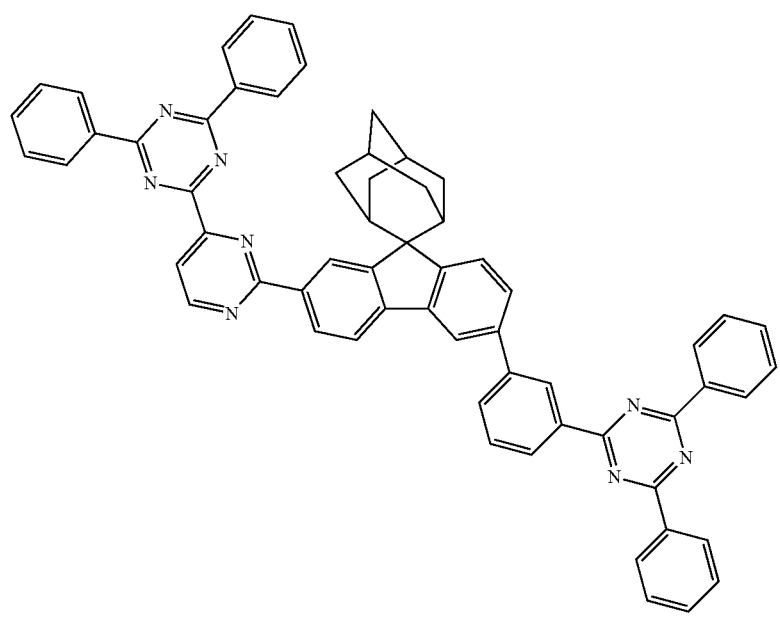
Compound 60
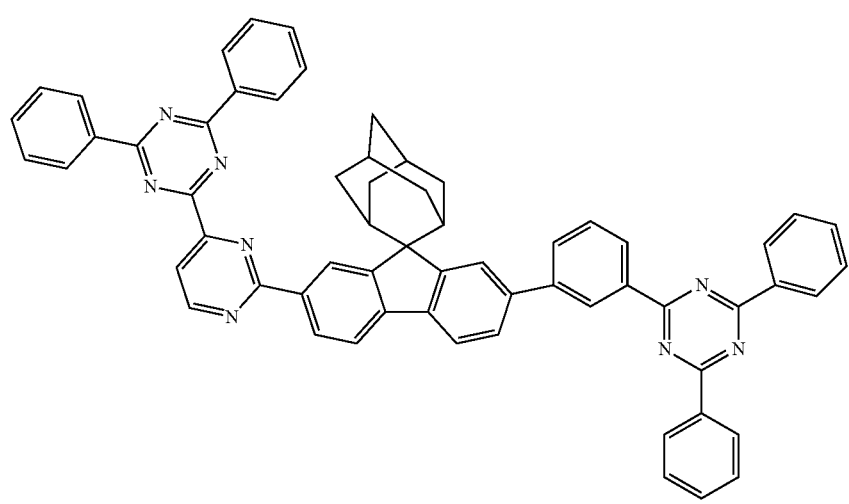

Compound 61
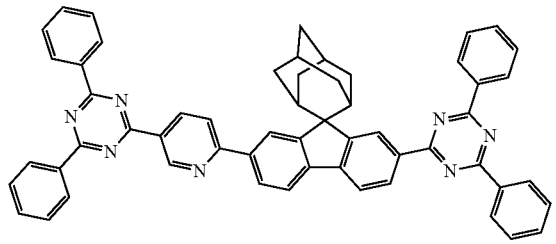
Compound 62
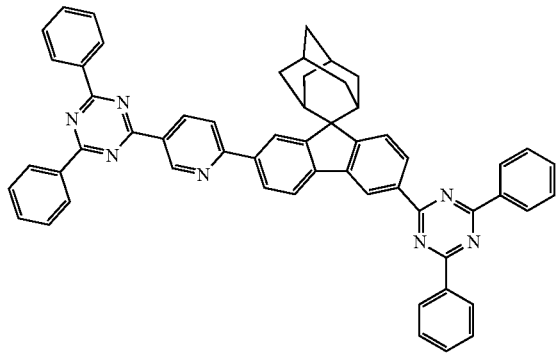
Compound 63
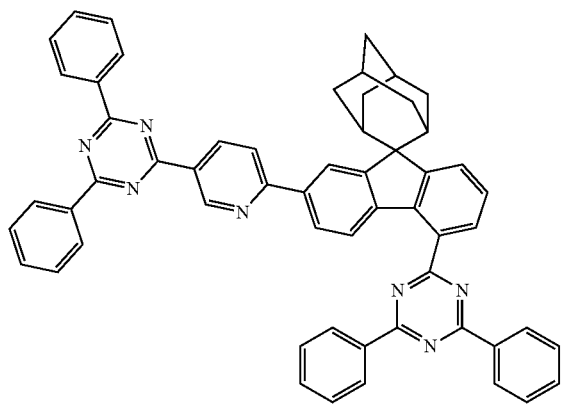
Compound 64
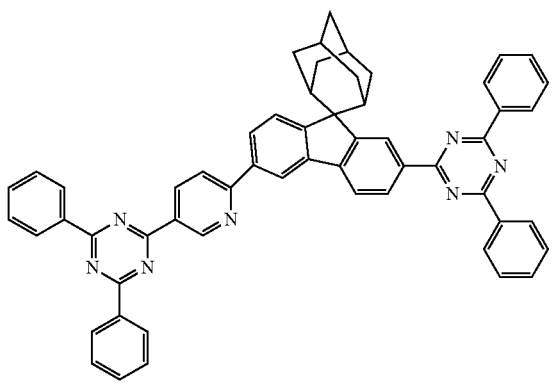
Compound 65
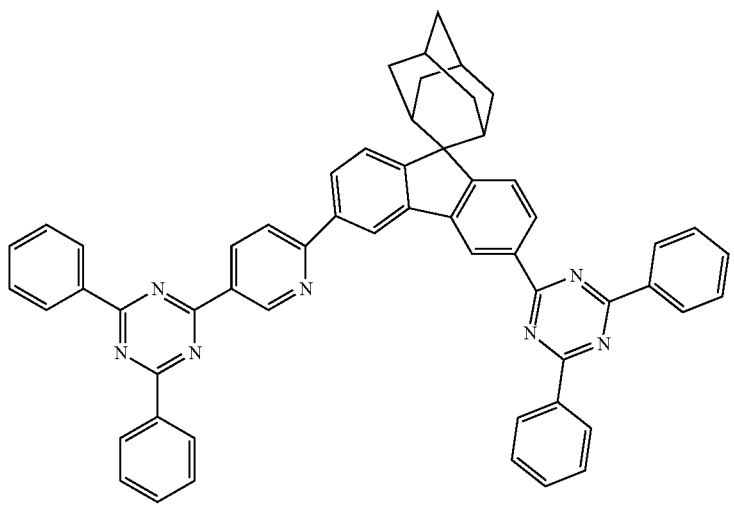

Compound 66
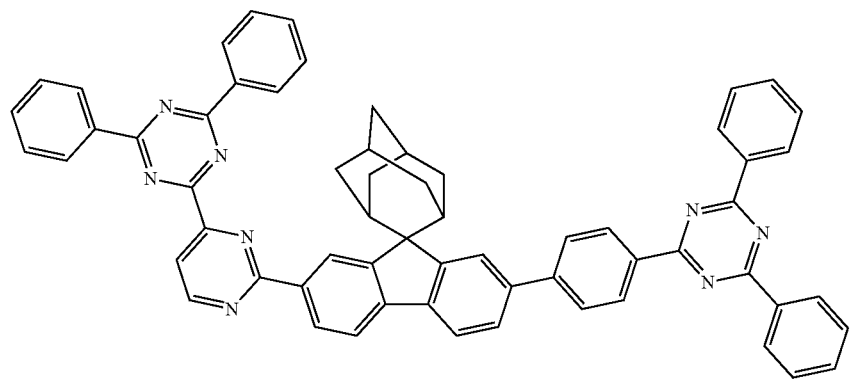
Compound 67
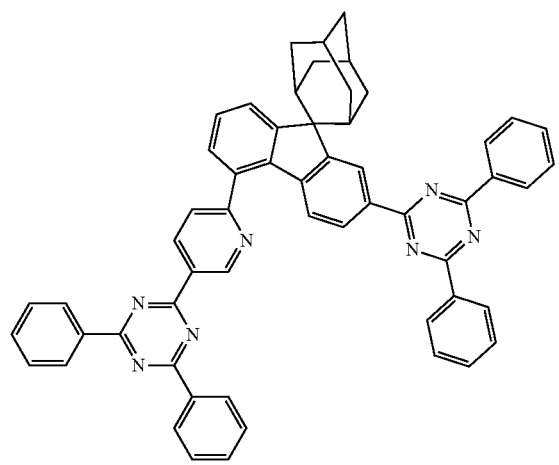
Compound 68
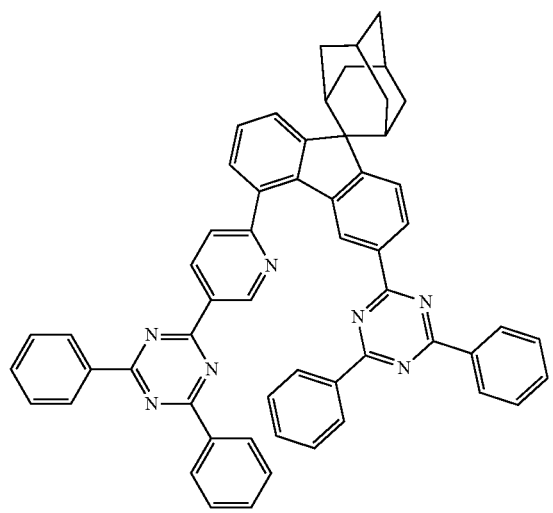
Compound 69
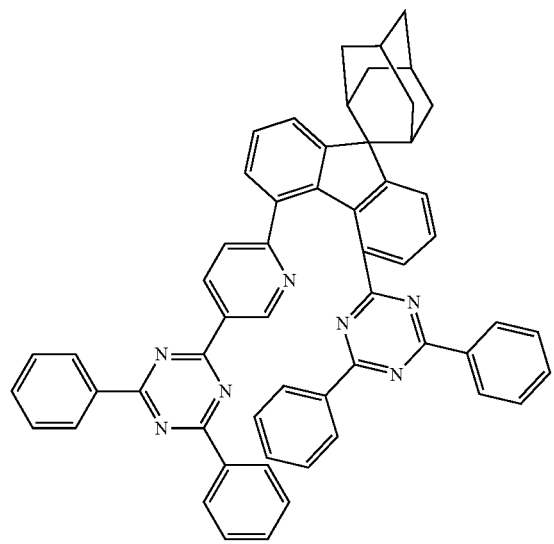

-continued
Compound 70
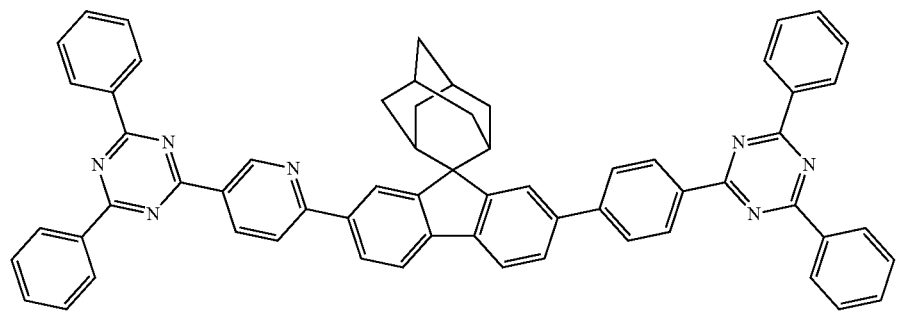
Compound 71
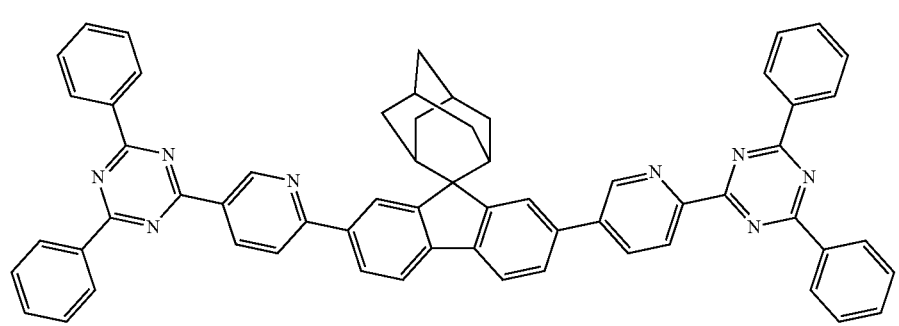
Compound 72
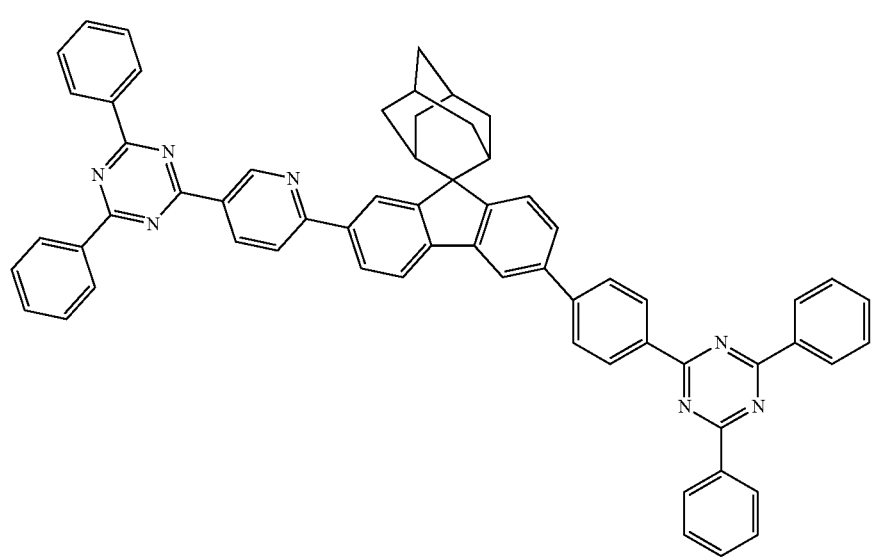

Compound 73
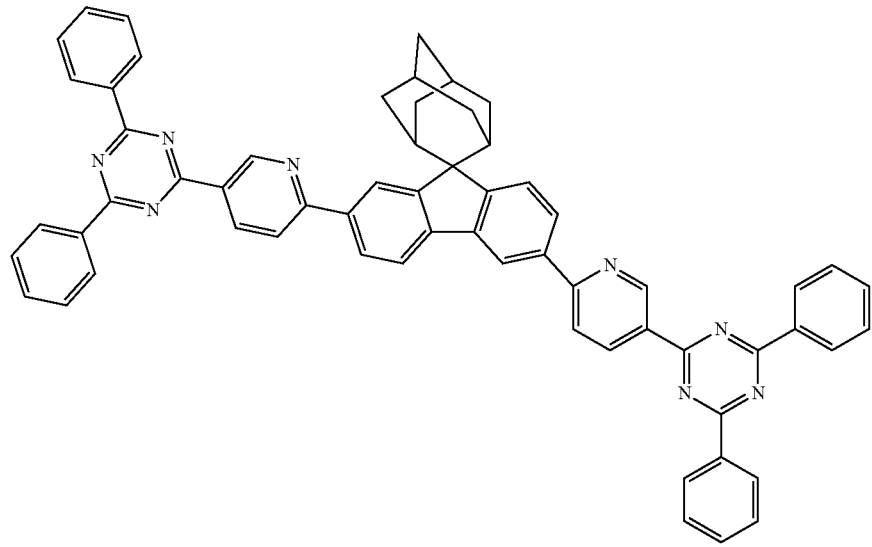
Compound 74
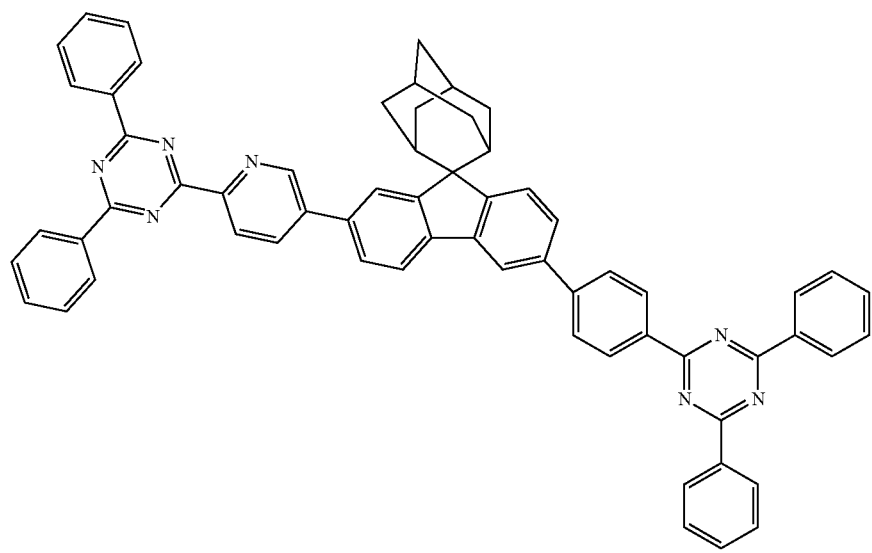
Compound 75
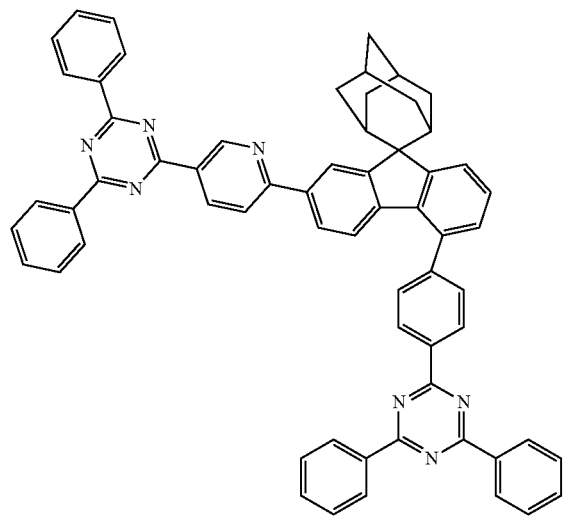
Compound 76
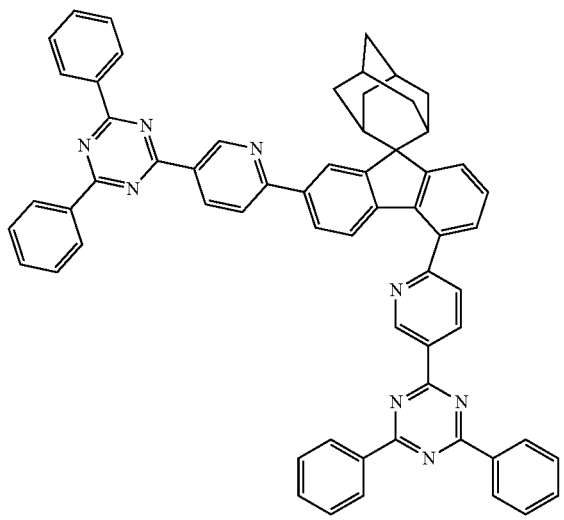

-continued
Compound 77
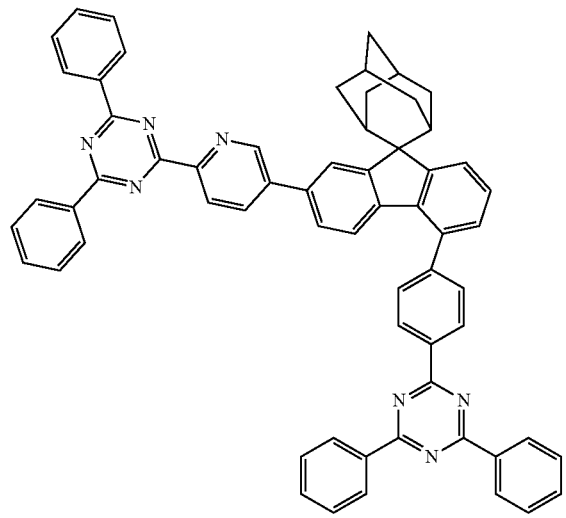
Compound 78
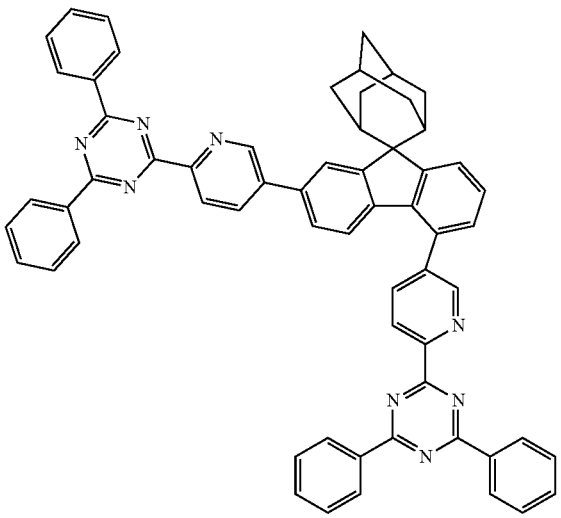
Compound 79
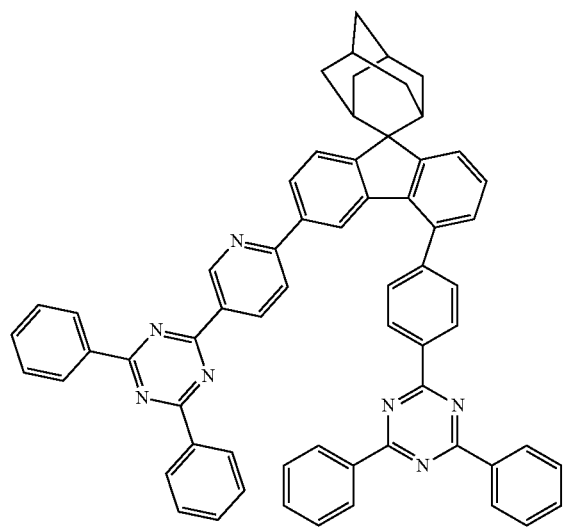
Compound 80
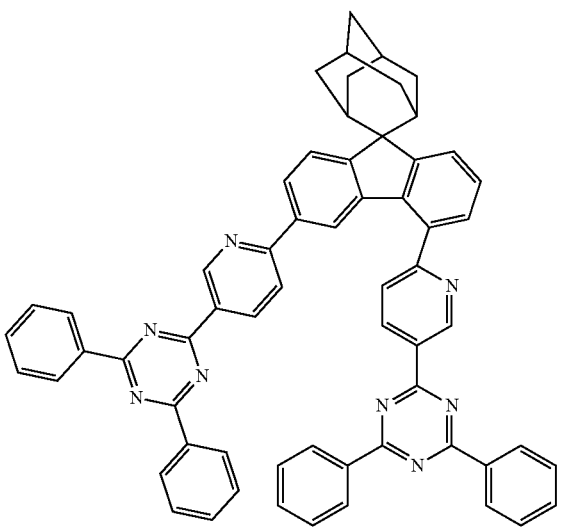
Compound 81
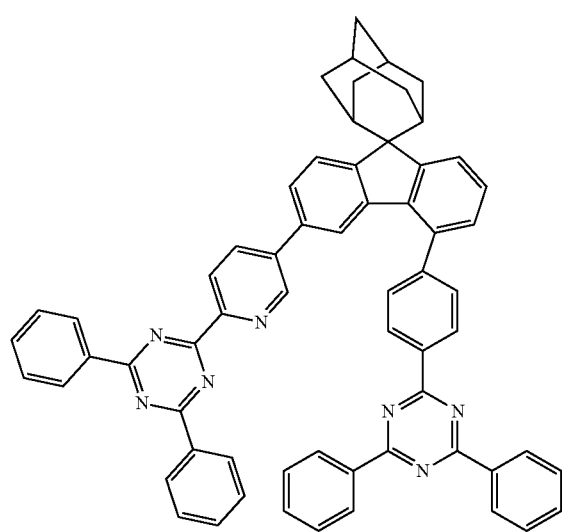
Compound 82

-continued
Compound 83
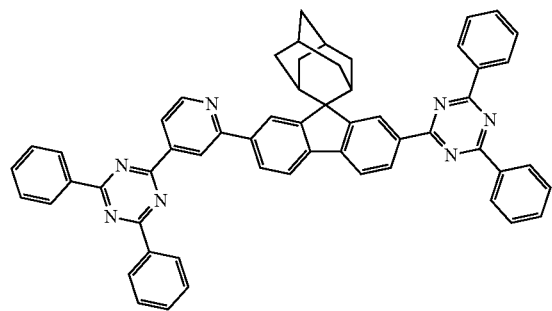
Compound 84
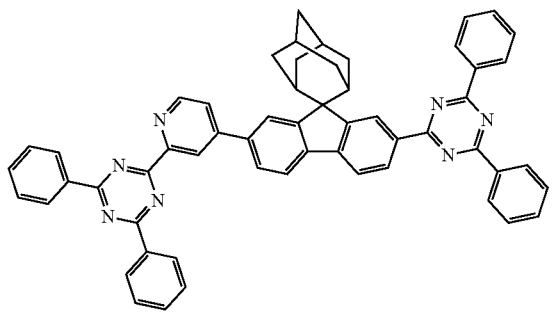
Compound 85
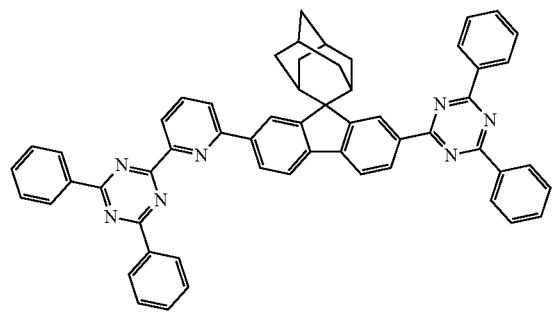
Compound 86
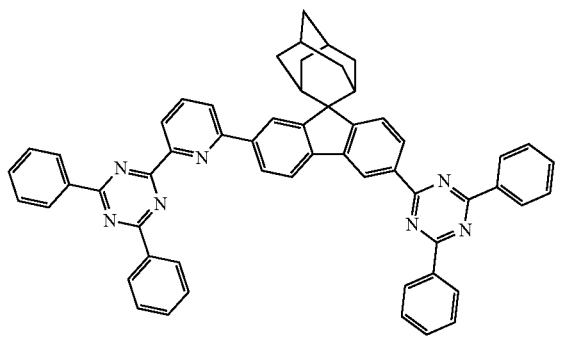
Compound 87
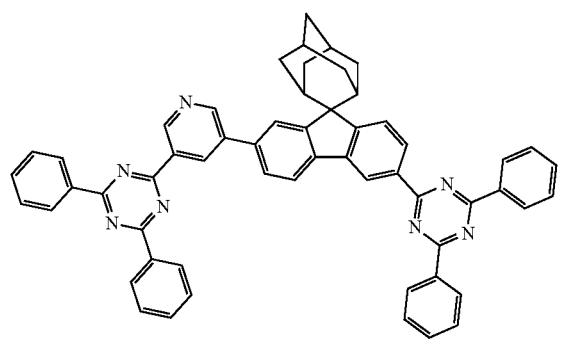
Compound 88
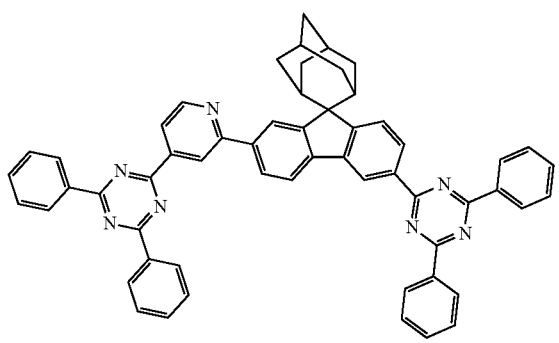
Compound 89
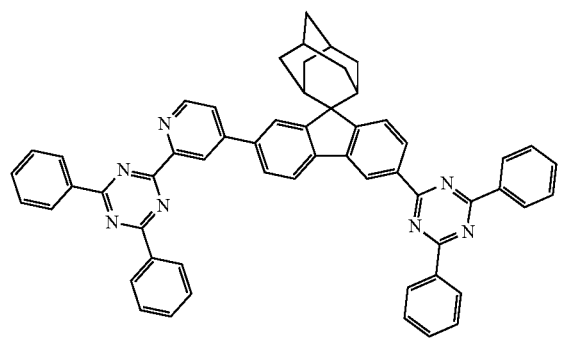
Compound 90
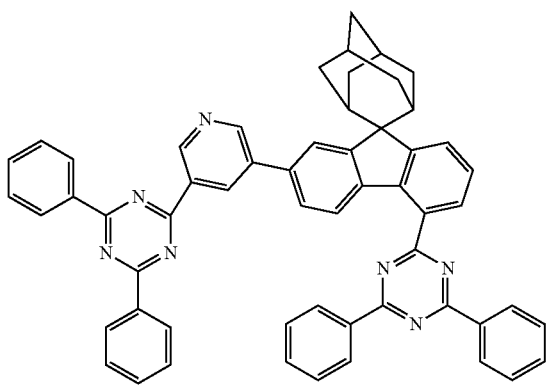

-continued
Compound 91
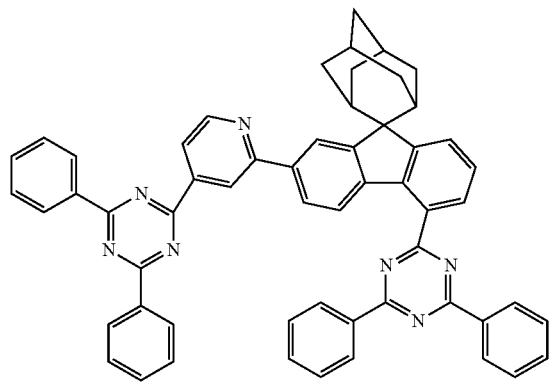
Compound 92
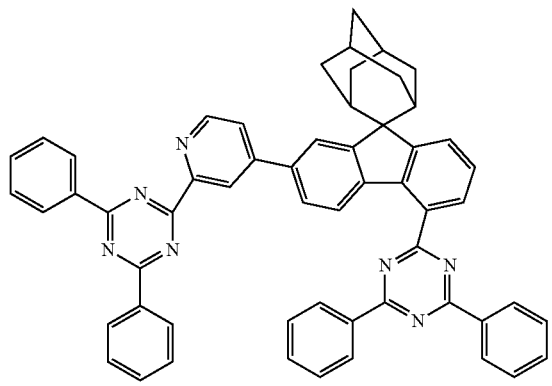
Compound 93
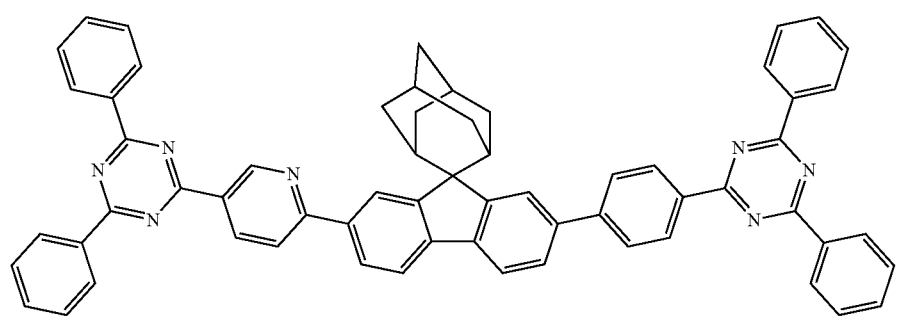
Compound 94
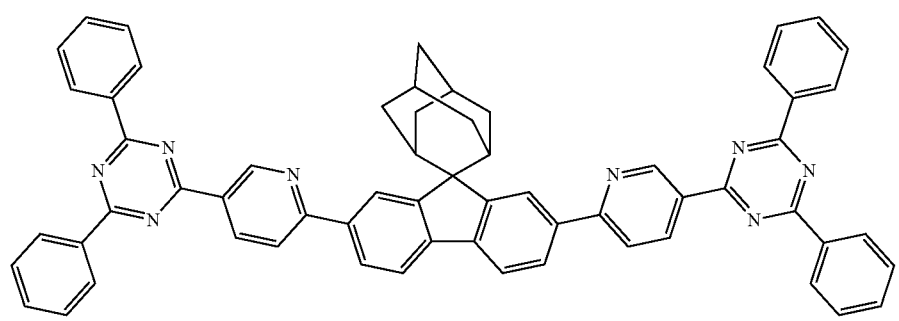
Compound 95
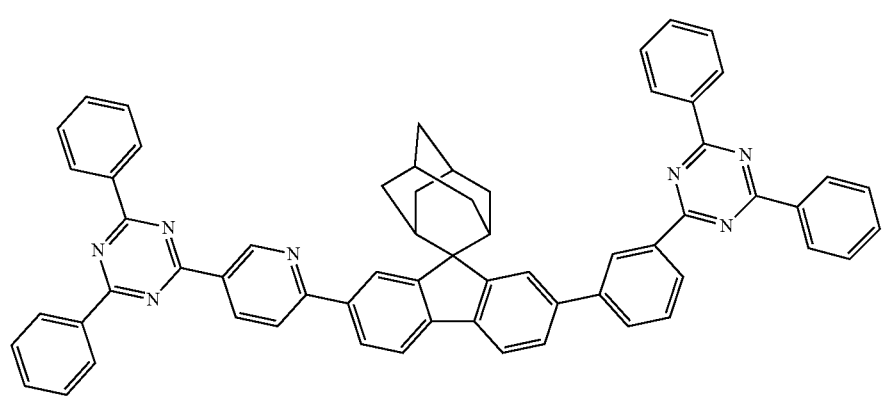

Compound 96
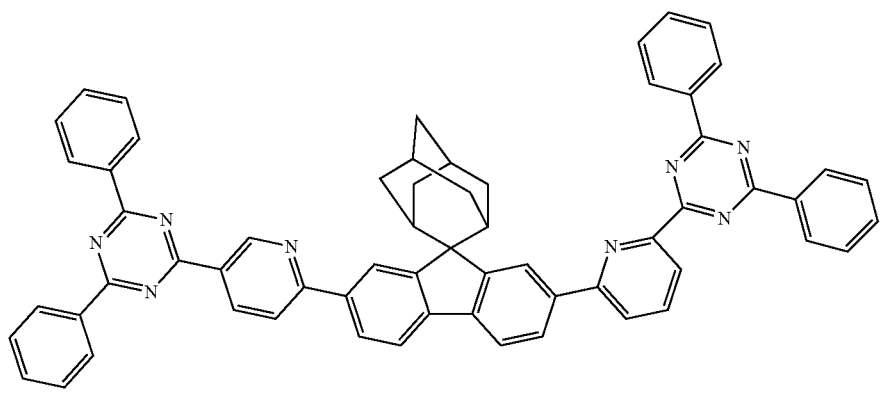
Compound 97
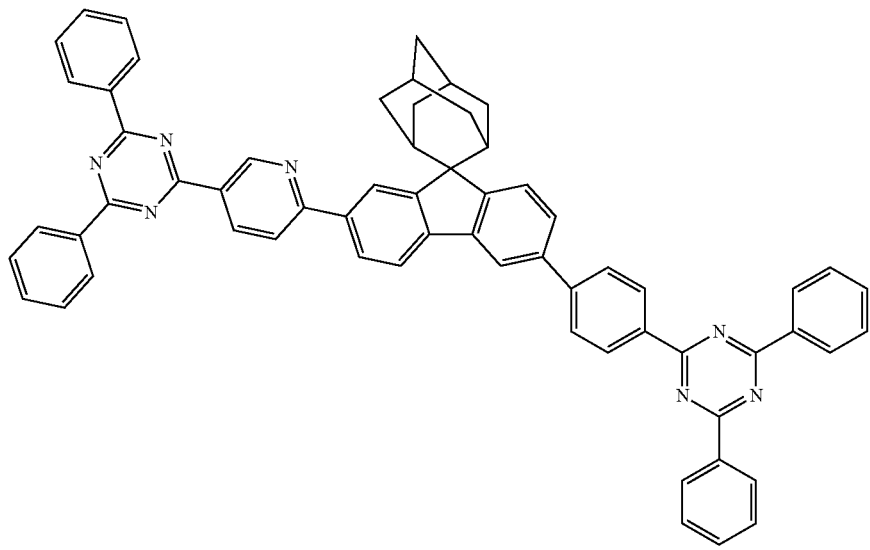
Compound 98
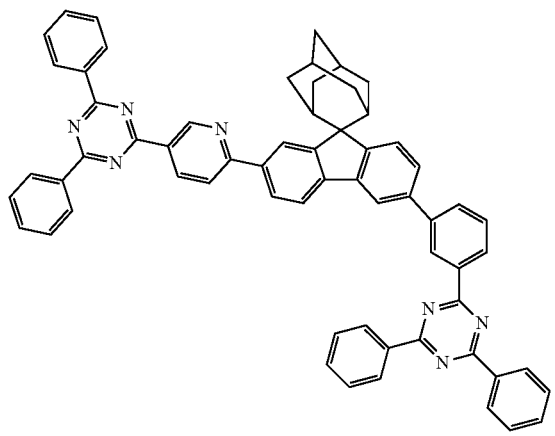
Compound 99
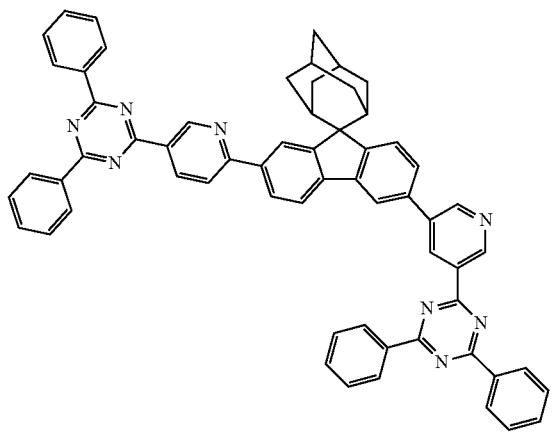

Compound 100
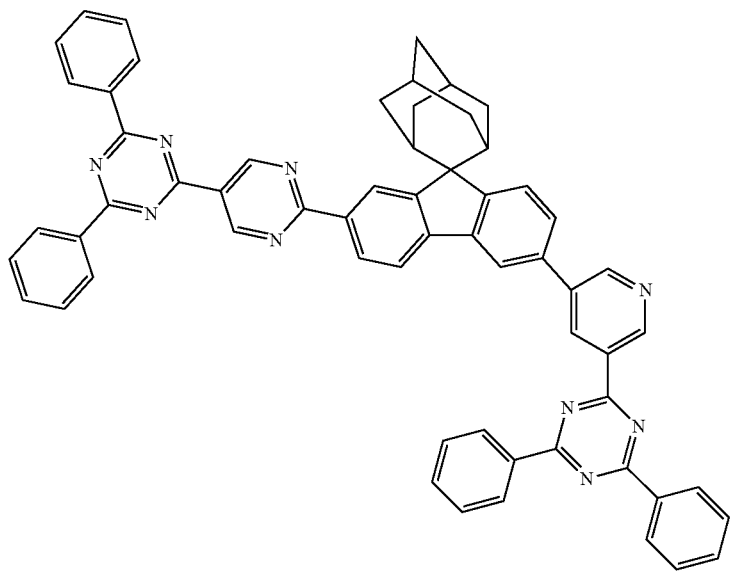
Compound N
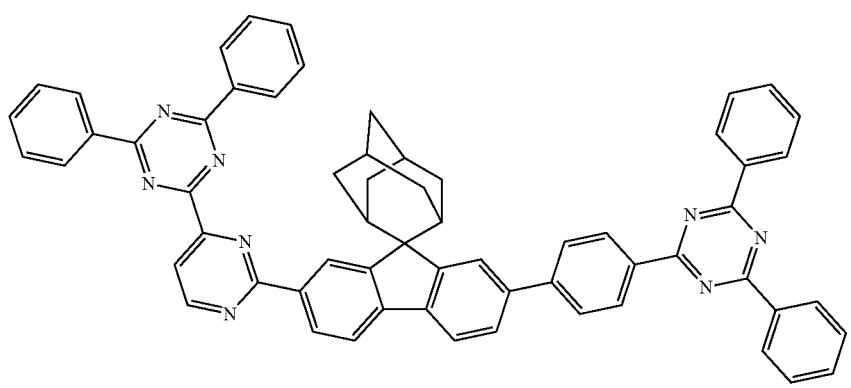
Compound O
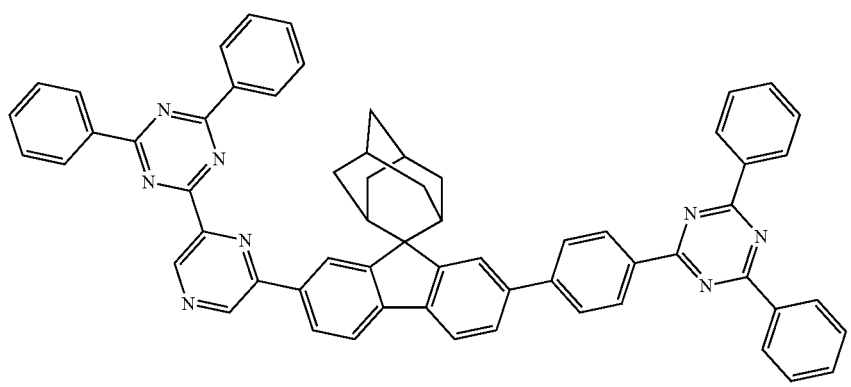

-continued
Compound P
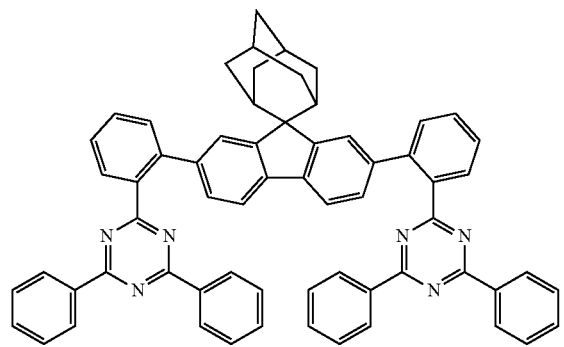
Compound Q
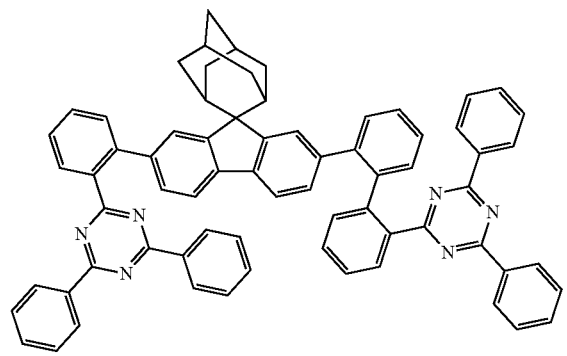
Compound R
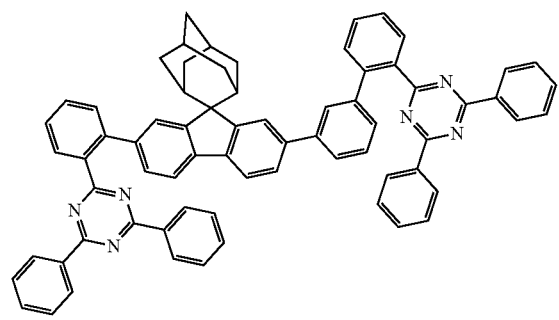
Compound S
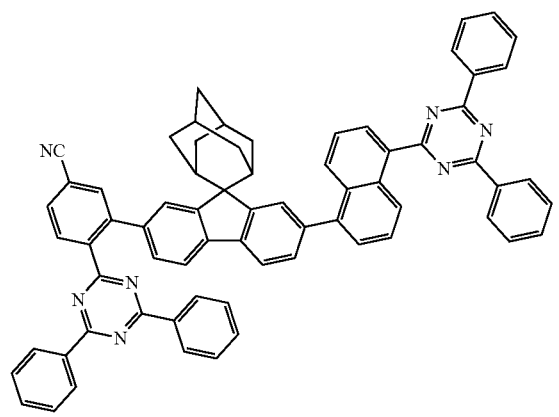
Compound T
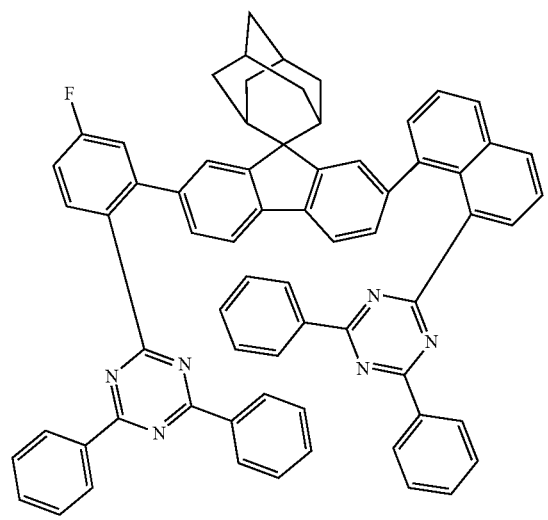
Compound U
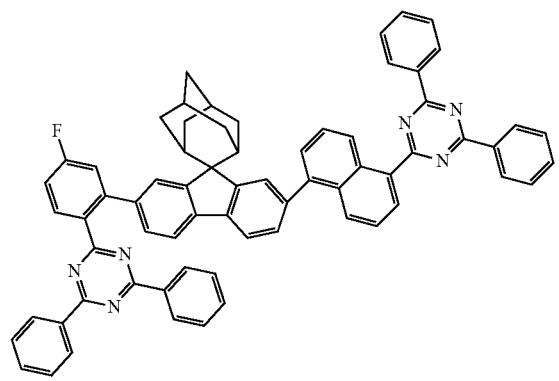

-continued
Compound V
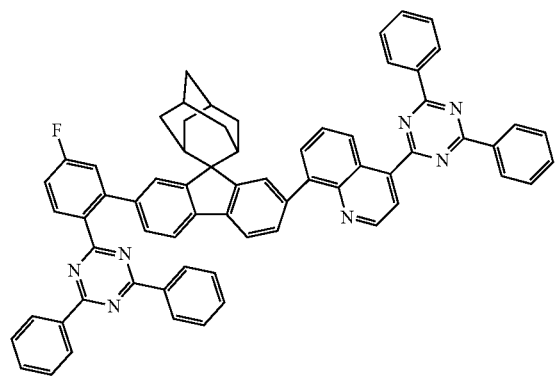
Compound W
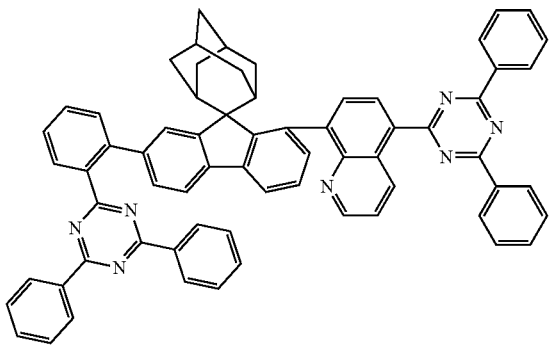
Compound X
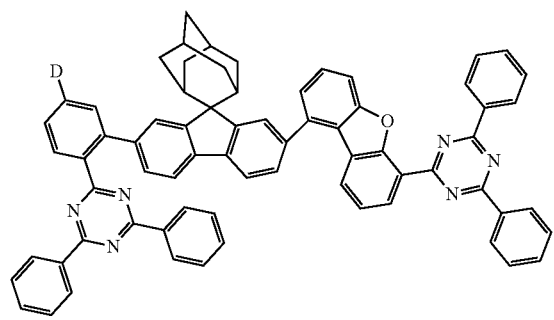
Compound Y
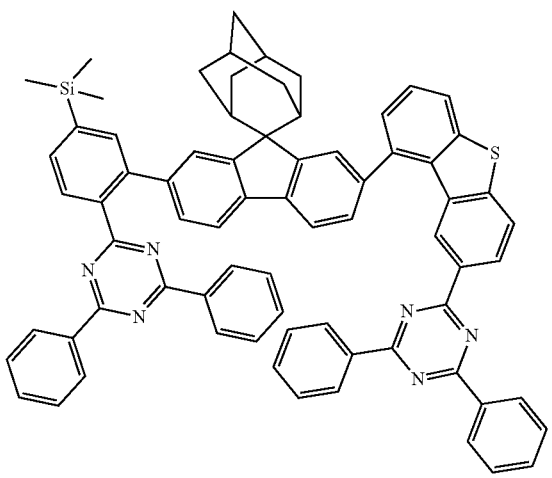
Compound Z
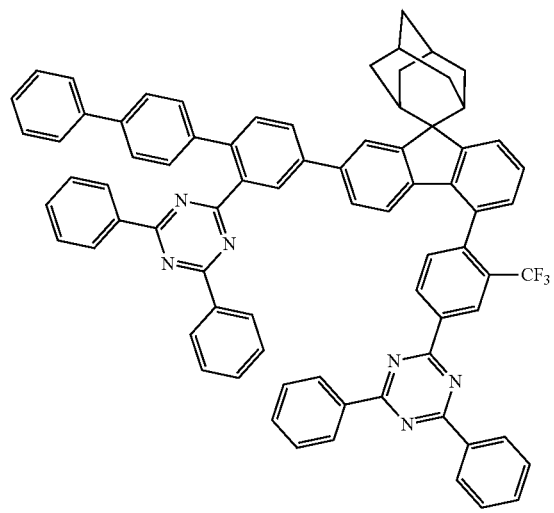
Compound Z-1
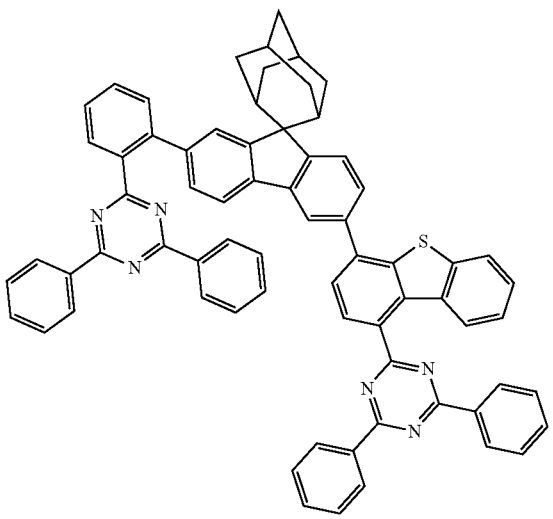

-continued
Compound Z-2
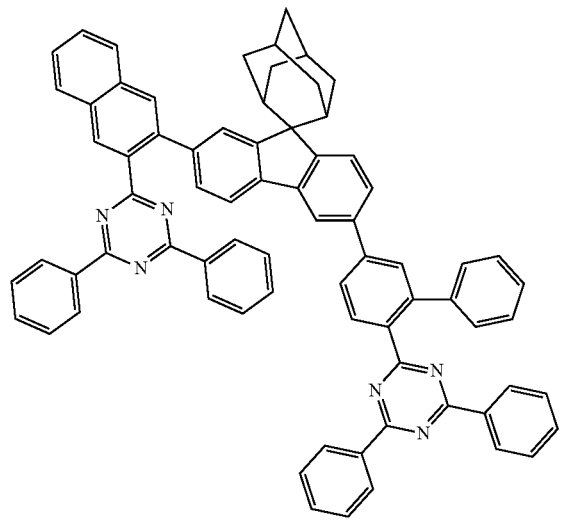
Compound Z-3
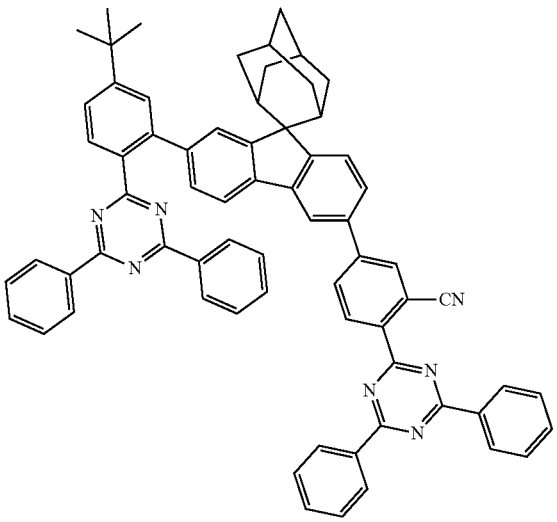
Compound Z-4
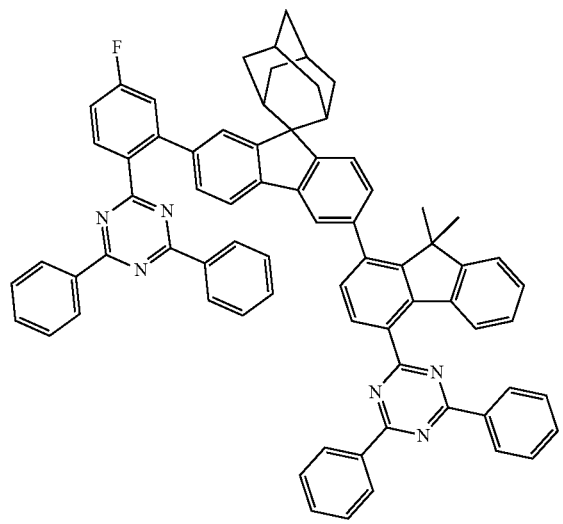
Compound Z-5
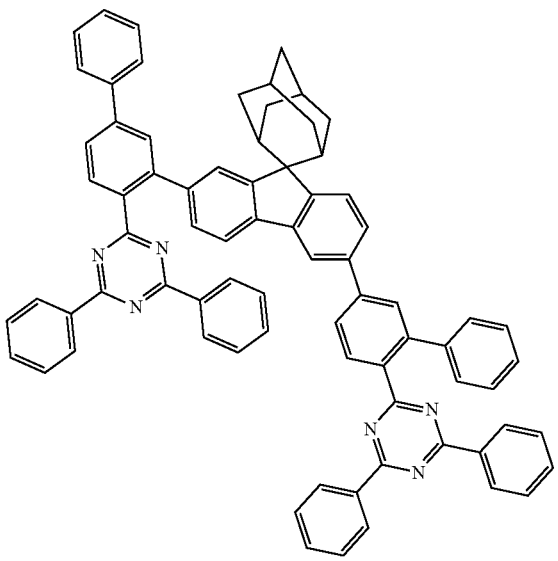
Compound Z-6
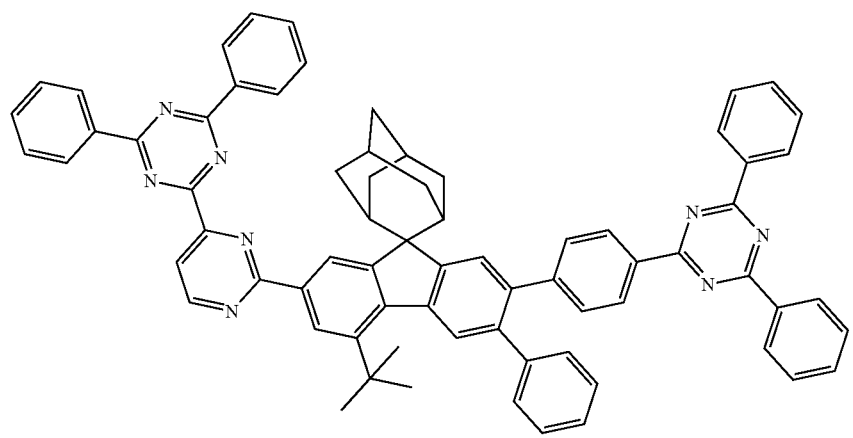

Compound Z-7
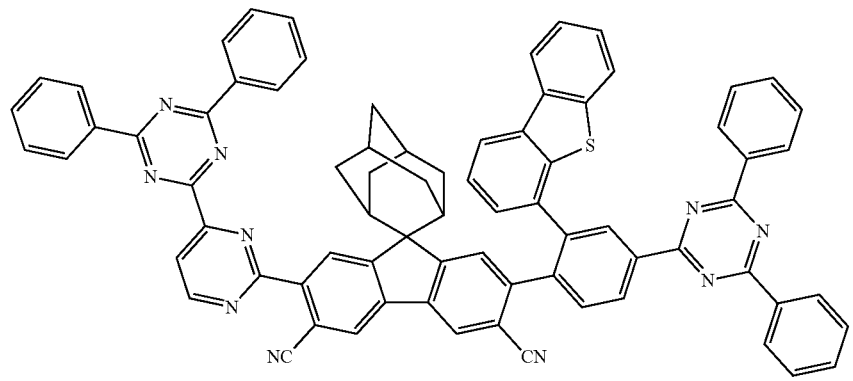
Compound Z-8
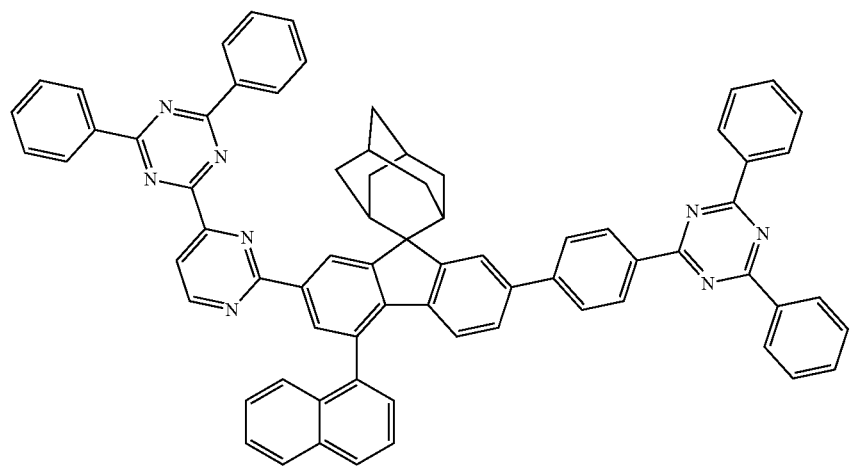
Compound Z-9
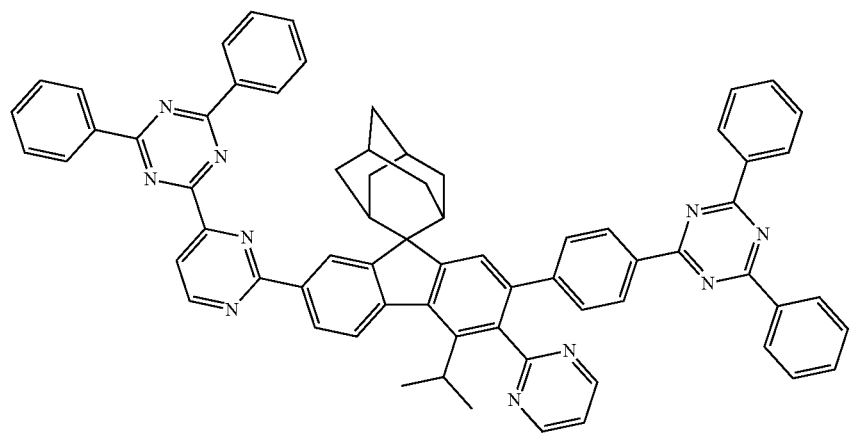

-continued
Compound Z-10
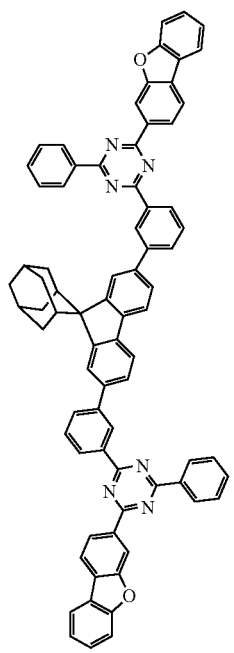
Compound Z-11
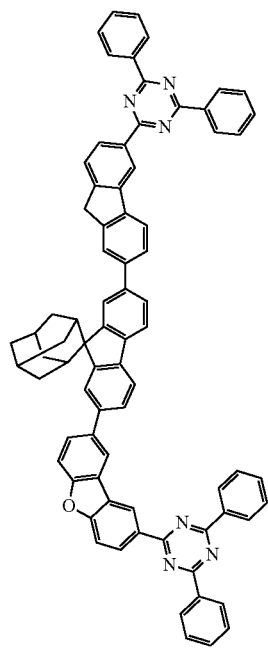
Compound Z-12
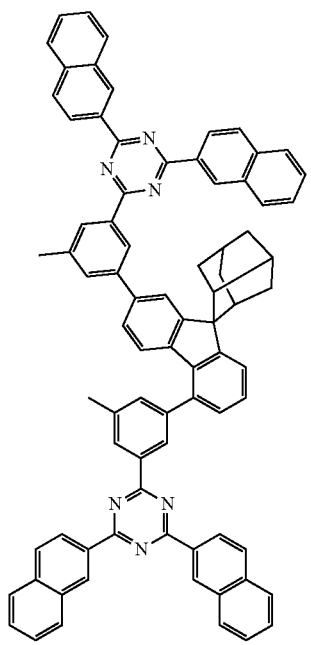
Compound Z-13
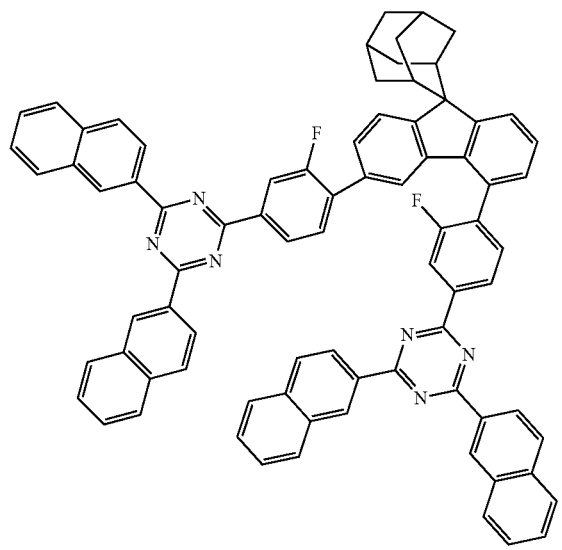

-continued
Compound Z-14
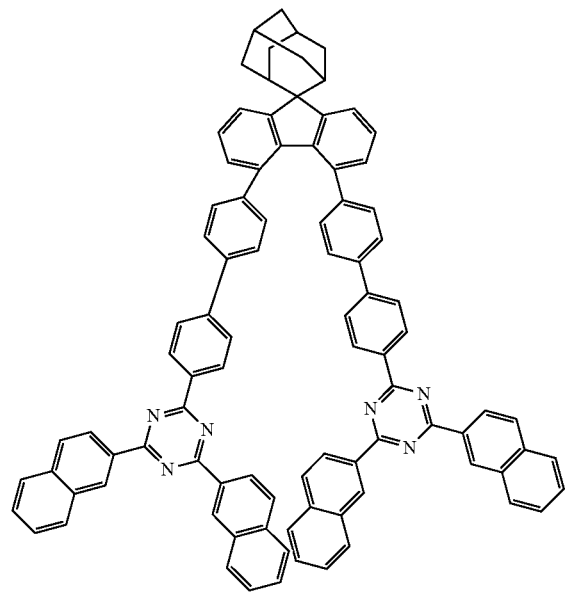
Compound Z-15
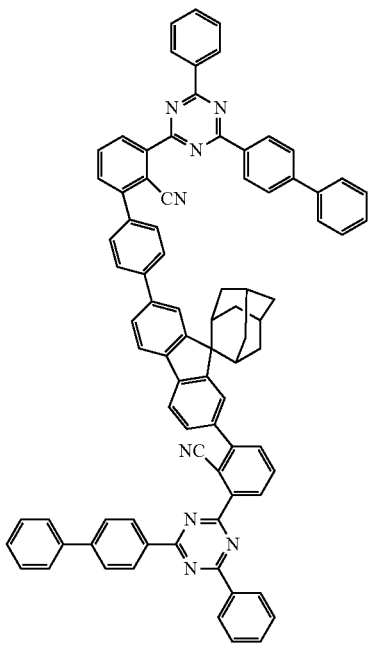
Compound Z-16
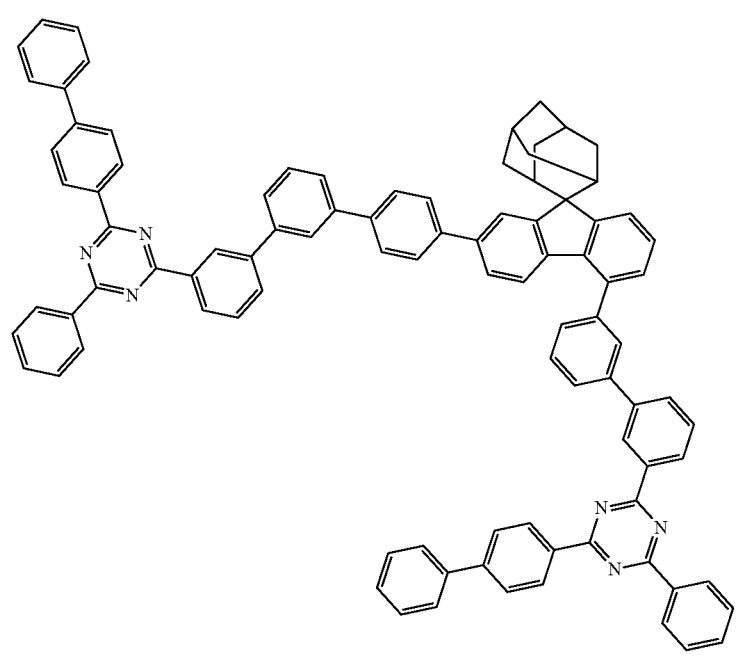

-continued
Compound Z-17
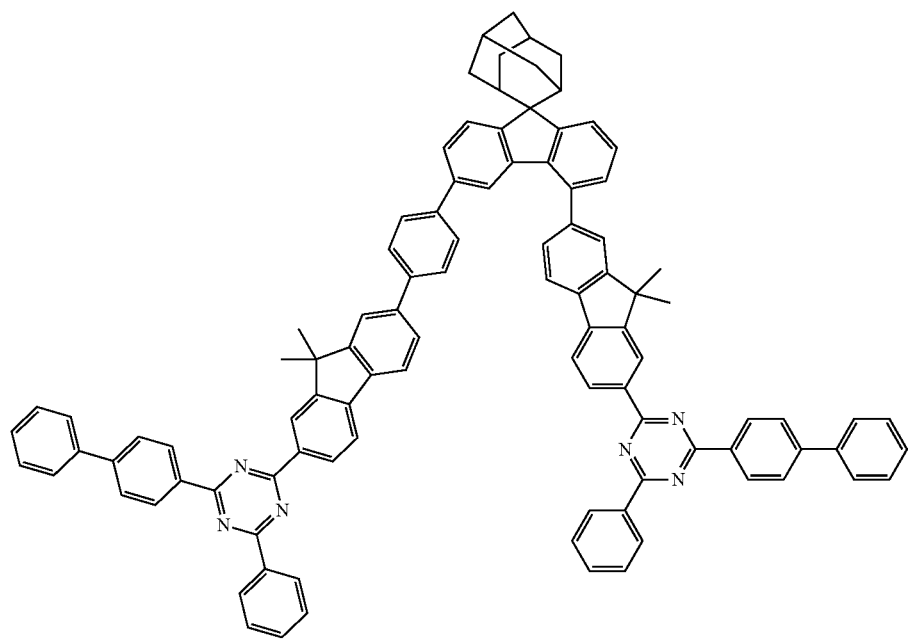
Compound Z-18
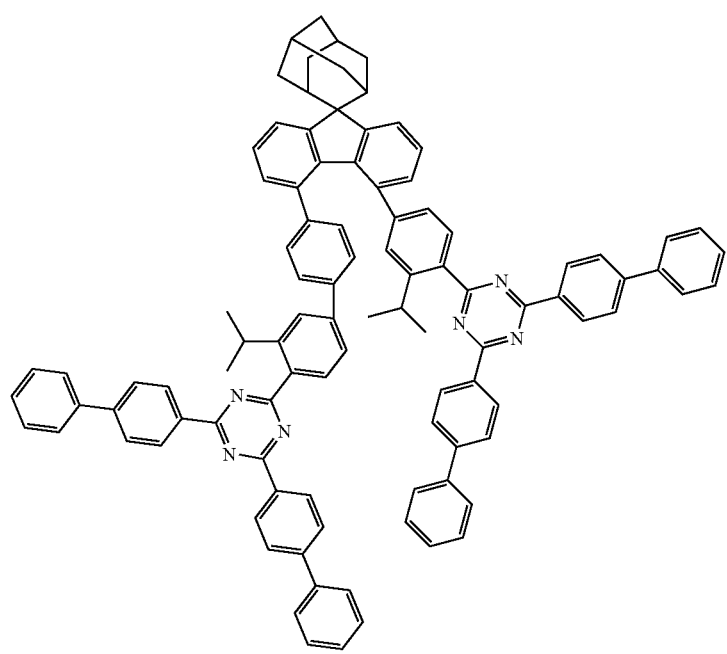

-continued
Compound Z-19
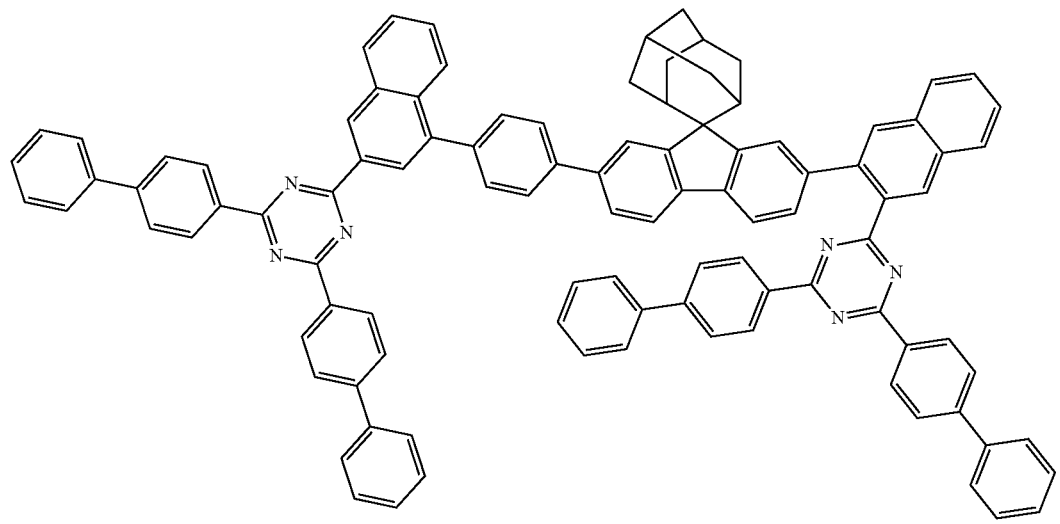
Compound Z-20
Compound Z-21
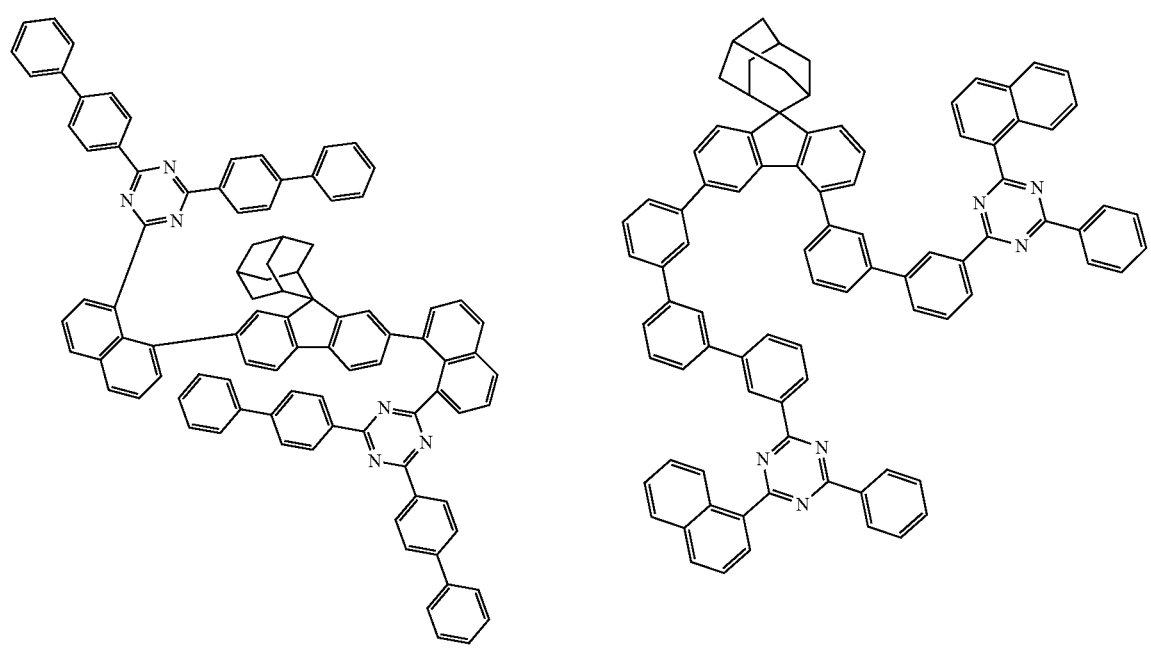

-continued
Compound Z-22
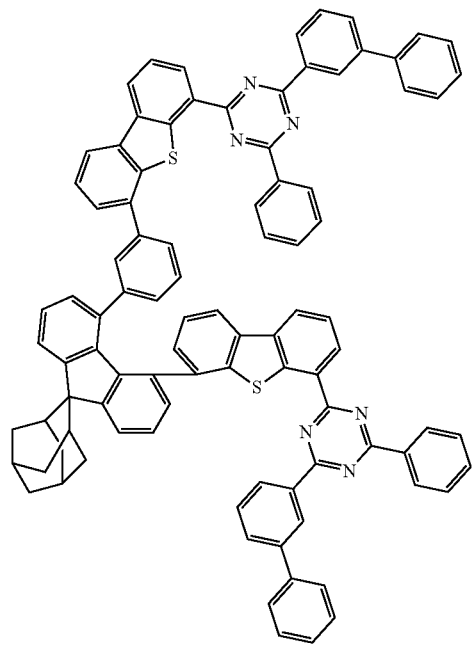
Compound Z-23
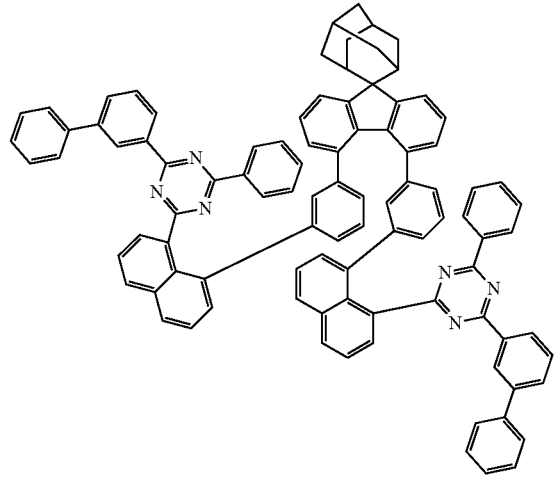
Compound Z-24
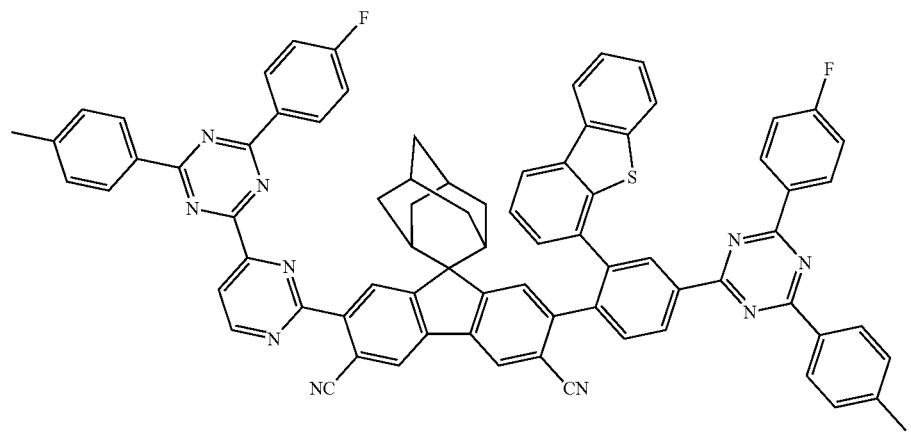
Compound Z-25
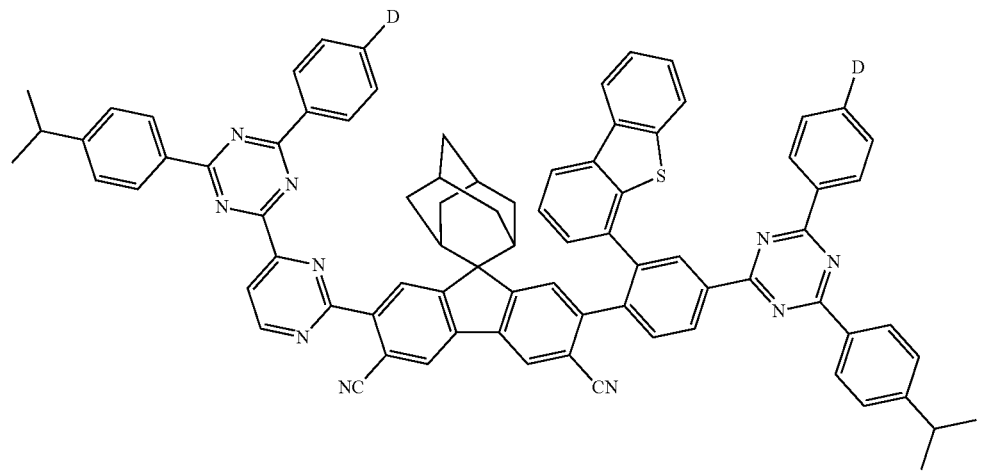

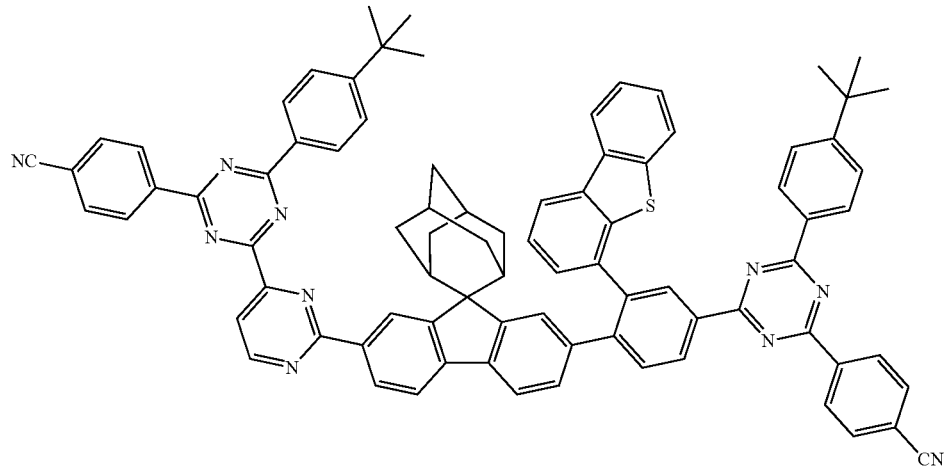

Compound Z-26

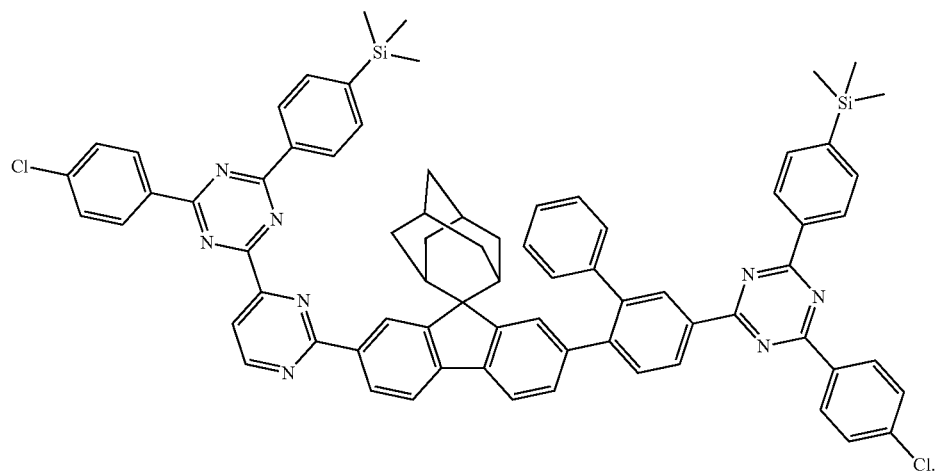

Compound Z-27

According to an embodiment of the present disclosure, provided is an electronic component, comprising an anode and a cathode oppositely arranged, and one or more functional layers arranged between the anode and cathode, wherein the functional layer comprises an electron transport layer, and the electron transport layer contains the organic compound.

In one embodiment, the electronic component is an organic electroluminescent device. As shown in FIG. 1, the organic electroluminescent device comprises an anode 100, a cathode 200 and a functional layer 300, wherein: the anode 100 and the cathode 200 are oppositely arranged, and the functional layer 300 is arranged between the anode 100 and the cathode 200. The functional layer 300 contains the organic compound described herein.

The material of the anode 100 may be metal, alloy or metallic oxide and the like, for example, it is either nickel, platinum, vanadium, chromium, copper, zinc, gold or their alloys, or zinc oxide, indium oxide, indium tin oxide (ITO) and indium zinc oxide (IZO); the material of the anode 100 may also be, but not limited to, a composition such as ZnO:Al, SnO$_2$:Sb, a conducting polymer (poly (3-methyl-thiophene), poly [3,4-(ethylidene-1,2-dioxyl) thiophene] (PEDT), polypyrrole and polyaniline) and the like. Optionally, the material of the anode 100 is indium tin oxide (ITO).

The material of the cathode 200 may be a metal or alloy material, for example, it is either, but not limited to, magnesium, calcium, sodium, potassium, titanium, aluminum, silver or their alloys, or multilayer materials, such as LiF/Al, Liq/Al, LiO$_2$/Al, LiF/Ca, LiF/Al, BaF$_2$/Ca and the like. Optionally, the material of the cathode 200 is aluminum.

The functional layer 300 may comprise a hole transport layer 320, a light-emitting layer 340 and an electron transport layer 350, wherein the light-emitting layer 340 is arranged at a side of the hole transport layer 320 away from the anode 100, and the electron transport layer 350 is arranged at a side of the light-emitting layer 340 near the cathode 200.

The light-emitting layer 340 consists of a single light-emitting material, or comprises a host material and a guest material. Optionally, the light-emitting layer 340 consists of a host material and a guest material, the holes injected into the light-emitting layer 340 and the electrons injected into the light-emitting layer 340 can be recombined at the light-emitting layer 340 to form excitons, the excitons transfer energy to the host material, and the host material transfers energy to the guest material, so that the guest material can emit light.

The host material of the light-emitting layer 340 may be a metal chelate compound, a diphenyl-vinyl derivative, an aromatic amine derivative, a dibenzofuran derivative or other types of materials, which is not specially restricted herein. In one embodiment of the disclosure, the host material of the light-emitting layer 340 is CBP. In another embodiment of the disclosure, the host material of the light-emitting layer 340 is α,β-ADN.

The guest material of the light-emitting layer 340 may be a compound with a condensed aryl ring or a derivative thereof, a compound with a heteroaryl ring or a derivative thereof, an aromatic amine derivative or other materials, which is not specially restricted herein. In one embodiment of the disclosure, the guest material of the light-emitting layer 340 is Ir(piq)$_2$(acac). In another embodiment of the disclosure, the guest material of the light-emitting layer 340 is BD-1.

The electron transport layer 350 is either a single-layer structure or a multi-layer structure, and the electron transport layer may comprise one or more electron transport materials which are the organic compounds of the present disclosure.

The functional layer 300 may also comprise a hole injection layer 310 which may be arranged between the hole transport layer 320 and the anode 100.

The functional layer 300 may also comprise an electron-blocking layer 330 which may be arranged between the hole transport layer 320 and the light-emitting layer 340.

The functional layer 300 may also comprise an electron injection layer 360 which may be arranged between the electron transport layer 350 and the cathode 200.

The hole transport layer 320 may comprise a first hole transport layer 3201 and a second hole transport layer 3202. Wherein the first hole transport layer 3201 covers the hole injection layer 310, and the second hole transport layer 3202 is arranged at a side of the first hole transport layer 3201 away from the hole injection layer 310. In one embodiment of the present disclosure, the first hole transport layer 3201 is PAPB (CAS: 934000-87-0) or the second hole transport layer 3202 is α-NPD (CAS 495416-60-9).

Figure 2:
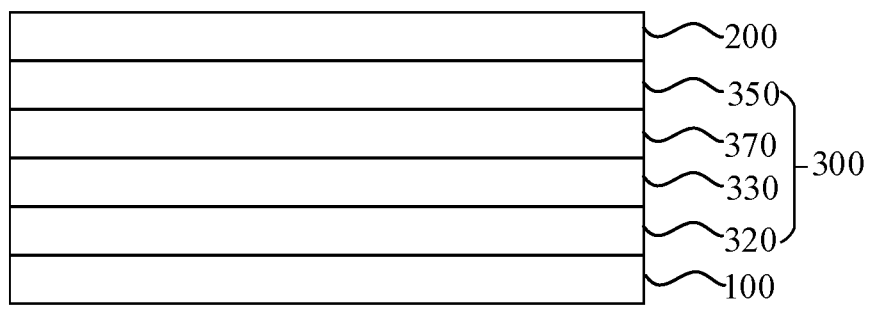
FIG. 2 shows a solar cell plate containing the organic compound of the present disclosure as an embodiment of the present disclosure.
Figure 3:
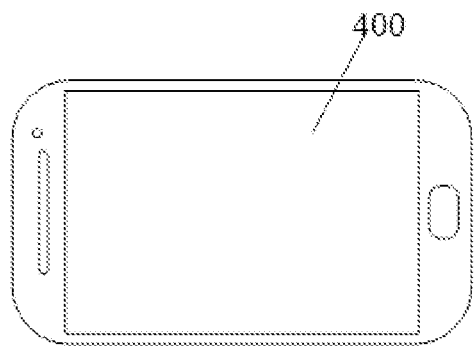
FIG. 3 shows a structural view of the electronic device as an embodiment of the present disclosure.

In another embodiment, the electronic component is a solar cell. As shown in FIG. 2, the solar cell comprises an anode 100, a cathode 200 and a functional layer 300, wherein: the anode 100 and the cathode 200 are oppositely arranged, the functional layer 300 is arranged between the anode 100 and the cathode 200, and the functional layer 300 contains the organic compound of the present disclosure.

All parts of the solar cell of the embodiment herein will be described in detail below.

The functional layer 300 may comprise a hole transport layer 320, a photoelectric conversion layer 370 and an electron transport layer 350, wherein the photoelectric conversion layer 370 is arranged at a side of the hole transport layer 320 away from the anode 100, the electron transport layer 350 is arranged at a side of the photoelectric conversion layer 370 near the cathode 200, and the electron transport layer 320 contains the organic compound of the present disclosure.

The functional layer 300 may also comprise an electron-blocking layer 330 which may be arranged between the hole transport layer 320 and the photoelectric conversion layer 370.

In addition, the solar cell may be an organic thin film solar cell.

Test Method:

According to the present disclosure, purification and/or determination are performed by using a silica gel chromatographic column and low-resolution mass spectrometry.

Chromatographic column: silica gel chromatographic column (silica gel (300-400 meshes), purchased from Qingdao Haiyang Chemical Factory).

Low-resolution mass spectrometry (MS): Agilent 6120 Quadrupole HPLC-M (column model: Zorbax SB-C18, 2.1× 30 mm, 3.5 microns, 6 min, flow rate was 0.6 mL/min; mobile phase: 5%-95% (proportion of CH$_3$CN containing 0.1% formic acid in H$_2$O containing 0.1% formic acid), UV detection at 210 nm/254 nm using electrospray ionization (ESI)).

Nuclear magnetic resonance hydrogen spectrum: Bruker 400 MHz Nuclear Magnetic Resonance Spectrometer, with CD$_2$Cl$_2$ as a solvent (in ppm) and TMS (0 ppm) as a reference standard at room temperature. When multiplet appears, the following abbreviations will be used: s (singlet), d (doublet), t (triplet), m (multiplet), br (broadened), dd (doublet of doublets), and dt (doublet of triplets).

The present disclosure will be described in more detail below in combination with the examples, but is not limited to this.

EXAMPLE

Unless otherwise specified, all the temperatures are in degrees Celsius in this description.

Unless otherwise specified, all the reagents used in the example were purchased from commodity suppliers and not further purified in use in this description.

Anhydrous tetrahydrofuran, dioxane and toluene ether used in the examples of the specification were all obtained by reflux drying with metal sodium; anhydrous dichloromethane and chloroform were obtained by reflux drying with calcium hydride; ethyl acetate, petroleum ether, n-hexane, N,N-dimethylacetamide and N,N-dimethylformamide were used after drying in advance with anhydrous sodium sulfate.

In the examples herein, unless otherwise stated, a reaction was generally performed under positive pressure of nitrogen or argon, or a drying tube was installed to an anhydrous solvent, reaction bottles were plugged with suitable rubber stoppers, the substrate was injected into the reaction bottles through a syringe, and all glassware was dried before use.

Preparation Example 1: Synthesis of Compound 15

1) Synthesis of Intermediate M1

100 g (i.e. 373.5 mmol) of 2-chloro-4,6-diphenyl-1,3,5-triazine were added into a three-necked flask containing 1 L of tetrahydrofuran (THF), 25.12 g (i.e. 392.20 mmol) of n-butyllithium (n-Buli) were added dropwise at −78° C., the temperature was kept after dropping was completed, then 40.85 g (i.e. 1120.5 mmol) of trimethyl borate were added dropwise, heated to room temperature after the temperature was continuously kept for 1 h, and stirred overnight. Hydrochloric acid (2 mol/L) was added, pH was adjusted to neutral, a white crude product was obtained after filtration, pulped with n-heptane, so that 72.1 g of white solid intermediate M1 were obtained (with a yield of 70%).

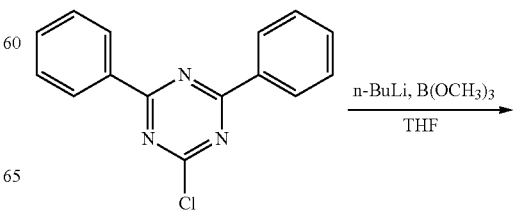

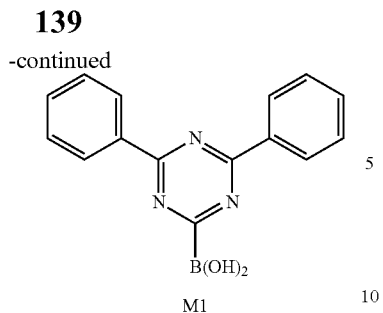

M1

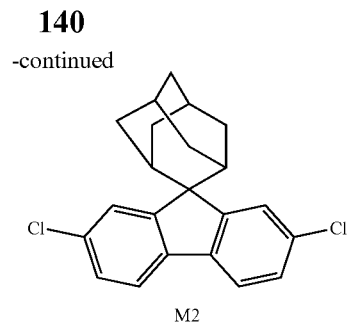

M2

2) Synthesis of Intermediate M2

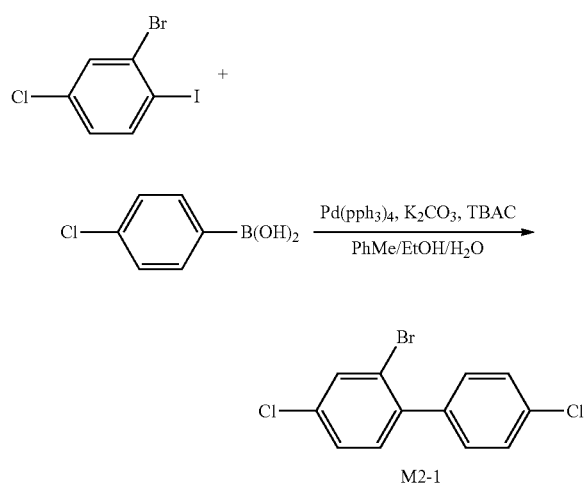

2.1) Synthesis of Intermediate M2-1

100 g (i.e. 315.1 mmol) of 2-bromo-4-chloro-1-iodobenzene, 49.27 g (i.e. 315.1 mmol) of 4-chlorophenylboronic acid, 18.21 g (i.e. 15.7 mmol) of tetrakis(triphenylphosphine)palladium (Pd(pph$_3$)$_4$), 87.1 g (i.e. 630.2 mmol) of potassium carbonate, 3.59 g (i.e. 15.7 mmol) of tetrabutyl ammonium chloride (TBAC), 800 mL of toluene (PhMe), 400 mL of ethanol (EtOH) and 200 mL of deionized water were added into a three-necked flask, heated to 78° C. under the nitrogen atmosphere and stirred for 8 hours; the reaction solution above was cooled to room temperature, 500 mL of methylbenzene was added for extraction. The combined organic phases were dried over anhydrous magnesium sulfate and filtered, the filtrate was concentrated in vacuo to obtain a crude product; the obtained crude product was purified by silica gel column chromatography and eluted with n-heptane, then purified by recrystallization using a mixture of dichloromethane and ethyl acetate, to obtain 75.16 g of intermediate M2-1 as a white solid (yield 79%).

2.2) Synthesis of Intermediate M2-2

100 g (i.e. 331.13 mmol) of intermediate M2-1 were added into a three-necked flask containing 1 L of THF, n-butyllithium (THF solution, 397.35 mmol) was added dropwise at −80° C. After addition, the reaction mixture was stirred at −80° C. for another 1 h, 39.78 g (i.e. 264.90 mmol) of adamantanone were added dropwise, the resulted mixture was stirred for 1 h, and then heated to room temperature and stirred overnight. Hydrochloric acid (2 mol/L) was added into the mixture to adjust the solution to neutral. A white crude product was obtained after filtration, then stirred with n-heptane, so that 86.52 g of intermediate M2-2 were obtained as a white solid (with a yield of 70%).

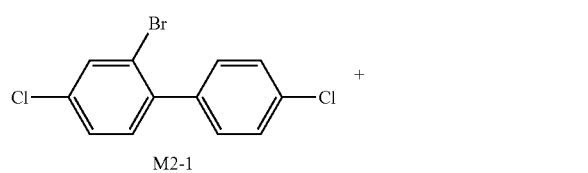

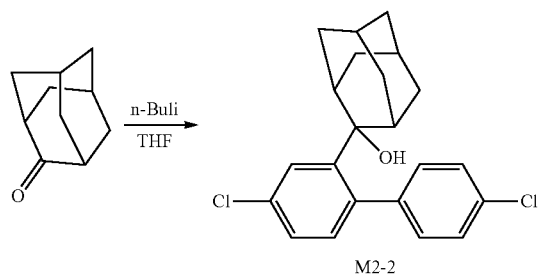

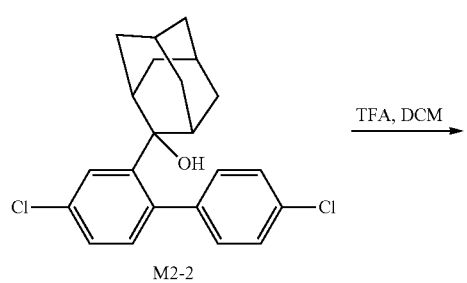

2.3) Synthesis of Intermediate M2

86.52 g (i.e. 231.77 mmol) of intermediate M2-2, 79.28 g (i.e. 695.31 mmol) of trifluoroacetic acid (TFA) and 900 mL of dichloromethane (DCM) were added into a three-necked flask and the mixture was stirred under the nitrogen atmosphere for 2 hours; then a sodium hydroxide aqueous solution (1M aqueous solution) was added, the reaction solution was adjusted to neutral. The separated organic phase was dried with anhydrous magnesium sulfate and filtered to obtain filtrate, the filtrate was concentrated in vacuo to obtain a crude product; the obtained crude product was purified by silica gel column chromatography and eluted with a mixture of dichloromethane and n-heptane (v/v=½), and 70.82 g of intermediate M2 was obtained as a white solid (yield: 86%).

3) Synthesis of Compound 15

1.0 g (i.e. 3.60 mmol) of intermediate M1, 1.29 g (1.80 mmol) of intermediate M2, 0.11 g (i.e. 0.09 mmol) of tetrakis(triphenylphosphine)palladium (Pd(pph$_3$)$_4$), 0.50 g (i.e. 3.61 mmol) of potassium carbonate, 0.02 g (i.e. 0.09 mmol) of tetrabutyl ammonium chloride (TBAC), 8 mL of toluene (PhMe), 4 mL of ethanol (EtOH) and 2 mL of deionized water were added into a three-necked flask, the mixture was heated to 78° C. under the nitrogen atmosphere and stirred for 8 hours. The reaction solution above was cooled to room temperature, 50 mL of methylbenzene was added for extraction. The combined organic phases were dried over anhydrous MgSO$_4$ and filtered. The filtrate was concentrated in vacuo to obtain a crude product. The obtained crude product was purified by silica gel column chromatography and eluted with n-heptane, then purified by recrystallization using a mixture of dichloromethane and ethyl acetate to obtain 1.01 g of compound 15 were obtained (yield 75%, LC-MS(ESI,pos.ion): m/z=749.3 ([M+H]$^+$)).

$^1$HNMR (400 MHz, CD$_2$Cl$_2$):9.75 (s, 21H), 8.89 (d, 2H), 8.83 (d, 8H), 8.13 (d, 2H), 7.68-7.62 (m, 12H), 3.27 (d, 4H), 2.50 (s, 2H), 2.18 (s, 2H), 2.04 (d, 4H), 1.81 (s, 2H).

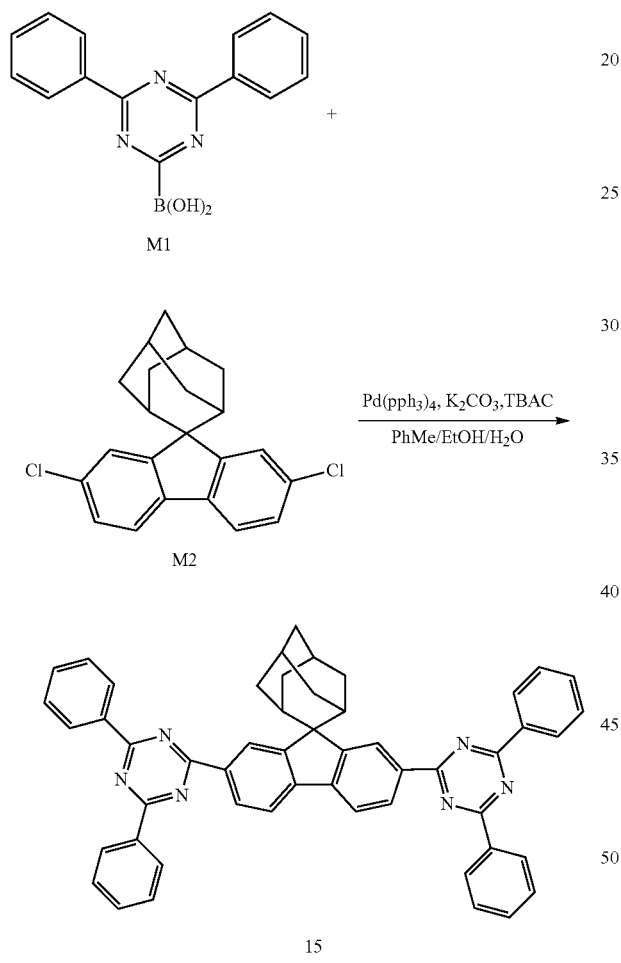

Preparation Example 2: Synthesis of Compound 17

The compound 17 was synthesized by the same method as in Preparation Example 1 (yield 76%, LC-MS (ESI, pos.ion): m/z=749.3 ([M+H]$^+$)), the difference was just that the raw materials 1 and 2 as follows were used respectively to replace 2-bromo-4-chloro-1-iodobenzene and 4-chlorophenylboronic acid used to prepare the intermediate M2 in Preparation Embodiment 1, thus the intermediate M3-1, intermediate M3-2 and intermediate M3 as follows were obtained, as shown in Table 1.

TABLE 1

| | |
|---|---|
| Raw material 1 | 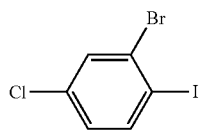 |
| Raw material 2 | 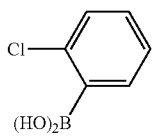 |
| Intermediate M3-1 | 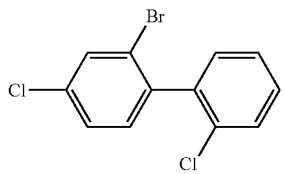 [SMILES: Clc1ccc(-c2ccccc2Cl)c(Br)c1] |
| Intermediate M3-2 | 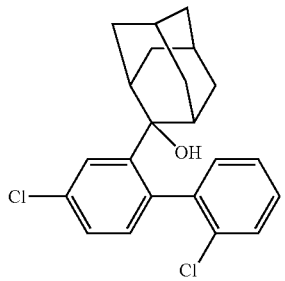 [SMILES: OC1(c2cc(Cl)ccc2-c2ccccc2Cl)C2CC3CC(C2)CC1C3] |
| Intermediate M3 (yield 85%) | 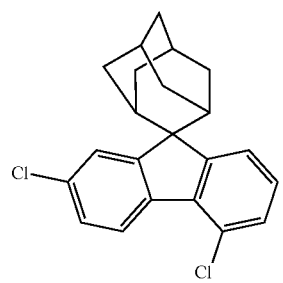 [SMILES: Clc1ccc2c(c1)C1(c3cccc(Cl)c3-2)C2CC3CC(C2)CC1C3] |

Then, the compound 17 prepared through the same coupling reaction as the last step of Preparation Example 1 is as follows:

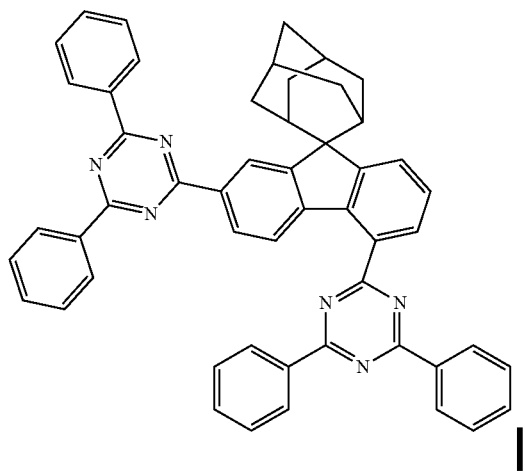

17

Preparation Example 3: Synthesis of Compound 19

The compound 19 was synthesized by the same method as in Preparation Example 1 (yield 74%, LC-MS (ESI, pos.ion): m/z=749.3 ([M+H]⁺)), the difference was just that the raw materials 3 and 4 as follows were used respectively to replace 2-bromo-4-chloro-1-iodobenzene and 4-chlorophenylboronic acid used to prepare the intermediate M2 in Preparation Example 1, thus the intermediate 4-1, intermediate 4-2 and intermediate 4 as follows were obtained, as shown in Table 2.

TABLE 2

| Raw material 3 | 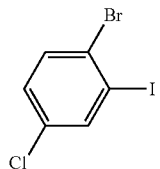 |
|---|---|
| Raw material 4 | 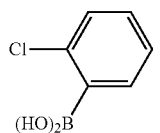 |
| Intermediate 4-1 | 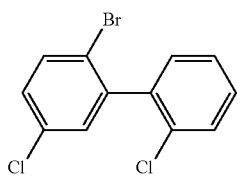 [SMILES: Clc1ccc(Br)c(-c2ccccc2Cl)c1] |
| Intermediate 4-2 | 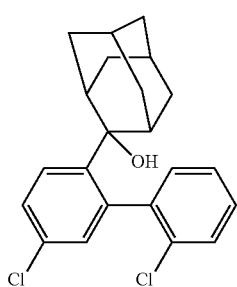 [SMILES: OC1(c2ccc(Cl)cc2-c2ccccc2Cl)C2CC3CC(C2)CC1C3] |

TABLE 2-continued

| Intermediate 4 (yield 84%) | 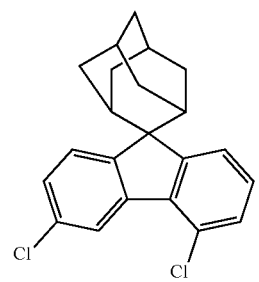 [SMILES: Clc1ccc2c(c1)-c1c(Cl)cccc1C21C2CC3CC(C2)CC1C3] |
|---|---|

Then, the compound 19 prepared through the same coupling reaction as the last step of Preparation Example 1 is as follows:

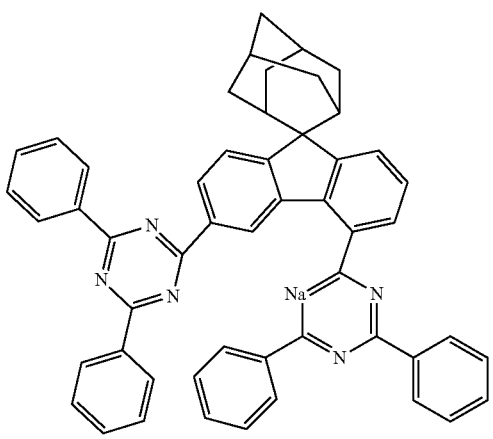

19

Preparation Example 4: Synthesis of Compound 20

The compound 20 (yield 75%, LC-MS (ESI, pos.ion): m/z=749.4 ([M+H]⁺) was synthesized by the same method as in Preparation Example 1, the difference was just that the raw materials 5 and 6 as follows were used respectively to replace 2-bromo-4-chloro-1-iodobenzene and 4-chlorophenylboronic acid used to prepare the intermediate 2 in Preparation Example 1, thus the intermediate M5-1, intermediate M5-2 and intermediate M5 as follows were obtained, as shown in Table 3.

TABLE 3

| Raw material 5 | 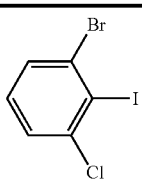 |
|---|---|
| Raw material 6 | 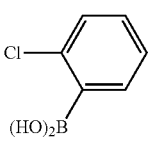 |

TABLE 3-continued

Intermediate M5-1

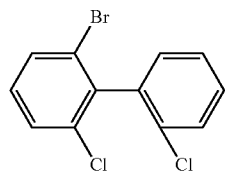 [SMILES: Clc1ccccc1-c1c(Cl)cccc1Br]

Intermediate M5-2

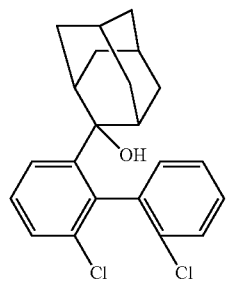 [SMILES: OC1(c2cccc(Cl)c2-c2ccccc2Cl)C2CC3CC(C2)CC1C3]

Intermediate M5
(yield 86%)

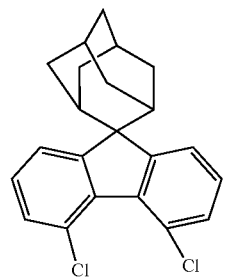 [SMILES: Clc1cccc2c1-c1c(Cl)cccc1C21C2CC3CC(C2)CC1C3]

The compound 20 prepare by the above method is as follows:

20

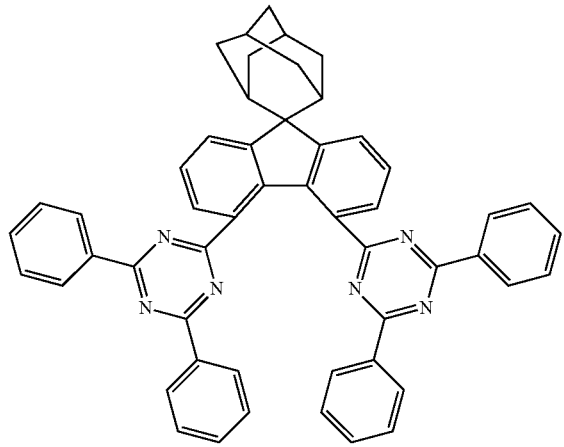

Preparation Example 5: Synthesis of Compound 21

The compound 21 (1.08 g, yield 73%, LC-MS (ESI, pos.ion): m/z=825.3 ([M+H]$^+$)) was prepared by the same method as in Preparation Example 1, the difference was just that the intermediate M2 (1.29 g, i.e. 1.80 mmol) used in Preparation Example 1 was replaced by a intermediate M2-A (0.78 g, i.e. 1.80 mmol) prepared as follows:

10 g (i.e. 28.14 mmol) of intermediate M2, 4.40 g (i.e. 28.14 mmol) of 4-chlorophenylboronic acid, 1.63 g (i.e. 1.41 mmol) of tetrakis(triphenylphosphine)palladium, 7.78 g (i.e. 56.29 mmol) of potassium carbonate, 0.32 g (i.e. 1.41 mmol) of tetrabutyl ammonium chloride, 80 mL of toluene (PhMe), 40 mL of ethanol and 20 mL of deionized water were added into a three-necked flask, the mixture was heated to 78° C. under the nitrogen atmosphere and stirred for 6 hours. The reaction solution above was cooled to room temperature, 100 mL of methylbenzene was added for extraction. The combined organic phases were dried over anhydrous MgSO$_4$ and filtered. The filtrate was concentrated in vacuo to obtain a crude product. The obtained crude product was purified by silica gel column chromatography and eluted with n-heptane, then purified by recrystallization using a mixture of dichloromethane and ethyl acetate, and 8.86 g of intermediate M2-A were obtained as a white solid (yield 73%).

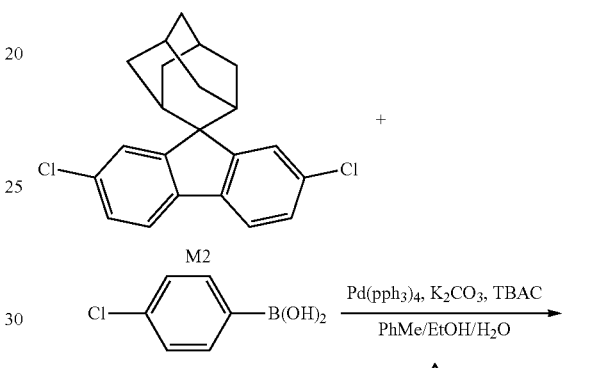

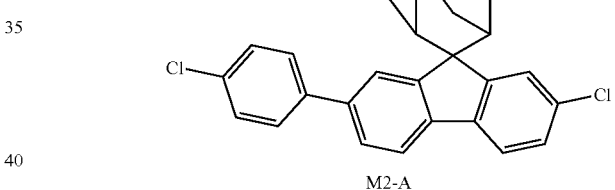

Then, the compound 21 prepared through the same coupling reaction as the last step of Preparation Example 1 is as follows:

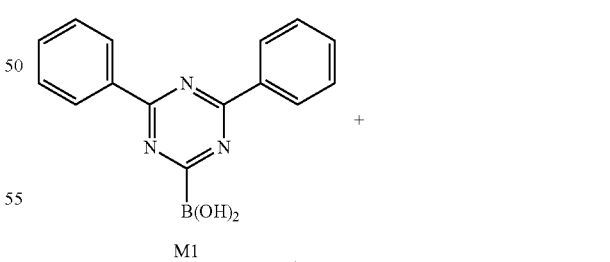

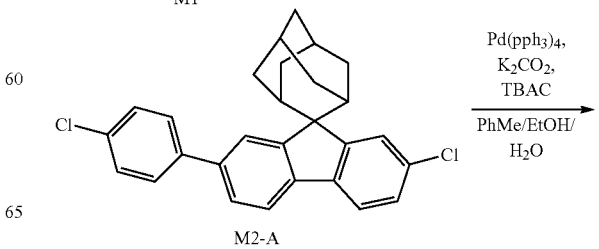

-continued

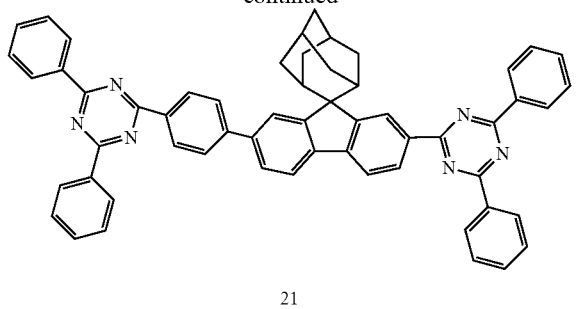

21

Preparation Example 6: Synthesis of Compound 23

The compound 23 (yield 72%, LC-MS (ESI, pos.ion): m/z=825.3 ([M+H]$^+$)) was prepared by the same method as in Preparation Example 5, the difference was just that the intermediate M2-A in Preparation Example 5 was replaced by the following intermediate M3-A which can be prepared with reference to M2-A.

M3-A

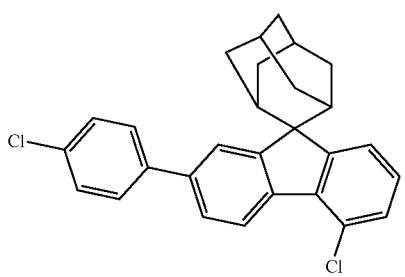

Then, the compound 23 prepared through the same coupling reaction as the last step of Preparation Example 1 is as follows:

23

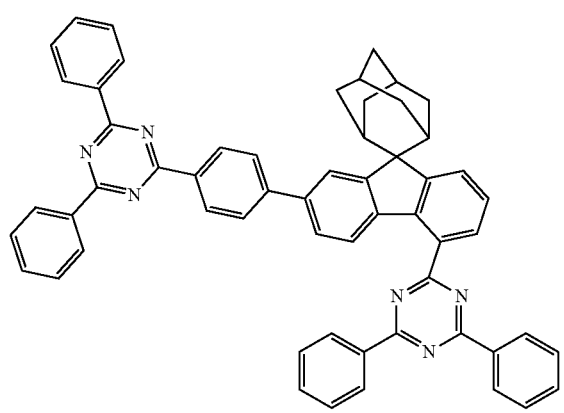

Preparation Example 7: Synthesis of Compound 26

The compound 26 (yield 71%, LC-MS (ESI, pos.ion): m/z=825.4 ([M+H]$^+$)) was prepared by the same method as in Preparation Example 5, the difference was just that the intermediate M2-A in Preparation Example 5 was replaced by the following intermediate M4-A which can be prepared with reference to M2-A.

M4-A

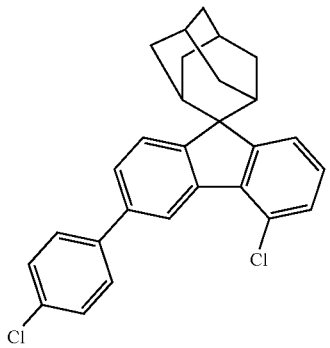

Then, the compound 26 prepared through the same coupling reaction as the last step of Preparation Example 1 is as follows:

26

Preparation Example 8: Synthesis of Compound 29

The compound 29 (yield 72%, LC-MS (ESI, pos.ion): m/z=825.4 ([M+H]$^+$)) was prepared by the same method as in Preparation Example 5, the difference was just that the intermediate M2-A in Preparation Example 5 was replaced by the following intermediate M5-A which can be prepared with reference to M2-A.

M5-A

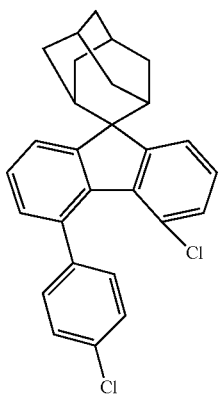

Then, the compound 29 prepared through the same coupling reaction as the last step of Preparation Example 1 is as follows:

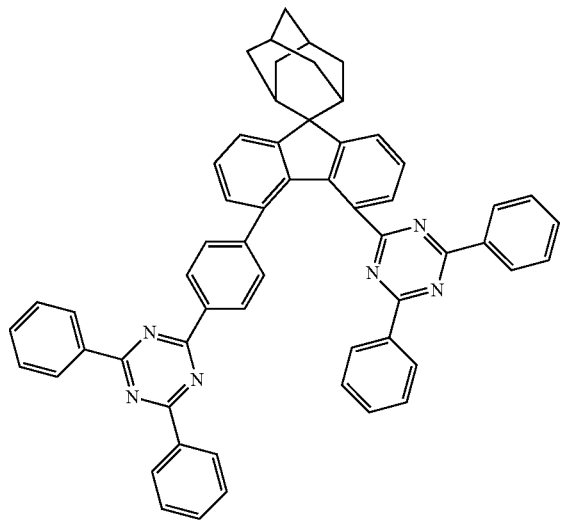

29

Preparation Example 9: Synthesis of Compound 34

The compound 34 (1.09 g, yield 74%, LC-MS (ESI, pos.ion): m/z=825.3 ([M+H]$^+$)) was prepared by the same method as in Preparation Example 5, the difference was just that the intermediate M2-A (1.29 g, i.e. 1.80 mmol) used in Preparation Example 5 was replaced by the intermediate M2-B (1.29 g, i.e. 1.80 Mmol), the synthesis and purification processes of the intermediate M2-B were consistent with or roughly the same as those of the intermediate M2-A, and the difference was just that 4-chlorophenylboronic acid (4.40 g, i.e. 28.14 mmol) was replaced by 3-chlorophenylboronic acid (4.40 g, i.e. 28.14 mmol) to obtain the intermediate M2-B (8.61 g, yield 71%).

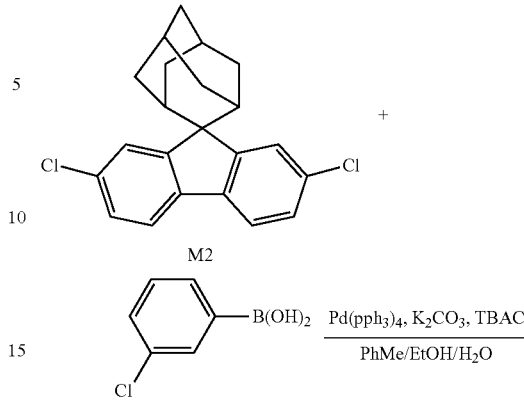

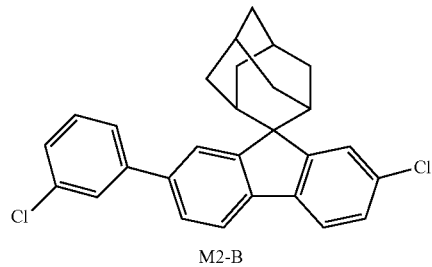

Then, the compound 34 prepared through the same coupling reaction as the last step of Preparation Example 1 is as follows:

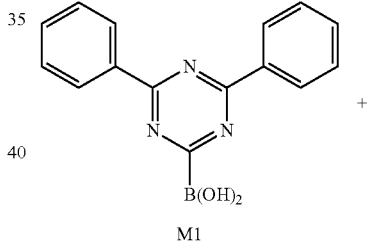

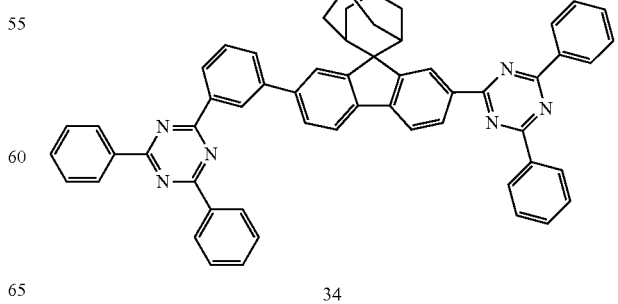

34

Preparation Example 10: Preparation of Compound 36

The compound 36 (yield 70%, LC-MS (ESI, pos.ion): m/z=825.3 ([M+H]⁺)) was prepared by the same method as in Preparation Example 9, the difference was just that the intermediate M2-B in Preparation Example 9 was replaced by the following intermediate M3-B.

M3-B

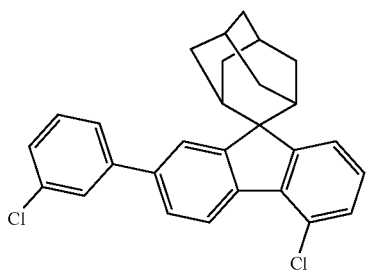

Then, the compound 36 prepared through the same coupling reaction as the last step of Preparation Example 1 is as follows:

36

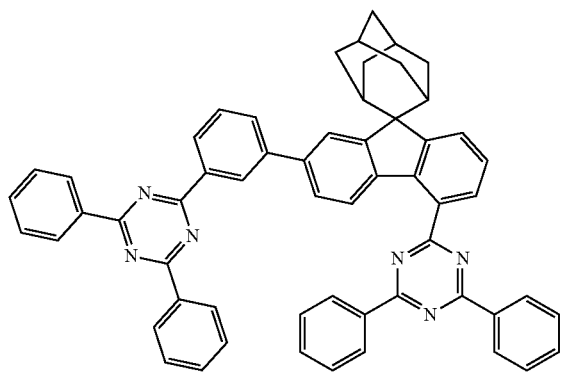

Preparation Example 11: Preparation of Compound 39

The compound 39 (yield 72%, LC-MS (ESI, pos.ion): m/z=825.4 ([M+H]⁺)) was prepared by the same method as in Preparation Example 9, the difference was just that the intermediate M2-B in Preparation Example 9 was replaced by the following intermediate M4-B. Intermediate M4-B may be prepared with reference to M2-A.

M4-B

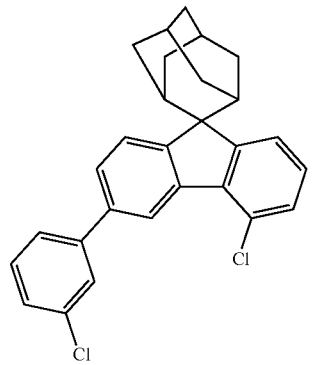

Then, the compound 39 prepared through the same coupling reaction as the last step of Preparation Example 1 is as follows:

39

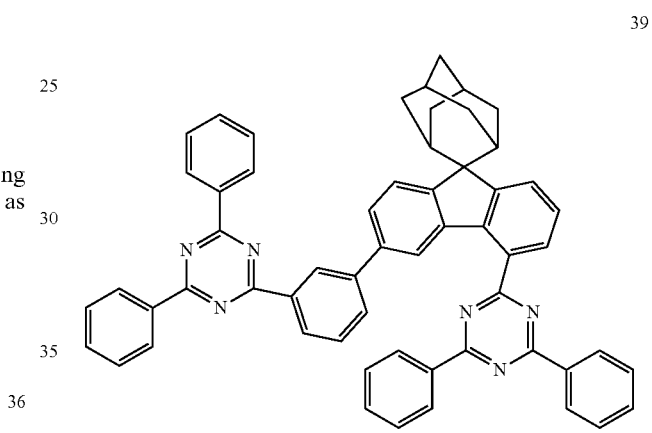

Preparation Example 12: Preparation of Compound 42

The compound 42 (yield 73%, LC-MS (ESI, pos.ion): m/z=825.4 ([M+H]⁺)) was prepared by the same method as in Preparation Example 9, the difference was just that the intermediate M2-B in Preparation Example 9 was replaced by the following intermediate M5-B. Intermediate M5-B may be prepared with reference to M2-A.

M5-B

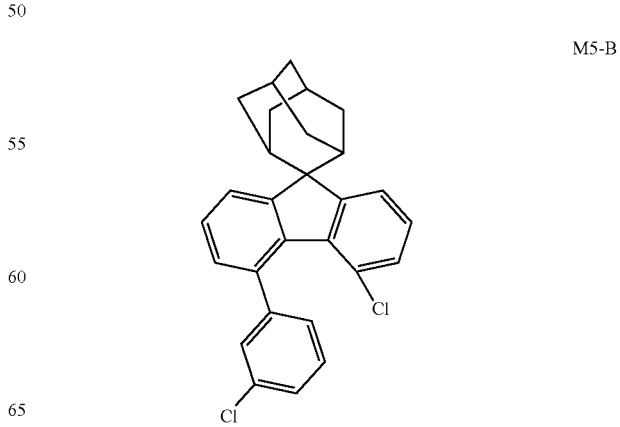

Then, the compound 42 prepared through the same coupling reaction as the last step of Preparation Example 1 is as follows:

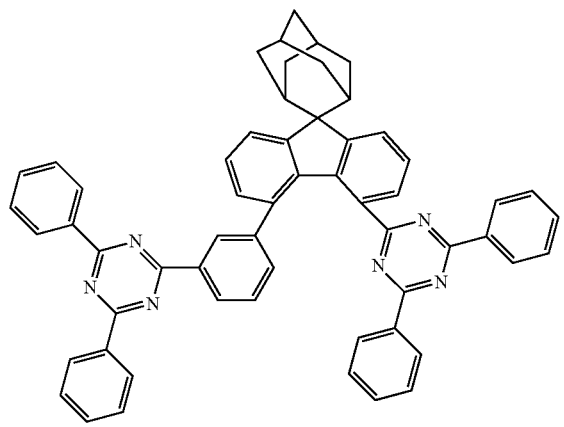

42

Preparation Example 13: Synthesis of Compound 43

The compound 43 (1.18 g, yield 73%, LC-MS (ESI, pos.ion): m/z=901.3 ([M+H]$^+$)) was prepared by the same method as in Preparation Example 5, the difference was just that the intermediate M2-A (1.29 g, i.e. 1.80 mmol) used in Preparation Example 5 was replaced by the intermediate M2-C (1.29 g, i.e. 1.80 mmol), the synthesis and purification processes of the intermediate M2-C were consistent with or roughly the same as those of the intermediate M2-A, and the difference was just that the feeding quantity of 4-chlorophenylboronic acid was increased from 4.40 g (i.e. 28.14 mmol) to 8.80 g (i.e. 56.29 mmol), so that the intermediate M2-C was obtained (9.71 g, yield 68%).

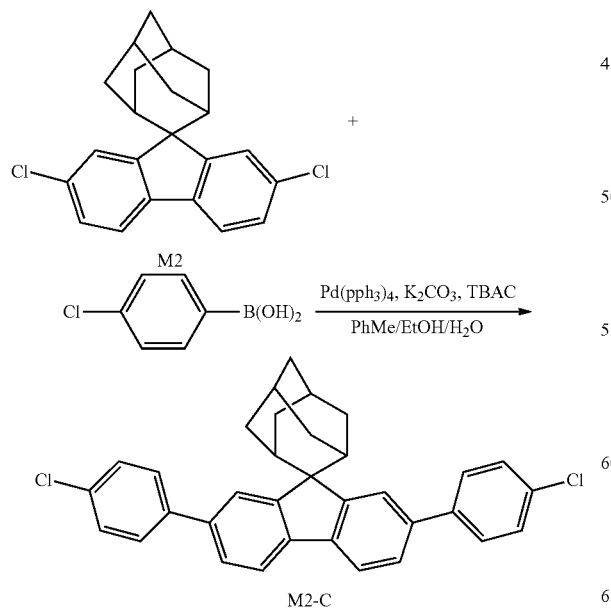

Then, the compound 43 prepared through the same coupling reaction as the last step of Preparation Example 1 is as follows:

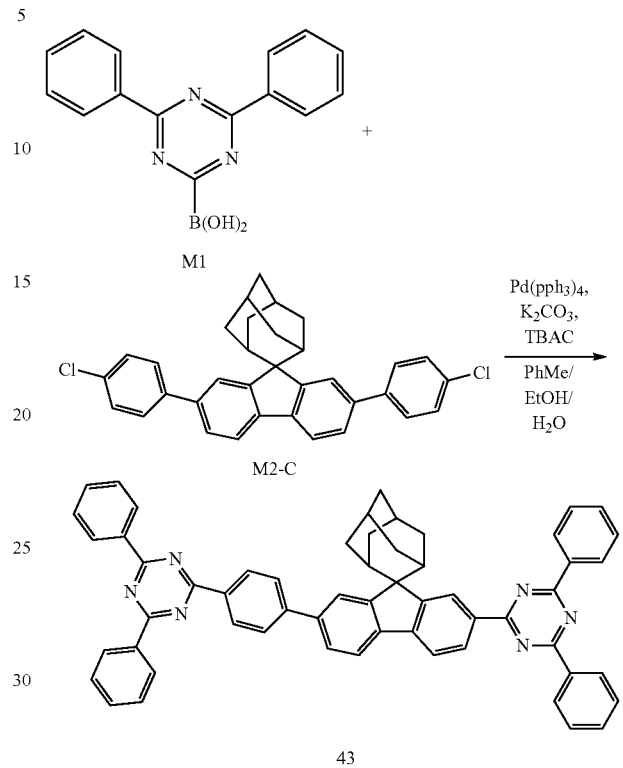

Preparation Example 14: Synthesis of Compound 47

The compound 47 (yield 70%, LC-MS (ESI, pos.ion): m/z=901.4 ([M+H]$^+$)) was prepared by the same method as in Preparation Example 13, the difference was just that the intermediate M2-C in Preparation Example 13 was replaced by the following intermediate M3-C which can be prepared with reference to M2-C.

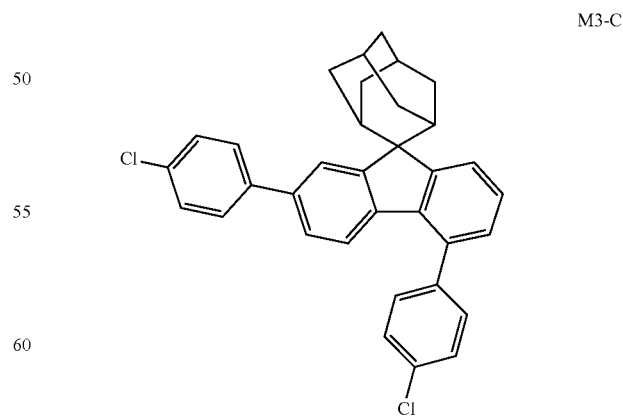

Then, the compound 47 prepared through the same coupling reaction as the last step of Preparation Example 1 is as follows:

47

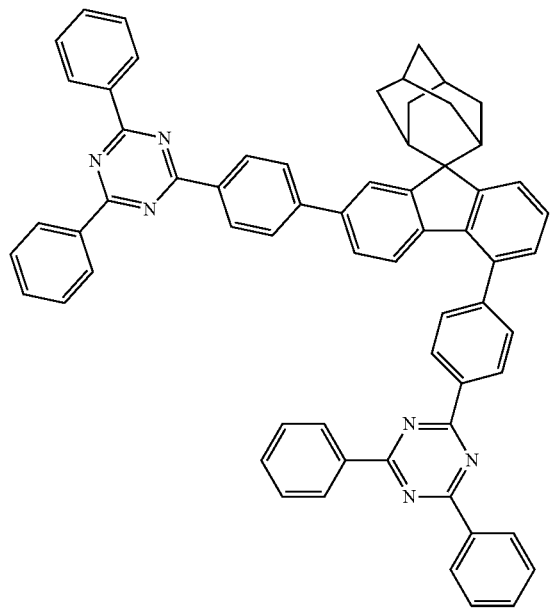

51

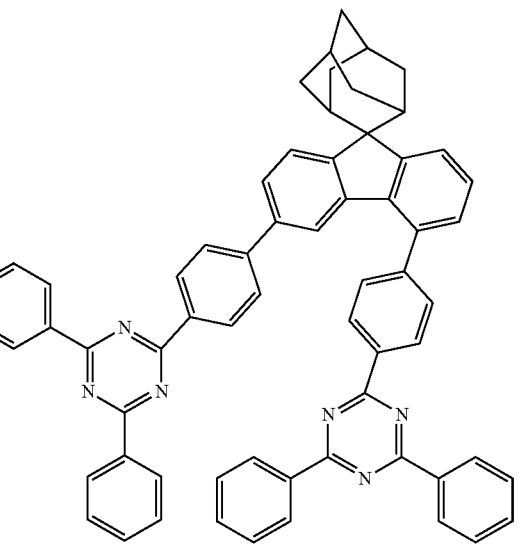

Preparation Example 15: Synthesis of Compound 51

The compound 51 (yield 71%, LC-MS (ESI, pos.ion): m/z=901.3 ([M+H]$^+$)) was prepared by the same method as in Preparation Example 13, the difference was just that the intermediate M2-C in Preparation Example 13 was replaced by the following intermediate M4-C which can be prepared with reference to M2-C.

Preparation Example 16: Synthesis of Compound 53

The compound 53 (yield 70%, LC-MS (ESI, pos.ion): m/z=901.4 ([M+H]$^+$)) was prepared by the same method as in Preparation Example 13, the difference was just that the intermediate M2-C in Preparation Example 13 was replaced by the following intermediate M5-C which can be prepared with reference to M2-C.

M4-C

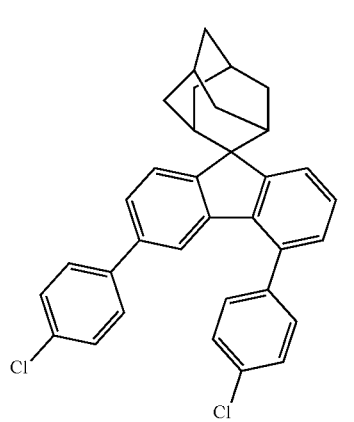

M5-C

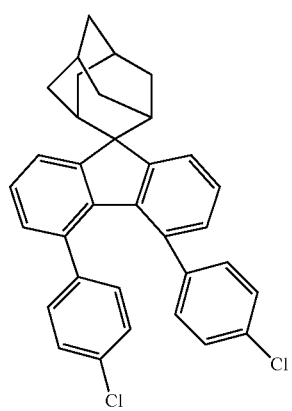

Then, the compound 51 prepared through the same coupling reaction as the last step of Preparation Example 1 is as follows:

Then, the compound 53 prepared through the same coupling reaction as the last step of Preparation Example 1 is as follows:

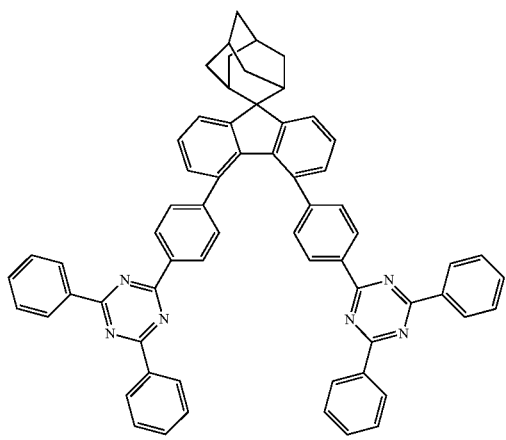

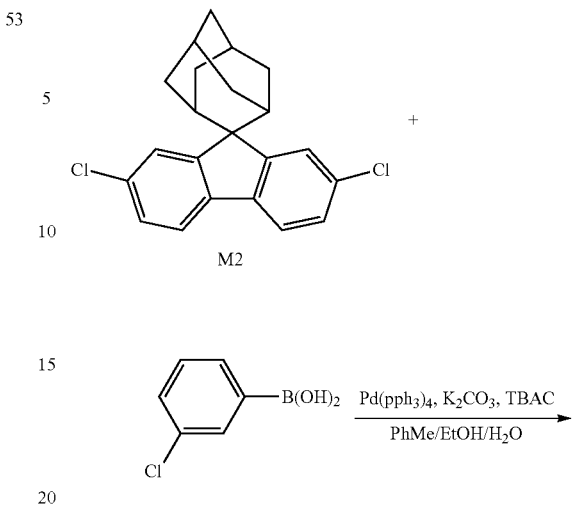

Preparation Example 17: Synthesis of Compound 60

The compound 60 (1.14 g, yield 71%, LC-MS (ESI, pos.ion): m/z=901.3 ([M+H]$^+$)) was prepared by the same method as in Preparation Example 1, the difference was just that the intermediate M2 (1.29 g, i.e. 1.80 mmol) used in Preparation Example 1 was replaced by the intermediate M2-D (0.91 g, i.e. 1.80 mmol).

The synthesis and purification processes of the intermediate M2-D were consistent with those of the intermediate M2-B in Preparation Example 9, the difference was just that the feeding quantity of 3-chlorophenylboronic acid was increased from 4.40 g (i.e. 28.14 Mmol) to 8.80 g (i.e. 56.29 Mmol) to obtain the intermediate M2-D (9.99 g, yield 70%).

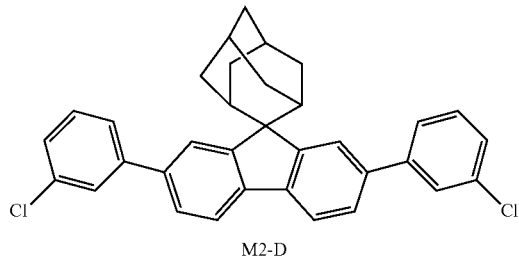

Then, the compound 60 prepared through the same coupling reaction as the last step of Preparation Example 1 is as follows:

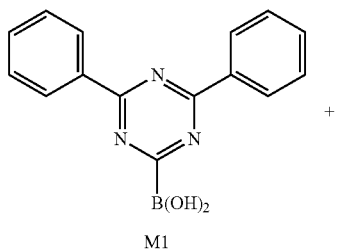

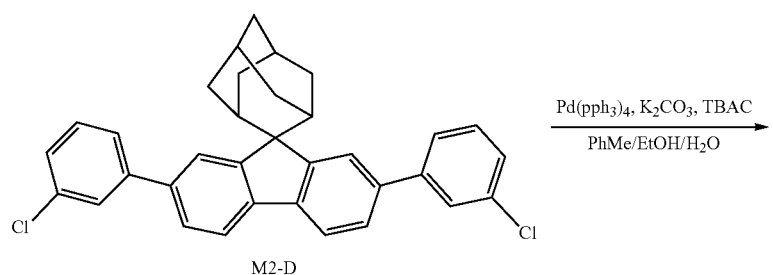

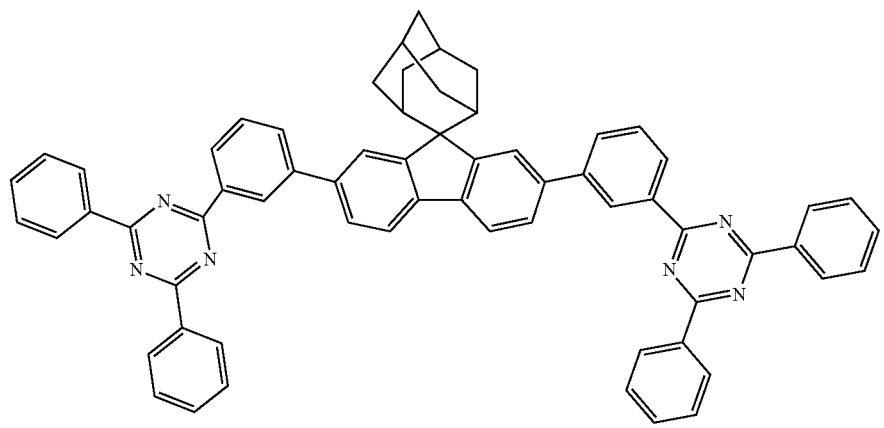

60

Preparation Example 18: Synthesis of Compound 58

The compound 58 (yield 72%, LC-MS (ESI, pos.ion): m/z=901.4 ([M+H]$^+$)) was prepared by the same method as in Preparation Example 17, the difference was just that the intermediate M2-D in Preparation Example 17 was replaced by the following intermediate M3-D which can be prepared with reference to M2-D.

M3-D

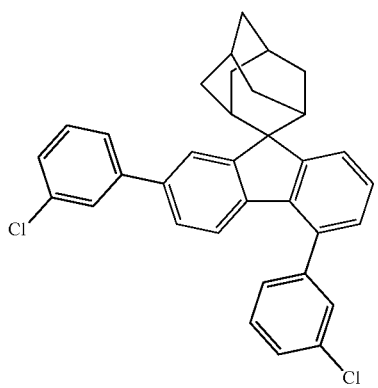

Then, the compound 58 prepared through the same coupling reaction as the last step of Preparation Example 1 is as follows:

58

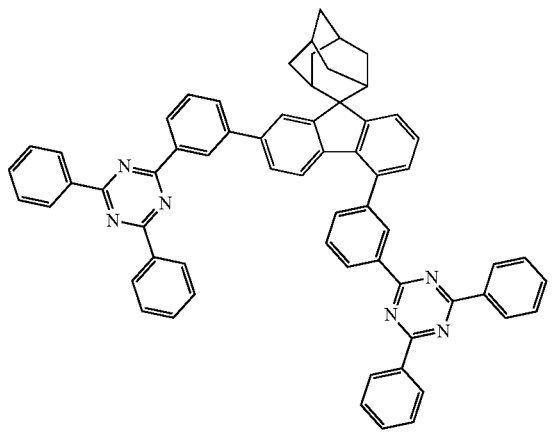

$^1$HNMR (400 MHz, CD$_2$Cl$_2$):9.23 (s, 1H), 9.04 (s, 1H), 8.89 (d, 8H), 8.58 (d, 1H), 8.54 (d, 1H), 7.84(d,1H), 7.75-7.71 (m, 2H), 7.76-7.53 (m, 16H), 7.44-7.36 (m, 2H), 7.20 (d,1H), 3.05 (d, 2H), 2.91 (d, 2H), 2.37 (d, 2H), 2.04 (s, 2H), 1.85-1.95 (m, 4H), 1.70 (s, 2H).

Preparation Example 19: Synthesis of Compound 56

The compound 56 (yield 70%, LC-MS (ESI, pos.ion): m/z=901.3 ([M+H]$^+$)) was prepared by the same method as in Preparation Example 17, the difference was just that the intermediate M2-D in Preparation Example 17 was replaced by the following intermediate M4-D which can be prepared with reference to M2-D.

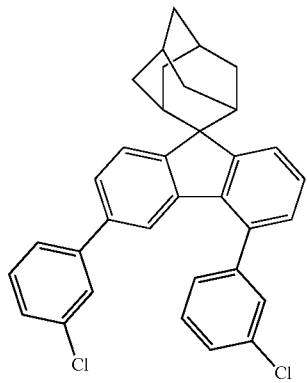

M4-D

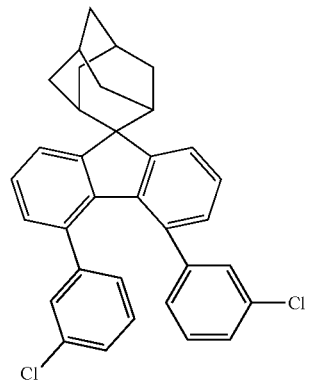

M5-D

Then, the compound 55 prepared through the same coupling reaction as the last step of Preparation Example 1 is as follows:

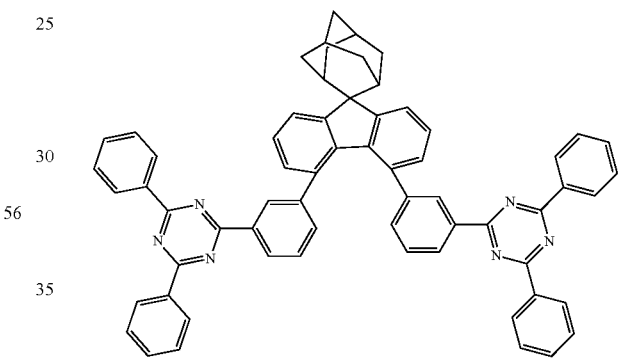

Compound 55

Then, the compound 56 prepared through the same coupling reaction as the last step of Preparation Example 1 is as follows:

56

[Structure of compound 56]

Preparation Example 20: Synthesis of Compound 55

The compound 55 (yield 71%, LC-MS (ESI, pos.ion): m/z=901.3 ([M+H]$^+$)) was prepared by the same method as in Preparation Example 17, the difference was just that the intermediate M2-D in Preparation Example 17 was replaced by the following intermediate M5-D which can be prepared with reference to M2-D.

Preparation Example 21: Synthesis of Compound 1

1.56 g (i.e. 3.60 mmol) of intermediate M6, 2.0 g of intermediate M1 (i.e. 7.22 mmol), 0.21 g (i.e. 0.18 mmol) of tetrakis(triphenylphosphine)palladium, 0.99 g (i.e. 7.22 mmol) of potassium carbonate, 0.04 g (i.e. 0.18 mmol) of tetrabutyl ammonium chloride, 8 mL of toluene, 4 mL of ethanol and 2 mL of deionized water were added into a three-necked flask, the mixture was heated to 78° C. under nitrogen atmosphere and stirred for 3 hours. The reaction solution was cooled to room temperature, 50 mL of methylbenzene was added for extraction. The combined organic phases were dried with anhydrous magnesium sulfate and filtered. The filtrate was concentrated in vacuo to obtain a crude product. The obtained crude product was purified by silica gel column chromatography and eluted with n-heptane, then purified by recrystallization using a mixture of a dichloromethane and ethyl acetate to obtain 2.16 g of compound 1 (yield 73%, LC-MS (ESI, pos.ion): m/z=825.4 ([M+H]$^+$)).

1) Synthesis of Intermediate M6

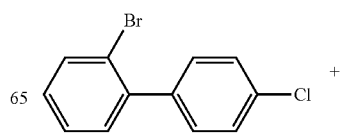

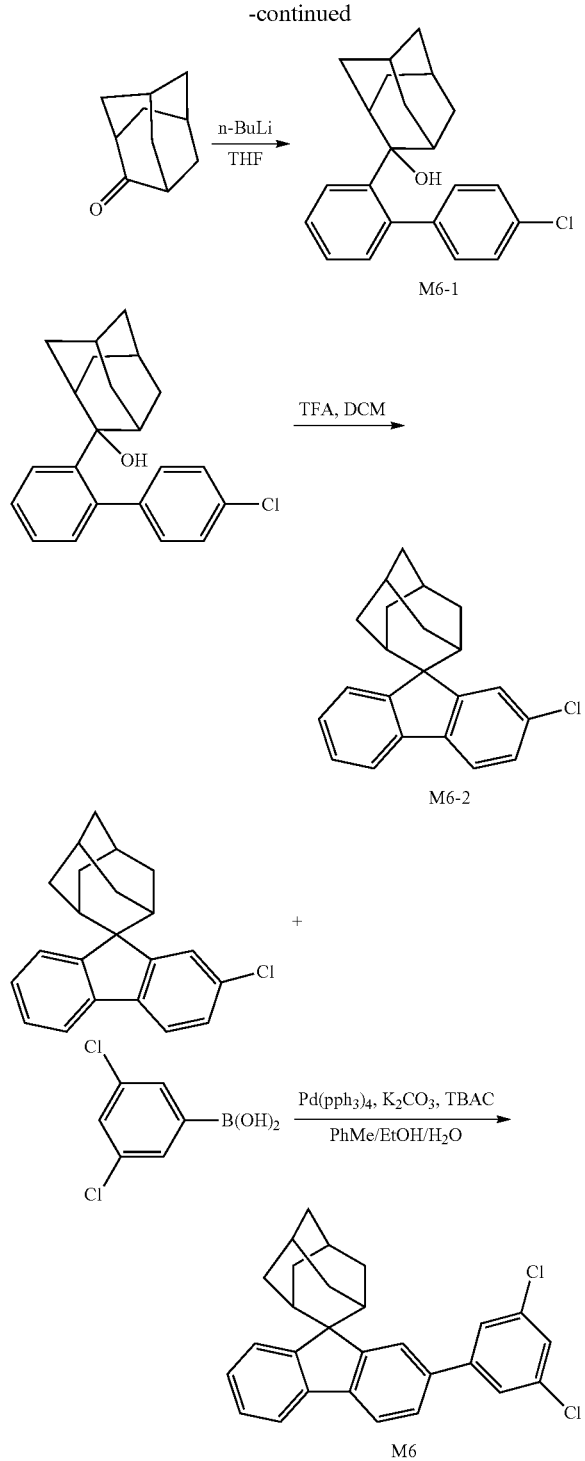

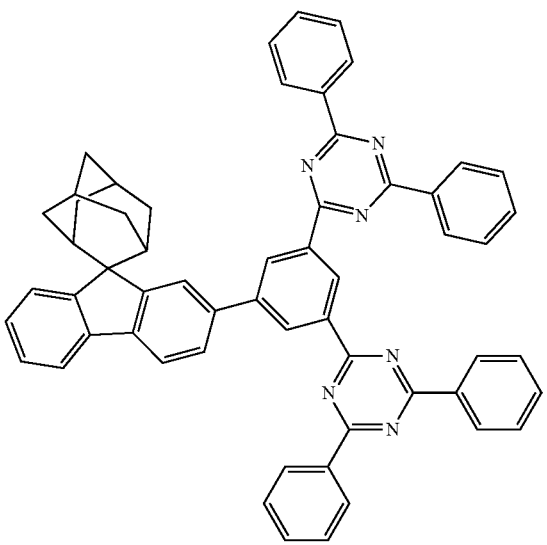

Compound 1 crude product was obtained after filtration. The crude product was stirred with n-heptane to obtain 12.76 g of intermediate M6-1 (yield 71%).

1.2) Synthesis of Intermediate M6-2

12.76 g (i.e. 37.65 mmol) of intermediate 6-1, 12.87 g (i.e. 112.95 mmol) of trifluoroacetic acid and 130 mL of dichloromethane were added into a round-bottom flask and stirred under nitrogen atmosphere for 2 hours. A sodium hydroxide aqueous solution was added until the reaction solution was neutral, the solution was extracted with 100 mL of dichloromethane. The organic phase was dried with anhydrous magnesium sulfate and filtered to obtain filtrate, the filtrate was concentrated in vacuo to obtain a crude product. The crude product was purified by silica gel column chromatography and eluted with a mixture of dichloromethane and n-heptane (v/v=⅓) to obtain 10.02 g of intermediate M6-2 (yield 83%).

1.3) Synthesis of Intermediate M6

10.02 g (i.e. 31.22 mmol) of intermediate 6-2, 5.95 g (i.e. 31.22 mmol) of 3,5-dichlorophenylboronic acid, 1.80 g (i.e. 1.56 mmol) of tetrakis(triphenylphosphine)palladium, 8.63 g (i.e. 62.44 mmol) of potassium carbonate, 0.36 g (i.e. 1.56 mmol) of tetrabutyl ammonium chloride, 80 mL of toluene, 40 mL of ethanol and 20 mL of deionized water were added into a three-necked flask, the mixture was heated to 78° C. under the nitrogen atmosphere and stirred for 5 hours. The reaction solution above was cooled to room temperature, 100 mL of methylbenzene was added for extraction.

The combined organic phases were dried with anhydrous magnesium sulfate and filtered. The filtrate was concentrated in vacuo to obtain a crude product; the obtained crude product was purified by silica gel column chromatography and eluted with n-heptane, then purified by recrystallization using a mixture of dichloromethane and ethyl acetate (v/v=⅕) to obtain 10.10 g of intermediate M6 (yield 75%). Then, the compound 1 prepared through the same coupling reaction as the last step of Preparation Example 1 is as follows:

1.1) Synthesis of Intermediate M6-1

20 g (i.e. 74.73 mmol) of 2-bromo-4-chlorobiphenyl were added into a three-necked flask containing 160 mL of THF, 5.74 g (i.e. 89.68 mmol) of n-butyllithium was added dropwise at −80° C. After addition, the reaction mixture was stirred at −80° C. for another 1 h, then 8.98 g (i.e. 59.79 mmol) of adamantanone were added dropwise, the resulted mixture was stirred for 1 h, and then moved to room temperature and stirred overnight. Hydrochloric acid (2 mol/L) was added, pH was adjusted to neutral, then a white $^1$HNMR (400 MHz, $CD_2Cl_2$):9.95 (s,1H), 9.31 (s, 2H), 8.79 (d, 8H), 8.13(s, 1H),7.85 (d,1H), 7.73 (d,1H),7.66-7.56

(m, 13H), 7.51-7.45 (m, 2H), 7.33-7.30(t,1H), 3.13 (d, 2H), 3.01 (d, 2H), 2.47 (d, 2H), 2.19 (s, 2H), 1.90-2.00 (m, 4H), 1.75 (s, 2H).

Preparation Example 22: Synthesis of Compound 2

The compound 2 (yield 70%, LC-MS (ESI, pos.ion): m/z–825.3 ([M+H]⁺)) was prepared by the same method as in Preparation Example 21, the difference was just that the intermediate M6 in Preparation Example 21 was replaced by the intermediate M7 as follows, wherein the synthesis and purification processes of the intermediate M7 were the same as those of the intermediate M6, and the difference was just that 2-bromo-4-chlorobiphenyl was replaced by 2-bromo-3-chlorobiphenyl to obtain the intermediate M7 (yield 72%).

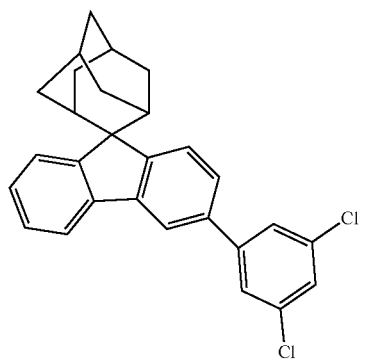

M7

Then, the compound 2 prepared through the same coupling reaction as the last step of Preparation Example 1 is as follows:

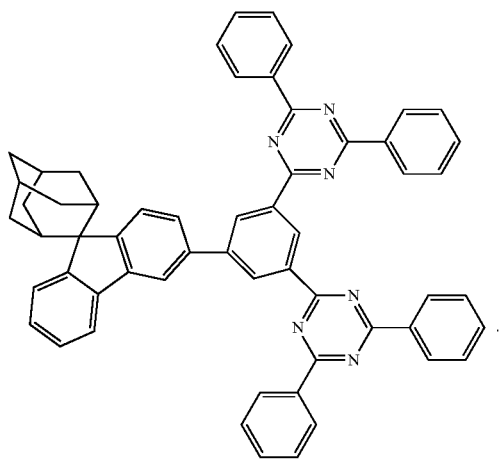

2

Preparation Example 23: Synthesis of Compound 3

The compound 3 (yield 71%, LC-MS (ESI, pos.ion): m/z=825.4 ([M+H]⁺)) was prepared by the same method as in Preparation Example 21, the difference was just that the intermediate M6 in Preparation Example 21 was replaced by the intermediate M8 as follows, wherein the synthesis and purification processes of the intermediate M8 were the same as those of the intermediate M6, and the difference was just that 2-bromo-4-chlorobiphenyl and 3,5-dichlorophenylboronic acid were replaced by 2-bromo-2-chlorobiphenyl and 3-chlorophenyl boronic acid respectively to obtain the intermediate M8 (yield 74%).

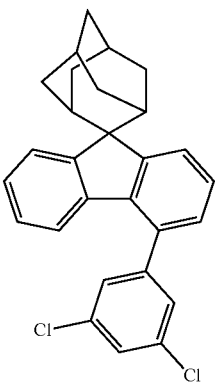

M8

Then, the compound 3 prepared through the same coupling reaction as the last step of Preparation Example 1 is as follows:

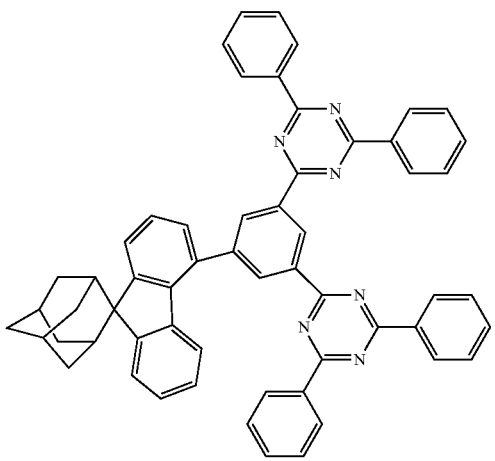

3

Preparation Example 24: Synthesis of Compound 14

The compound 14 (yield 73%, LC-MS (ESI, pos.ion): m/z=901.3 ([M+H]⁺)) was prepared by the same method as in Preparation Example 21, the difference was just that the intermediate M6 in Preparation Example 21 was replaced by the intermediate M9 as follows, wherein the synthesis and purification processes of the intermediate M9 were the same as those of the intermediate M6, and the difference was just that 2-bromo-4-chlorobiphenyl and 3,5-dichlorophenylboronic acid were replaced by 2-bromo-3-chlorobiphenyl and 3,4-dichlorobiphenyl-4'-boric acid respectively to obtain the intermediate M9 (yield 70%).

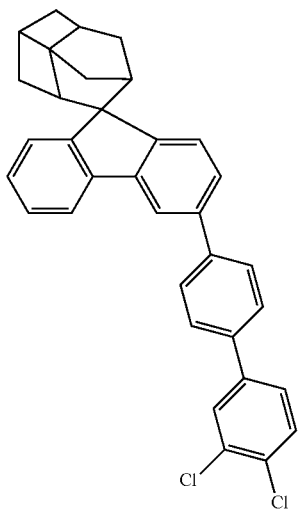

M9

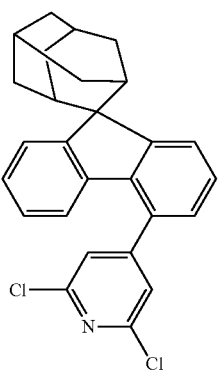

M10

Then, the compound 7 prepared through the same coupling reaction as the last step of Preparation Example 1 is as follows:

Then, the compound 14 prepared through the same coupling reaction as the last step of Preparation Example 1 is as follows:

Compound 7

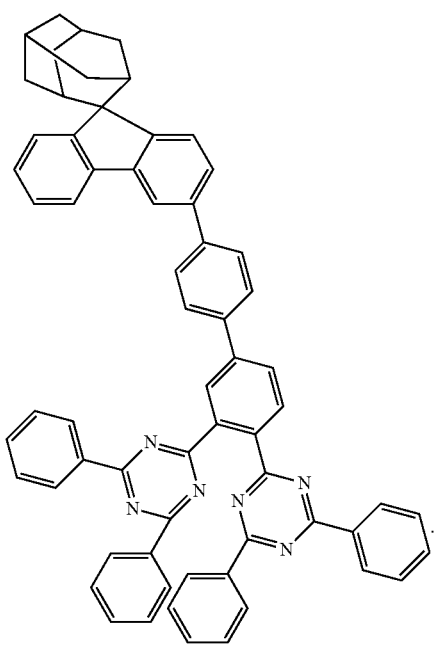

14

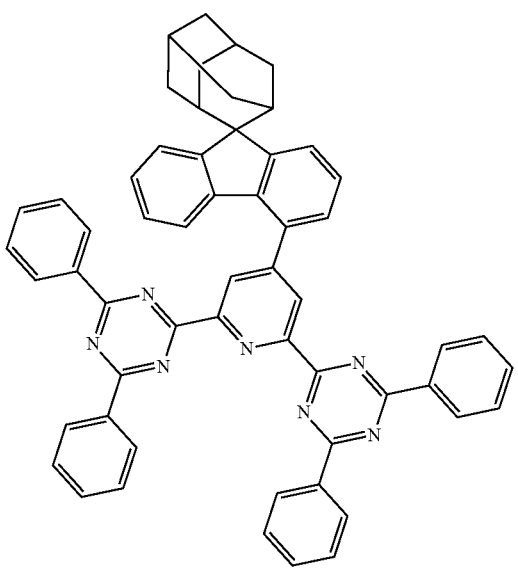

Preparation of Intermediates in Preparation Examples 26 to 45

The intermediate was prepared as follows:

Step (1):

Preparation Example 25: Synthesis of Compound 7

The compound 7 (yield 70%, LC-MS (ESI, pos.ion): m/z=826.5 ([M+H]⁺)) was prepared by the same method as in Preparation Example 21, the difference was just that the intermediate M6 in Preparation Example 21 was replaced by the intermediate M10 as follows, wherein the synthesis and purification processes of the intermediate M10 were the same as those of the intermediate M6, and the difference was just that 2-bromo-4-chlorobiphenyl and 3,5-dichlorophenyl-boronic acid were replaced by 2-bromo-2-chlorobiphenyl and 2,6-dichloropyridine-4-boric acid respectively to obtain the intermediate M10.

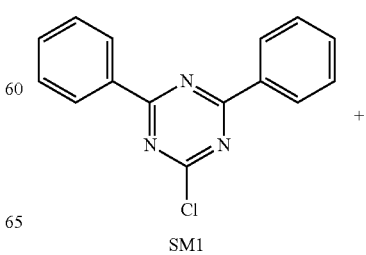

SM1

+

-continued

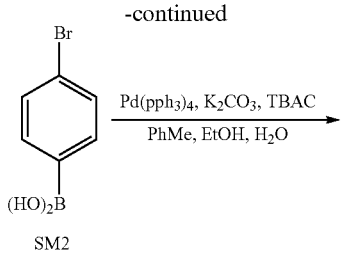

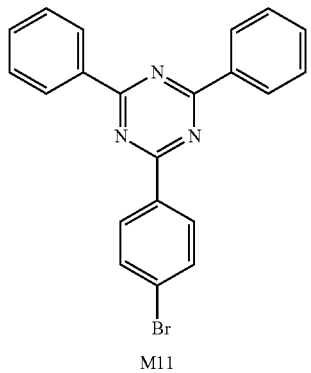

SM1 (30 g, 112.05 mmol), SM2 (22.50 g, 112.05 mmol), tetrakis(triphenylphosphine)palladium (6.47 g, 5.60 mmol), potassium carbonate (46.39 g, 336.7 mmol), tetrabutyl ammonium chloride (1.56 g, 5.60 mmol), toluene (240 mL), ethanol (120 mL) and deionized water (60 mL) were added into a three-necked flask, the mixture was heated to 78° C. under nitrogen atmosphere and stirred for 8 hours. The reaction solution above was cooled to room temperature, toluene (150 mL) was added for extraction. The combined organic phases were dried with anhydrous magnesium sulfate and filtered. The filtrate was concentrated in vacuo to obtain a crude product. The obtained crude product was purified by silica gel column chromatography and eluted with n-heptane, then purified by recrystallization using a mixture of a dichloromethane and ethyl acetate (v/v=⅓) to obtain an intermediate M11 (34.8 g, yield 80%).

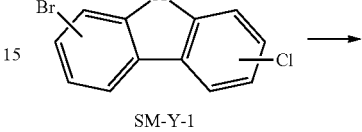

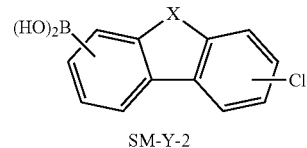

An intermediate SM-Y-2 series was synthesized by the same synthesis method as that of the intermediate M11, wherein Y may be 1, 2 or 3, the difference was that an intermediate SM-Y-1 was used instead of the starting material SM1, and the only corresponding intermediate SM-Y-2 may be prepared from each intermediate SM-Y-1. The prepared intermediate SM-Y-2 is shown in Table 4.

TABLE 4

| SM-Y-1 (CAS) | SM-Y-2 | Mass (g) | Yield (%) |
|---|---|---|---|
| ![dibenzofuran Br Cl] CAS:1360145-45-4 | ![dibenzofuran (HO)₂B Cl] SM-1-2 | 4.35 | 56 |
| ![fluorene Br Cl] CAS:605630-37-3 | ![fluorene (HO)₂B Cl] SM-2-2 | 4.85 | 59 |
| ![dibenzothiophene Br Cl] CAS:1332939-29-3 | ![dibenzothiophene B(OH)₂ Cl] SM-3-2 | 4.26 | 53 |

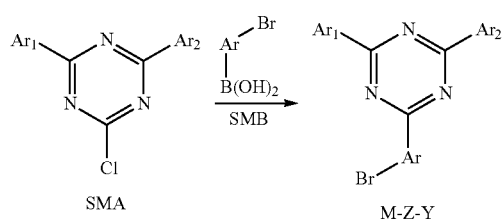

In the specific preparation process, the intermediate M-Z—Y series was synthesized by the same method as that of the intermediate M11, wherein Y may be 2 to 16, and the difference was that the compound SMA was used instead of the starting material SM1 for preparing the intermediate M11, and the compound SMB was used instead of SM2 for preparing the intermediate –11; the compound SMA may be SM1, 2-chloro-4,6-bis (naphthalene-2-yl)-1,3,5-triazine, 2-(4-biphenyl)-4-chloro-6-benzene-1,3,5-triazine, 2,4-bis ((1,1'-biphenyl)-4-yl)-6-chloro-1,3,5-triazine, 2-chloro-4-(1-naphthyl)-6-phenyl-1,3,5-triazine, 2-((1,1'-biphenyl)-3-yl)-4-chloro-6-phenyl-1,3,5-triazine, 2-chloro-4,6-di-p-tolyl-1,3,5-triazine or 2-chloro-4,6-bis(4-tert-butylphenyl)-1,3,5-triazine. The compound SMB may be (3-bromo-5-methylphenyl) boric acid, (4-bromo-3-fluorophenyl) boric acid, (3-bromo-2-cyanophenyl) boric acid, (3'-bromo-(1,1'-biphenyl)-4-yl) boric acid, (4'-bromo-(1,1' biphenyl)-4-yl) boric acid, (4-bromo-2-isopropylphenyl) boric acid, (3-bromonaphthalene-2-yl) boric acid, (8-bromonaphthalene-2-yl) boric acid, (3'-bromo-(1,1'-biphenyl)-3-yl) boric acid, 2-bromo-phenylboronic acid, SM-1-2, SM-2-2 or SM-3-2; the only corresponding intermediate M-Z—Y may be prepared from a combination of each of the compounds SMA and SMB, and the prepared intermediate M-Z—Y is shown in Table 5.

TABLE 5

Structural formula, mass and yield of intermediate M-Z-Y

| SMA | SMB | Intermediate-Z-Y | Mass (g) | Yield (%) |
|---|---|---|---|---|
| | SM-1-2 | M-Z-1 | 33.06 | 76 |
| | | M-Z-2 | 29.87 | 75 |

TABLE 5-continued

Structural formula, mass and yield of intermediate M-Z-Y

| SMA | SMB | Intermediate-Z-Y | Mass (g) | Yield (%) |
|---|---|---|---|---|
| | (structure) | M-Z-3 | 29.00 | 75 |
| | (structure) | M-Z-4 | 33.60 | 73 |
| (structure) | (structure) | M-Z-5 | 30.38 | 75 |

TABLE 5-continued
Structural formula, mass and yield of intermediate M-Z-Y
| SMA | SMB | Intermediate-Z-Y | Mass (g) | Yield (%) |
|---|---|---|---|---|
| | 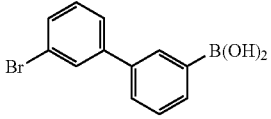 | 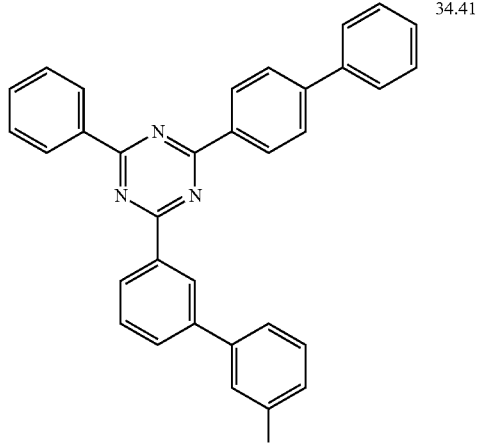<br>M-Z-6 | 34.41 | 72 |
| | <br>SM-2-2 | 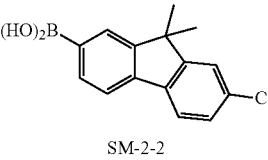<br>M-Z-7 | 29.16 | 72 |
| 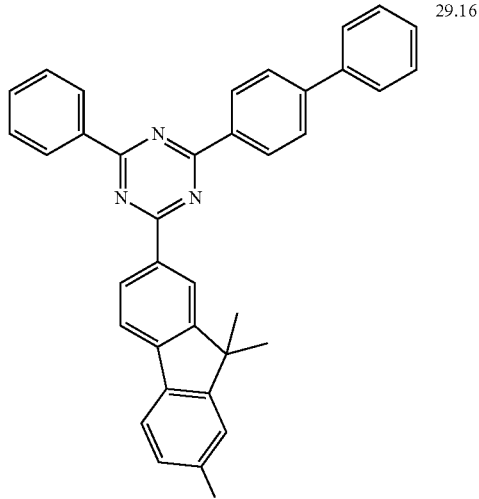 | 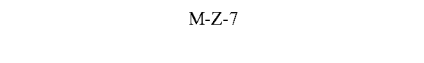 | 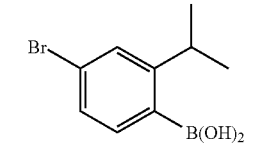<br>M-Z-8 | 28.95 | 75 |

TABLE 5-continued

Structural formula, mass and yield of intermediate M-Z-Y

| SMA | SMB | Intermediate-Z-Y | Mass (g) | Yield (%) |
|---|---|---|---|---|
| | (3-bromonaphthalen-2-yl)boronic acid | M-Z-9 | 29.94 | 71 |
| | (8-bromonaphthalen-1-yl)boronic acid | M-Z-10 | 29.52 | 70 |
| 2-chloro-4-(naphthalen-1-yl)-6-phenyl-1,3,5-triazine | (3'-bromo-[1,1'-biphenyl]-3-yl)boronic acid | M-Z-11 | 34.96 | 72 |
| 2-([1,1'-biphenyl]-3-yl)-4-chloro-6-phenyl-1,3,5-triazine | SM-3-2 | M-Z-12 | 29.57 | 73 |

TABLE 5-continued
Structural formula, mass and yield of intermediate M-Z-Y
| SMA | SMB | Intermediate-Z-Y | Mass (g) | Yield (%) |
|---|---|---|---|---|
| | 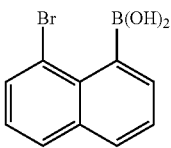 | 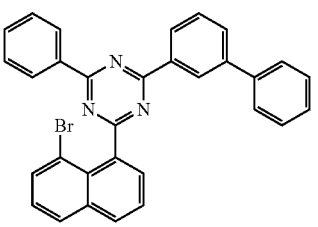 M-Z-13 | 31.41 | 70 |
| 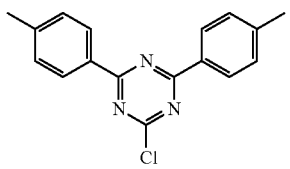 | 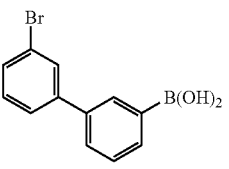 | 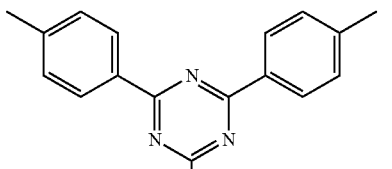 M-Z-14 | 34.95 | 70 |
| | 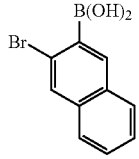 | 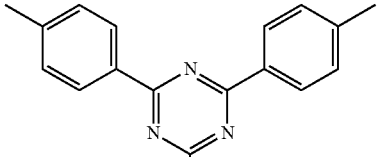 M-Z-15 | 34.05 | 72 |
| 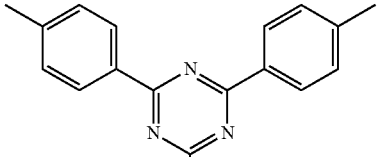 | 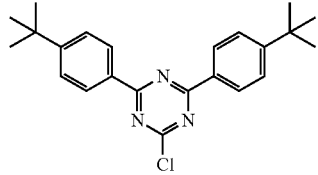 | 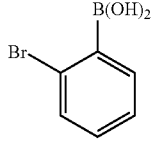 M-Z-16 | 29.55 | 70 |

Step (2):

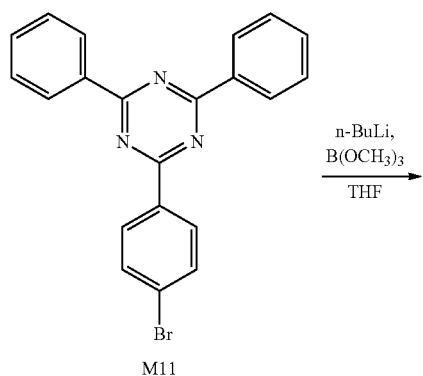

The intermediate M11 (20 g, 51.51 mmol) was added into a three-necked flask containing THF(1 L), n-butyllithium (3.46 g, 54.08 mmol) was added dropwise at −78° C., the temperature was kept for 1 h after dropping was completed, then trimethyl borate (8.02 g, 77.26 mmol) was added dropwise, then the mixture was heated to room temperature after the temperature was continuously kept for 1 h, and stirred overnight. Hydrochloric acid (2 mol/L) was added, pH was adjusted to neutral, a white crude product was obtained after filtration, pulped with n-heptane with amount three times as much as that of the crude product, so that a white solid intermediate M12 was obtained (11.82 g, yield 65%).

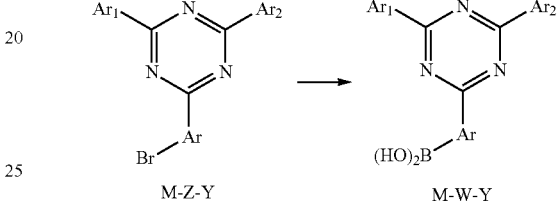

In an embodiment, an intermediate M-W—Y was synthesized by the same synthesis method as that of the intermediate M12, wherein Y may be 1 to 19 (the intermediate M-Z-17, intermediate M-Z-18 and intermediate M-Z-19 were raw materials purchased directly), the difference was that an intermediate M-Z—Y was used instead of the intermediate M11, and the only corresponding intermediate M-W—Y may be prepared from each intermediate M-Z—Y. The prepared intermediate M-W—Y is shown in Table 6.

TABLE 6

| Structural formula, mass and yield of intermediate M-W-Y | | | |
|---|---|---|---|
| Intermediate M-Z-Y | Intermediate M-W-Y | Mass (g) | Yield (%) |
| M-Z1 | M-W-1 | 10.35 | 64 |

TABLE 6-continued

Structural formula, mass and yield of intermediate M-W-Y

| Intermediate M-Z-Y | Intermediate M-W-Y | Mass (g) | Yield (%) |
|---|---|---|---|
| M-Z-2 | M-W-2 | 11.69 | 63 |
| M-Z-3 | M-W-3 | 12.06 | 65 |
| M-Z-4 | M-W-4 | 11.81 | 63 |

TABLE 6-continued

Structural formula, mass and yield of intermediate M-W-Y

| Intermediate M-Z-Y | Intermediate M-W-Y | Mass (g) | Yield (%) |
|---|---|---|---|
| M-Z-5 | M-W-5 | 12.01 | 65 |
| M-Z-6 | M-W-6 | 11.22 | 60 |
| M-Z-7 | M-W-7 | 11.83 | 64 |

TABLE 6-continued
Structural formula, mass and yield of intermediate M-W-Y
| Intermediate M-Z-Y | Intermediate M-W-Y | Mass (g) | Yield (%) |
|---|---|---|---|
| 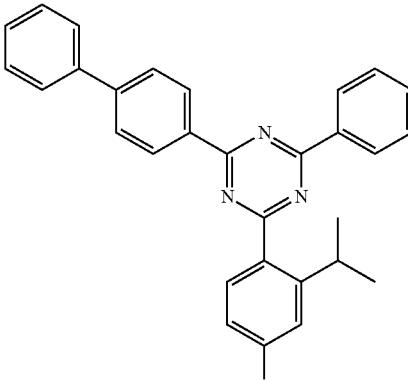<br>M-Z-8 | 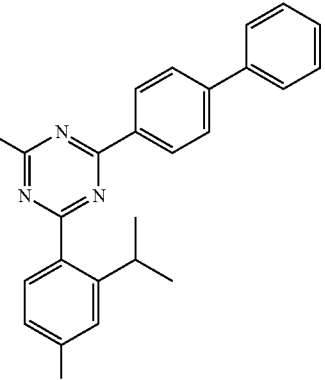<br>M-W-8 | 11.78 | 63 |
| 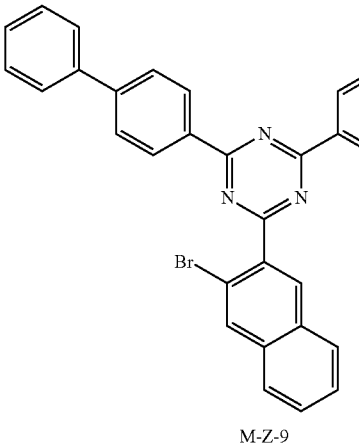<br>M-Z-9 | 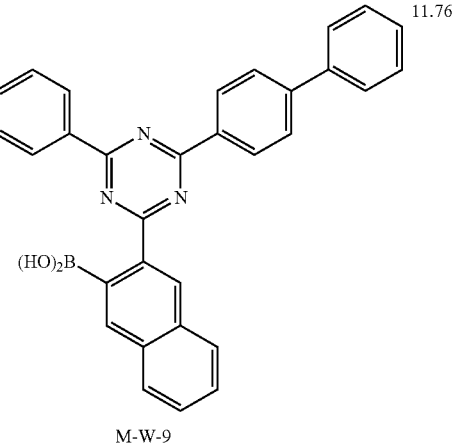<br>M-W-9 | 11.76 | 63 |
| 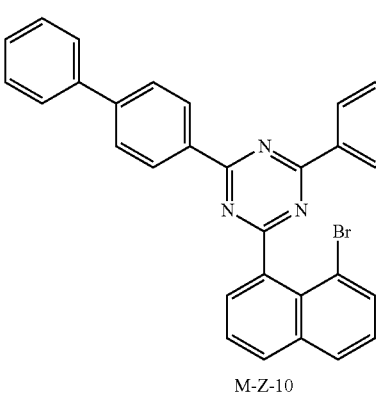<br>M-Z-10 | 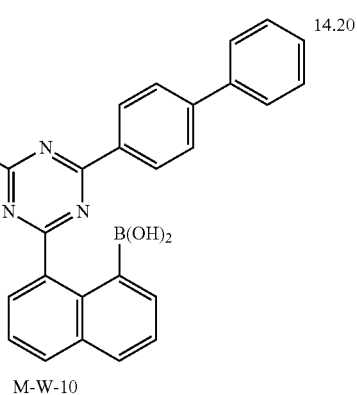<br>M-W-10 | 14.20 | 65 |

TABLE 6-continued
Structural formula, mass and yield of intermediate M-W-Y
| Intermediate M-Z-Y | Intermediate M-W-Y | Mass (g) | Yield (%) |
|---|---|---|---|
| 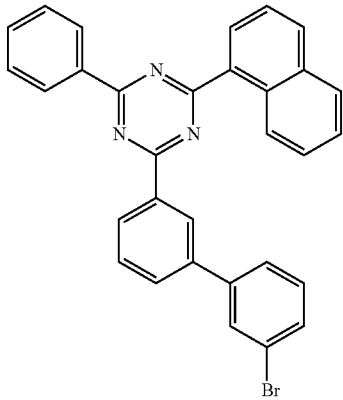 M-Z-11 | 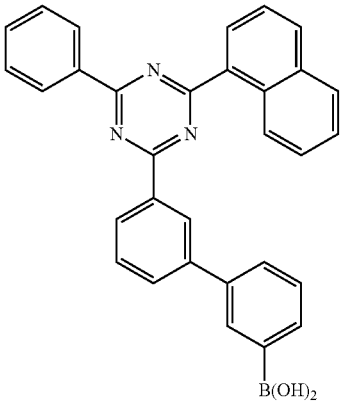 M-W-11 | 11.55 | 62 |
| 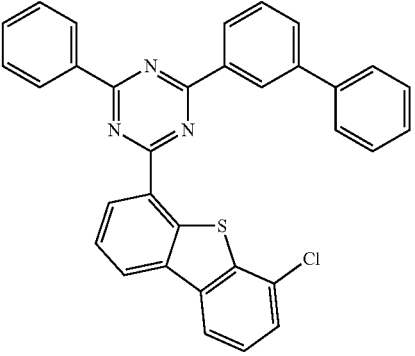 M-Z-12 | 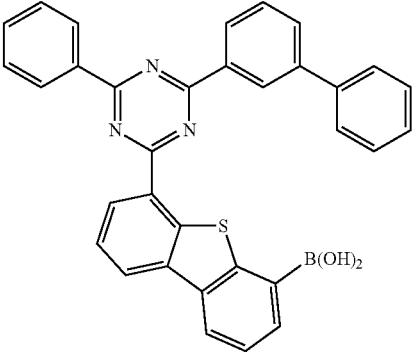 M-W-12 | 12.01 | 62 |
| 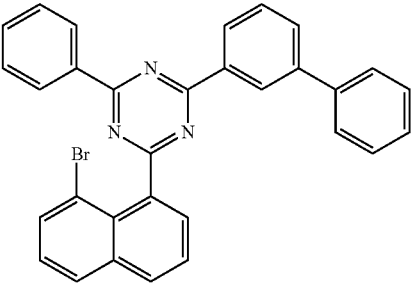 M-Z-13 | 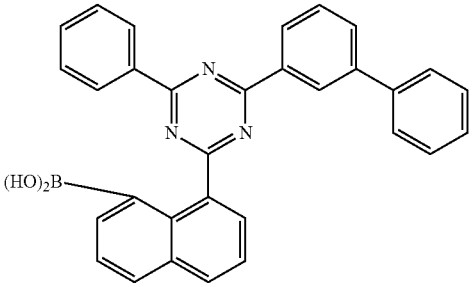 M-W-13 | 11.74 | 63 |
| 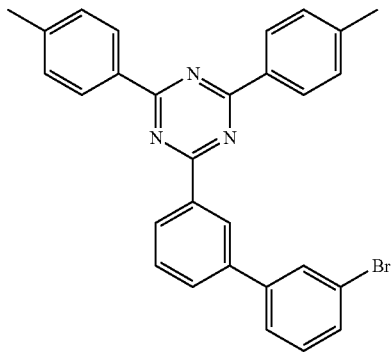 M-Z-14 | 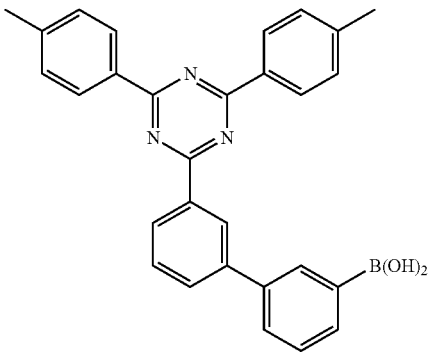 M-W-14 | 12.07 | 65 |

TABLE 6-continued

Structural formula, mass and yield of intermediate M-W-Y

| Intermediate M-Z-Y | Intermediate M-W-Y | Mass (g) | Yield (%) |
|---|---|---|---|
| M-Z-15 | M-W-15 | 11.65 | 63 |
| M-Z-16 | M-W-16 | 11.35 | 62 |
| M-Z-17 | M-W-17 | 10.32 | 61 |
| M-Z-18 | M-W-18 | 10.05 | 60 |

TABLE 6-continued
Structural formula, mass and yield of intermediate M-W-Y
| Intermediate M-Z-Y | Intermediate M-W-Y | Mass (g) | Yield (%) |
|---|---|---|---|
| M-Z-19 | M-W-19 | 9.98 | 59 |
Preparation Example 26: Synthesis of Compound Z-10
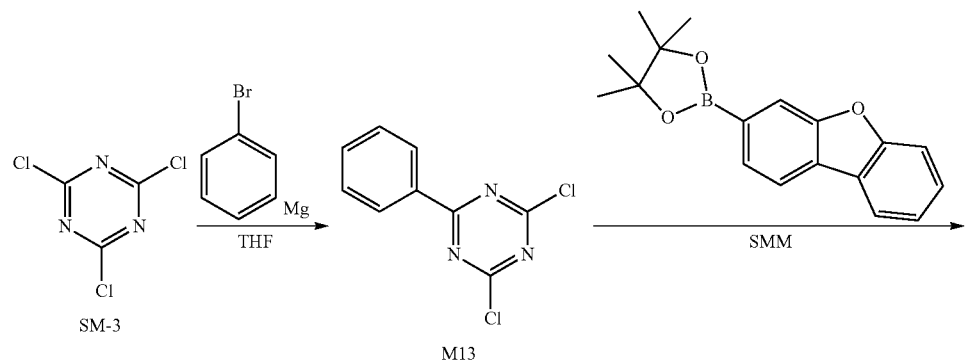
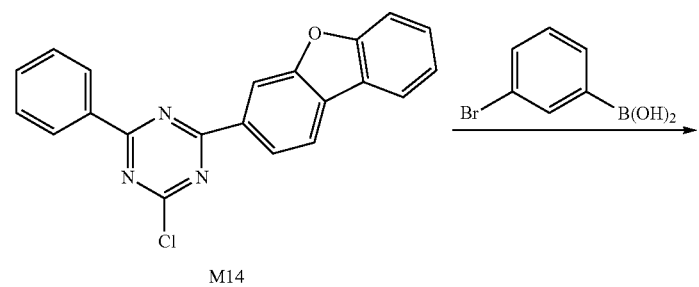
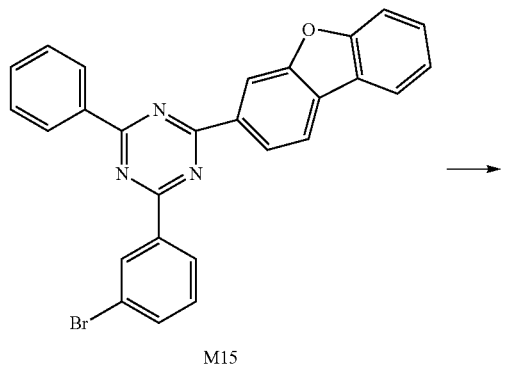

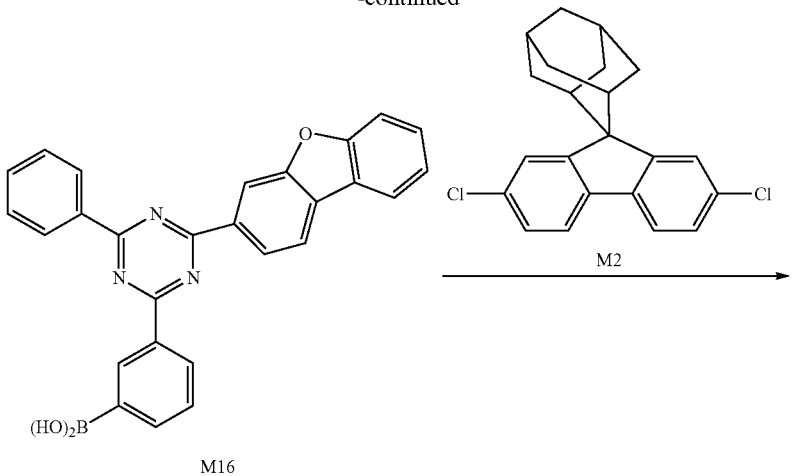

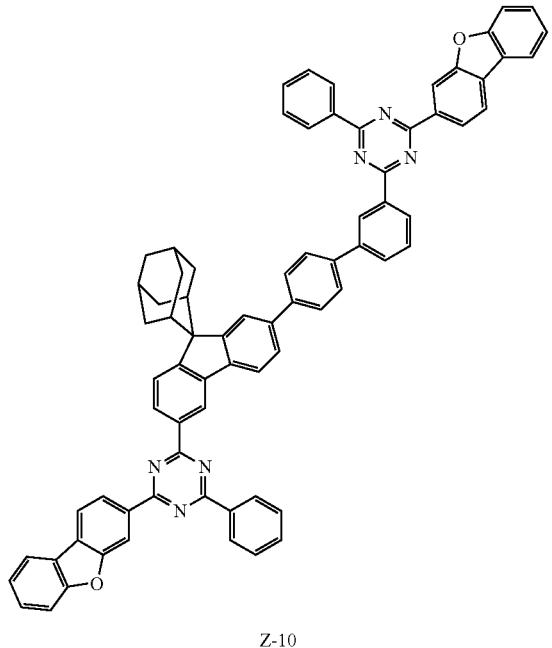 [SMILES: c1ccc(-c2nc(-c3cccc(-c4ccc(-c5ccc6c(c5)C5(c7ccc(-c8nc(-c9ccccc9)nc(-c9ccc%10c(c9)oc9ccccc9%10)n8)cc7-6)C6CC7CC(C6)CC5C7)cc4)c3)nc(-c3ccc4c(c3)oc3ccccc34)n2)cc1]

Z-10

Preparation of Intermediate M13:

2,4,6-trichloro-1,3,5-triazine (100 g, 542.27 mmol) and 800 mL anhydrous tetrahydrofuran were put into a 3 L reaction flask and the mixture was stirred at 0° C. under nitrogen atmosphere. 97.93 ml (1 mol/L) of phenyl magnesium bromide (which may be obtained from a reaction of bromobenzene and magnesium metal) was added into the flask dropwise, the reaction mixture was heated naturally to room temperature and stirred for 1 hour. 2 mol/L of aqueous hydrochloric acid solution was added to the above reaction solution, and then the resulted mixture was washed with dichloromethane and ultrapure water. The separated organic phase was dried over anhydrous magnesium sulfate, and then filtrated through silica gel, the filtrate was concentrated in vacuo to obtain a crude product. The crude product was purified by recrystallization using a mixture of dichloromethane and n-heptane to obtain an intermediate M13 (98 g, yield 80%).

Preparation of Intermediate M14:

The intermediate M13 (98 g, 433.44 mmol), SMM (127.51 g, 433.44 mmol), 1000 ml of anhydrous tetrahydrofuran, palladium acetate (2.92 g, 13.0 mmol), 2-dicyclohexylphosphino-2,4,6-triisopropylbiphenyl (12.39 g, 26.00 mmol) and potassium acetate (127.61 g, 1300.31 mmol) were put into a 3 L reaction flask, the mixture was heated to reflux under nitrogen atmosphere and stirred for 2 hours. The reaction solution was cooled to room temperature, extracted with dichloromethane and washed with ultrapure water in turn. After drying with anhydrous magnesium sulfate and filtration, the filtrate was concentrated under reduced pressure to obtain a crude product. The obtained crude product was purified by silica gel column and eluted with a mixture of dichloromethane and n-heptane to obtain intermediate M14 (124.06 g, yield 80%).

Preparation of Intermediate M15:

The intermediate-M14 (76.68 g, 214.30 mmol), 3-bromophenylboronic acid (43.03 g, 214.31 mmol) and 620 ml of 1,4-dioxane were put into a L reaction flask, stirred at 60° C. in a nitrogen atmosphere, tetrakis(triphenylphosphine)palladium (12.38 g, 10.72 mmol) and 50 mL of potassium carbonate (59.24 g, 428.62 mmol) aqueous solution were added, heated and refluxed, stirred overnight. The reaction solution was cooled to room temperature, the solid was washed with methanol and ultrapure water, and recrystallized by toluene, so that the intermediate M15 was obtained (82 g, yield 80%).

Preparation of Intermediate M16:

The intermediate M15 (82, 171.4 mmol) was added into a three-necked flask containing THF(1 L), n-butyllithium (11.6 g; 179.9 mmol) was added dropwise at −78° C., the temperature was kept for 1 h after dropping was completed, then trimethyl borate (27.51 g, 257.1 mmol) was added dropwise. The mixture was stirred for another 1 h, and then heated to room temperature, and stirred overnight. Hydrochloric acid (2 mol/L) was added, to adjust pH to neutral. A white crude product was obtained after filtration, stirred with n-heptane with amount three times as much as that of the crude product, so that a white solid intermediate M16 (45.5 g, yield 60%) was obtained.

Synthesis of Compound Z-10:

The intermediate-M16 (10 g, 22.55 mmol), intermediate-M2 (4.0 g, 11.28 mmol), tetrakis(triphenylphosphine) palladium (1.30 g, 1.13 mmol), potassium carbonate (9.34 g, 67.67 mmol), tetrabutyl ammonium chloride (0.31 g, 1.13 mmol), toluene (80 mL), ethanol (40 mL) and deionized water (20 mL) were added into a three-necked flask, the mixture was heated to 78° C. under the nitrogen atmosphere and stirred for 8 hours. The reaction solution above was cooled to room temperature, toluene (150 mL) was added for extraction. The combined organic phases were dried with anhydrous magnesium sulfate and filtered. The filtrate was concentrated in vacuo to obtain a crude product. The obtained crude product was purified by silica gel column chromatography and eluted with n-heptane, then purified by recrystallization using a mixture of a dichloromethane and ethyl acetate (v/v=1/5) to obtain the compound Z-10 (9.14 g, yield 75%) m/z=1081.4 $[M+H]^+$.

Preparation Examples 27 to 45

In the following preparation examples, compounds M-Y and Z—X were synthesized by the same synthesis method as that of the compound (Z-10), wherein Y may be 18-23, and X was 11-23, the difference was that the intermediate MP was used instead of the intermediate M2, the intermediate M-W—Y was used instead of the intermediate M16, and the only corresponding compound may be prepared from every two intermediates. As shown in Table 7 below.

TABLE 7

| Intermediate MP | Intermediate M-W-Y | Compound Z-X | Mass (g) | Yield (%) | Mass spectrum (m/z) |
|---|---|---|---|---|---|
| M2 | M-W-1 | Z-11 | 8.99 | 73 | 1081.4 |

TABLE 7-continued

| Intermediate MP | Intermediate M-W-Y | Compound Z-X | Mass (g) | Yield (%) | Mass spectrum (m/z) |
|---|---|---|---|---|---|
| M3 | M-W-2 | Z-12 | 9.32 | 76 | 1129.4 |

TABLE 7-continued
| Intermediate MP | Intermediate M-W-Y | Compound Z-X | Mass (g) | Yield (%) | Mass spectrum (m/z) |
|---|---|---|---|---|---|
| 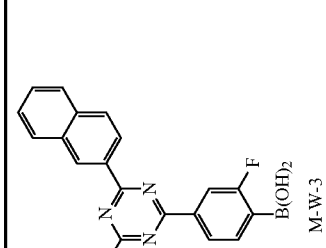<br>M4 | 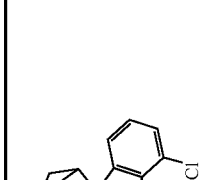<br>M-W-3 | 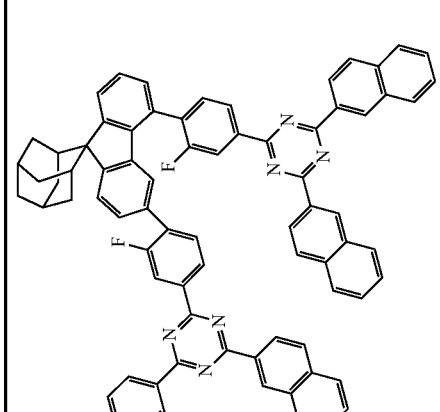<br>Z-13 | 9.56 | 77 | 1137.4 |

TABLE 7-continued
| Intermediate MP | Intermediate M-W-Y | Compound Z-X | Mass (g) | Yield (%) | Mass spectrum (m/z) |
|---|---|---|---|---|---|
| 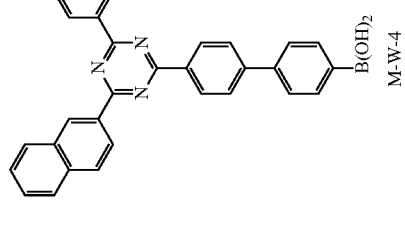 M5 | 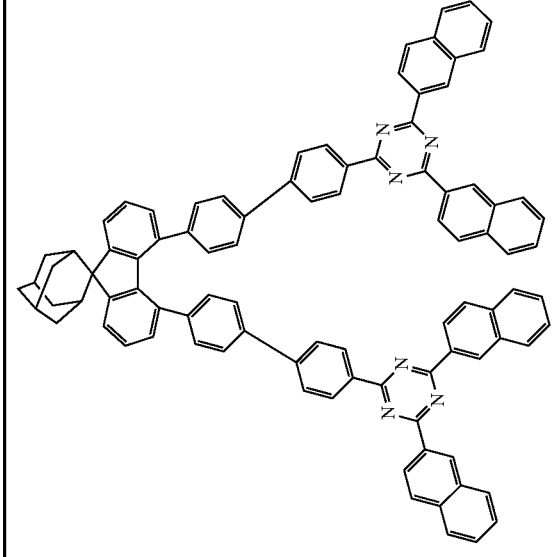 M-W-4 | 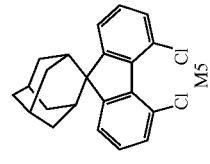 Z-14 | 9.31 | 76 | 1253.5 |

TABLE 7-continued
| Intermediate MP | Intermediate M-W-Y | Compound Z-X | Mass (g) | Yield (%) | Mass spectrum (m/z) |
|---|---|---|---|---|---|
| 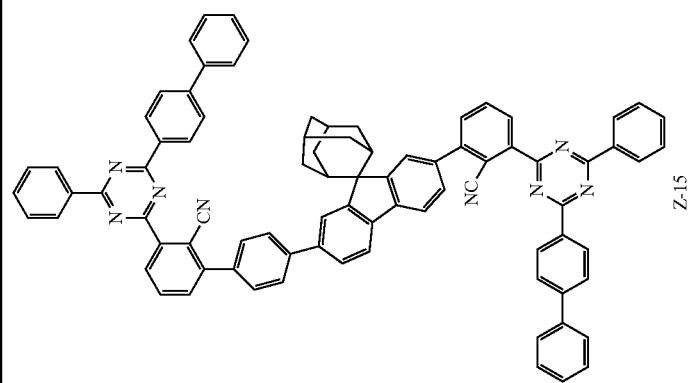 M2-A | 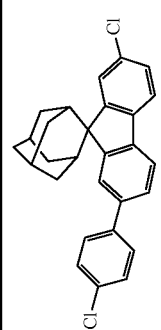 M-W-5 | Z-15 | 9.03 | 70 | 1179.4 |

TABLE 7-continued
| Intermediate MP | Intermediate M-W-Y | Compound Z-X | Mass (g) | Yield (%) | Mass spectrum (m/z) |
|---|---|---|---|---|---|
| M3-A 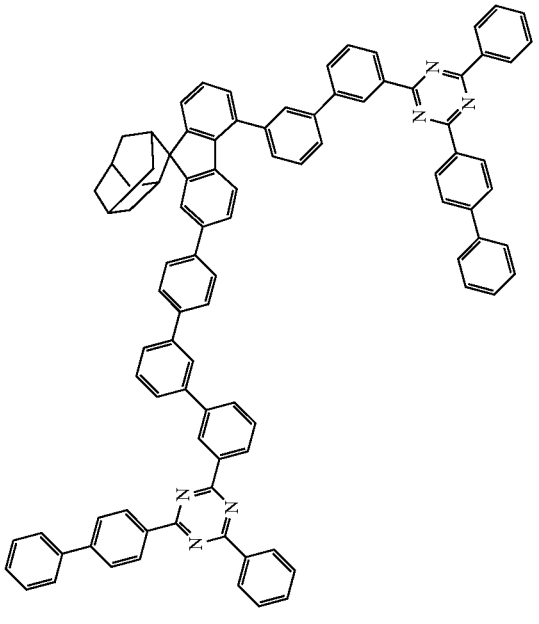 | M-W-6 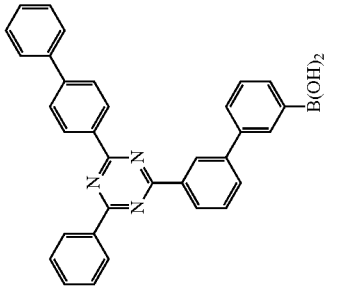 | Z-16 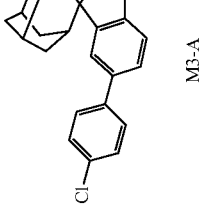 | 9.65 | 74 | 1282.5 |

TABLE 7-continued
| Intermediate MP | Intermediate M-W-Y | Compound Z-X | Mass (g) | Yield (%) | Mass spectrum (m/z) |
|---|---|---|---|---|---|
| 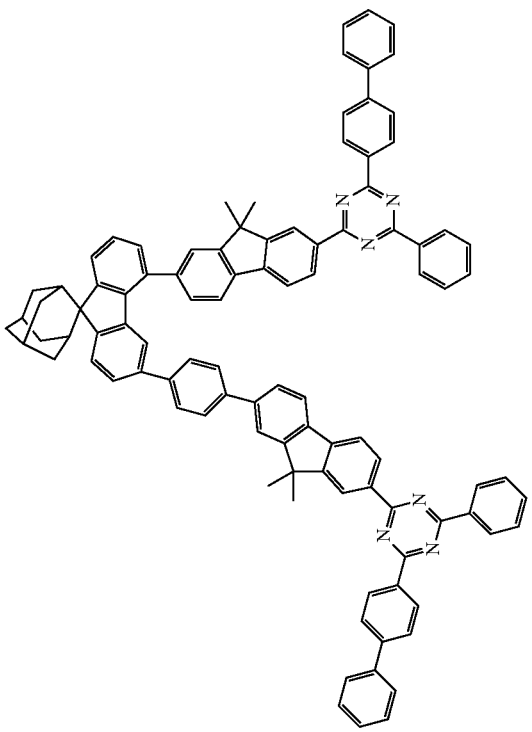 M4-A |  M-W-7 | 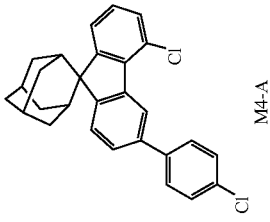 Z-17 | 9.63 | 71 | 1362.6 |

TABLE 7-continued

| Intermediate MP | Intermediate M-W-Y | Compound Z-X | Mass (g) | Yield (%) | Mass spectrum (m/z) |
|---|---|---|---|---|---|
| M5-A | M-W-8 | Z-18 | 9.82 | 73 | 1366.5 |
| M2-B | M-W-9 | Z-19 | 9.77 | 70 | 1382.5 |

TABLE 7-continued
| Intermediate MP | Intermediate M-W-Y | Compound Z-X | Mass (g) | Yield (%) | Mass spectrum (m/z) |
|---|---|---|---|---|---|
| M2 | M-W-10 | Z-20 | 9.69 | 71 | 1306.5 |
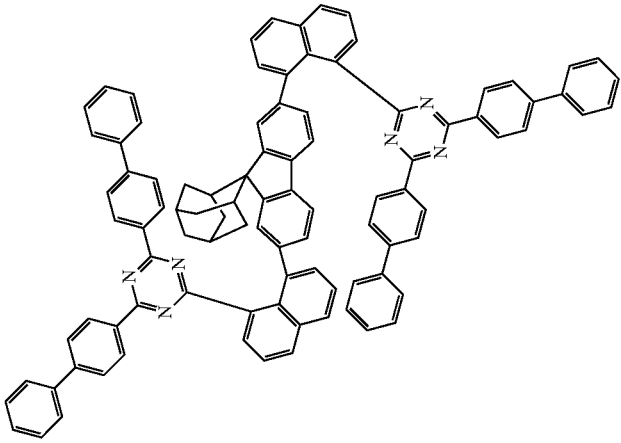

TABLE 7-continued

| Intermediate MP | Intermediate M-W-Y | Compound Z-X | Mass (g) | Yield (%) | Mass spectrum (m/z) |
|---|---|---|---|---|---|
| M4-B | M-W-11 | Z-21 | 9.13 | 74 | 1229.5 |

TABLE 7-continued
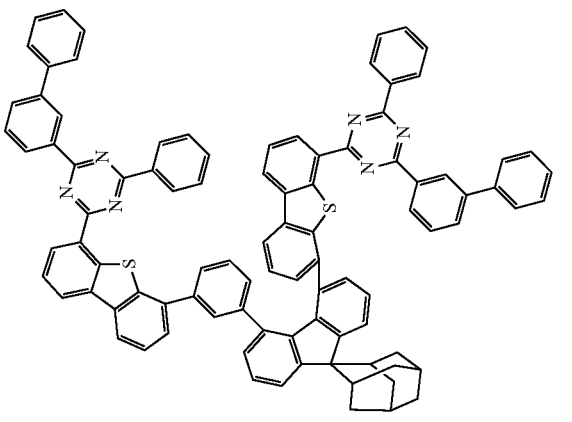

TABLE 7-continued

| Intermediate MP | Intermediate M-W-Y | Compound Z-X | Mass (g) | Yield (%) | Mass spectrum (m/z) |
|---|---|---|---|---|---|
| M5-D | M-W-13 | Z-23 | 9.33 | 72 | 1306.5 |
| M6 | M-W-14 | M-18 | 9.56 | 76 | 1185.5 |

TABLE 7-continued

| Intermediate MP | Intermediate M-W-Y | Compound Z-X | Mass (g) | Yield (%) | Mass spectrum (m/z) |
|---|---|---|---|---|---|
| | M-W-15 | M-19 | 9.62 | 76 | 1133.5 |
| | M-W-16 | M-20 | 9.35 | 73 | 1201.6 |

TABLE 7-continued

| Intermediate MP | Intermediate M-W-Y | Compound Z-X | Mass (g) | Yield (%) | Mass spectrum (m/z) |
|---|---|---|---|---|---|
| M8 | M-W-17 | M-21 | 9.37 | 83 | 823.3 |
|  | M-W-18 | M-22 | 9.56 | 85 | 821.3 |

TABLE 7-continued

| Intermediate MP | Intermediate M-W-Y | Compound Z-X | Mass (g) | Yield (%) | Mass spectrum (m/z) |
|---|---|---|---|---|---|
| | M-W-19 | M-23 | 9.32 | 81 | 8.75 |

¹HNMR characterization data of the compound M-23 in the above table: ¹HNMR (400 MHz, $CD_2Cl_2$):9.89 (s,1H), 9.31 (s, 2H), 8.79 (d, 4H), 8.56 (d, 4H), 8.16-8.12 (m, 5H), 7.85 (d, 1H), 7.73(d, 1H),7.66-7.56 (m, 7H), 7.51-7.47 (m, 2H), 7.32 (t,1H), 3.28 (d, 2H), 3.10 (d, 2H), 2.56 (d, 2H), 2.09 (s, 2H), 1.90 (d, 2H), 1.78 (d, 2H), 1.85 (s, 2H).

Example 1: Fabrication of Blue Organic Electroluminescent Devices

The anode was prepared through the following process: an ITO substrate (manufactured by Corning) with a thickness of 1500 Å was cut into the dimension of 40 mm×40 mm×0.7 mm, the substrate was prepared into an experimental substrate having a cathode, a anode and insulation layer patterns by photoetching procedure, and surface treatment was performed by ultraviolet ozone and $O_2:N_2$ plasma to increase the work function of the anode (experimental substrate) and remove scum.

HAT-CN was vacuum deposited on the experimental substrate (anode) to form a hole injection layer (HIL) with a thickness of 100 Å, and the compound NPB was vacuum deposited on the hole injection layer to form a hole transport layer (HTL) with a thickness of 850 Å.

The compound TCTA was vapor deposited on HTL as an electron-blocking layer (EBL) with a thickness of 100 Å.

Organic electroluminescent layer (EML) with a thickness of 220 Å was formed by vapor deposition on EBL with α,β-ADN as the host material doped with BD-1 (the ratio of host material to dopant was the film thickness ratio of 100:3).

Compound 15 and LiQ were vapor deposited on EML as an electron transport layer (ETL) at the film thickness ratio of 1:1 with a thickness of 350 Å.

Metal Yb was vapor deposited on ETL as an electron injection layer (EIL) with a thickness of 10 Å.

Silver magnesium film layer (the film thickness ratio of silver to magnesium was 10:1) was vapor deposited on the EIL as the cathode with a thickness of 110 Å.

Compound CP-1 was vapor deposited on the cathode as a light extraction layer (CPL) with a thickness of 630 Å.

The compounds used in the embodiment are as follows:

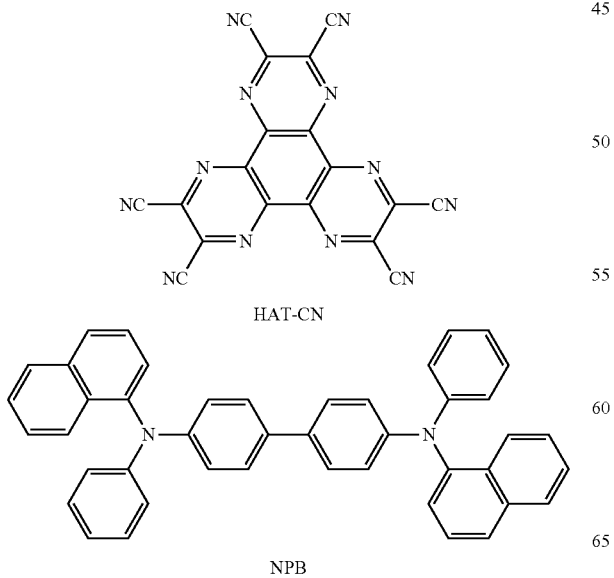

HAT-CN

NPB

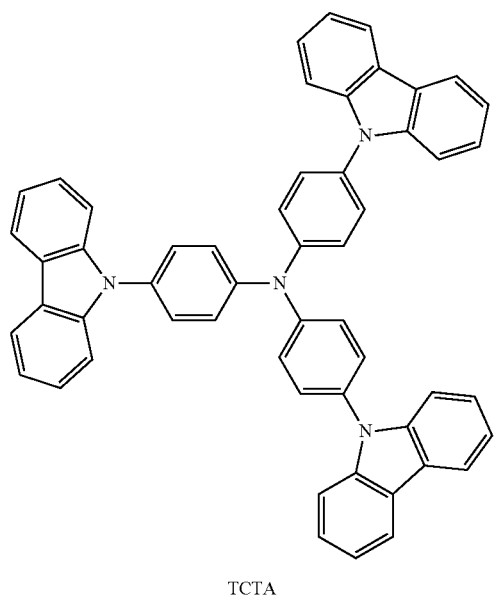

TCTA

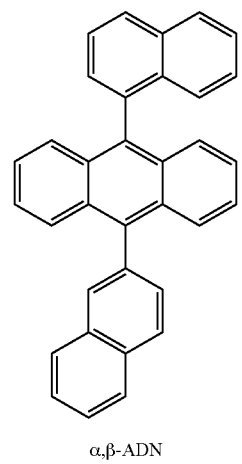

α,β-ADN

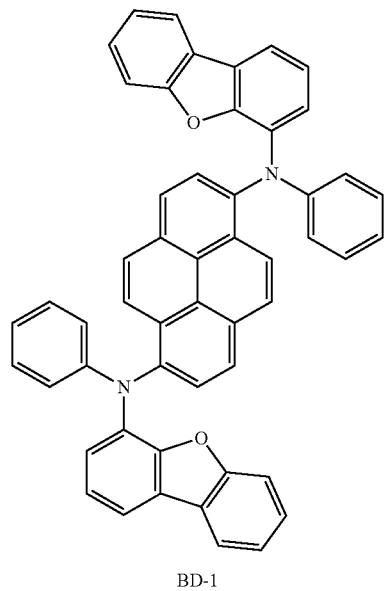

BD-1

-continued

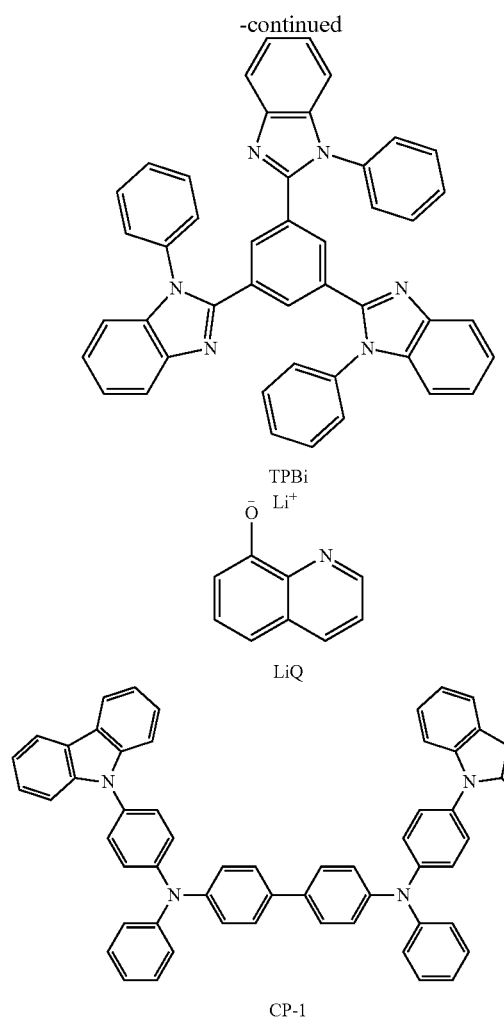

TPBi

LiQ

CP-1

Examples 2 to 45

The organic electroluminescent device in Examples 2 to 45 was prepared by the same preparation process as that in Example 1, and the difference was just that the compound 15 in the electron transport layer (ETL) of Example 1 was replaced by the compound in Table 8 below.

Comparative Example 1

The organic electroluminescent device in Comparative Example 1 was prepared by the same preparation process as that in Example 1, and the difference was just that the compound 15 in the electron transport layer (ETL) of Example 1 was replaced by a compound A' as follows.

Comparative Example 2

The organic electroluminescent device in Comparative Example 2 was prepared by the same preparation process as that in Example 1, and the difference was just that the compound 15 in the electron transport layer (ETL) of Example 1 was replaced by a compound B' as follows.

Comparative Example 3

The organic electroluminescent device in Comparative Example 3 was prepared by the same preparation process as that in Example 1, and the difference was just that the compound 15 in the electron transport layer (ETL) of Example 1 was replaced by a compound C' as follows.

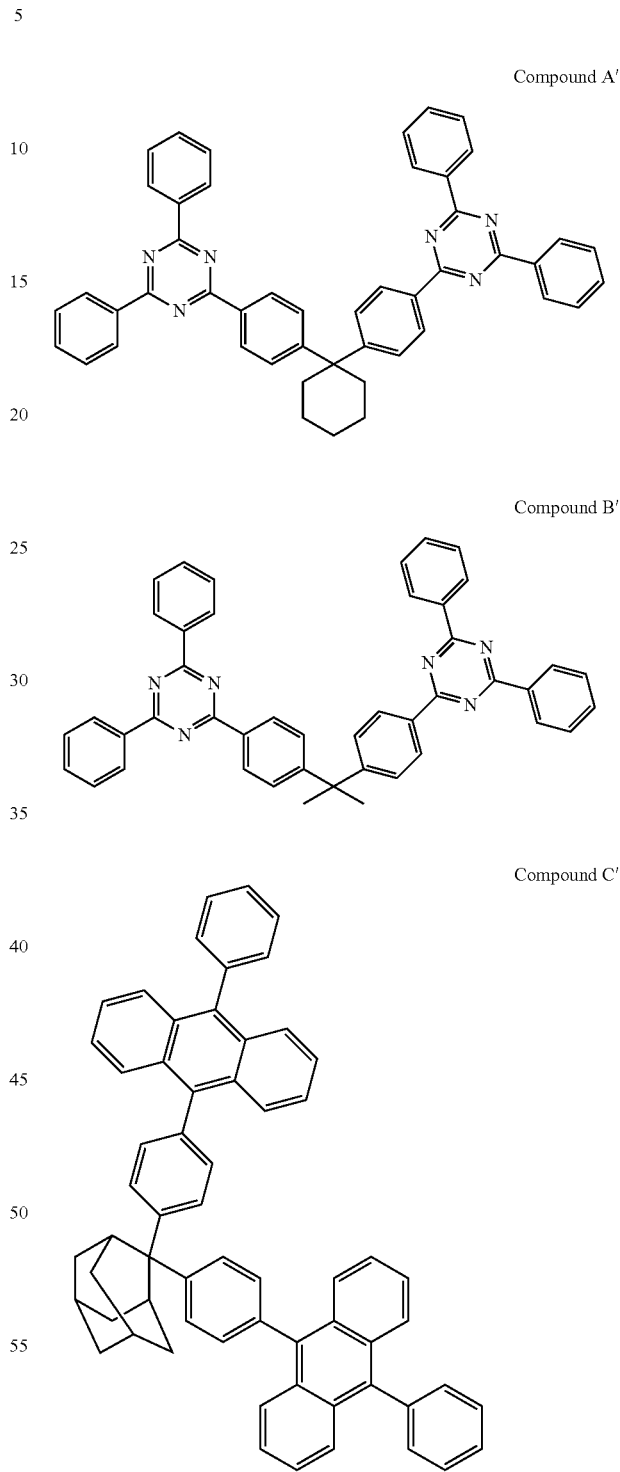

The performance of the organic electroluminescent devices of Examples 1 to 45 and Comparative Examples 1 to 3 were tested, wherein the IVL data compared the test results at 10 mA/cm$^2$, and the lifespan was the test result at the current density of 15 mA/cm$^2$. The test results are shown in Table 8 below.

TABLE 8

Performance Test Results of Organic Electroluminescent Devices

| Example | Compound | Volt (V) | Cd/A | EQE (%) | CIEy | T95 (h) |
|---|---|---|---|---|---|---|
| Example 1 | Compound 15 | 3.81 | 6.7 | 13.9 | 0.047 | 209 |
| Example 2 | Compound 17 | 3.84 | 6.8 | 14.0 | 0.046 | 211 |
| Example 3 | Compound 19 | 3.89 | 6.3 | 13.1 | 0.048 | 219 |
| Example 4 | Compound 20 | 3.88 | 6.5 | 13.5 | 0.046 | 219 |
| Example 5 | Compound 21 | 3.82 | 6.5 | 13.6 | 0.047 | 209 |
| Example 6 | Compound 23 | 3.84 | 6.9 | 14.3 | 0.048 | 212 |
| Example 7 | Compound 26 | 3.91 | 6.6 | 13.8 | 0.046 | 204 |
| Example 8 | Compound 29 | 3.84 | 6.9 | 14.2 | 0.046 | 216 |
| Example 9 | Compound 34 | 3.87 | 6.3 | 13.1 | 0.047 | 208 |
| Example 10 | Compound 36 | 3.91 | 6.8 | 14.1 | 0.048 | 216 |
| Example 11 | Compound 39 | 3.85 | 6.7 | 13.9 | 0.046 | 209 |
| Example 12 | Compound 42 | 3.89 | 6.4 | 13.5 | 0.047 | 211 |
| Example 13 | Compound 43 | 3.83 | 6.8 | 13.8 | 0.046 | 219 |
| Example 14 | Compound 47 | 3.83 | 6.5 | 13.5 | 0.046 | 203 |
| Example 15 | Compound 51 | 3.91 | 6.6 | 13.7 | 0.048 | 219 |
| Example 16 | Compound 53 | 3.92 | 6.5 | 13.6 | 0.046 | 232 |
| Example 17 | Compound 60 | 3.88 | 6.3 | 13.4 | 0.047 | 205 |
| Example 18 | Compound 58 | 3.86 | 6.4 | 13.5 | 0.046 | 210 |
| Example 19 | Compound 56 | 3.91 | 6.6 | 13.7 | 0.048 | 216 |
| Example 20 | Compound 55 | 3.90 | 6.5 | 13.6 | 0.048 | 212 |
| Example 21 | Compound 1 | 3.89 | 6.3 | 13.4 | 0.047 | 213 |
| Example 22 | Compound 2 | 3.88 | 6.6 | 13.8 | 0.046 | 208 |
| Example 23 | Compound 3 | 3.86 | 6.4 | 13.5 | 0.047 | 216 |
| Example 24 | Compound 7 | 3.85 | 6.5 | 13.6 | 0.048 | 215 |
| Example 25 | Compound 14 | 3.83 | 6.4 | 13.4 | 0.048 | 216 |
| Example 26 | Compound Z-10 | 3.90 | 6.8 | 13.9 | 0.048 | 218 |
| Example 27 | Compound Z-11 | 3.83 | 6.4 | 13.2 | 0.046 | 220 |
| Example 28 | Compound Z-12 | 3.91 | 6.7 | 13.8 | 0.047 | 208 |
| Example 29 | Compound Z-13 | 3.80 | 6.6 | 13.6 | 0.046 | 196 |
| Example 30 | Compound Z-14 | 3.81 | 6.8 | 14.0 | 0.046 | 200 |
| Example 31 | Compound Z-15 | 3.87 | 6.9 | 14.2 | 0.048 | 217 |
| Example 32 | Compound Z-16 | 3.96 | 6.4 | 13.2 | 0.046 | 179 |
| Example 33 | Compound Z-17 | 3.95 | 6.5 | 13.4 | 0.047 | 181 |
| Example 34 | Compound Z-18 | 3.98 | 6.3 | 13.0 | 0.046 | 183 |
| Example 35 | Compound Z-19 | 3.97 | 6.4 | 13.2 | 0.048 | 175 |
| Example 36 | Compound Z-20 | 3.96 | 6.5 | 13.4 | 0.048 | 180 |
| Example 37 | Compound Z-21 | 3.86 | 6.7 | 13.4 | 0.047 | 205 |
| Example 38 | Compound Z-22 | 3.98 | 6.3 | 13.0 | 0.046 | 206 |
| Example 39 | Compound Z-23 | 3.97 | 6.4 | 13.2 | 0.047 | 195 |
| Example 40 | Compound M-18 | 3.92 | 6.8 | 13.9 | 0.048 | 200 |
| Example 41 | Compound M-19 | 3.90 | 6.8 | 14.0 | 0.048 | 220 |
| Example 42 | Compound M-20 | 3.88 | 6.4 | 13.2 | 0.046 | 207 |
| Example 43 | Compound M-21 | 3.87 | 6.4 | 13.2 | 0.048 | 215 |
| Example 44 | Compound M-22 | 3.83 | 6.7 | 13.7 | 0.048 | 207 |
| Example 45 | Compound M-23 | 3.90 | 6.8 | 13.9 | 0.047 | 218 |
| Comparative Example 1 | Compound A' | 4.15 | 4.4 | 9.1 | 0.046 | 147 |
| Comparative Example 2 | Compound B' | 4.21 | 5.2 | 10.8 | 0.047 | 155 |
| Comparative Example 3 | Compound C' | 4.13 | 4.6 | 9.5 | 0.047 | 148 |

According to the results of Table 1, compared with Comparative Examples 1 to 3 using the known compounds A', B' and C', the operating voltage of the organic electroluminescent device in Examples 1 to 45 using the compound of the present disclosure as the electron transport layer (ETL) is reduced by at most 0.41 V, the luminous efficiency (Cd/A) is increased by at least 21.2%, the external quantum efficiency is increased by at least 20.4%, the lifespan is increased by at least 12.9%, and the T95 lifespan can be increased by at most 85 h.

The organic compound according to the present disclosure effectively improves the glass transition temperature of the material and the lifespan of the material in the device through the adamantane-fluorene group in the structure, the further introduced heteroaryl can further improve the performance of the device, and such compounds have the advantages of enhancing electron injection and transport and improving device efficiency. By using the organic compound of the present disclosure in the organic electroluminescent device, the driving voltage, luminous efficiency and lifespan of the electroluminescent device can be improved, and in particular, the lifespan and luminous efficiency of the device can be significantly improved.

The invention claimed is:

1. An organic compound represented by formula 1' as follows:

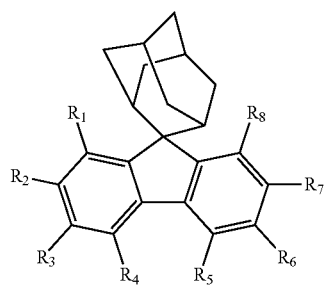

Formula 1' wherein, one of $R_1$ to $R_4$ is

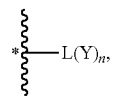

$*-L(Y)_n$, and the other three are each independently hydrogen, deuterium, fluorine, chlorine, bromine, cyano, phenyl, naphthyl, dimethylfluorenyl, dibenzothienyl, dibenzofuranyl, pyrimidinyl, methyl, ethyl, isopropyl or tert-butyl;

one of $R_5$ to $R_8$ is

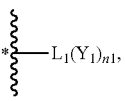

$*-L_1(Y_1)_{n1}$, and the other three are each independently hydrogen, deuterium, fluorine, chlorine, bromine, cyano, phenyl, naphthyl, dimethylfluorenyl, dibenzothienyl, dibenzofuranyl, pyrimidinyl, methyl, ethyl, isopropyl or tert-butyl;

each of n and $n_1$ is independently 0, 1 or 2, and $n+n_1=2$;

wherein each of Y and $Y_1$ is independently

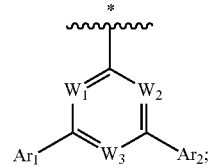

$W_1$ is $C(R^{w1})$ or N, $W_2$ is $C(R^{w2})$ or N, $W_3$ is $C(R^{w3})$ or N, and at least one of $W_1$, $W_2$ and $W_3$ is N;

$R^{w1}$, $R^{w2}$ and $R^{w3}$ are the same as or different from each other, and are each independently hydrogen, deuterium, fluorine, chlorine, bromine, or cyano;

$Ar_1$ and $Ar_2$ are the same as or different from each other, and are each independently hydrogen, deuterium or a substituted or unsubstituted group as follows:

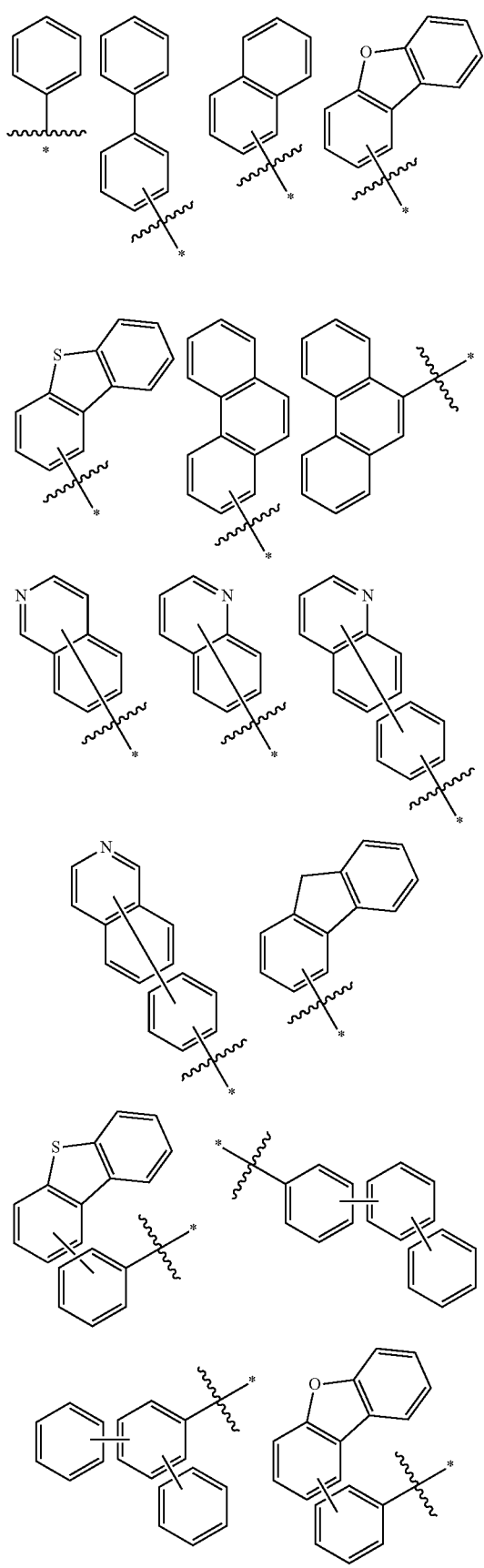
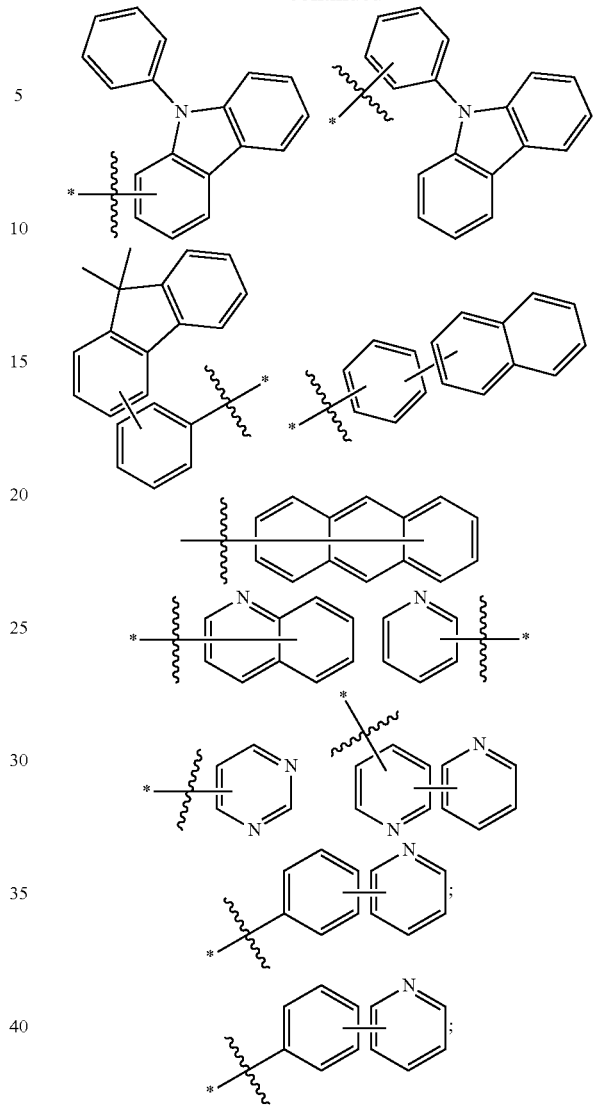

the above groups are optionally substituted by 0, 1, 2, 3, 4 or 5 substituents selected from deuterium, fluorine, chlorine, cyano, C1-C4 alkyl, C1-C4 alkoxyl, C1-C4 haloalkyl, C3-C9 alkylsilyl, C3-C10 cycloalkyl, C6-C12 aryl and C3-C12 heteroaryl;

wherein L and $L_1$ are the same as or different from each other, and are each independently selected from hydrogen, deuterium, a single bond and the groups as follows: substituted or unsubstituted phenylene, substituted or unsubstituted biphenylene, substituted or unsubstituted terphenylene, substituted or unsubstituted quaterphenylene, substituted or unsubstituted quinquephenylene, substituted or unsubstituted naphthylene, substituted or unsubstituted dinaphthylphenylene, substituted or unsubstituted naphthyl-phenylene, substituted or unsubstituted fluorenylene, substituted or unsubstituted phenanthrylene, substituted or unsubstituted anthrylene, substituted or unsubstituted triazinylene, substituted or unsubstituted pyrimidylene, substituted or unsubstituted pyridinylene, substituted or unsubstituted pyrazylene, substituted or unsubstituted dibenzothienylene, substituted or unsubstituted dibenzofuranylene, substituted or unsubstituted phenyl-dibenzothienylene, substituted or unsubstituted phenyl-dibenzofuranylene, substituted or unsubstituted phenyl-carbazolylene, N-phenylcarbazolylene, substituted or unsubstituted quinolylene and substituted or unsubstituted phenanthrolinylene;

the substituents of L and $L_1$ are the same as or different from each other, and are each independently selected from the group consisting of deuterium, fluorine, chlorine, bromine, cyano, C1-C4 alkyl, C1-C3 haloalkyl, phenyl, naphthyl, fluorenyl, C3-C12 heteroaryl, C3-C12 alkylsilyl and C3-C10 cycloalkyl.

2. The organic compound according to claim 1, wherein $Ar_1$ and $Ar_2$ are the same as or different from each other, and are each independently hydrogen, or a substituted or unsubstituted group as follows:

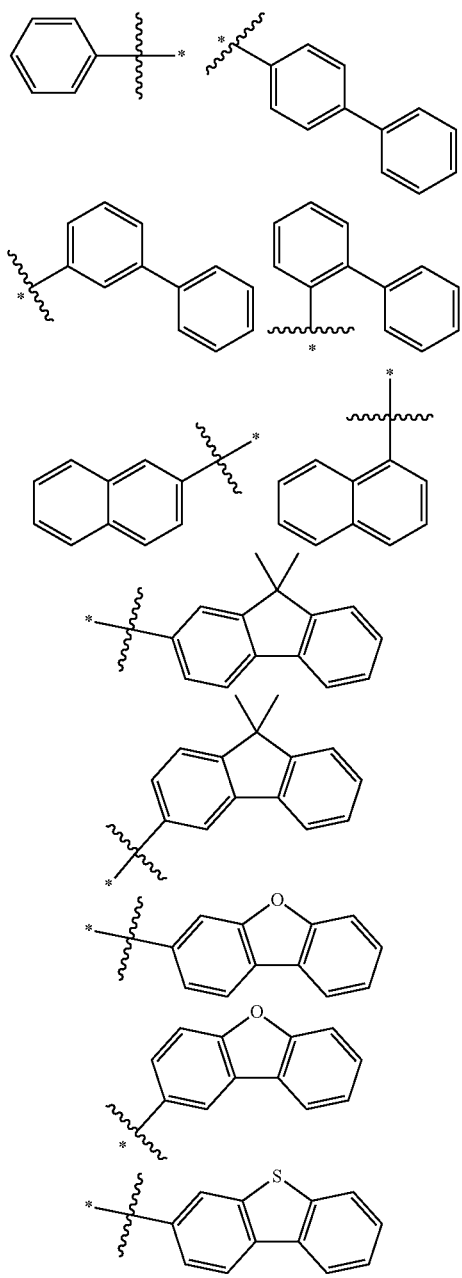

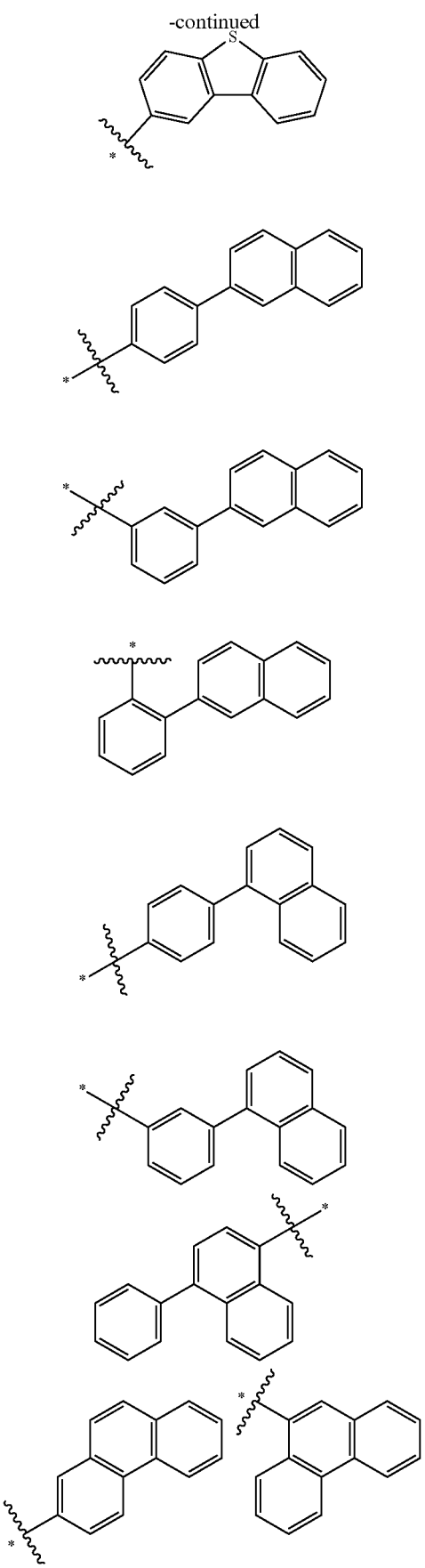

-continued
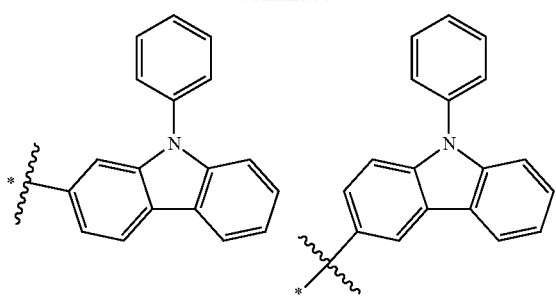
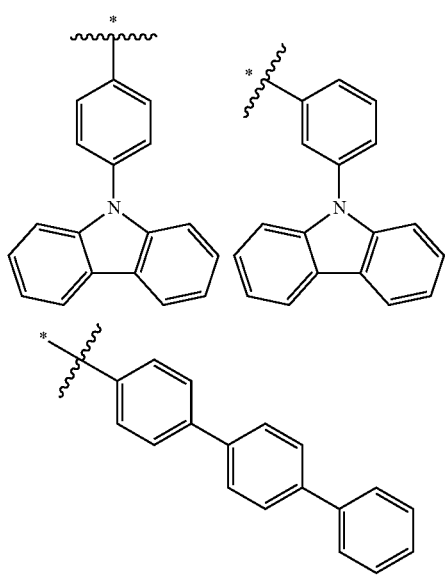
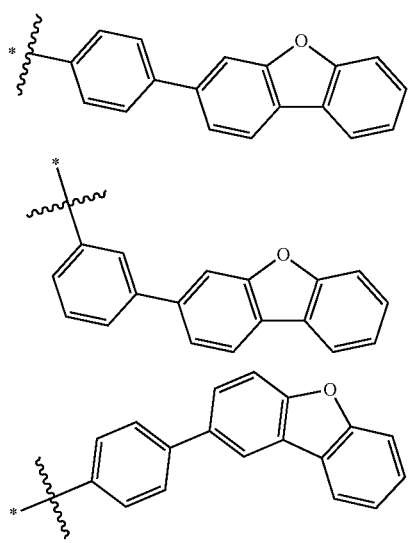
-continued
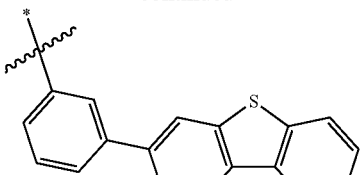
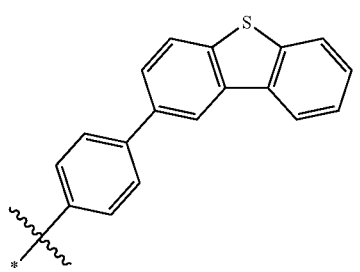
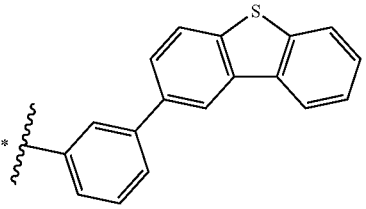
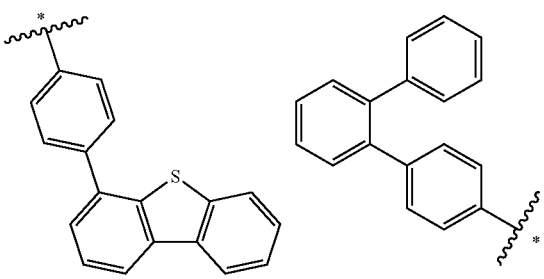
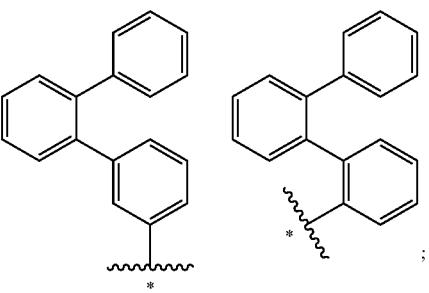
the above groups are optionally substituted by 0, 1, 2 or 3 substituents selected from deuterium, fluorine, chlorine, bromine, cyano, C1-C4 alkyl, C1-C3 haloalkyl, phenyl, naphthyl and dimethylfluorenyl.
3. The organic compound according to claim 1, wherein the organic compound is an organic compound represented by formula 1 as follows:

Formula 1

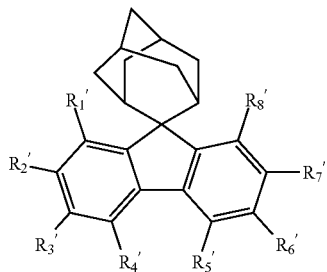

wherein, one of $R_1'$ to $R_4'$ is

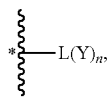

and the other three are each independently hydrogen, deuterium, fluorine, chlorine, bromine, cyano, phenyl, naphthyl, dimethylfluorenyl, dibenzothienyl, dibenzofuranyl, pyrimidinyl, methyl, ethyl, isopropyl or tert-butyl;

one of $R_5'$ to $R_8'$ is

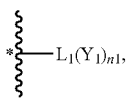

and the other three are each independently hydrogen, deuterium, fluorine, chlorine, bromine, cyano, phenyl, naphthyl, dimethylfluorenyl, dibenzothienyl, dibenzofuranyl, pyrimidinyl, methyl, ethyl, isopropyl or tert-butyl;

$n_1$ is 0, and n is 2;

Y is selected from the following structure:

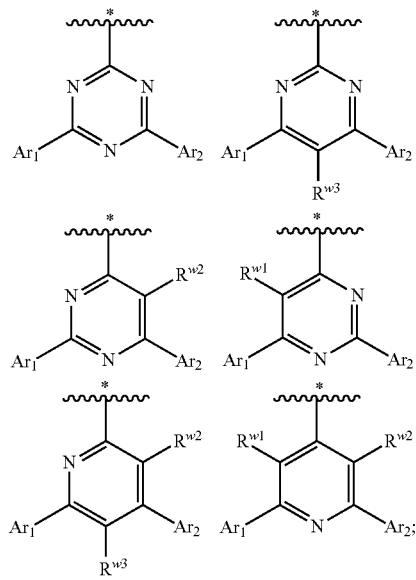

$L_1$ is hydrogen or deuterium;

$R^{w1}$, $R^{w2}$ and $R^{w3}$ are the same as or different from each other, and are independently hydrogen, deuterium, fluorine, chlorine, bromine, or cyano.

4. The organic compound according to claim 1, wherein the L is selected from the following groups: substituted or unsubstituted phenylene, substituted or unsubstituted biphenylene, substituted or unsubstituted terphenylene, substituted or unsubstituted quaterphenylene, substituted or unsubstituted quinquephenylene, substituted or unsubstituted naphthylene, substituted or unsubstituted naphthylphenylene, substituted or unsubstituted dinaphthylphenylene, substituted or unsubstituted fluorenylene, substituted or unsubstituted phenanthrylene, substituted or unsubstituted anthrylene, substituted or unsubstituted triazinylene, substituted or unsubstituted pyrimidylene, substituted or unsubstituted pyridinylene, substituted or unsubstituted pyrazylene, substituted or unsubstituted phenyl-dibenzofuranylene, substituted or unsubstituted phenyl-dibenzothienylene, substituted or unsubstituted dibenzothienylene, substituted or unsubstituted dibenzofuranylene, substituted or unsubstituted carbazolylene, N-phenylcarbazolylene, substituted or unsubstituted quinolylene, substituted or unsubstituted phenanthrolinylene;

the substituent of L is selected from the group consisting of deuterium, fluorine, chlorine, bromine, cyano, C1-C4 alkyl, C1-C3 haloalkyl, phenyl, naphthyl, fluorenyl, C12 heteroaryl, C3 alkylsilyl, cyclopentyl and cyclohexyl.

5. The organic compound according to claim 3, wherein the L is selected from the following groups:

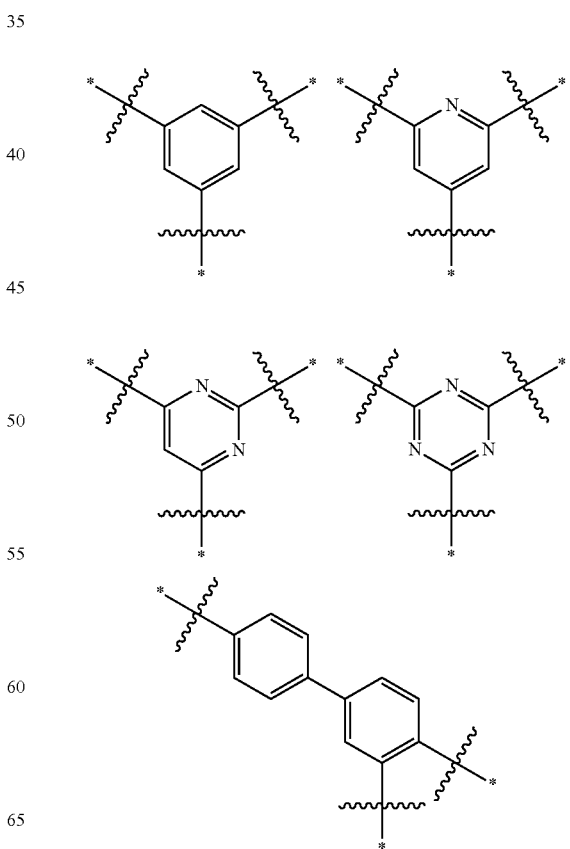

243
-continued
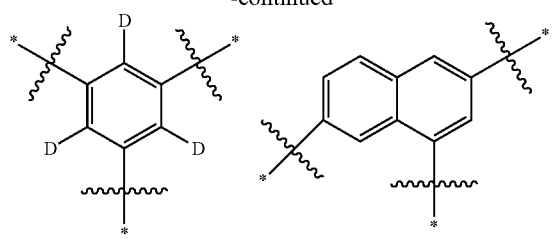
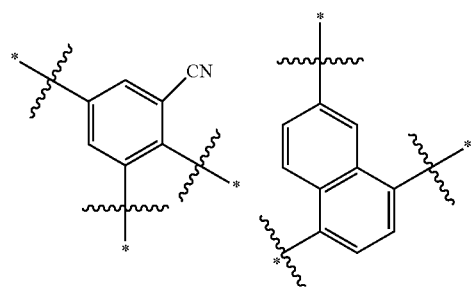
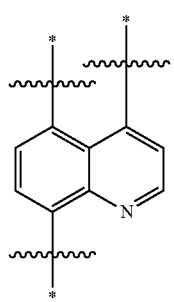
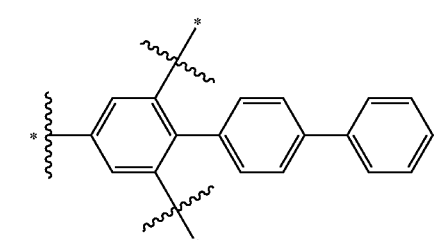
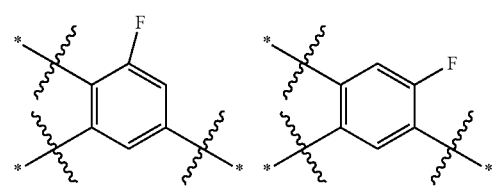
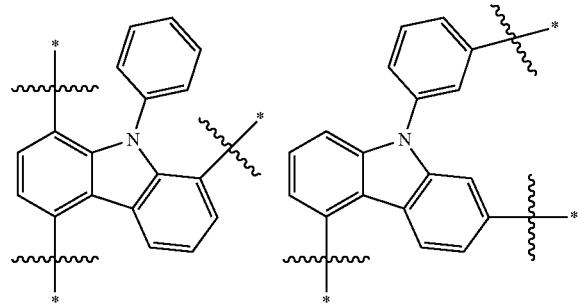
244
-continued
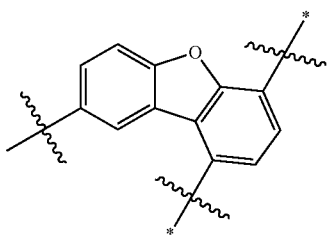
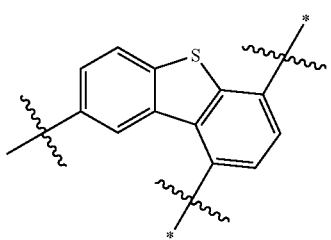
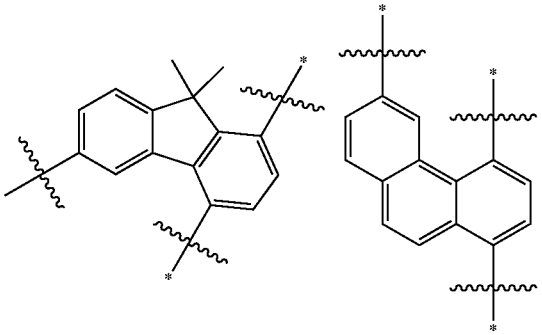
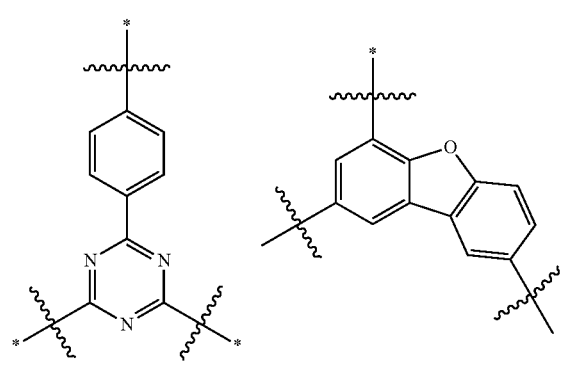
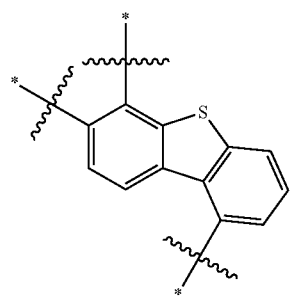

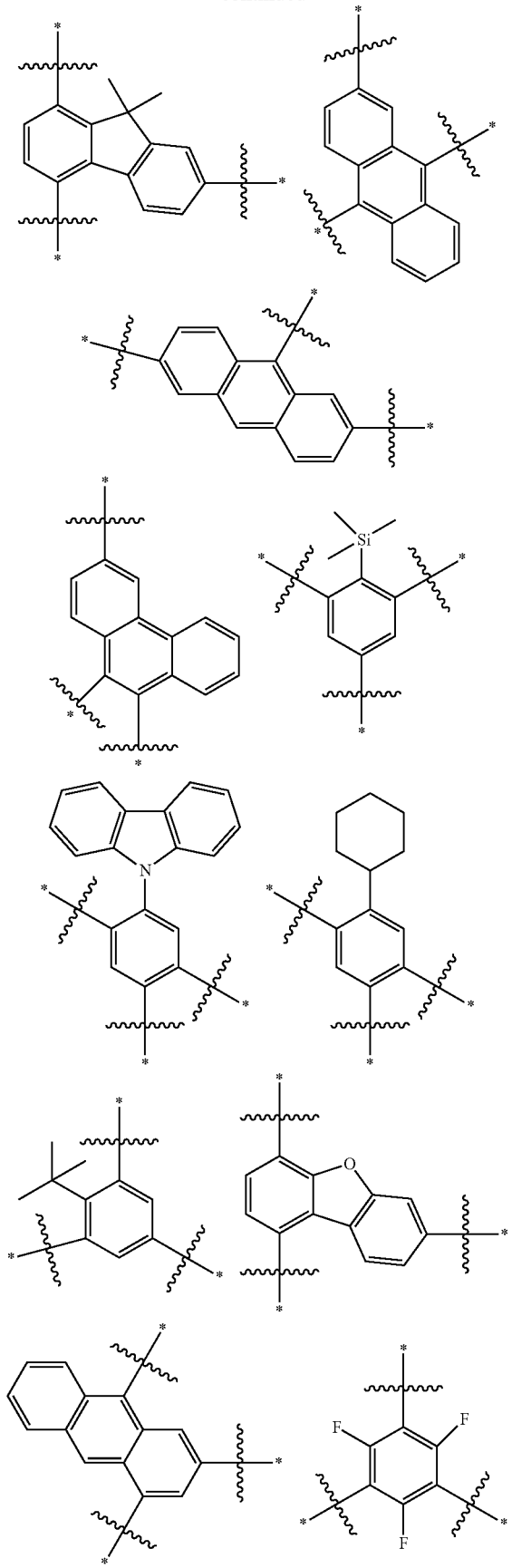
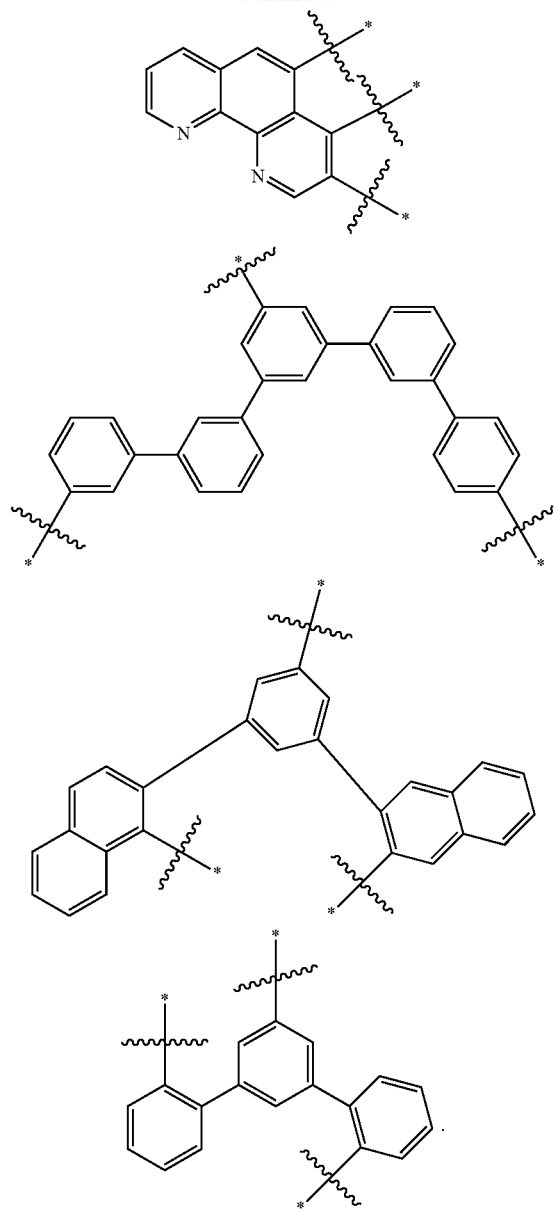
6. The organic compound according to claim 1, wherein the organic compound is an organic compound represented by formula 2 as follows:
Formula 2
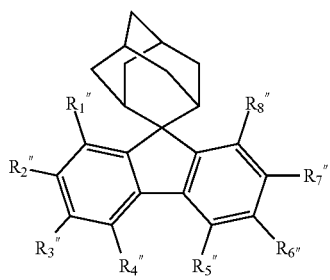

wherein, one of $R_1''$ to $R_4''$ is

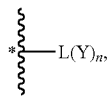

and the other three are each independently hydrogen, deuterium, fluorine, chlorine, bromine, cyano, phenyl, naphthyl, dimethylfluorenyl, dibenzothienyl, dibenzofuranyl, pyrimidinyl, methyl, ethyl, isopropyl or tert-butyl;

one of $R_5''$ to $R_8''$ is

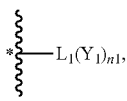

and the other three are each independently hydrogen, deuterium, fluorine, chlorine, bromine, cyano, phenyl, naphthyl, dimethylfluorenyl, dibenzothienyl, dibenzofuranyl, pyrimidinyl, methyl, ethyl, isopropyl, or tert-butyl;

both $n_1$ and n are 1;

Y and $Y_1$ are each independently selected from:

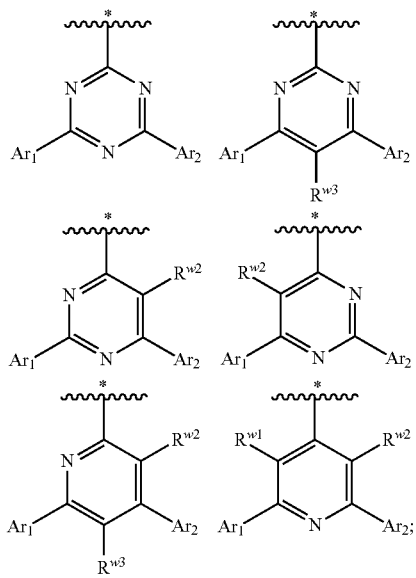

$R^{w1}$, $R^{w2}$ and $R^{w3}$ are the same as or different from each other, and are each independently hydrogen, deuterium, fluorine, chlorine, bromine, or cyano.

7. The organic compound according to claim 1, wherein L and $L_1$ are the same as or different from each other, and are each independently selected from a single bond, or a substituted or unsubstituted group as follows:

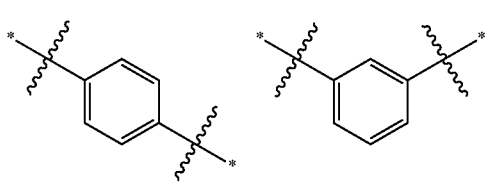

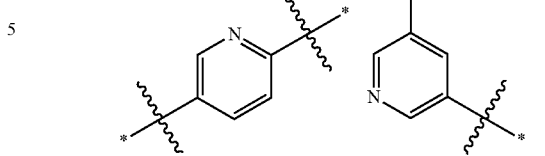

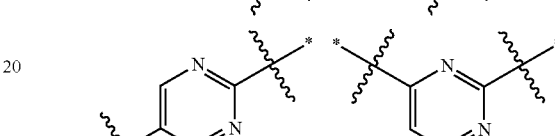

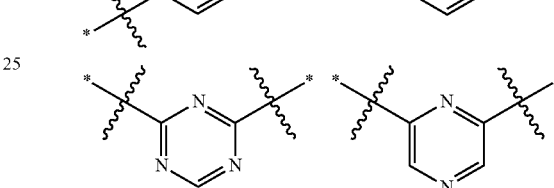

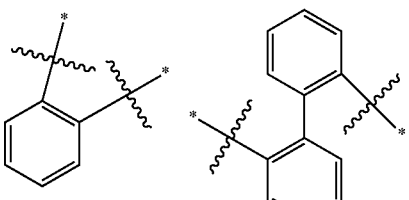

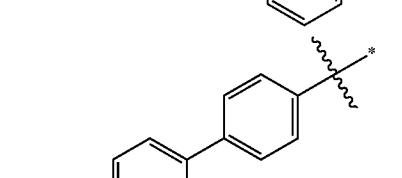

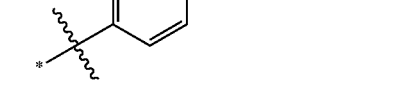

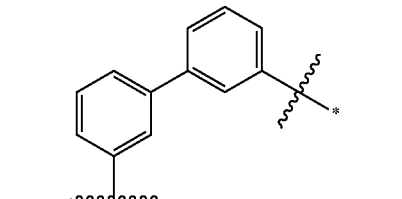

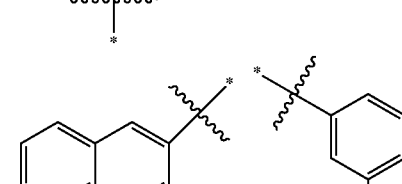

-continued
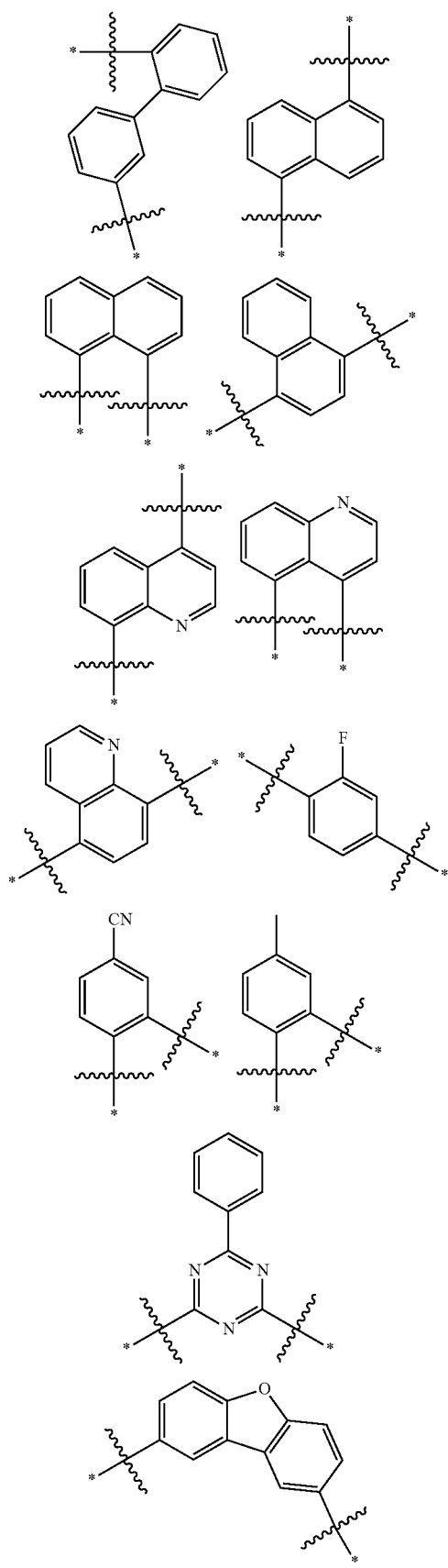
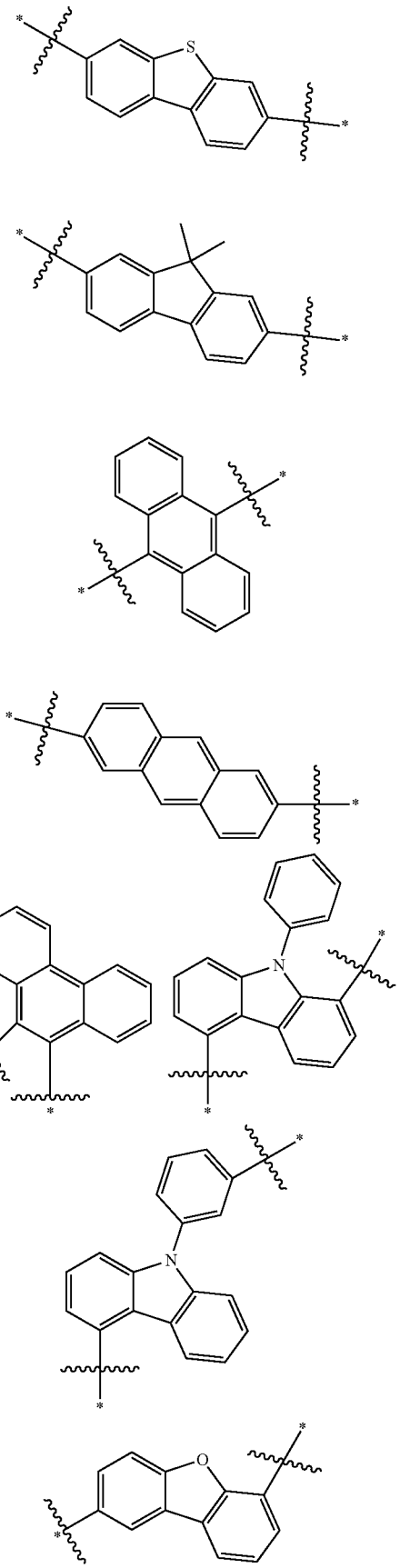

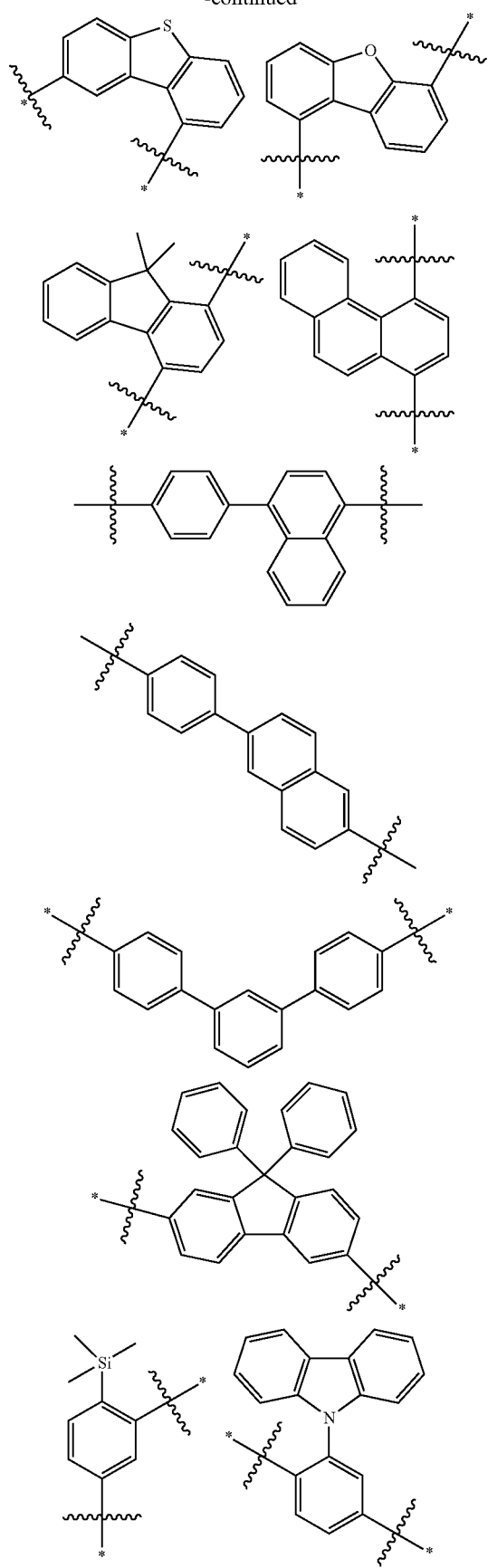
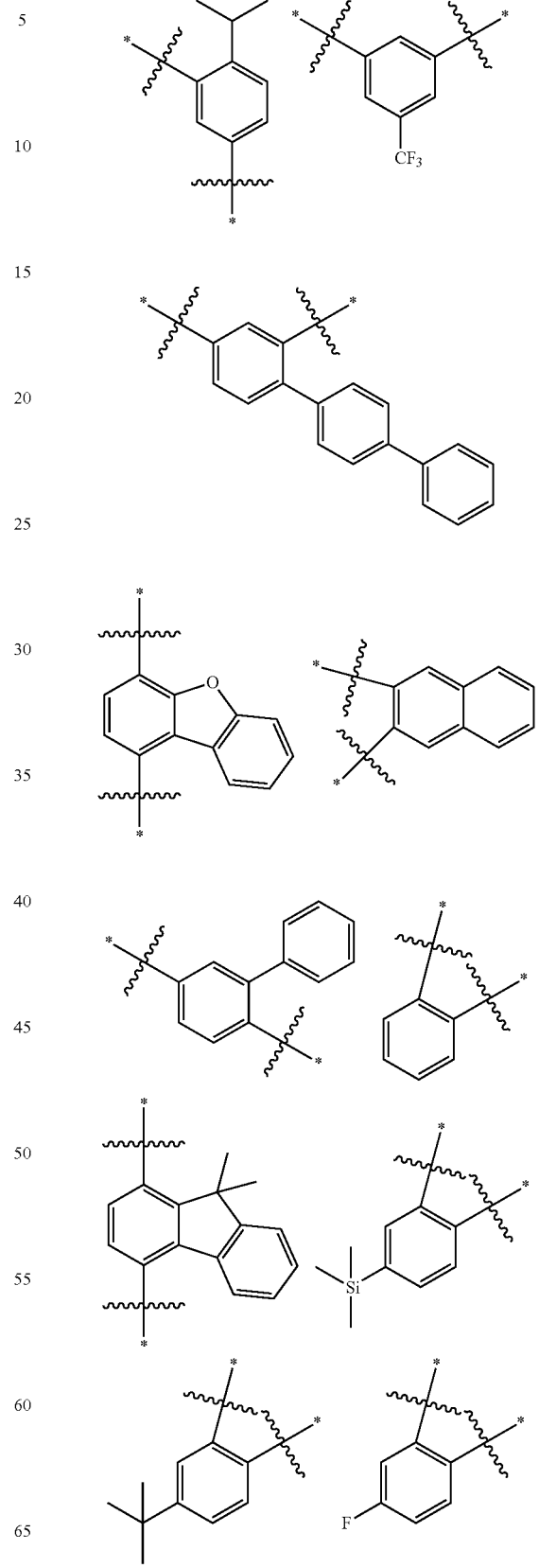

253
-continued

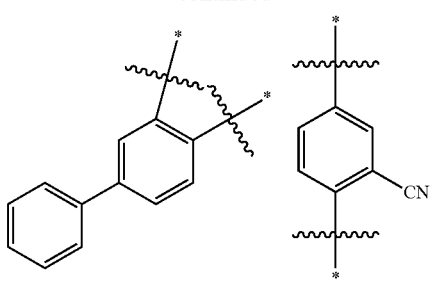

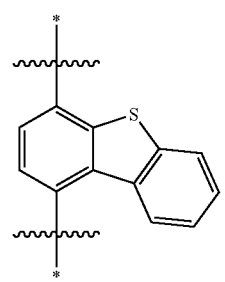

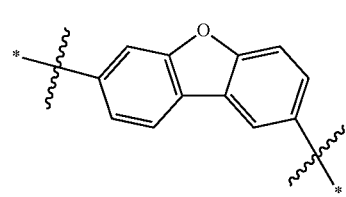

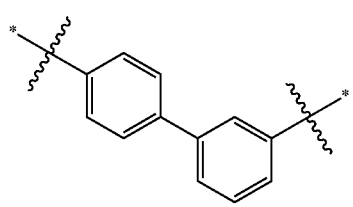

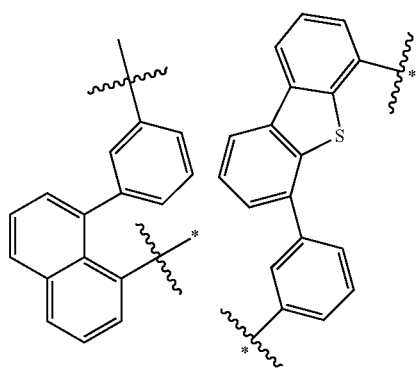

254
-continued

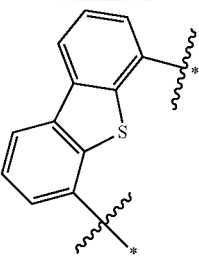

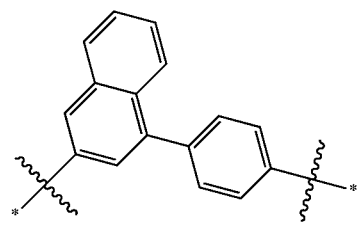

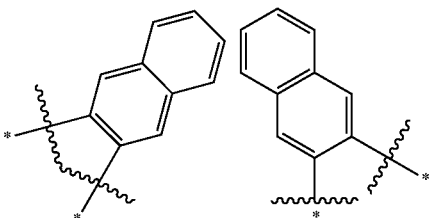

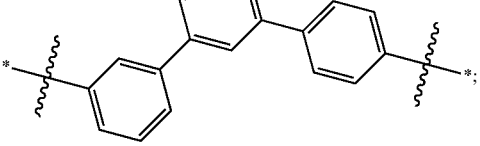

the above groups are optionally substituted by 0, 1, 2 or 3 substituents selected from deuterium, fluorine, chlorine, cyano, methyl, ethyl, isopropyl, tert-butyl, cyclopentyl, cyclohexyl, trifluoromethyl and trimethylsilyl.

8. The organic compound according to claim 6, wherein the organic compound represented by formula 2 is selected from any of the following:

Compound 15
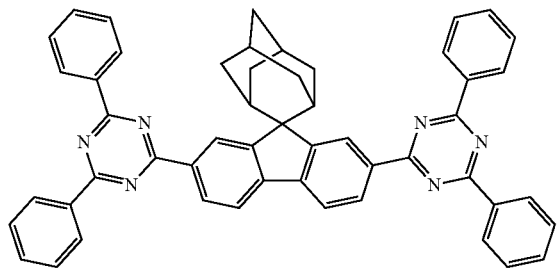
Compound 16
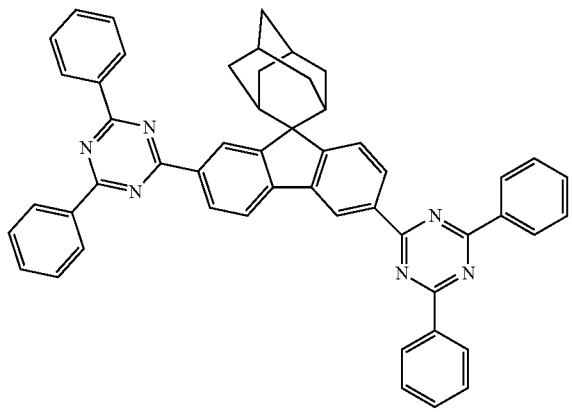
Compound 17
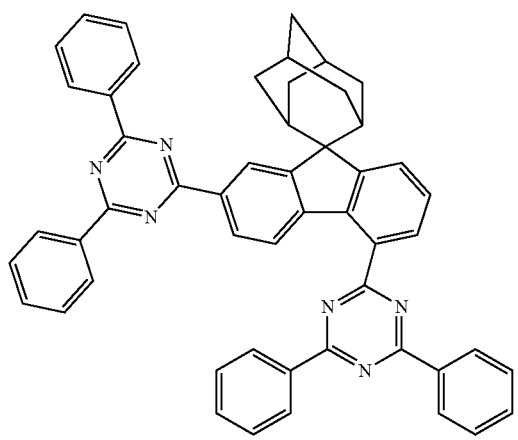
Compound 18
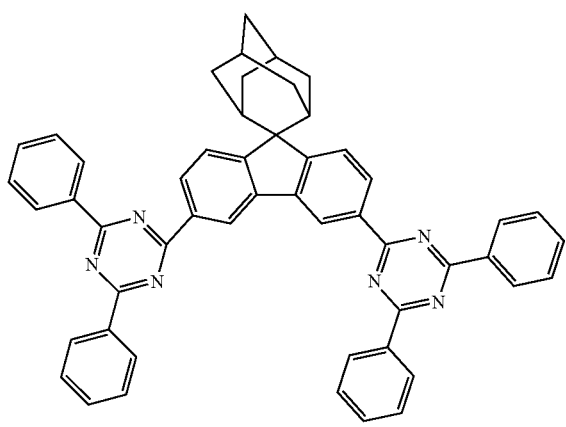
Compound 19
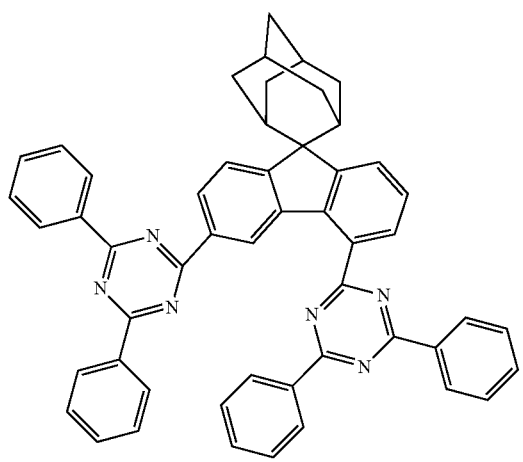
Compound 20
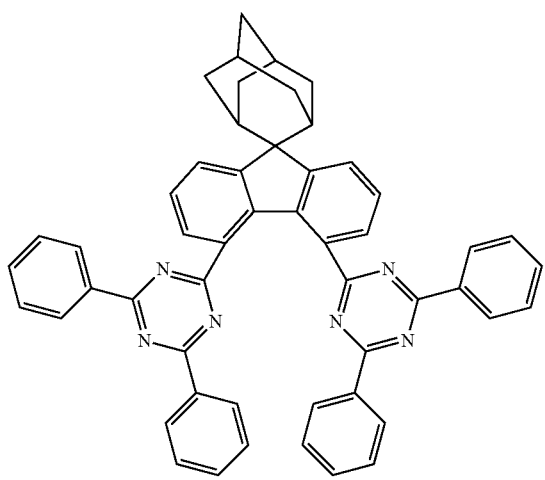

-continued
Compound 21
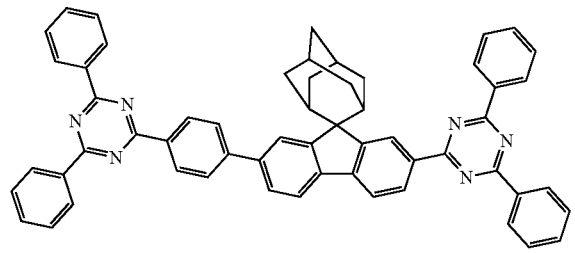
Compound 22
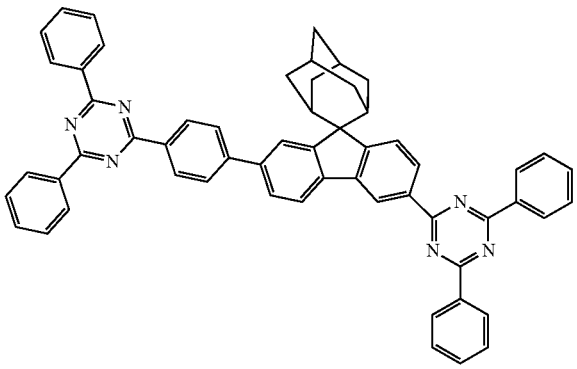
Compound 23
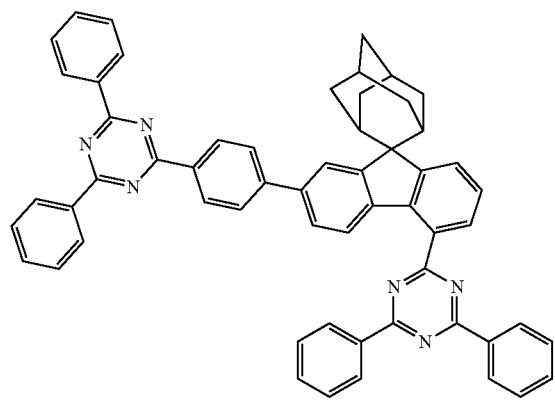
Compound 24
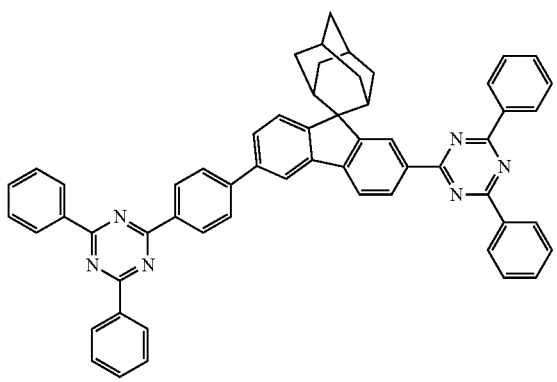
Compound 25
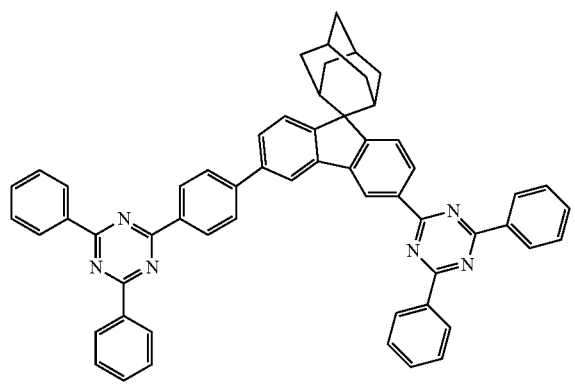
Compound 26
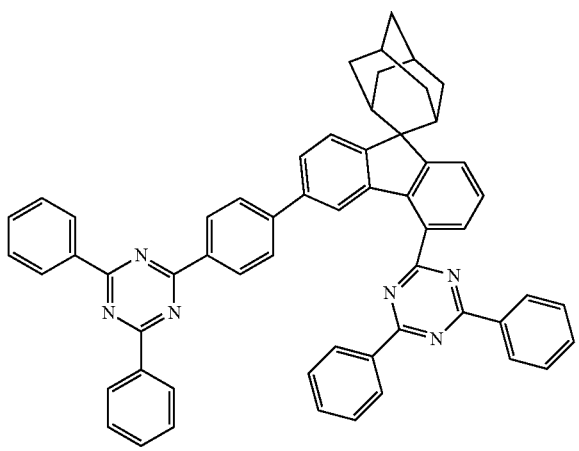

-continued
Compound 27
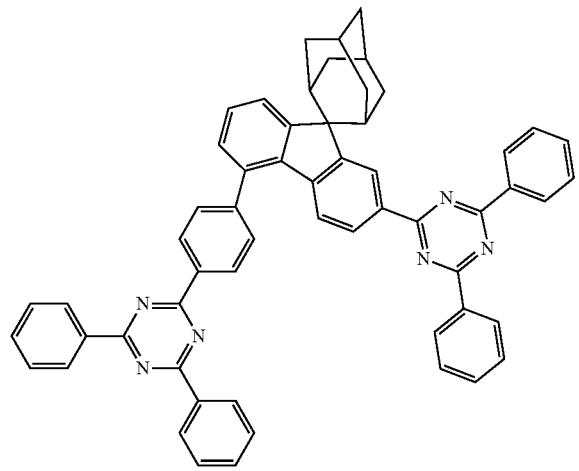
Compound 28
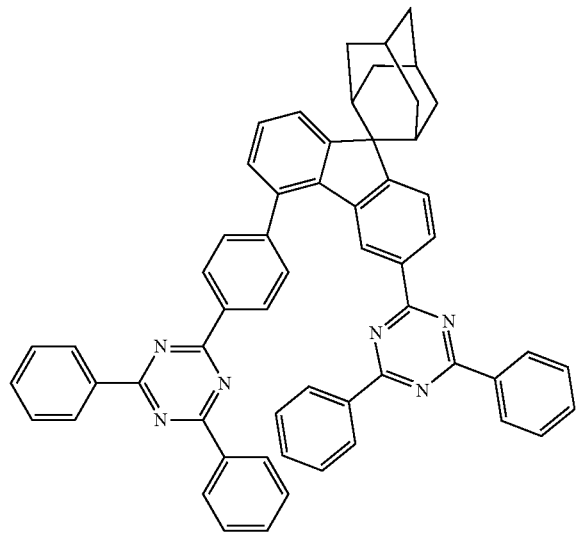
Compound 29
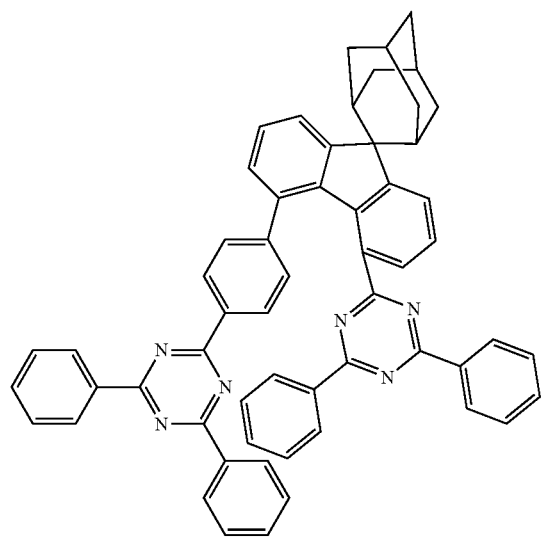
Compound 30
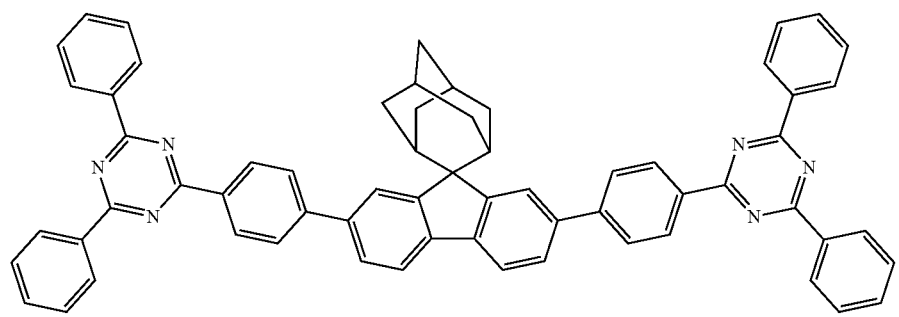

-continued
Compound 31
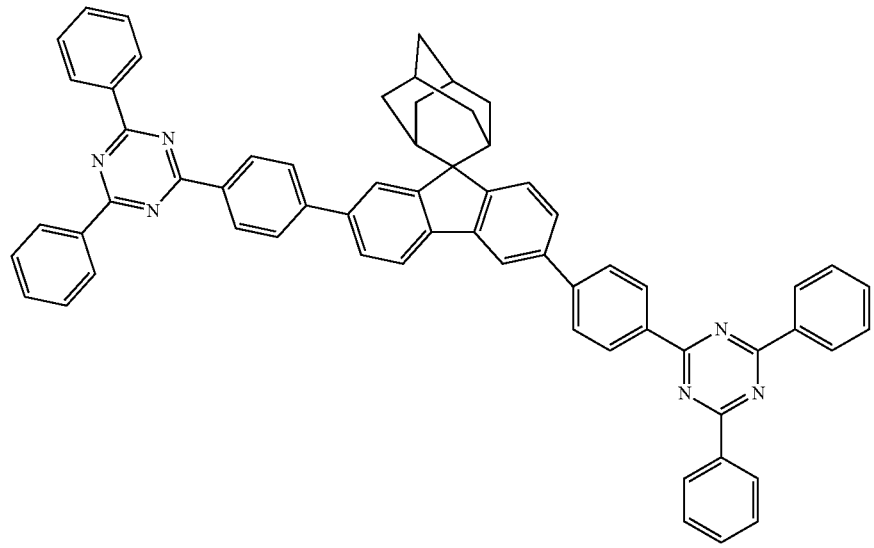
Compound 32
Compound 33
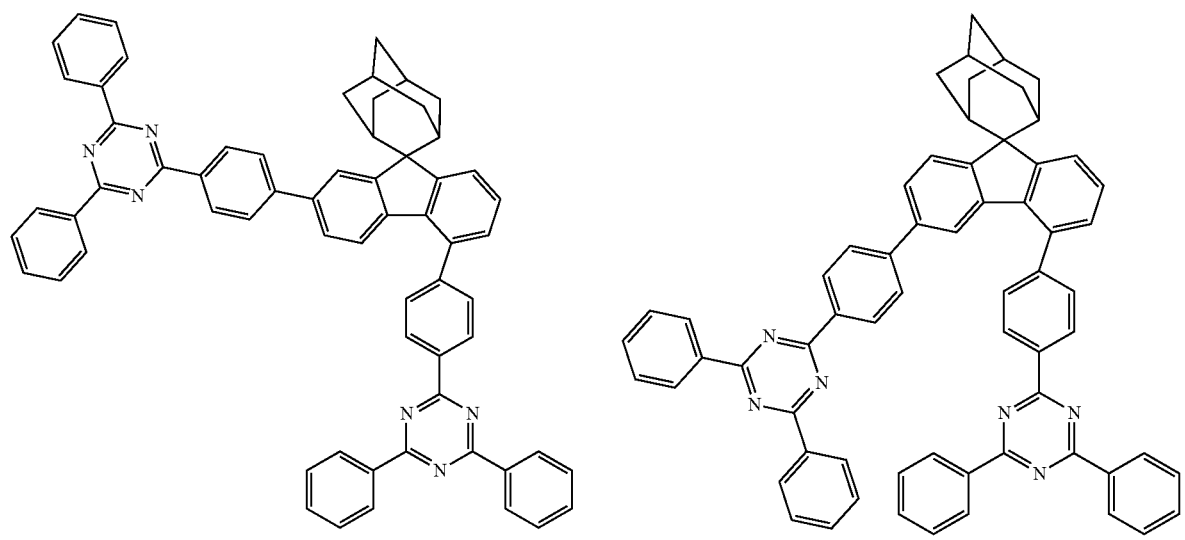
Compound 34
Compound 35
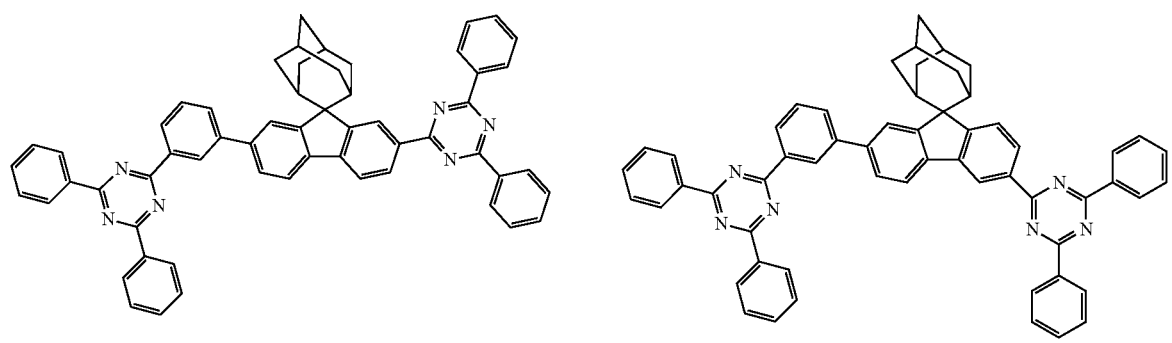

-continued
Compound 36
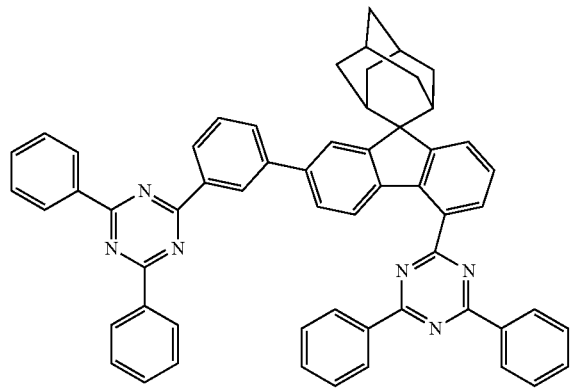
Compound 37
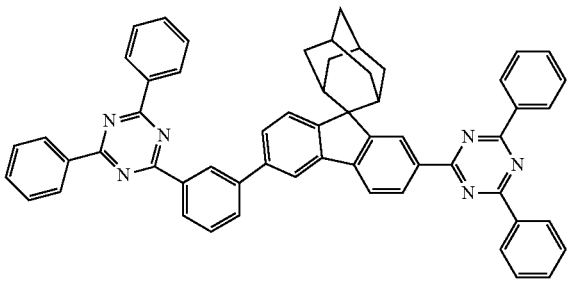
Compound 38
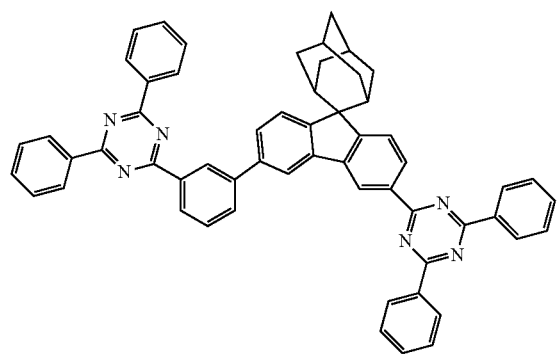
Compound 39
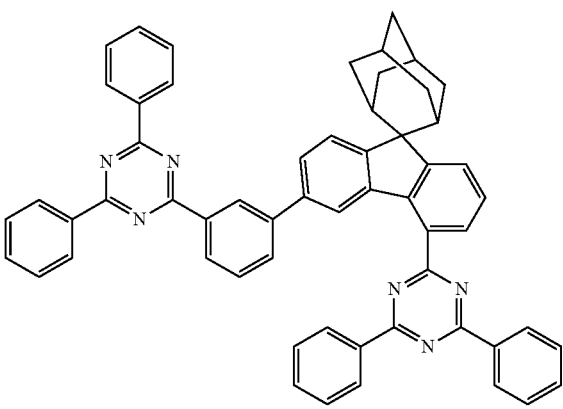
Compound 40
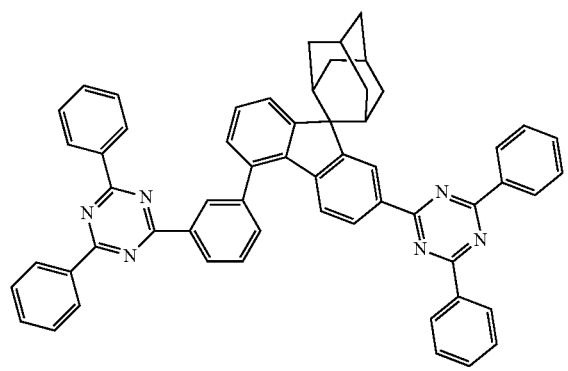
Compound 41
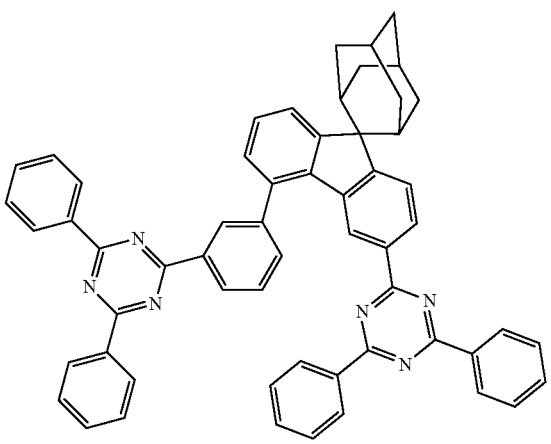

Compound 42
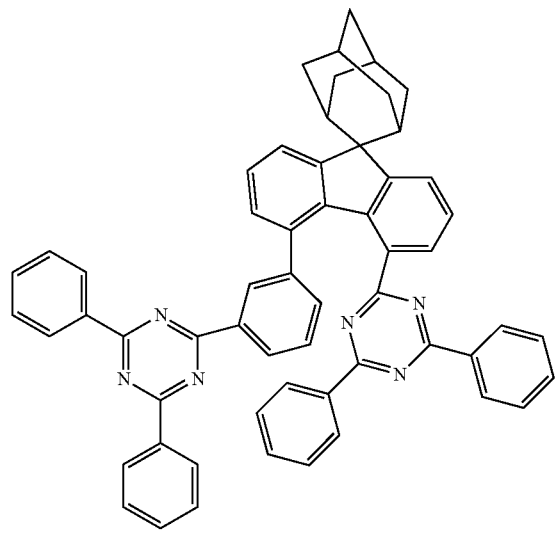
Compound 43
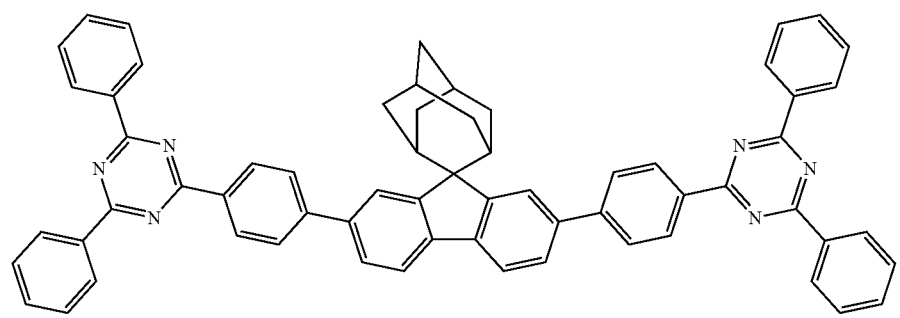
Compound 44
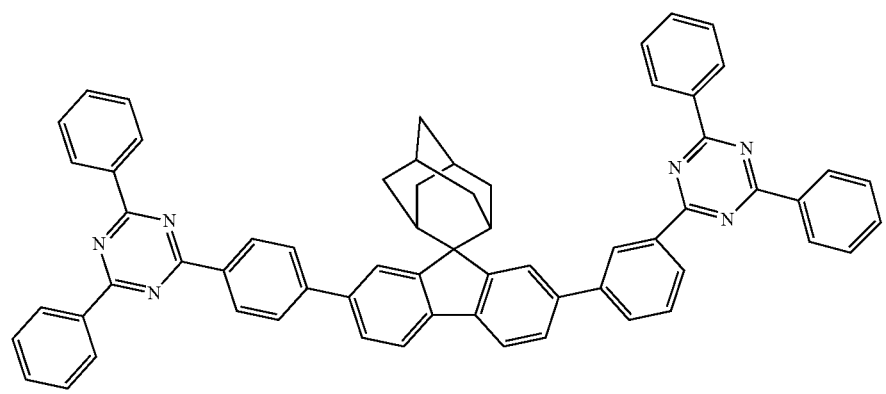

Compound 45
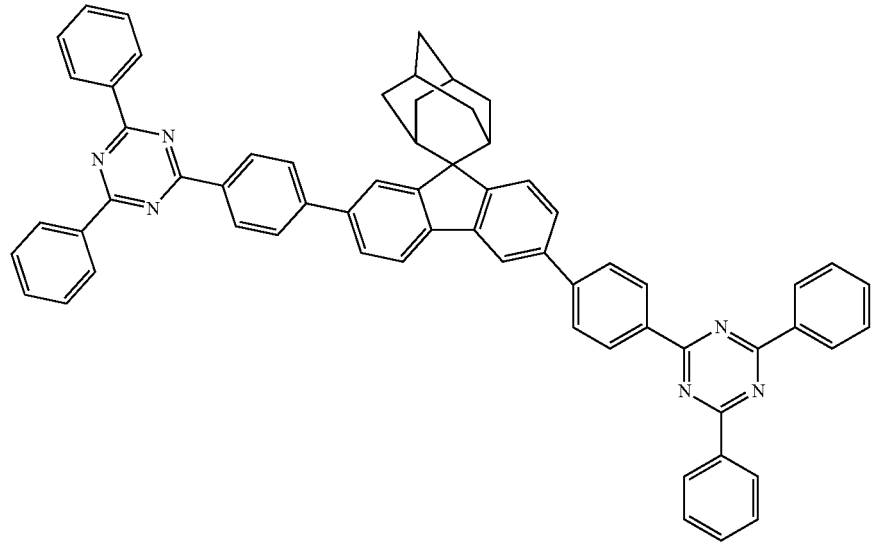
Compound 46
Compound 47
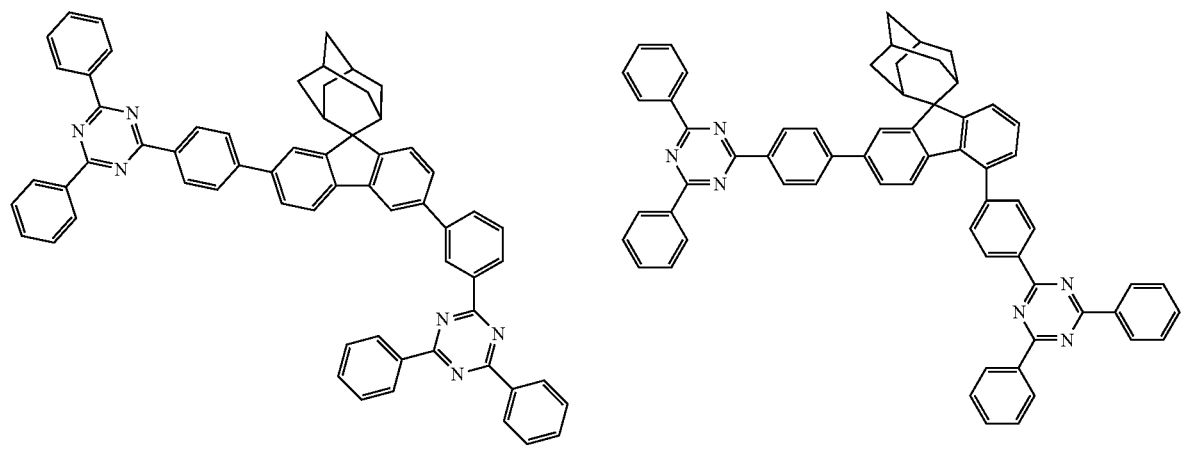
Compound 48
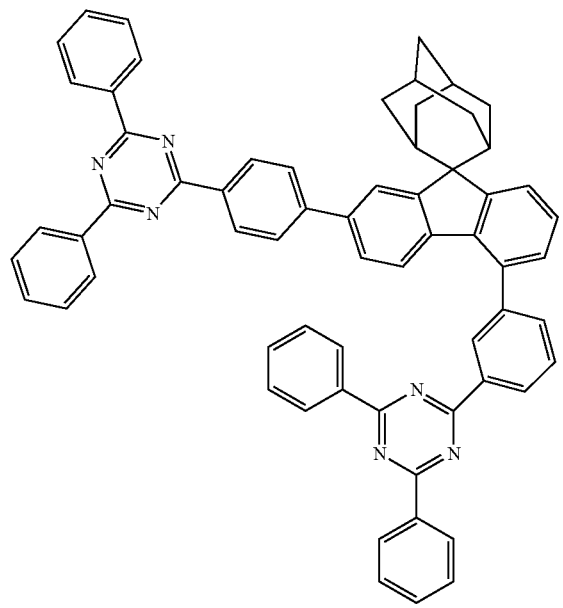

-continued
Compound 49
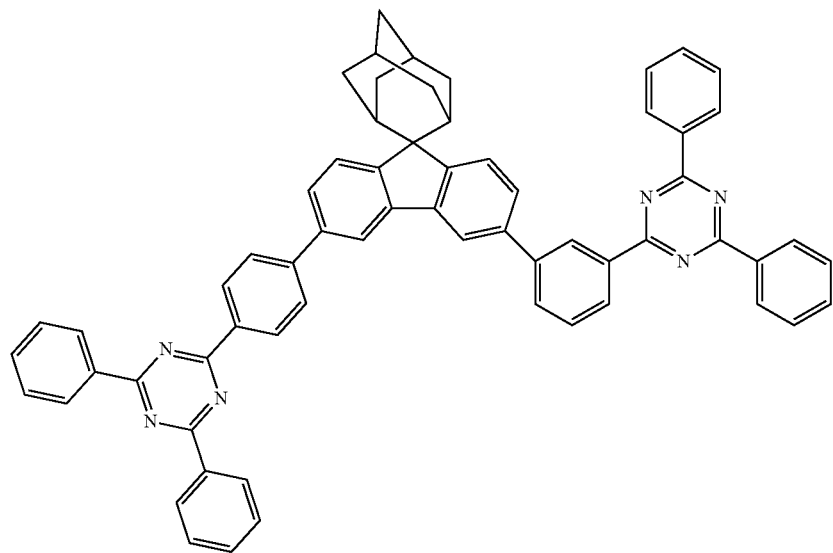
Compound 50 Compound 51
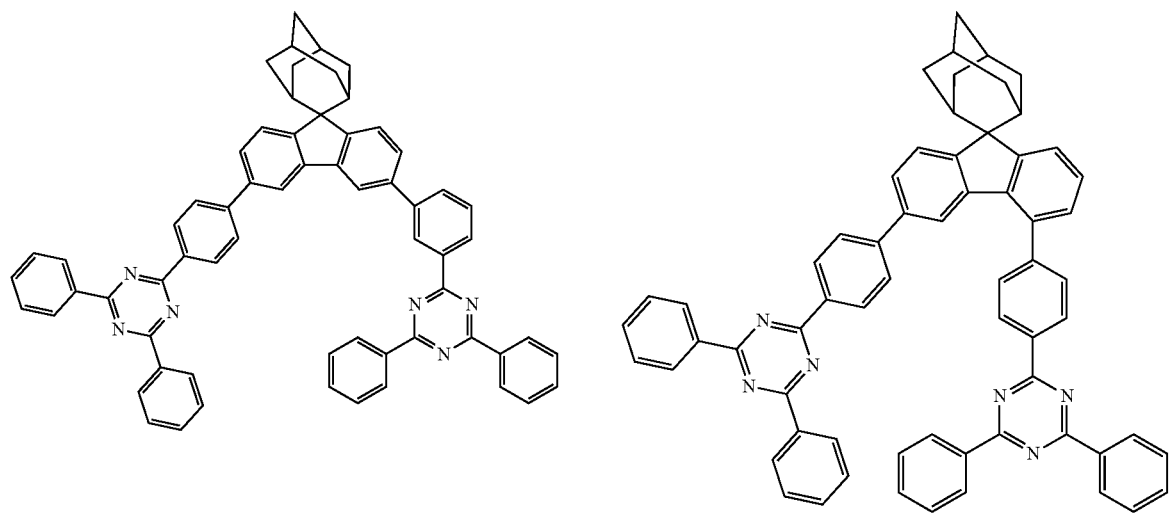

-continued
Compound 52
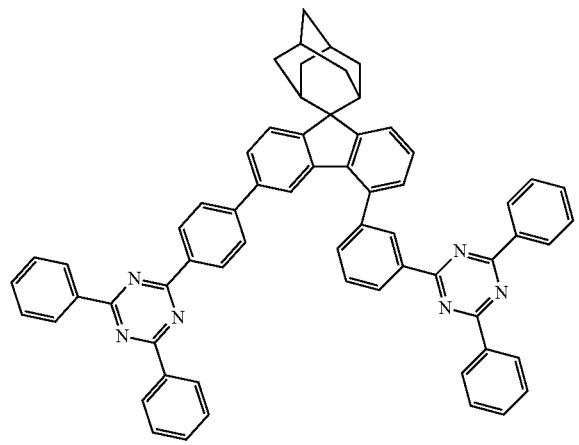
Compound 53
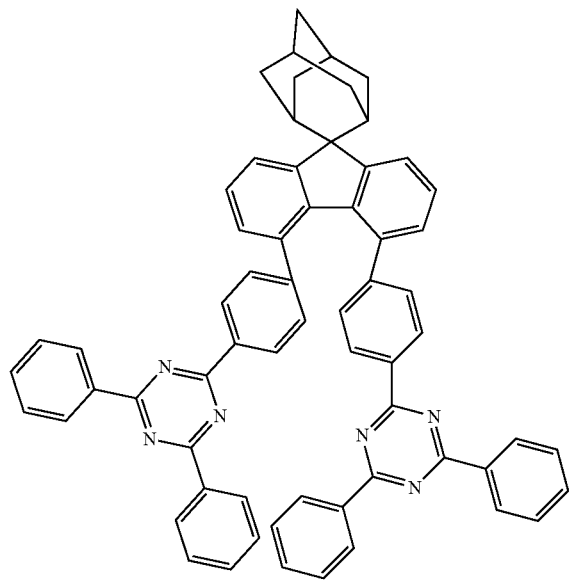
Compound 54
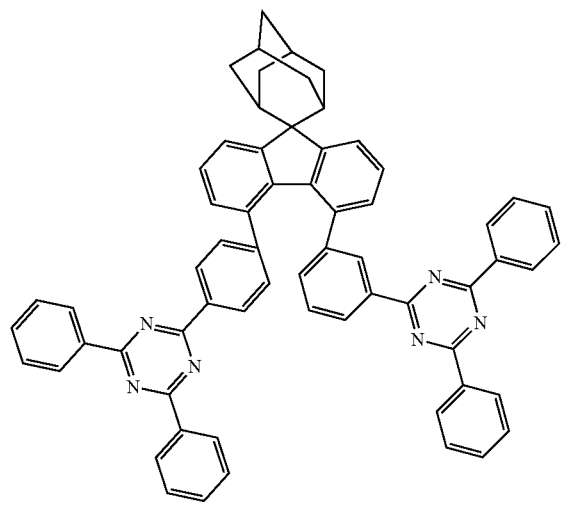
Compound 55
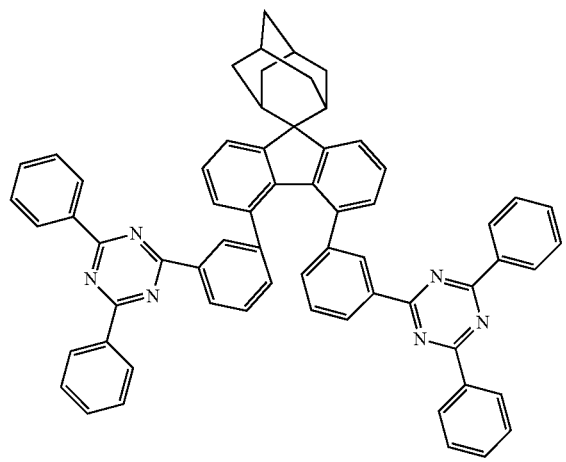
Compound 56
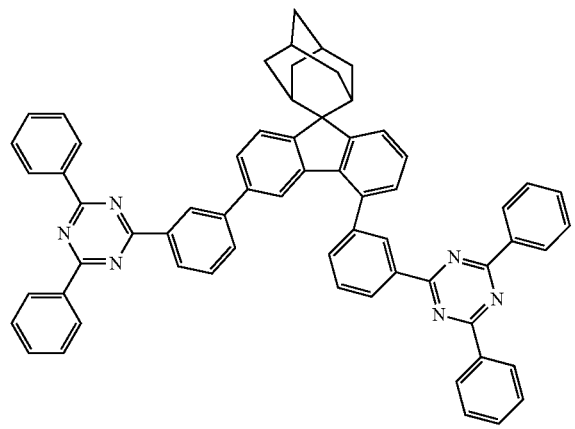
Compound 57
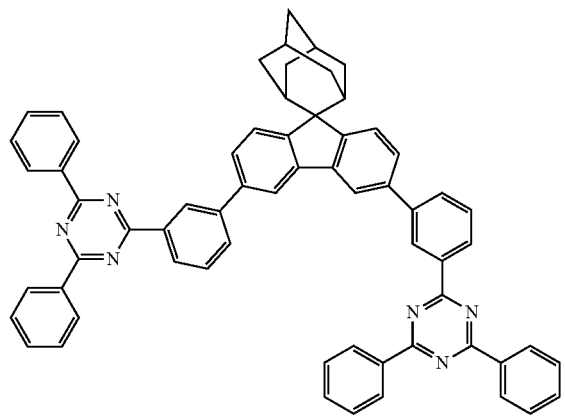

Compound 58
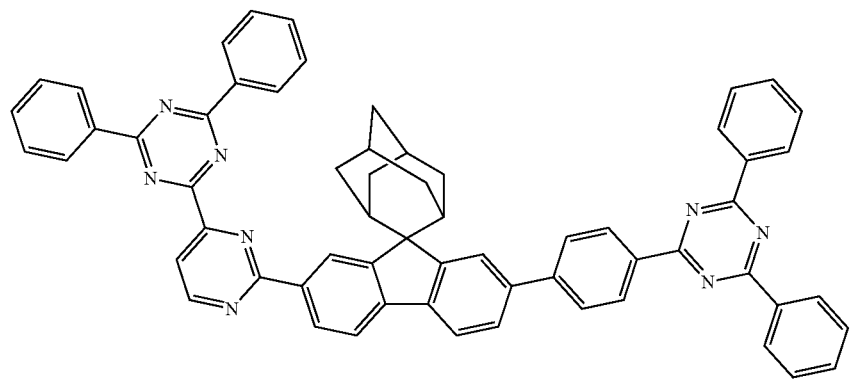
Compound 59
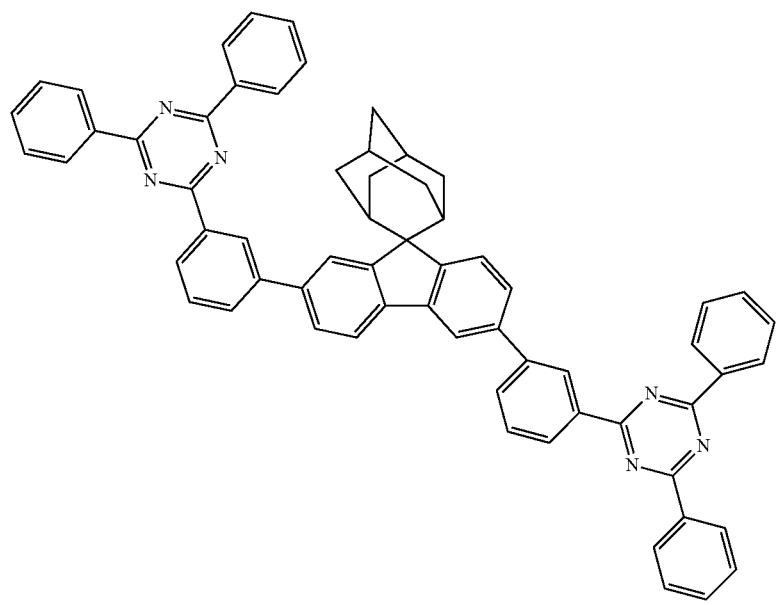
Compound 60
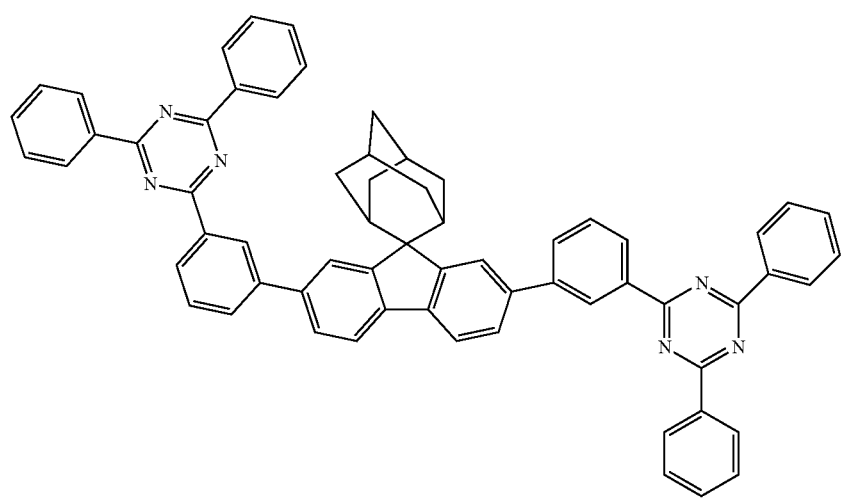

-continued
Compound 61
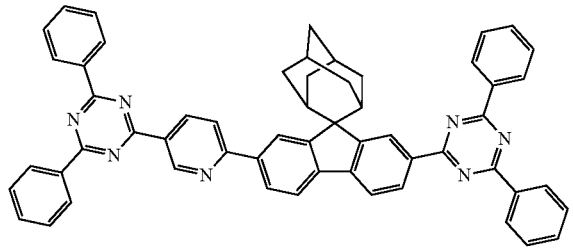
Compound 62
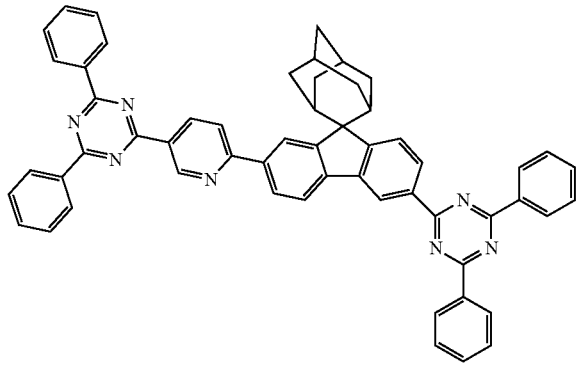
Compound 63
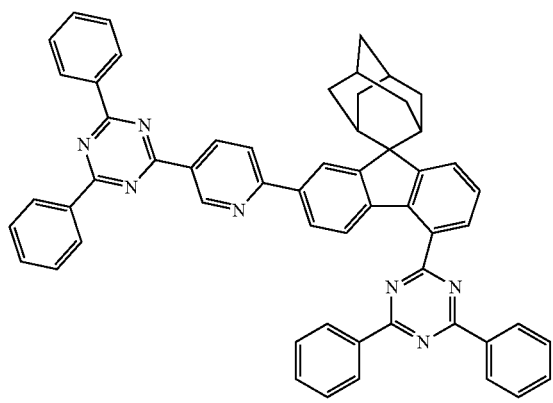
Compound 64
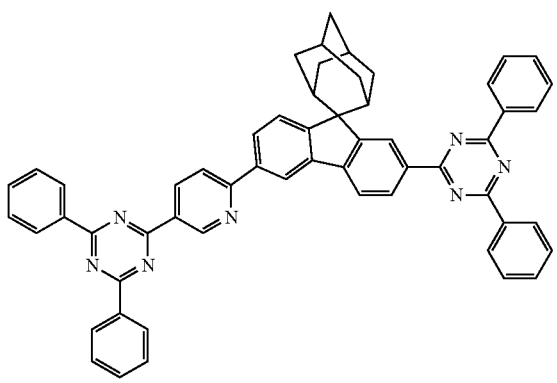
Compound 65
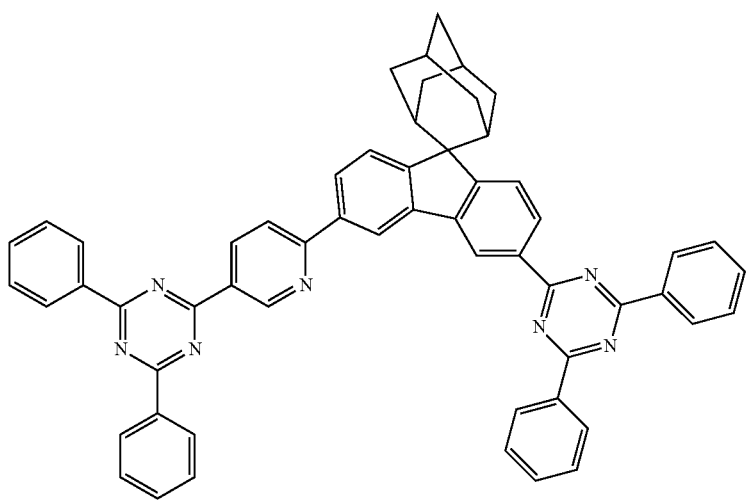

Compound 66
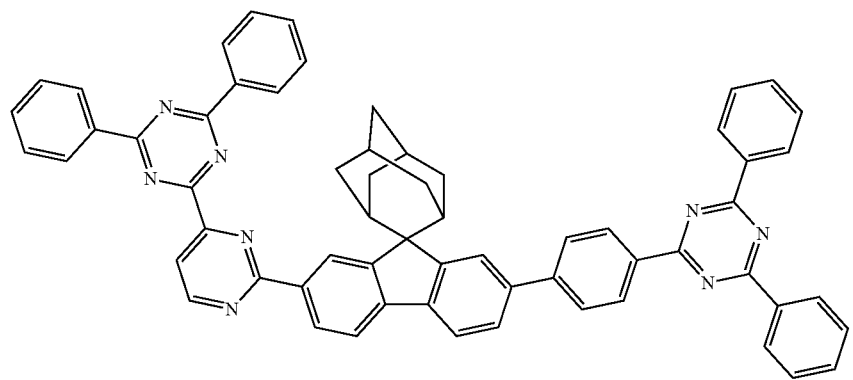
Compound 67
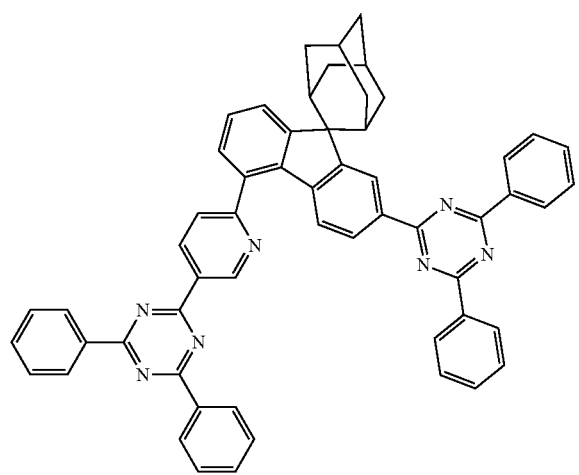
Compound 68
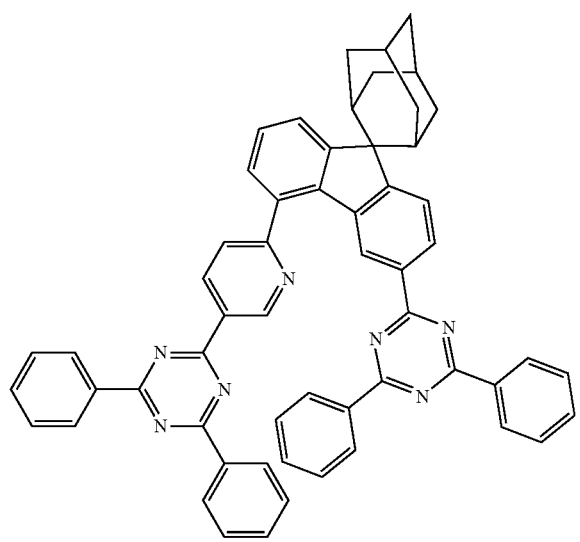
Compound 69
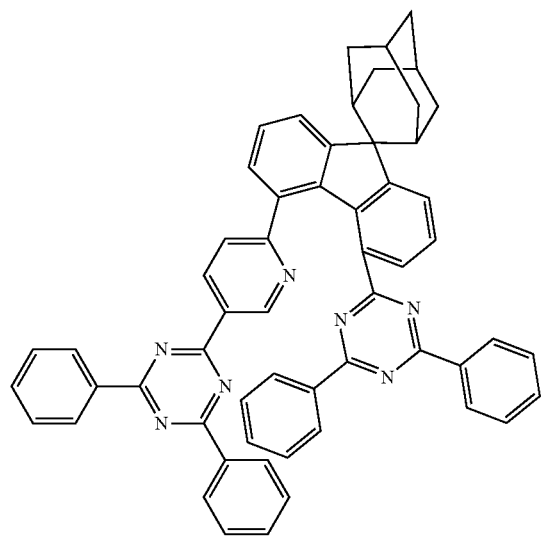

Compound 70
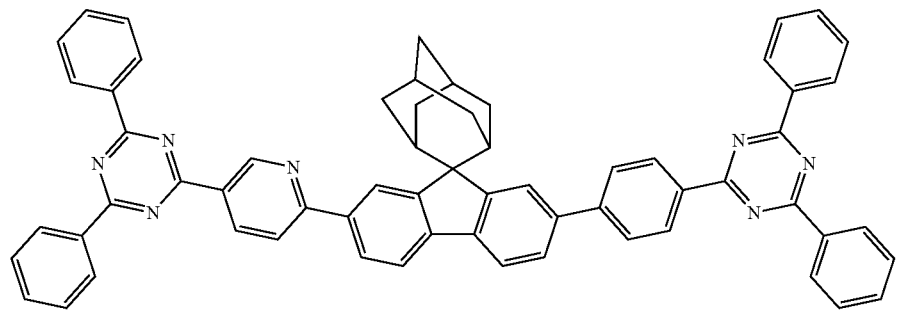
Compound 71
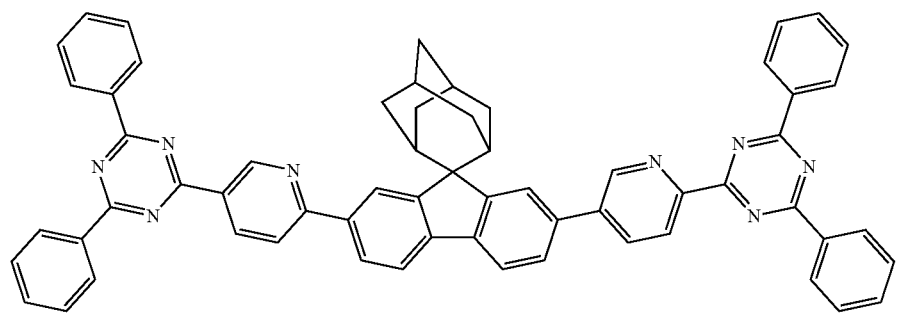
Compound 72
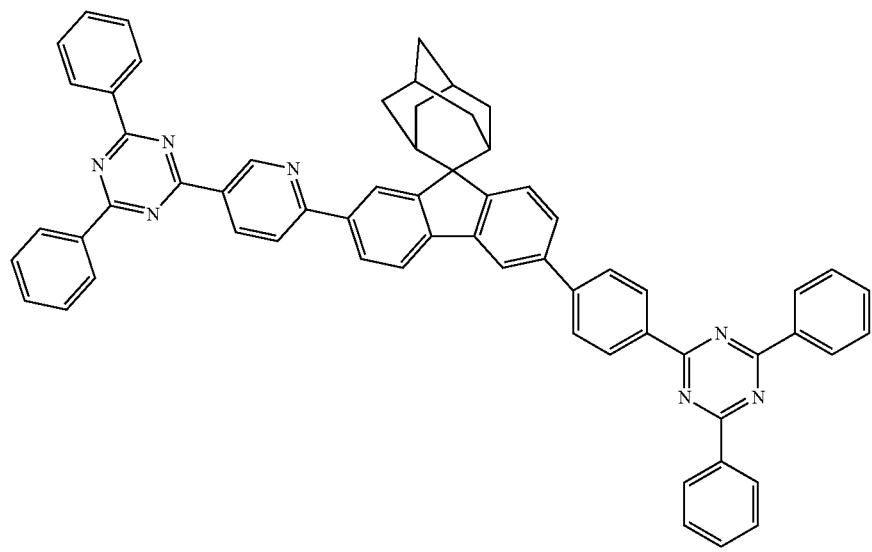

Compound 73
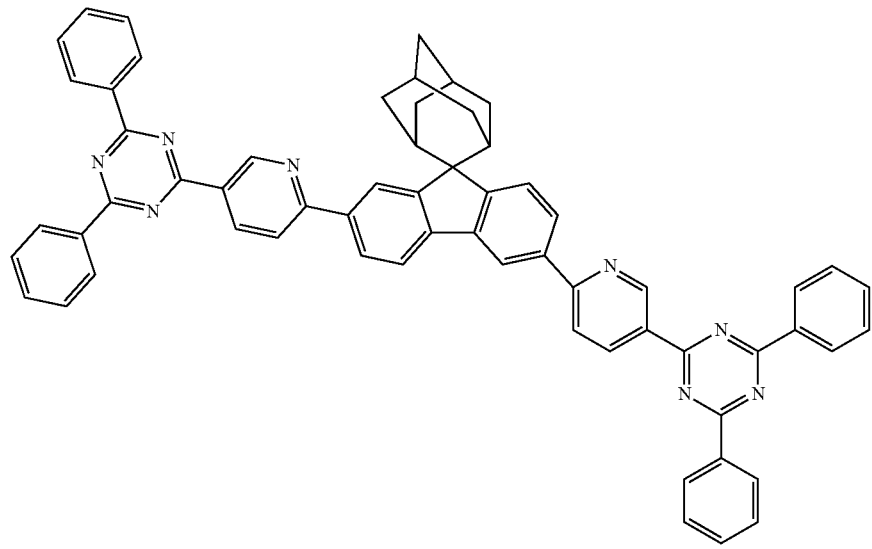
Compound 74
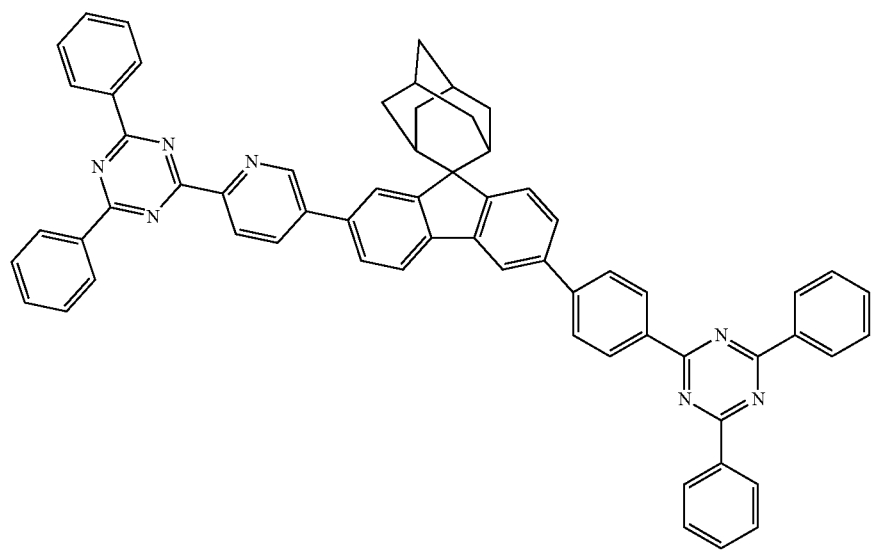
Compound 75
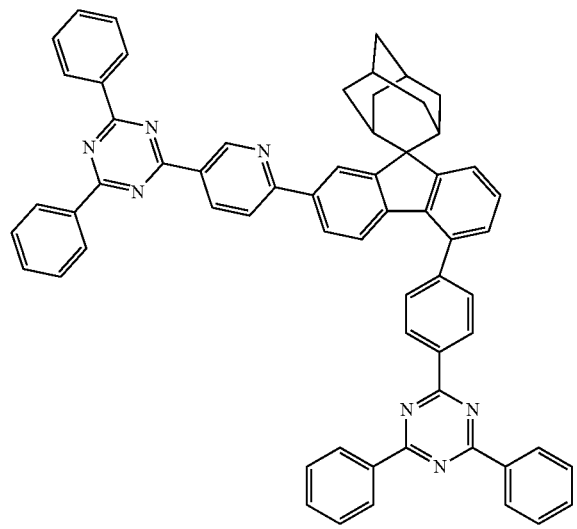
Compound 76
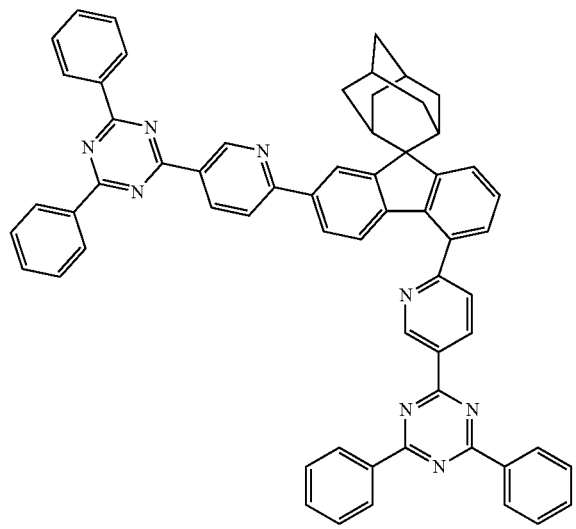

-continued
Compound 77
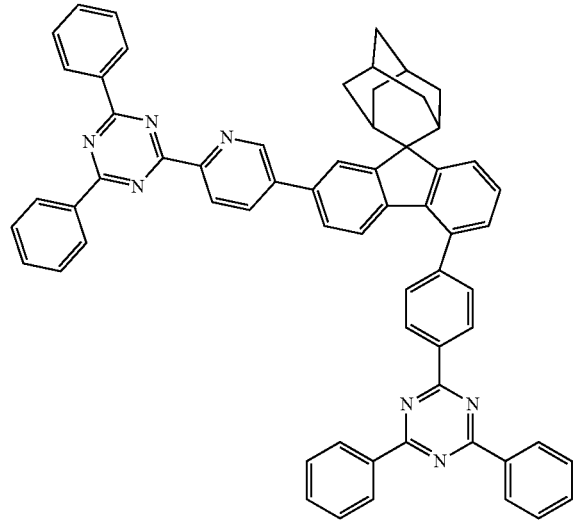
Compound 78
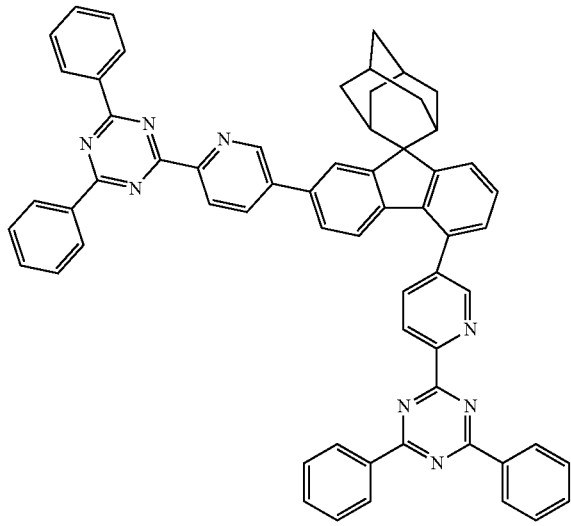
Compound 79
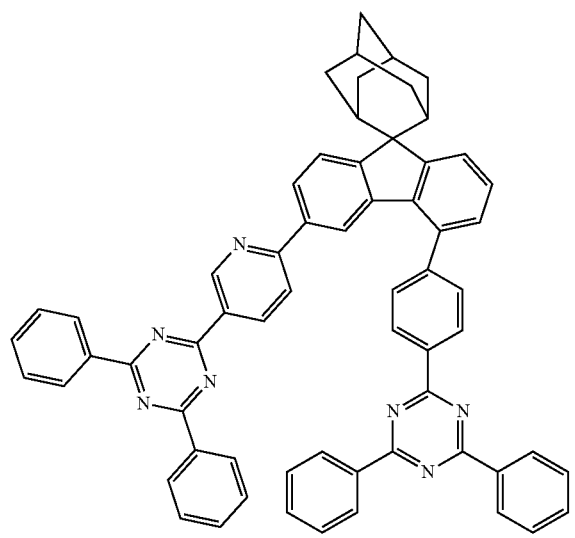
Compound 80
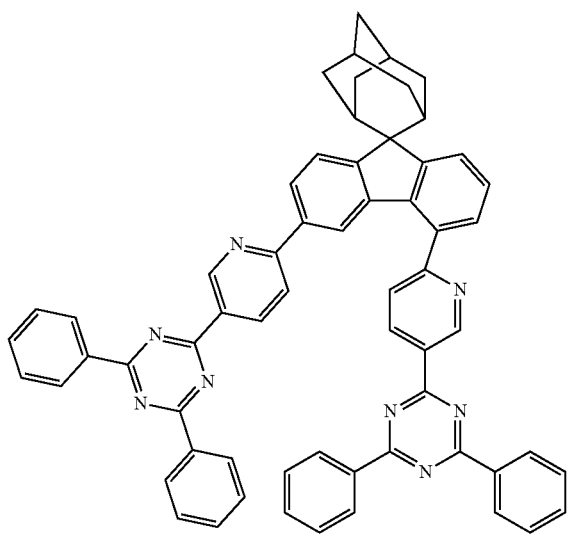
Compound 81
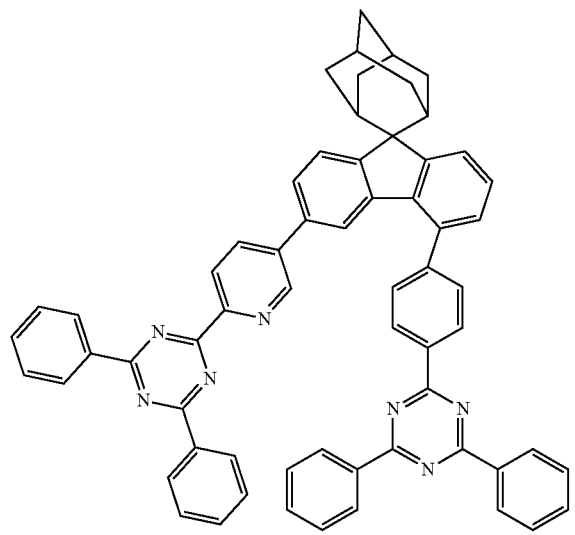
Compound 82
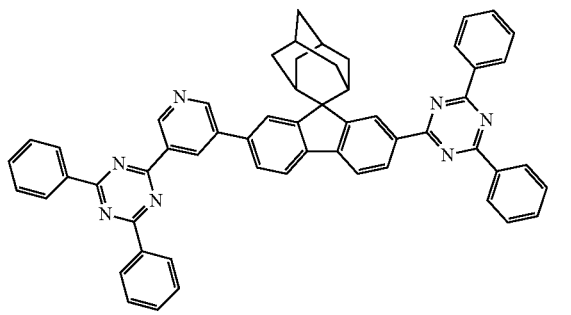

-continued
Compound 83
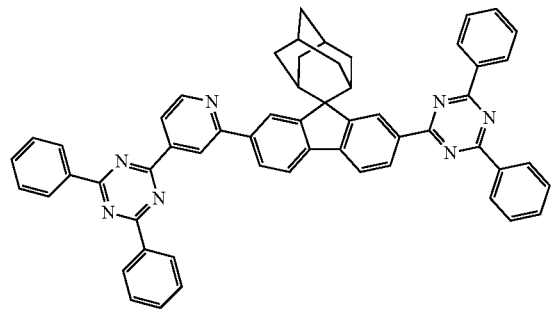
Compound 84
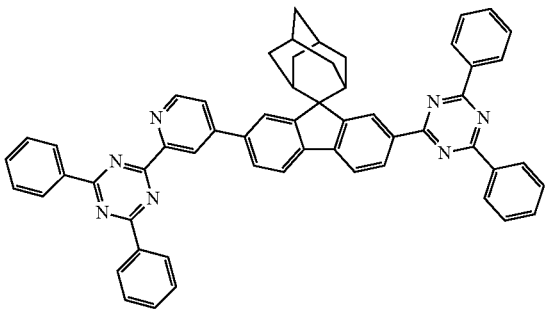
Compound 85
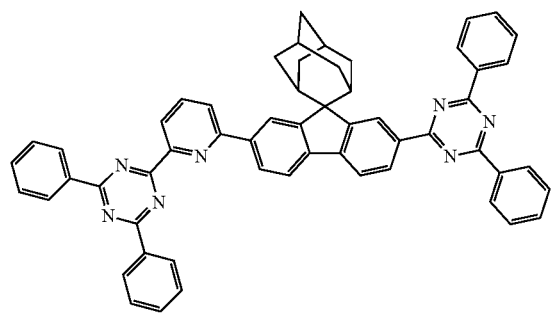
Compound 86
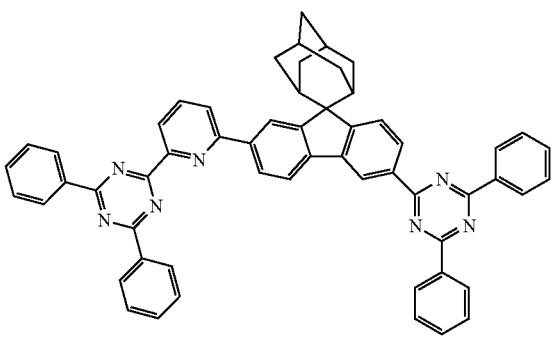
Compound 87
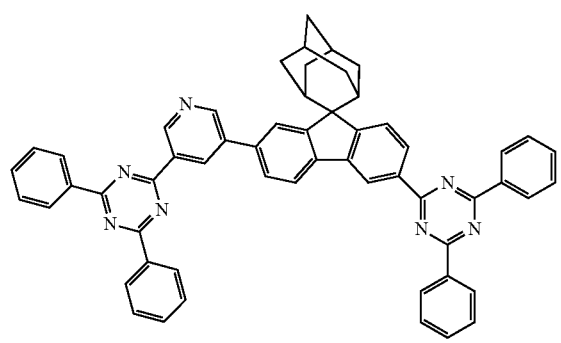
Compound 88
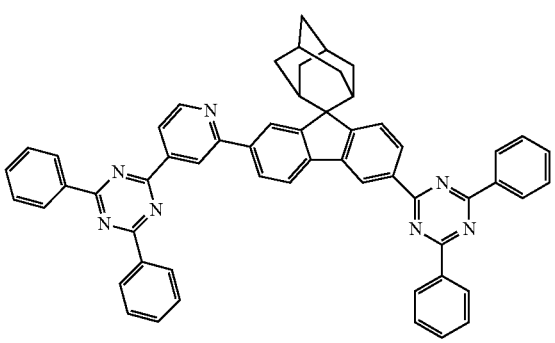
Compound 89
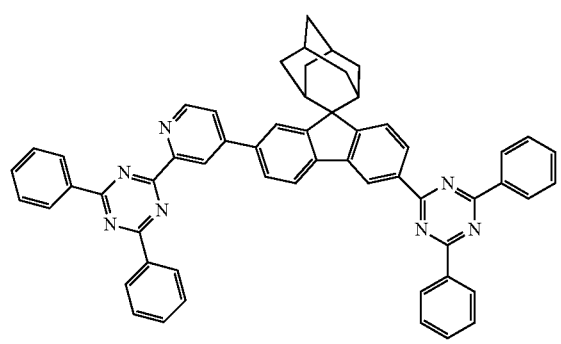
Compound 90
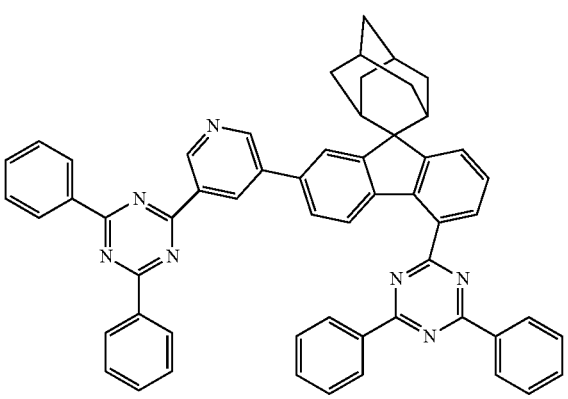

-continued
Compound 91
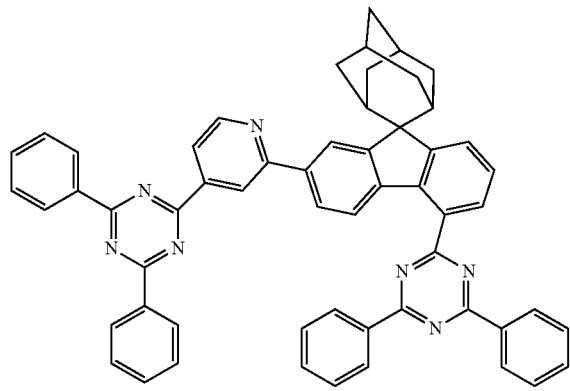
Compound 92
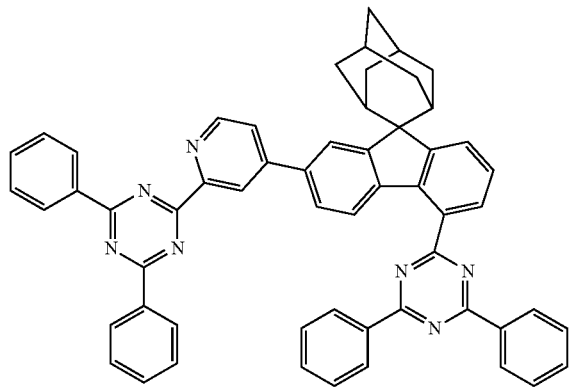
Compound 93
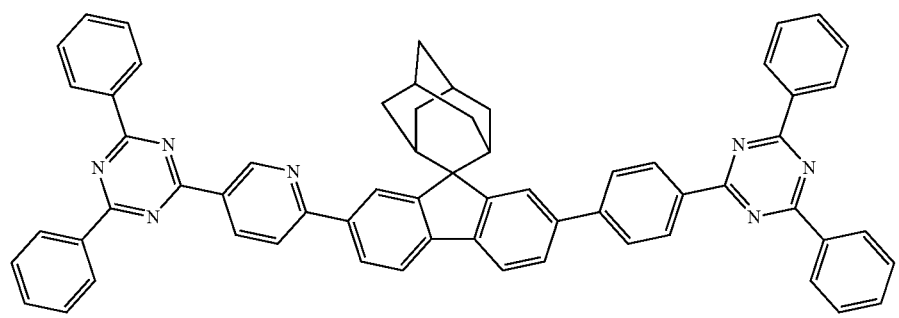
Compound 94
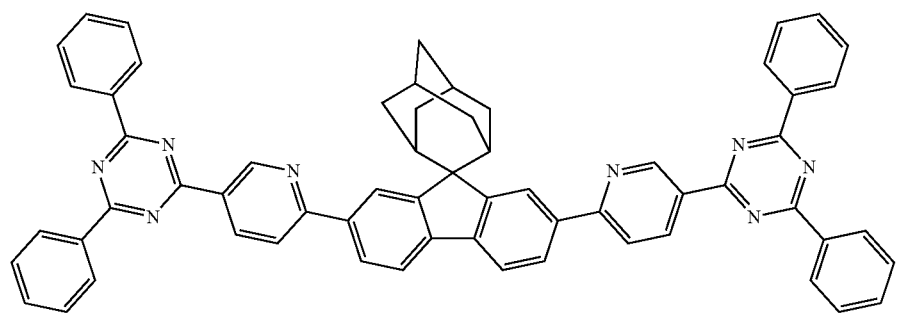
Compound 95
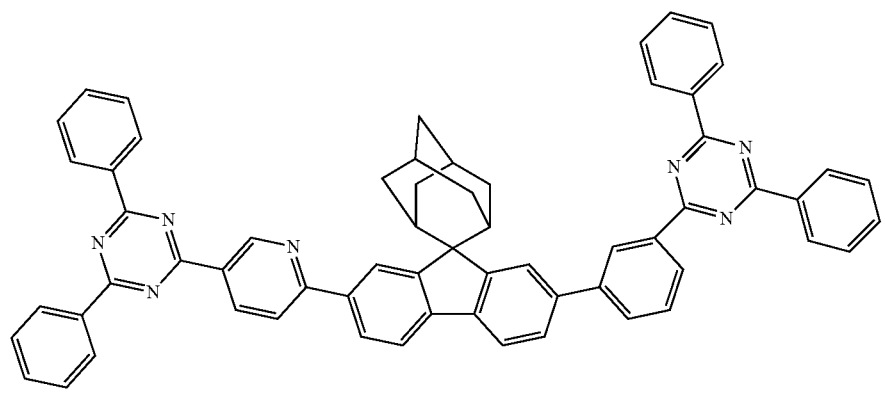

Compound 96
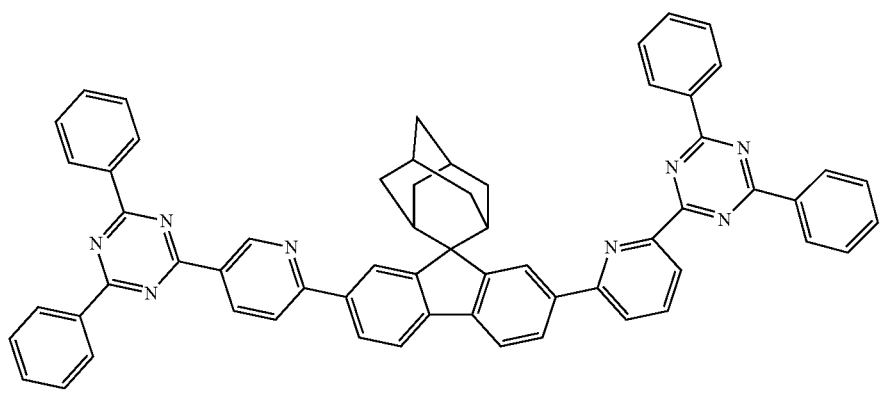
Compound 97
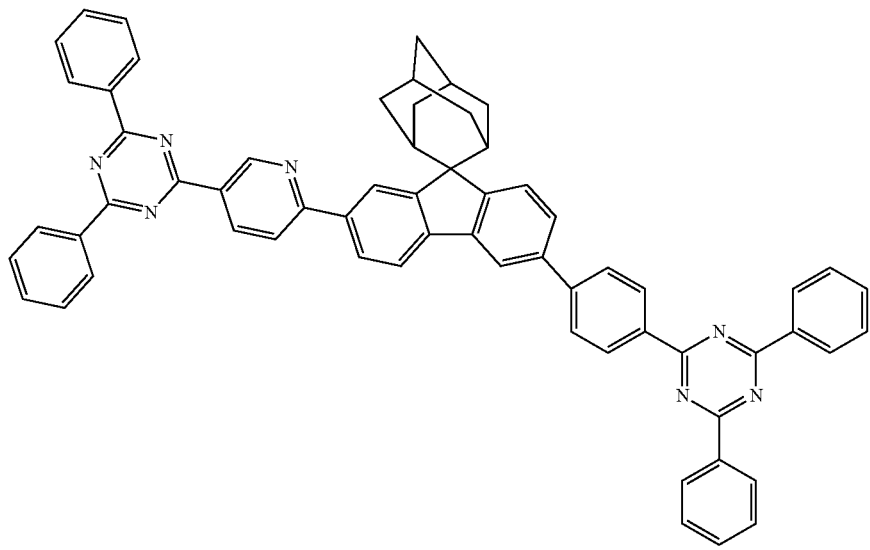
Compound 98
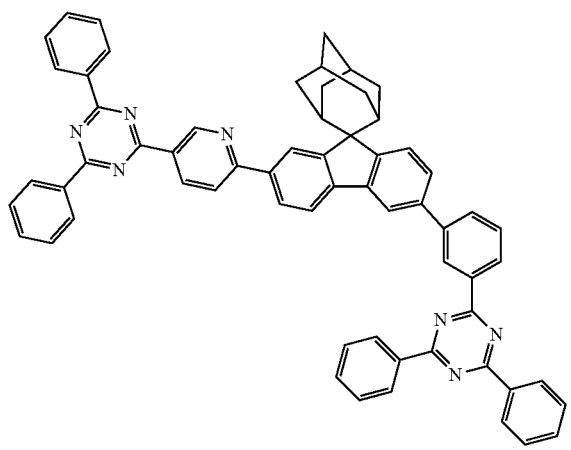
Compound 99
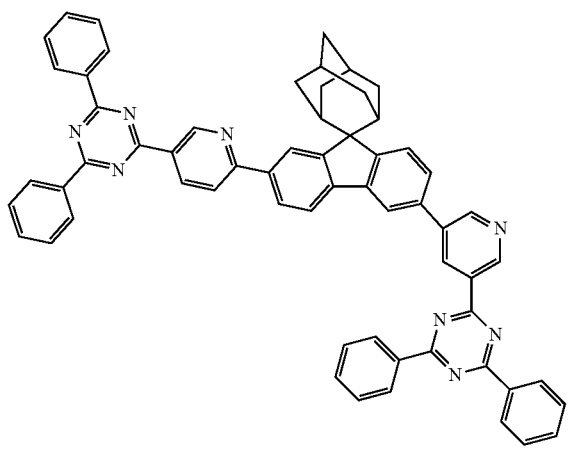

-continued
Compound 100
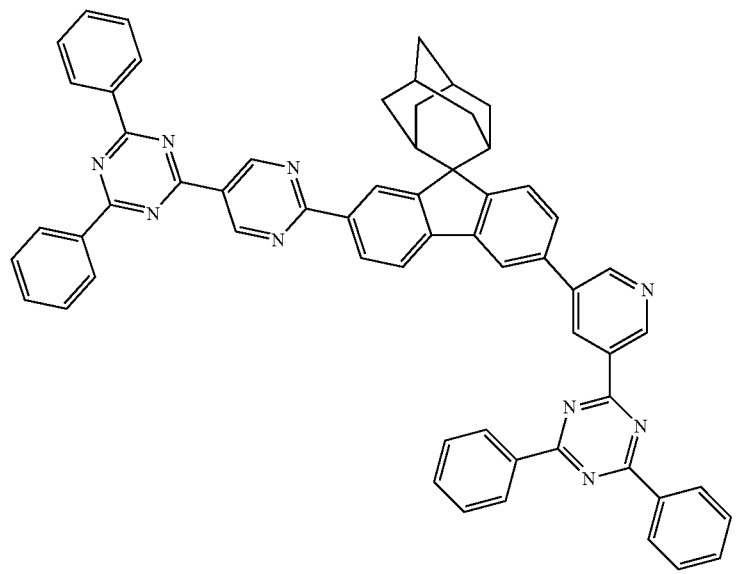
Compound N
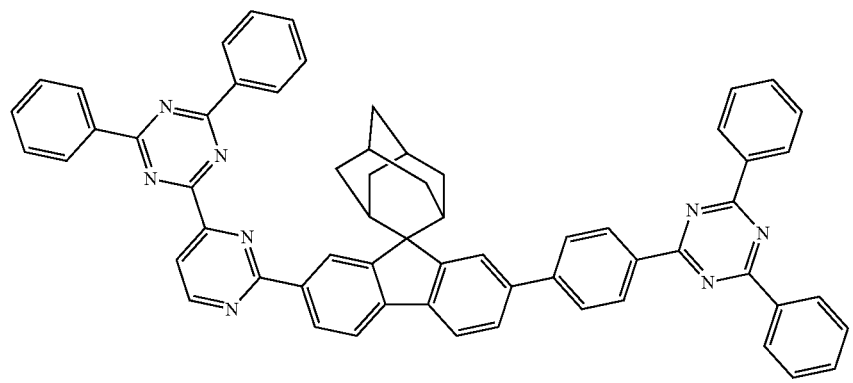
Compound O
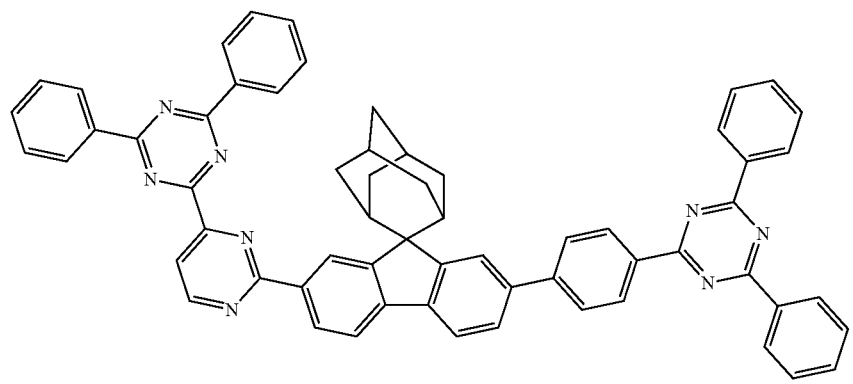

-continued
Compound P
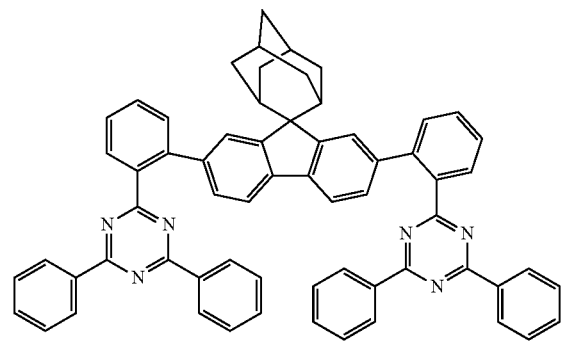
Compound Q
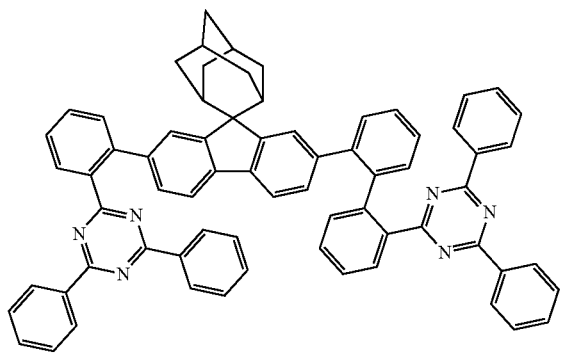
Compound R
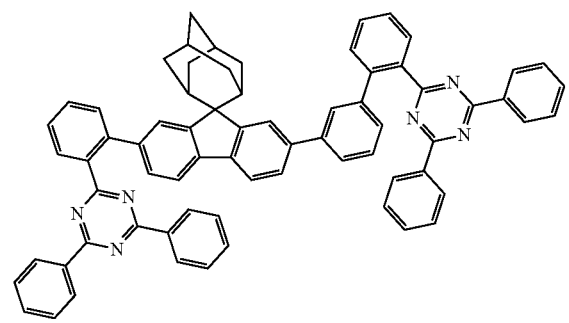
Compound S
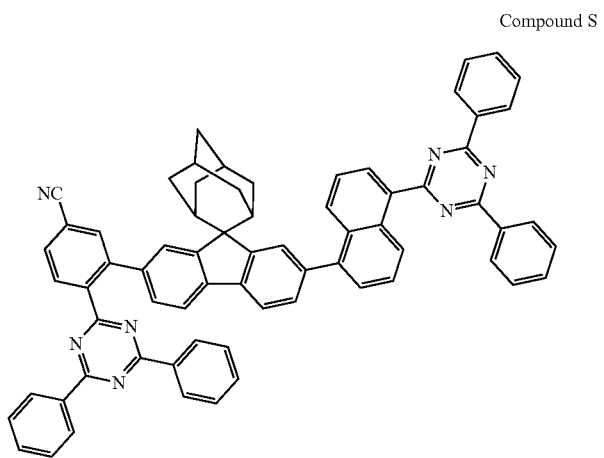
Compound T
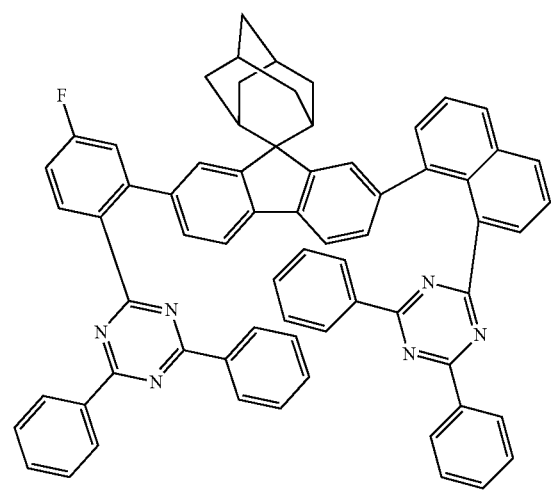
Compound U
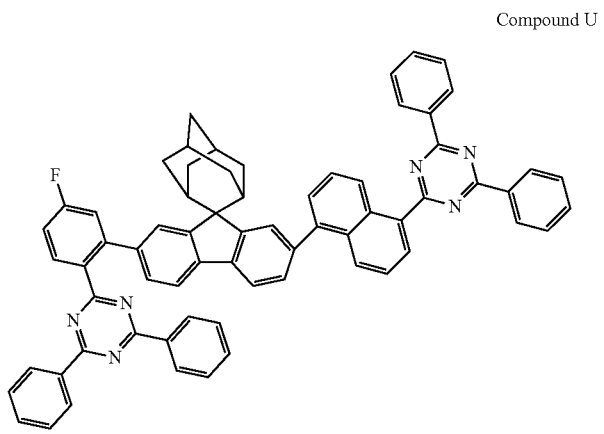

Compound V
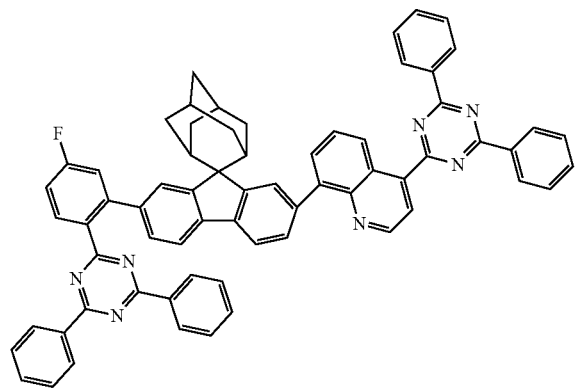
Compound W
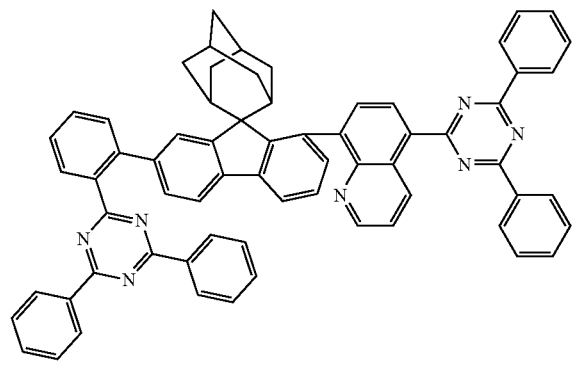
Compound X
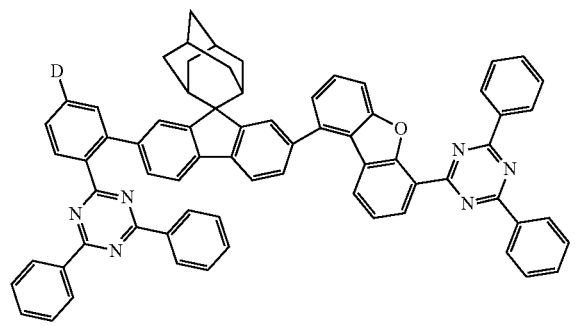
Compound Y
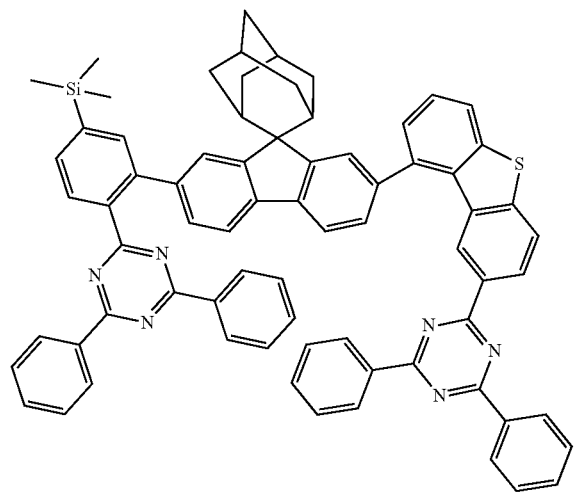
Compound Z
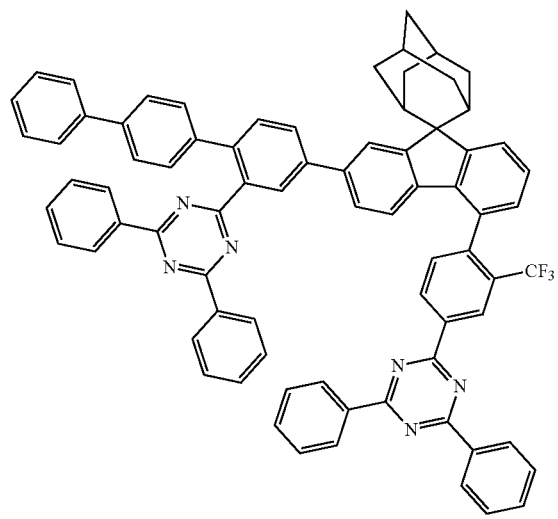
Compound Z-1
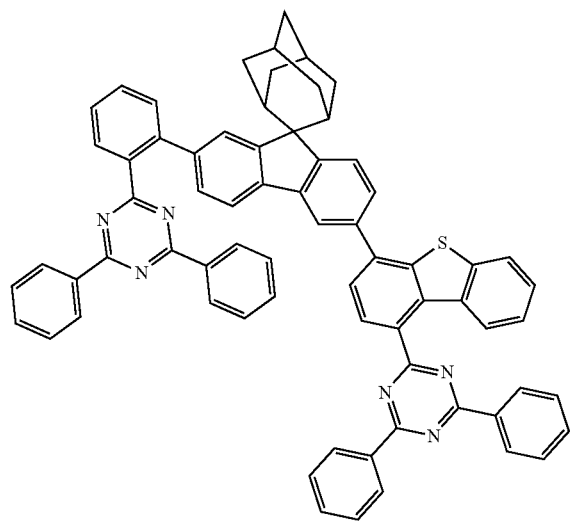

Compound Z-2
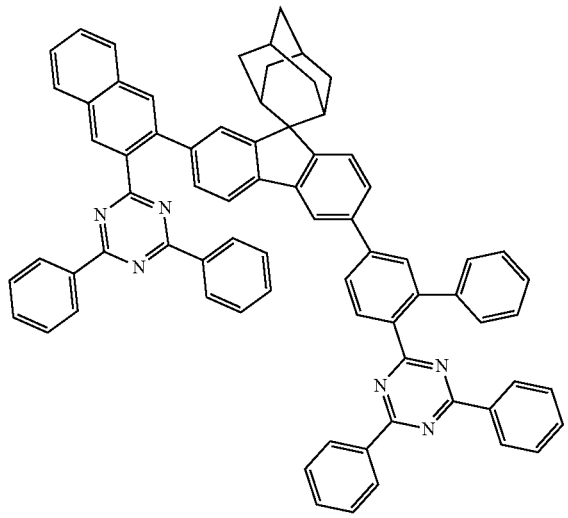
Compound Z-3
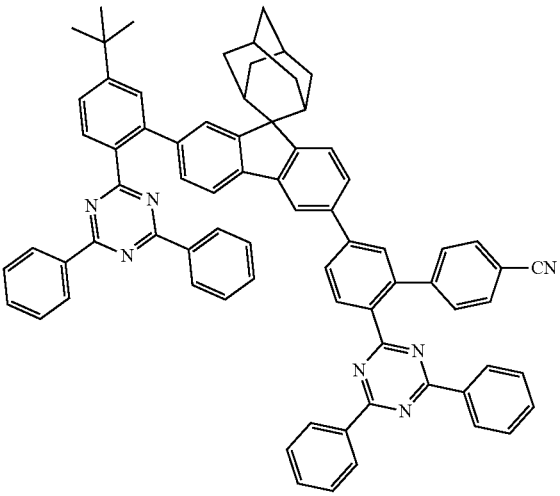
Compound Z-4
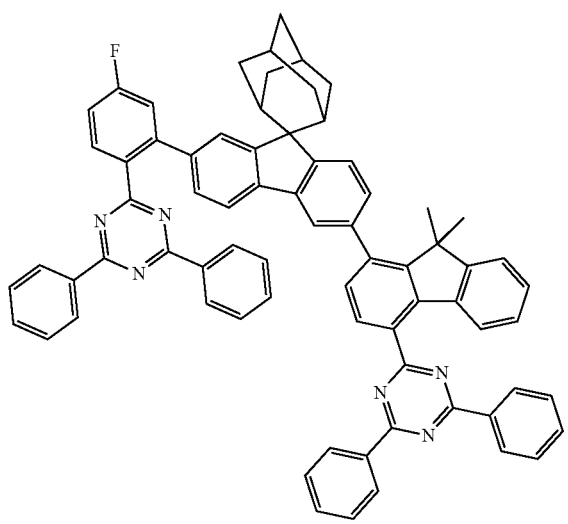
Compound Z-5
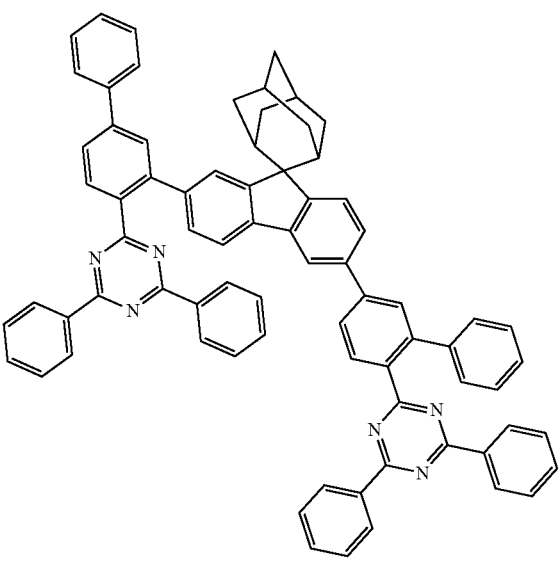
Compound Z-6
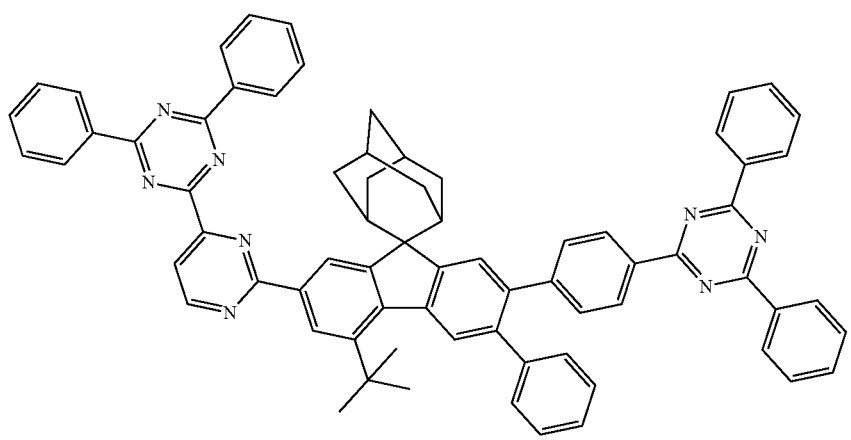

Compound Z-7
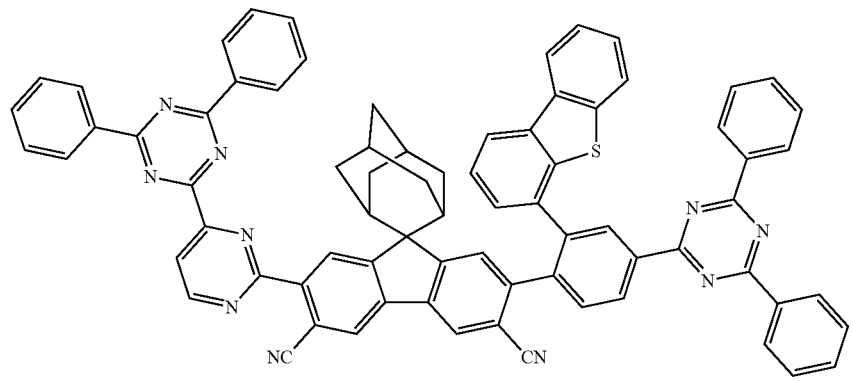
Compound Z-8
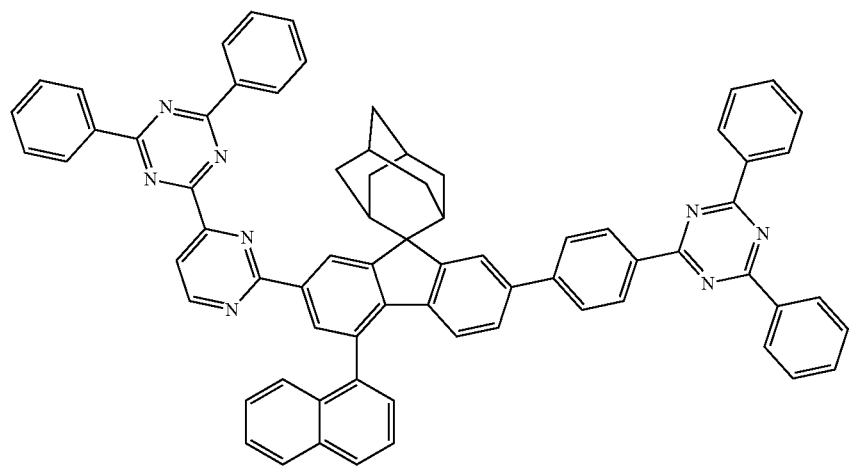
Compound Z-9
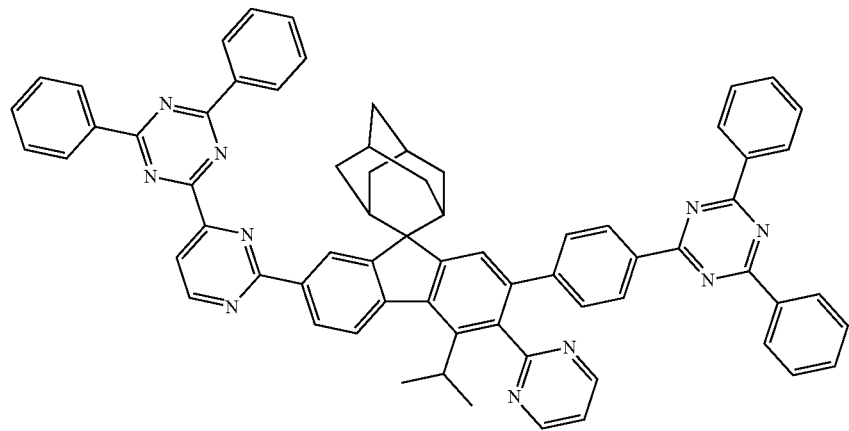

Compound Z-10
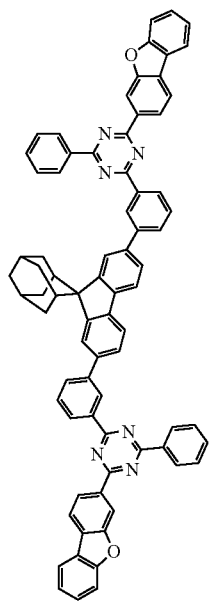
Compound Z-11
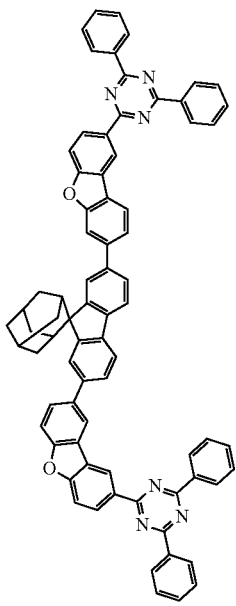
Compound Z-12
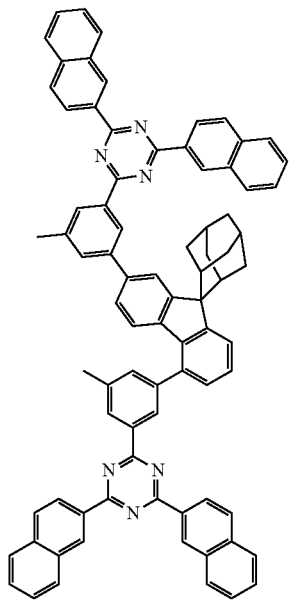
Compound Z-13
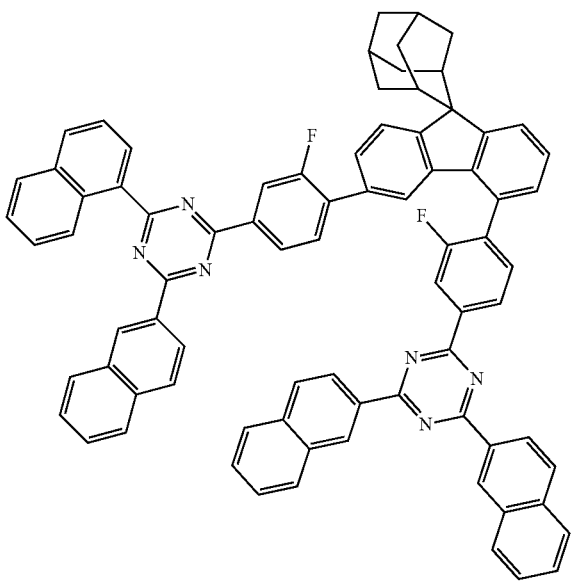

Compound Z-14
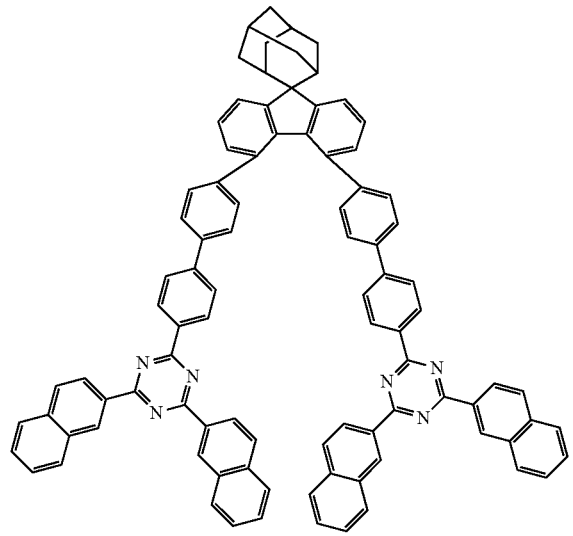
Compound Z-15
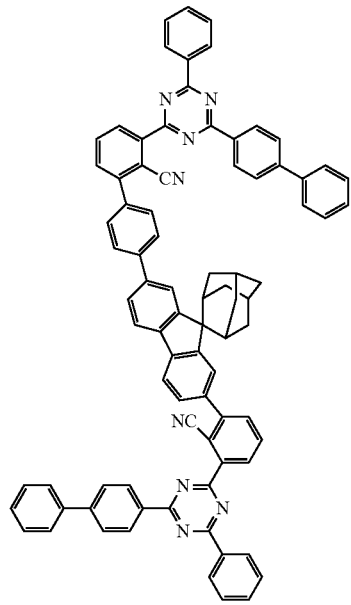
Compound Z-16
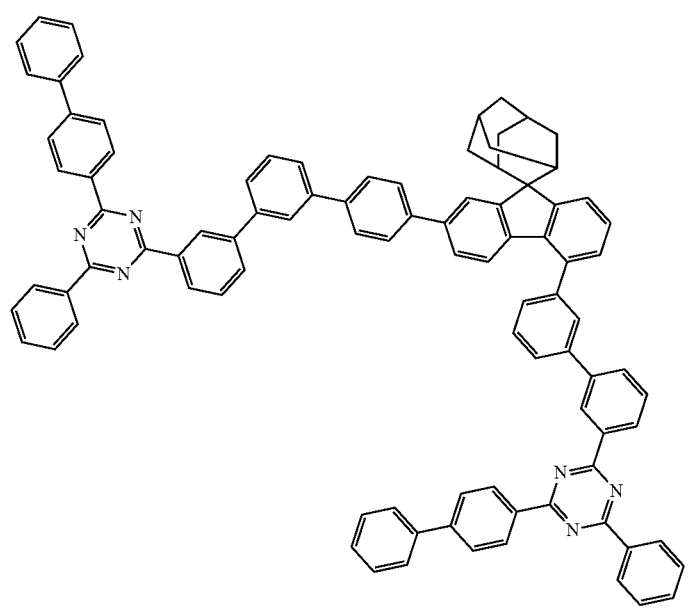

Compound Z-17
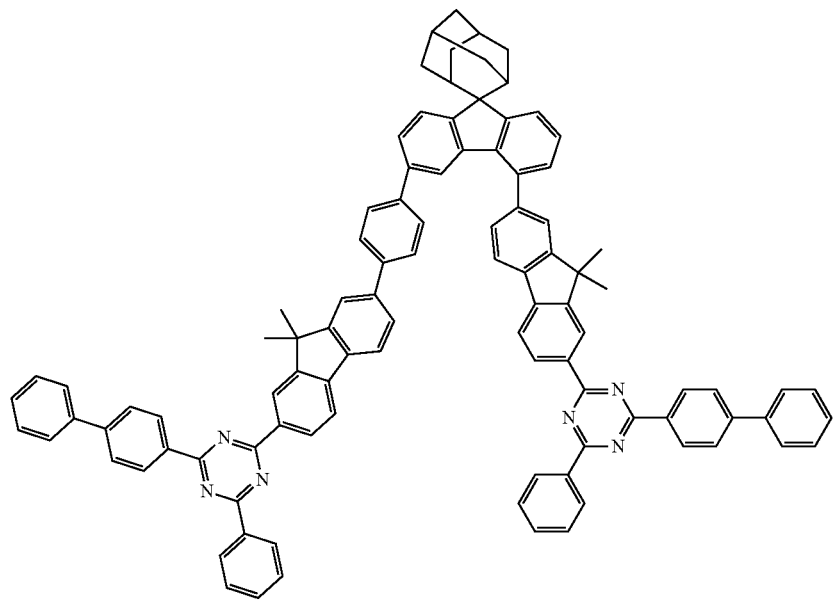
Compound Z-18
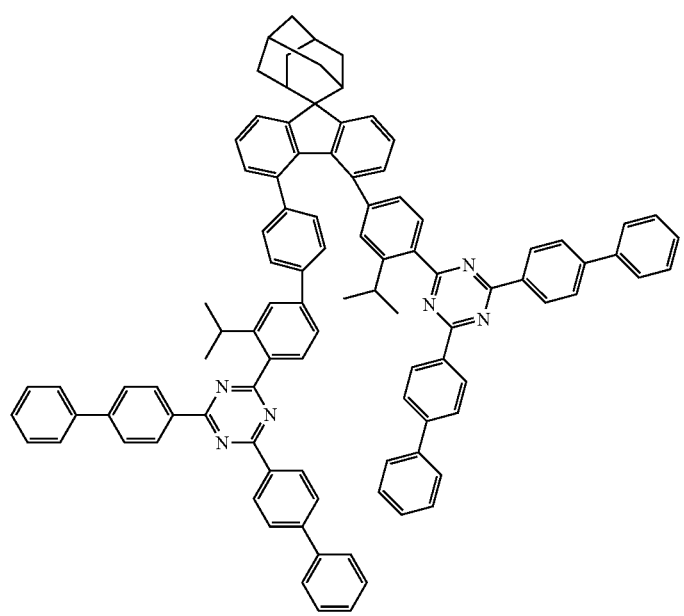

Compound Z-19
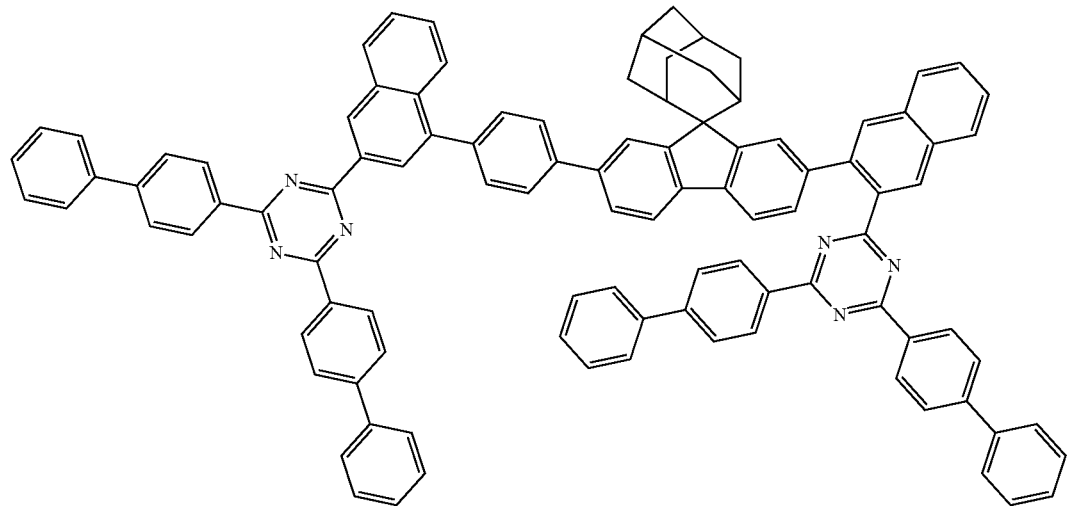
Compound Z-20
Compound Z-21
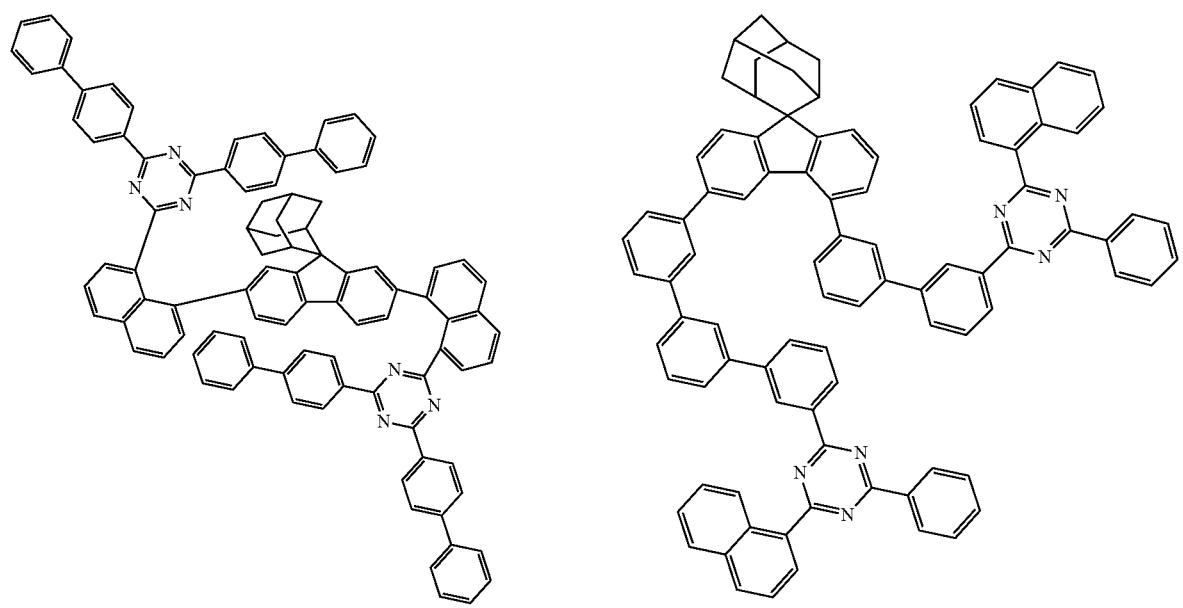

-continued
Compound Z-22
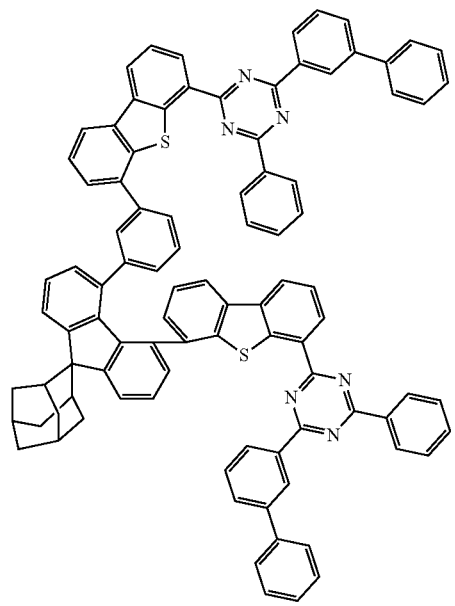
Compound Z-23
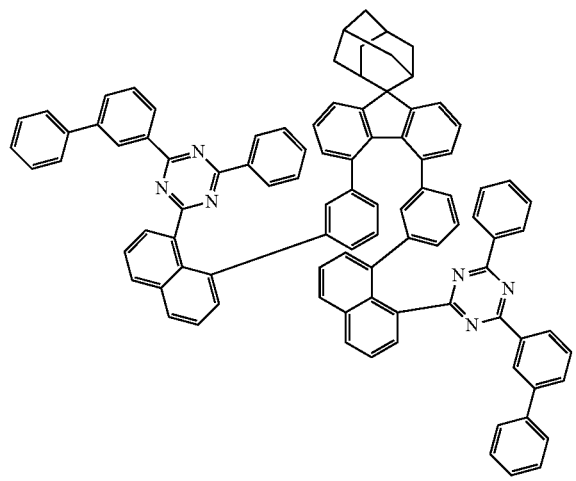
Compound Z-24
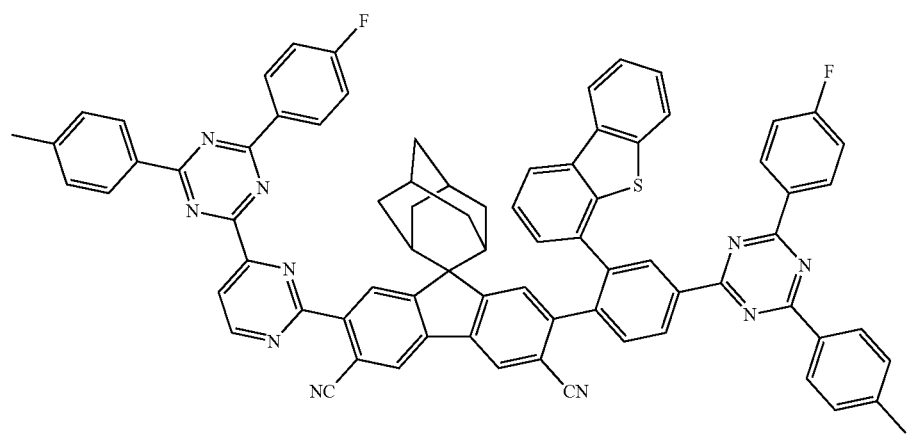
Compound Z-25
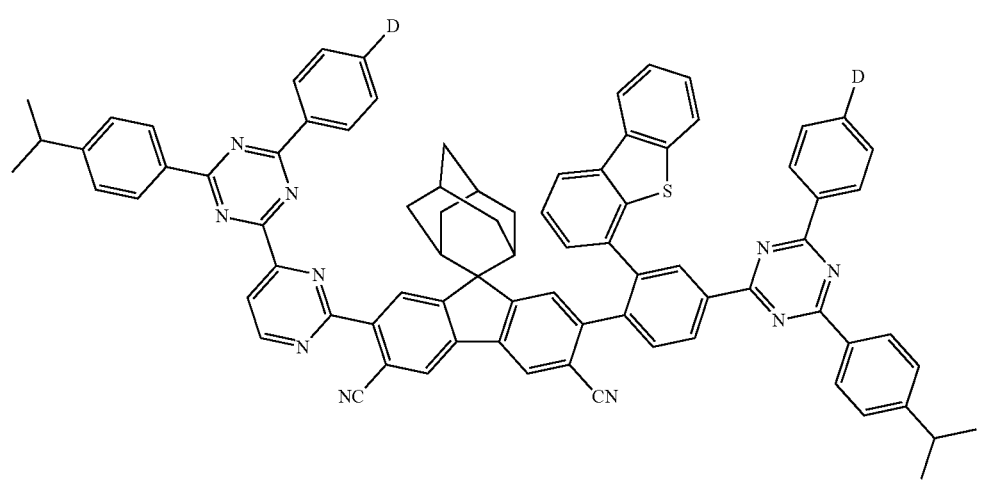

Compound Z-26

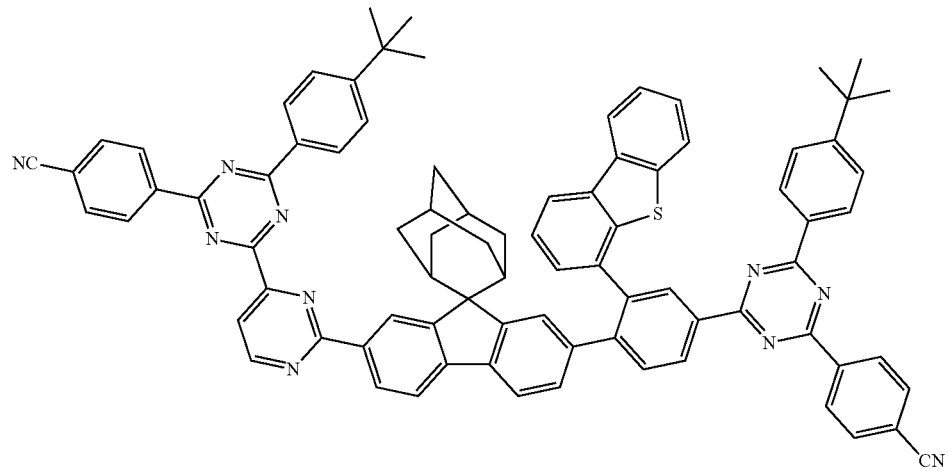

Compound Z-27

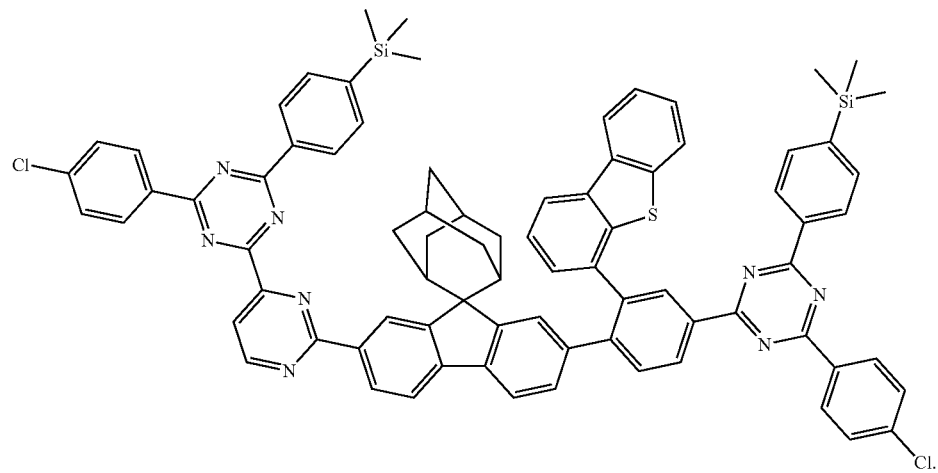

9. An electronic component, comprising an anode, a cathode and one or more functional layer(s) arranged between the anode and the cathode, wherein one or more layers in the functional layer contain the organic compound represented by claim 1.

10. The electronic component according to claim 9, wherein the functional layer comprises an electron transport layer, and the electron transport layer contains the organic compound.

11. An electronic device, comprising the electronic component according to claim 9.

12. An electronic device, comprising the electronic component according to claim 10.

13. The organic compound according to claim 3, wherein the organic compound represented by formula 1 is selected from any of the following:

Compound 1
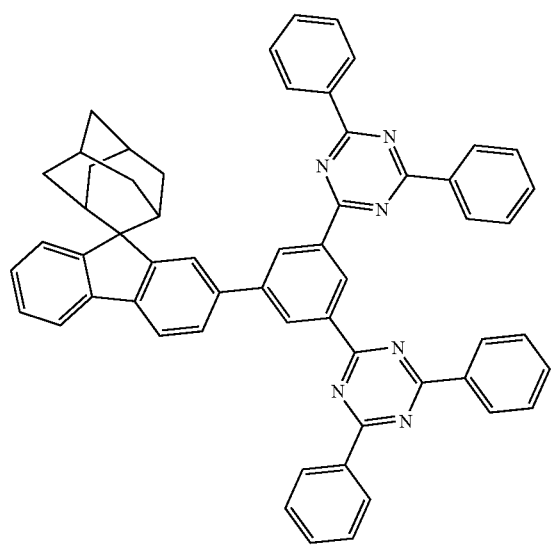
Compound 2
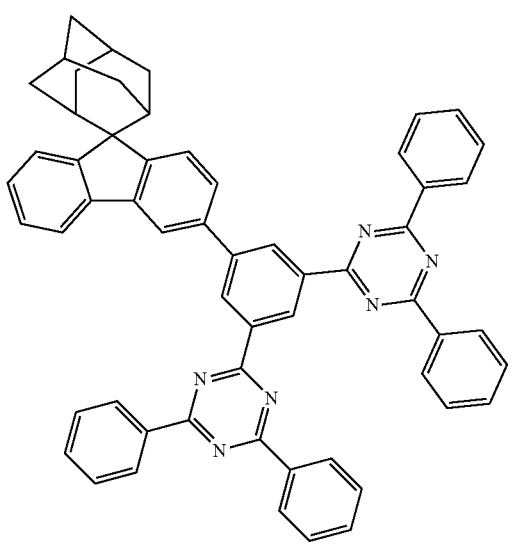
Compound 3
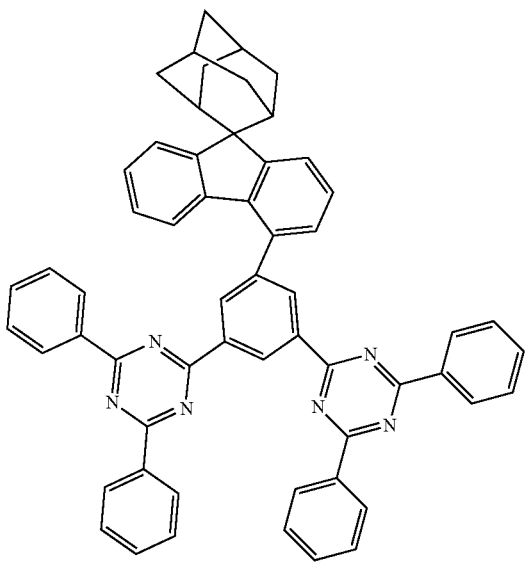
Compound 4
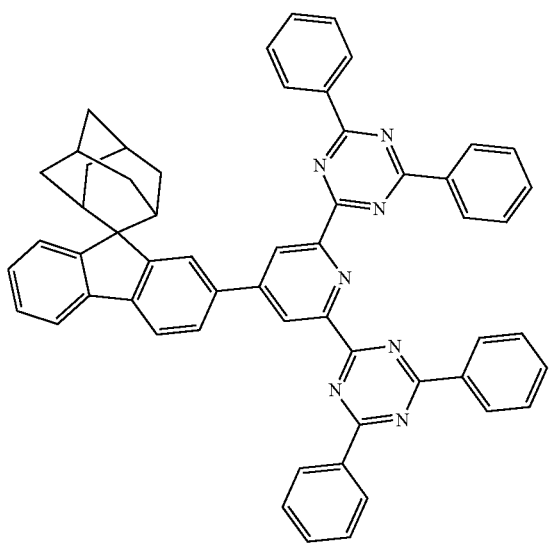

Compound 5
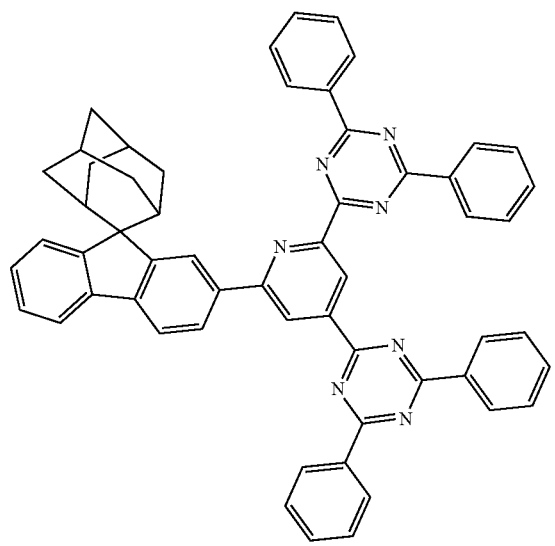
Compound 7
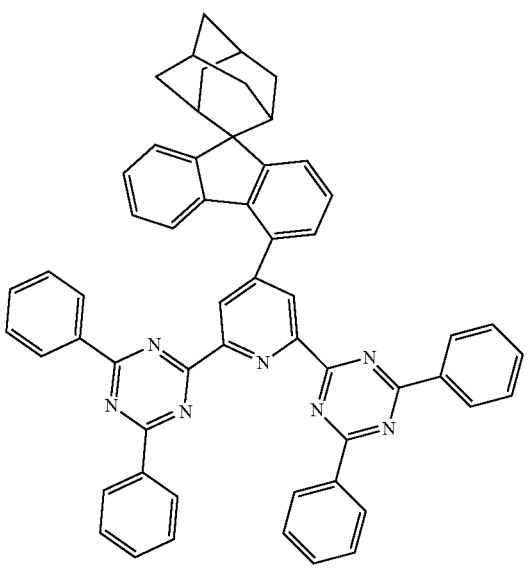
Compound 6
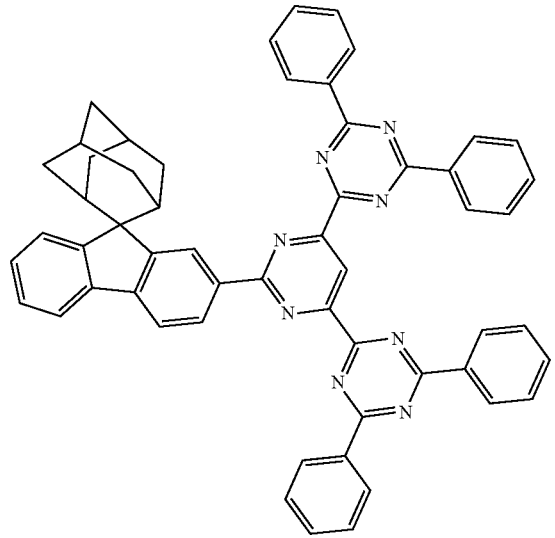
Compound 8
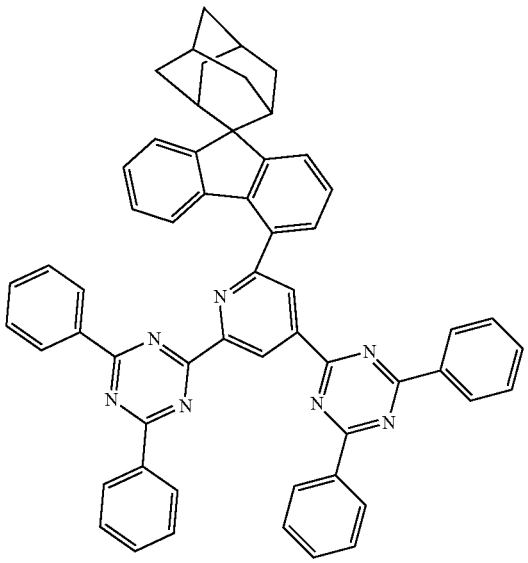

Compound 9
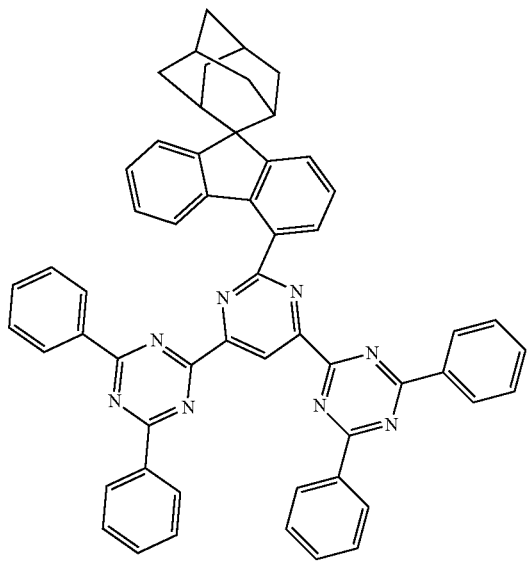
Compound 10
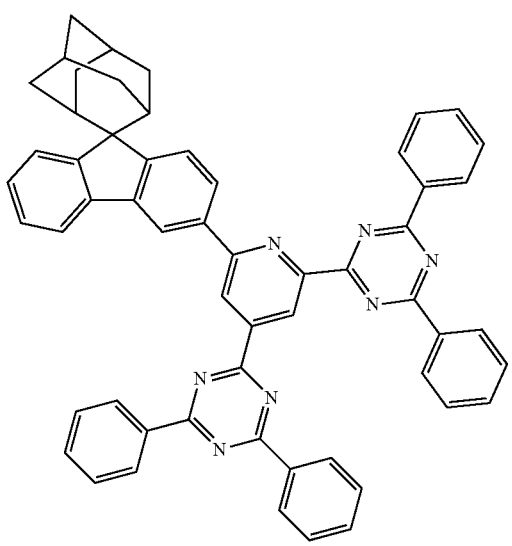
Compound 11
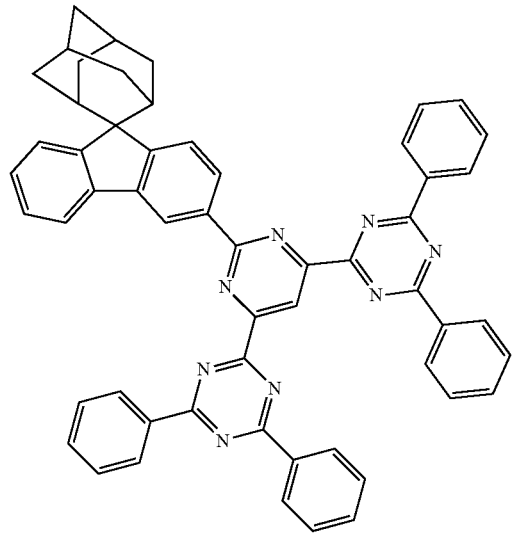
Compound 12
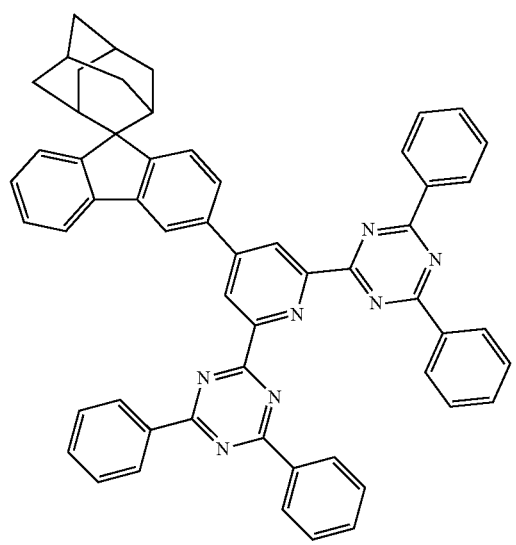
Compound 13
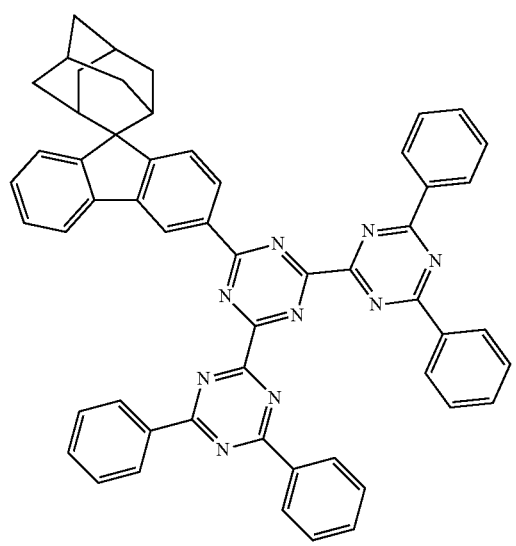

Compound 14
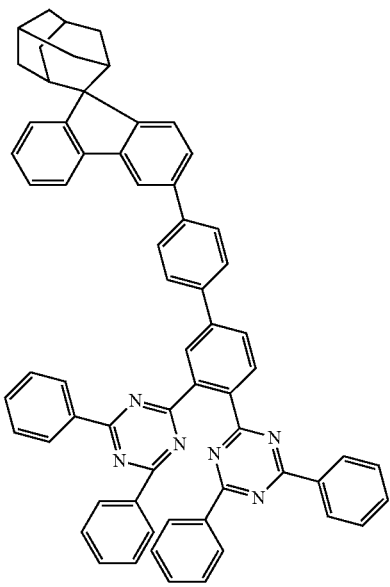
Compound C
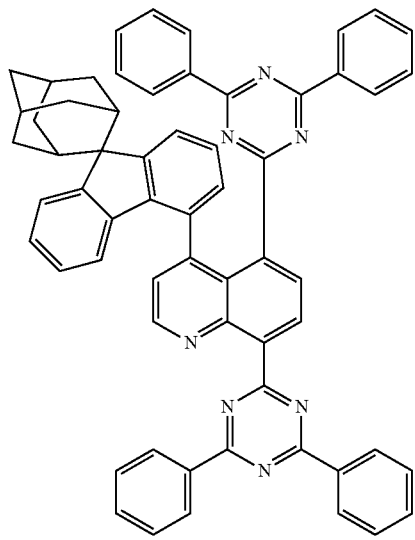
Compound A
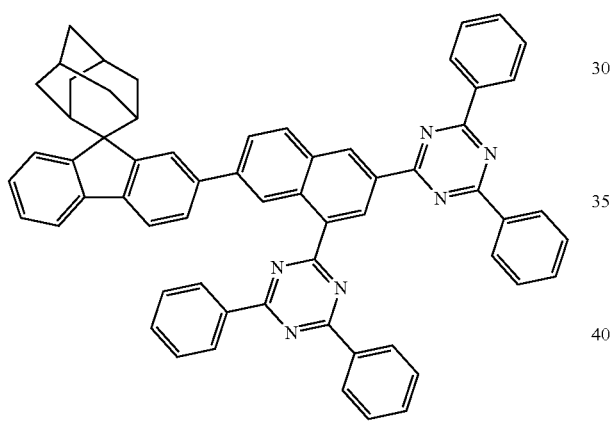
Compound B
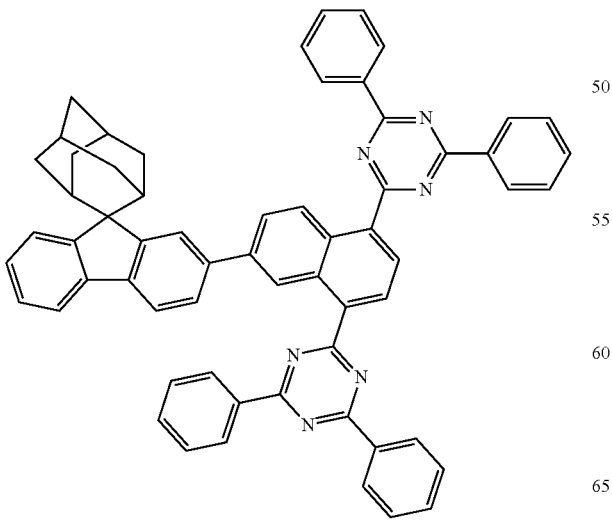
Compound D
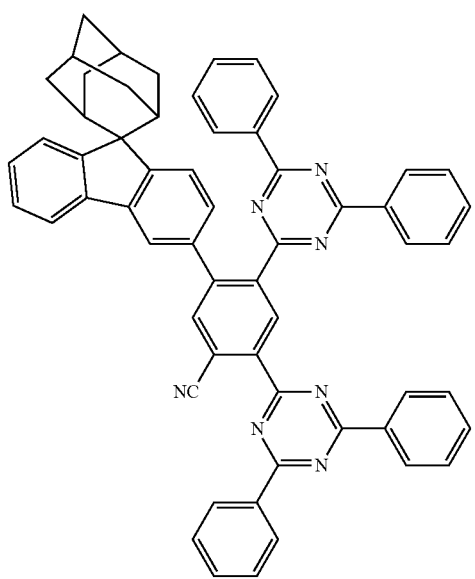

Compound E
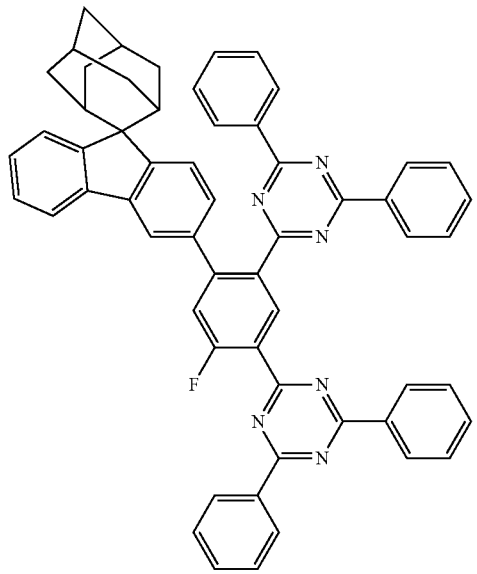
Compound F
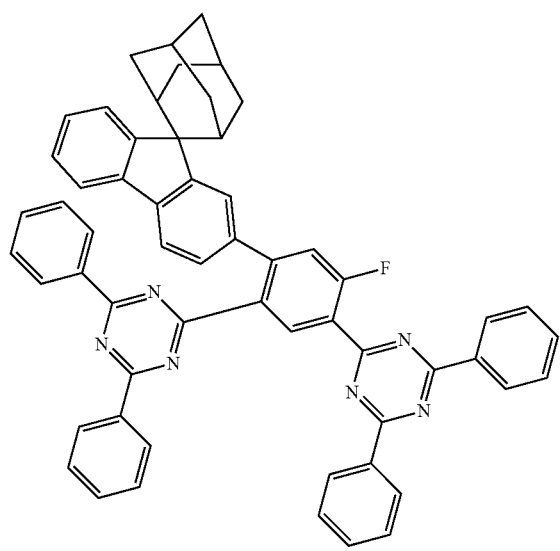
Compound G
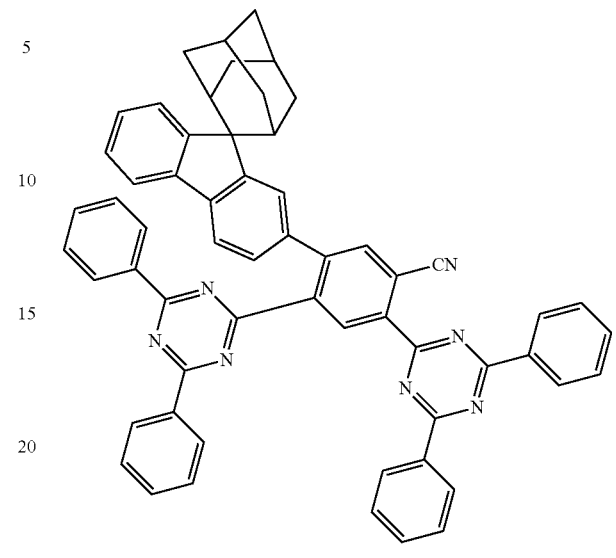
Compound H
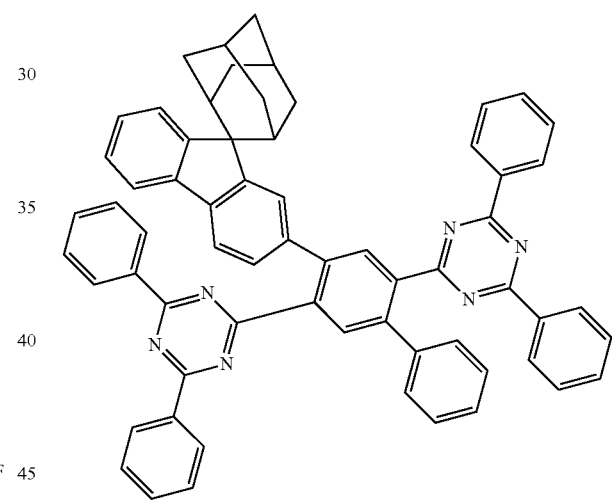
Compound I
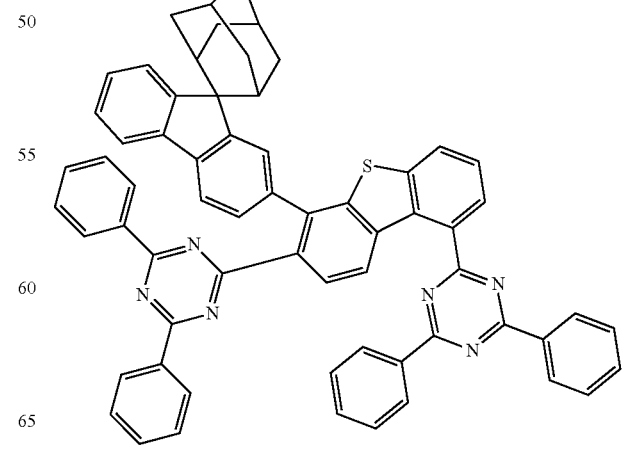

Compound J
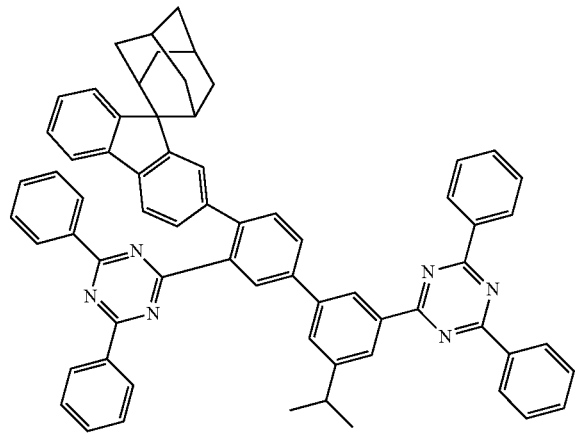
Compound K
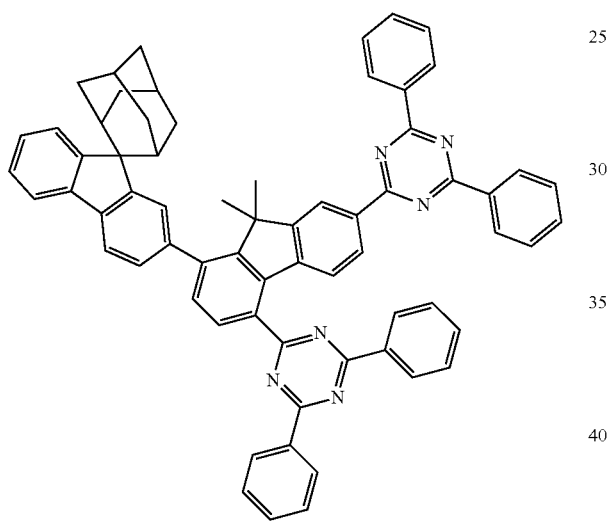
Compound L
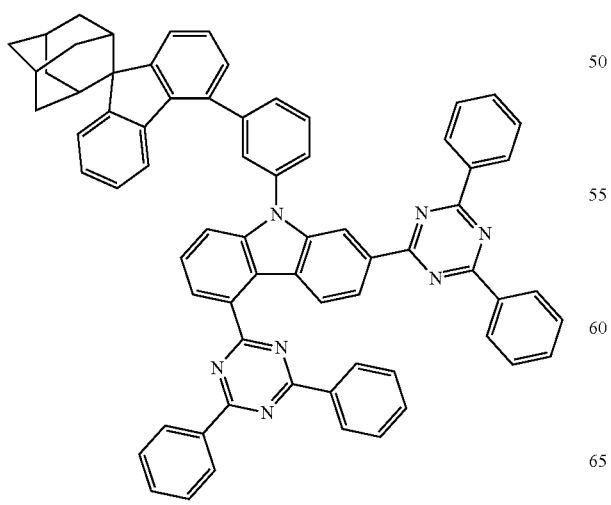
Compound M
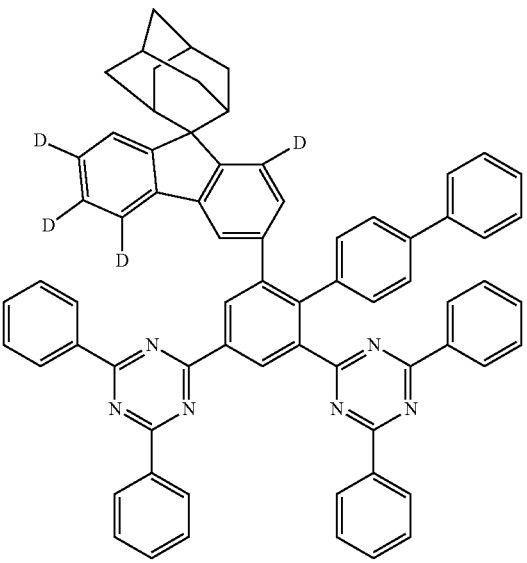
Compound M-1
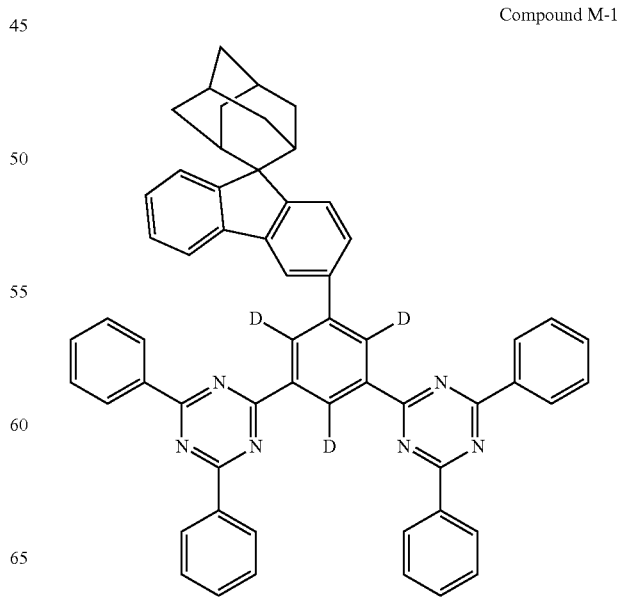

Compound M-2
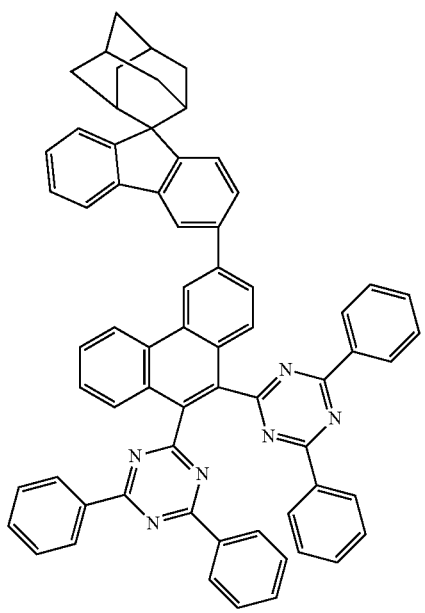
Compound M-5
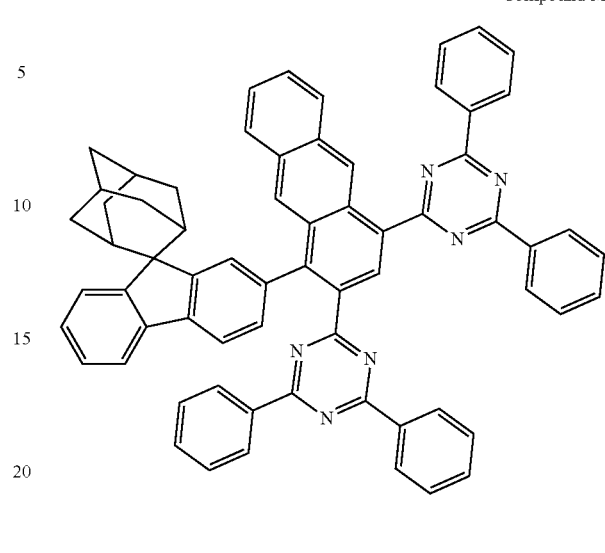
Compound M-3
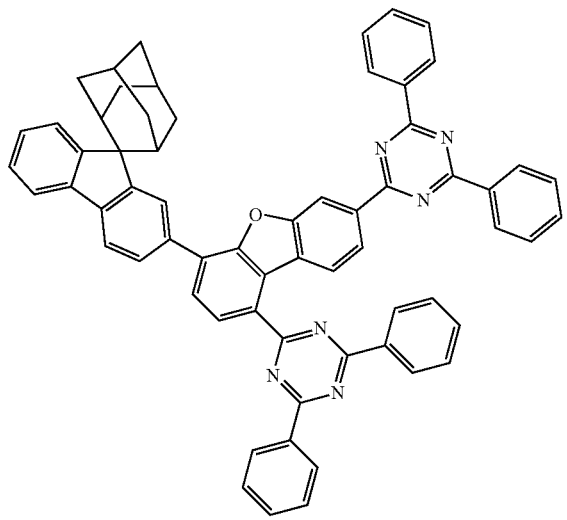
Compound M-6
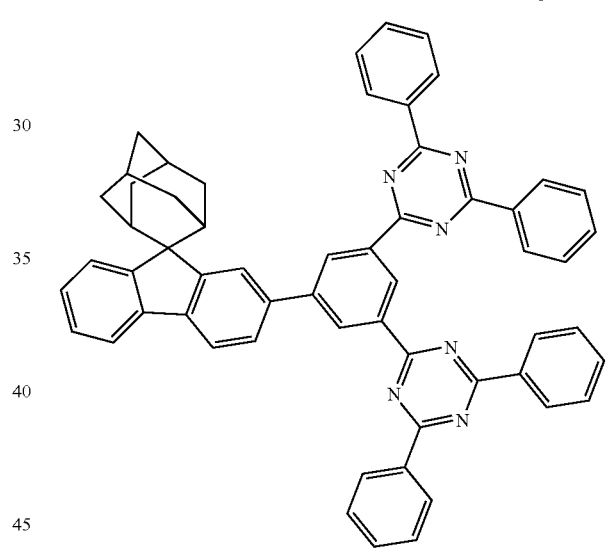
Compound M-4
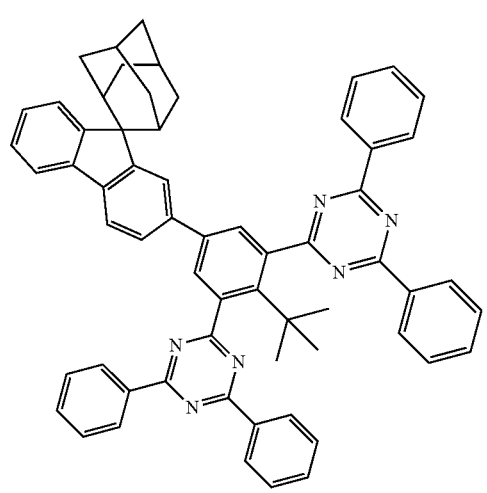
Compound M-7
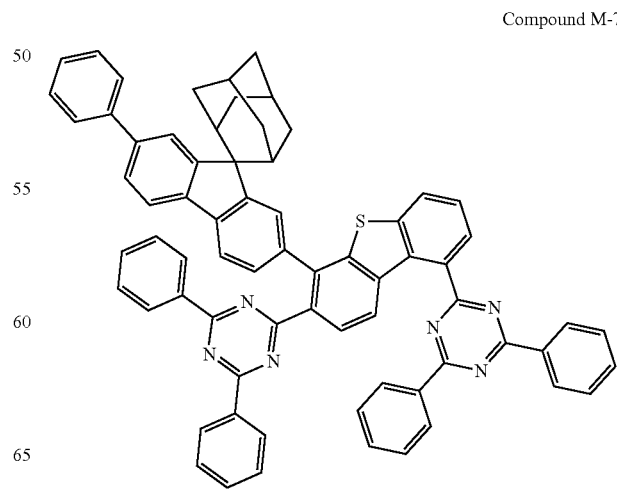

-continued
Compound M-8
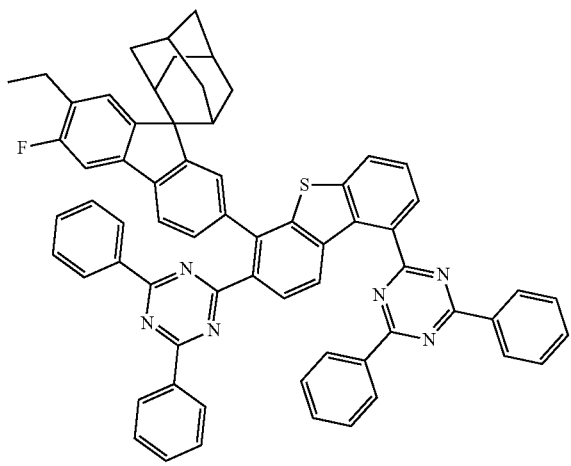
Compound M-9
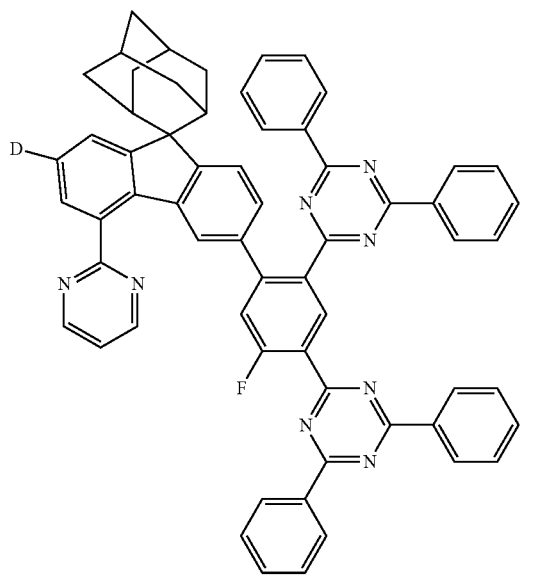
Compound M-10
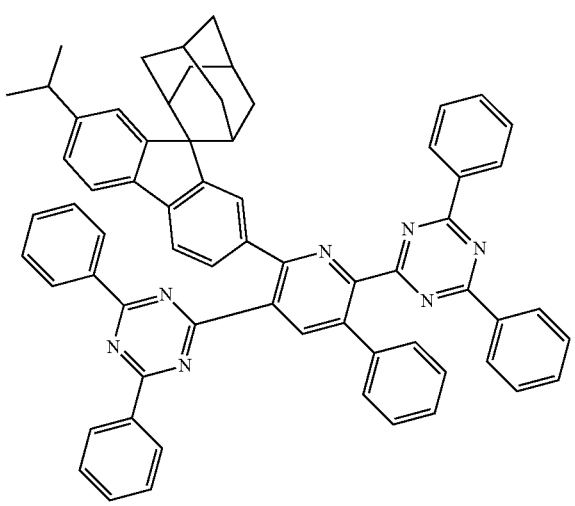
-continued
Compound M-11
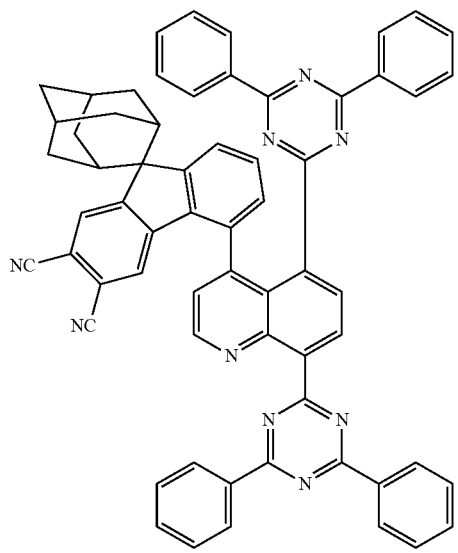
Compound M-12
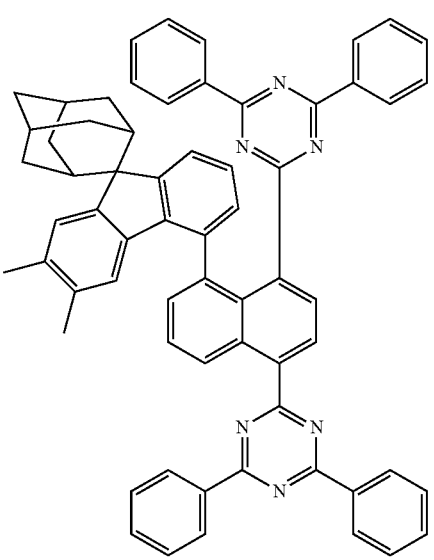

Compound M-13
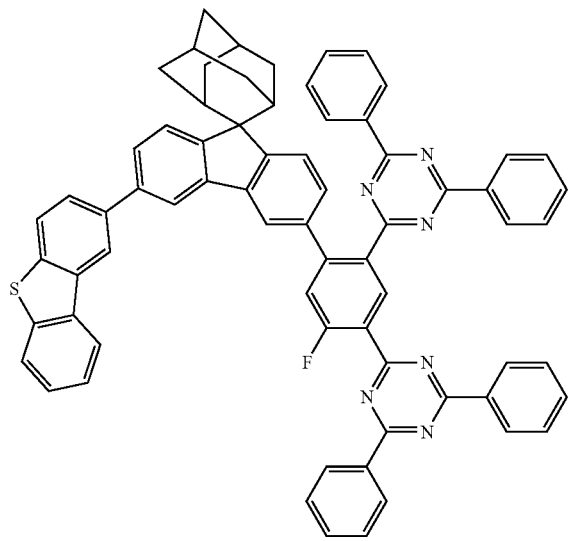
Compound M-14
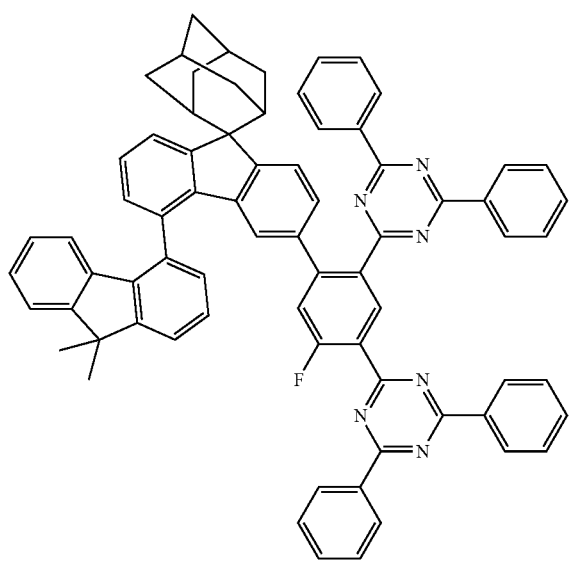
Compound M-15
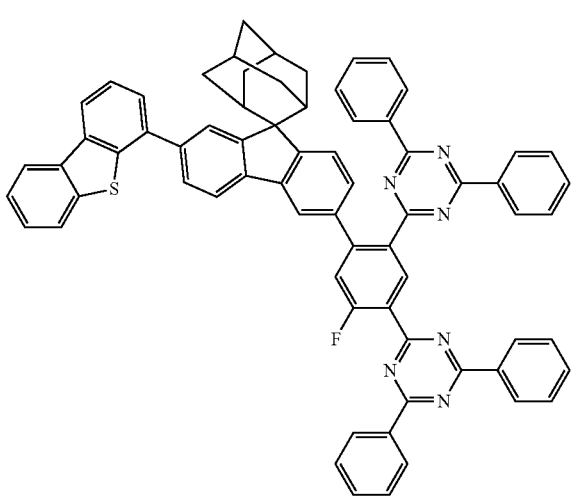
Compound M-16
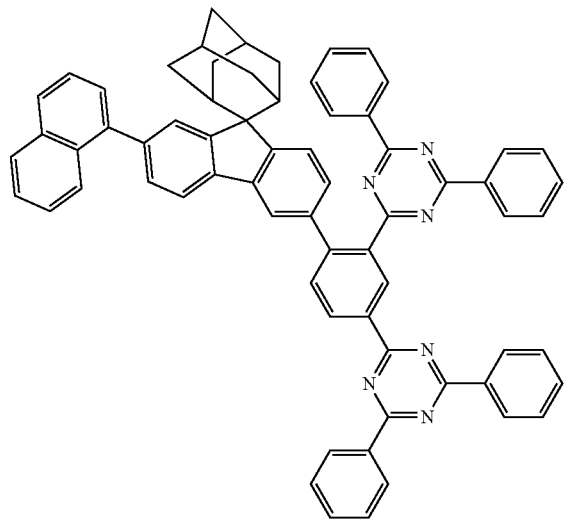
Compound M-17
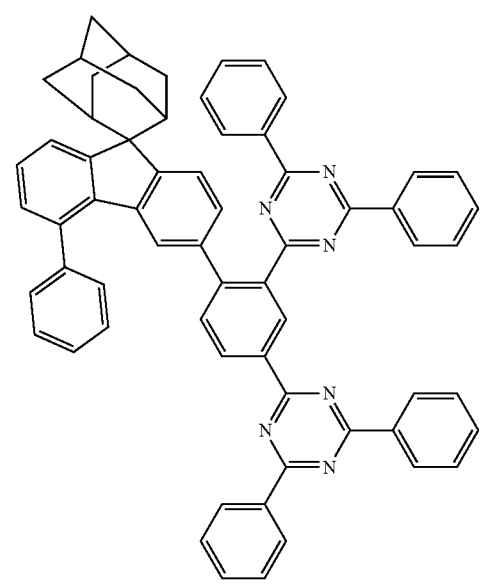
Compound M-18
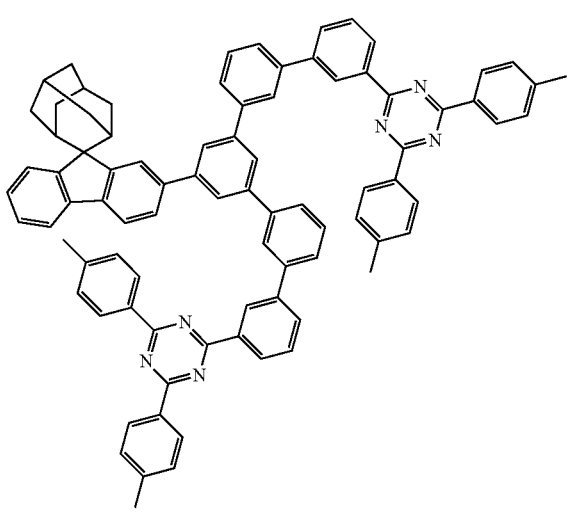

Compound M-19
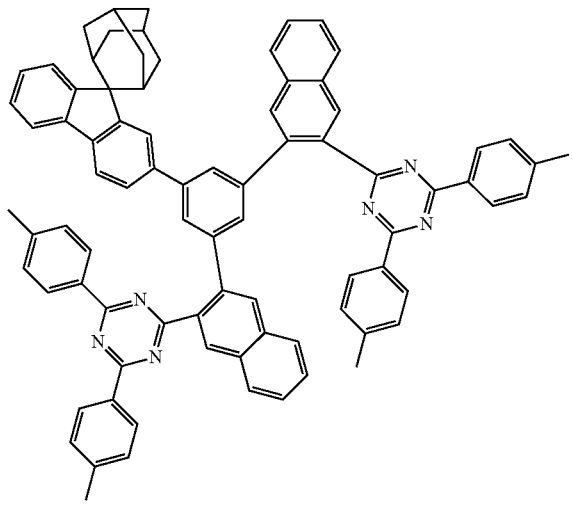
Compound M-20
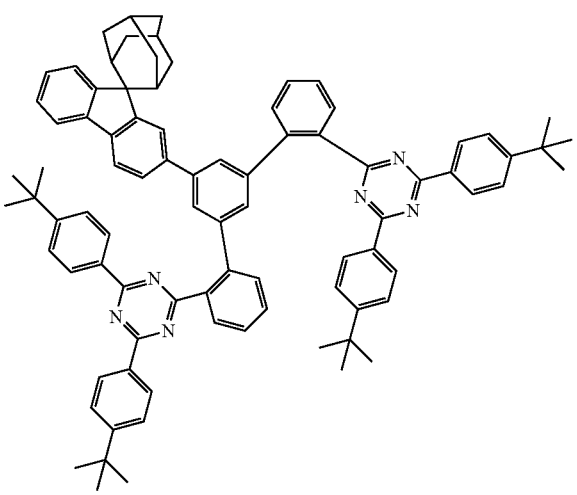
Compound M-21
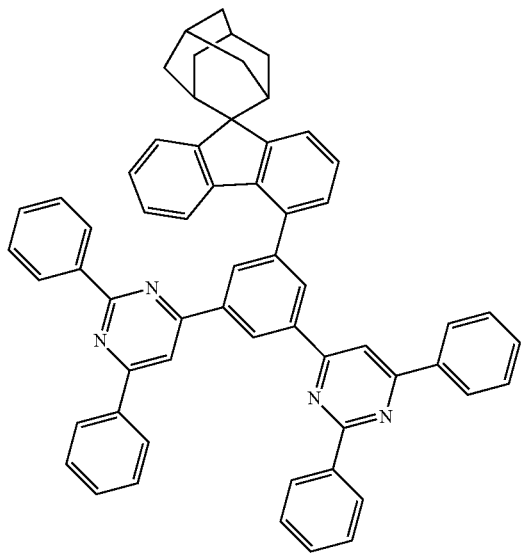
Compound M-22
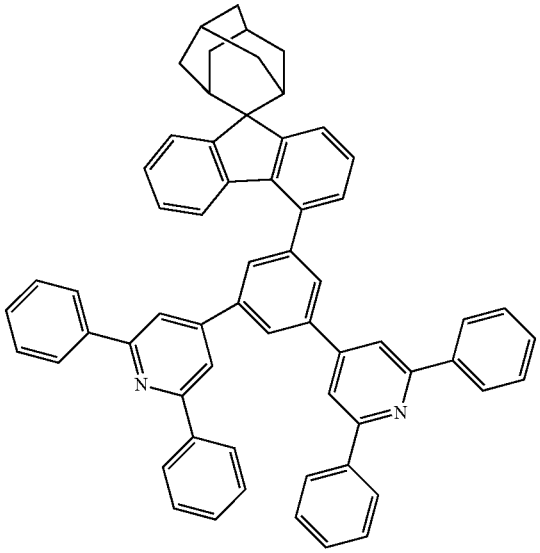
Compound M-23
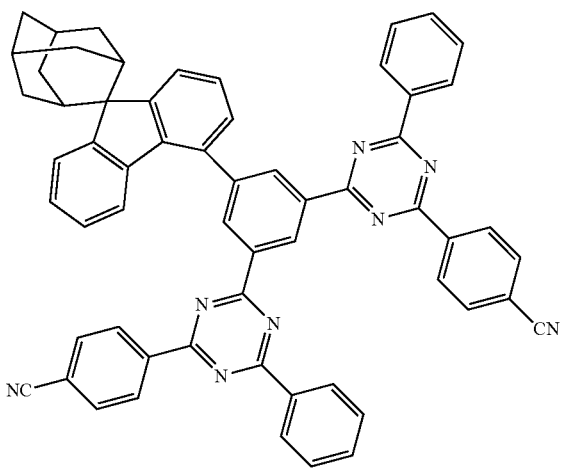
Compound M-24
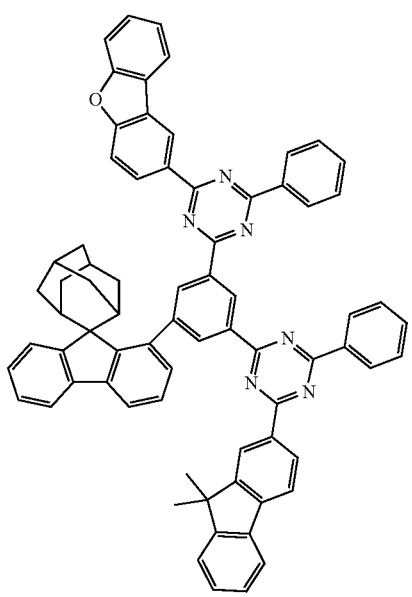

Compound M-25
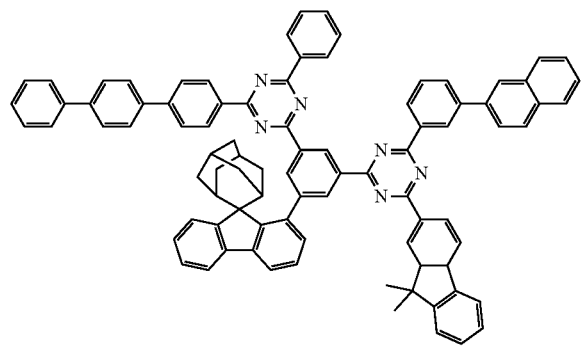
Compound M-26
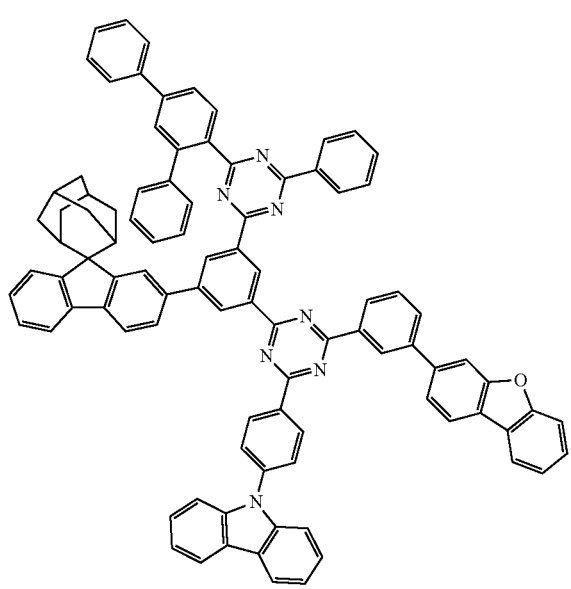
Compound M-27
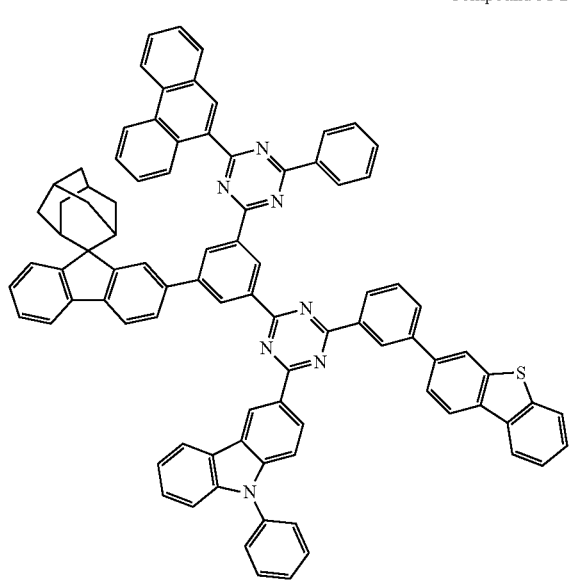
Compound M-28
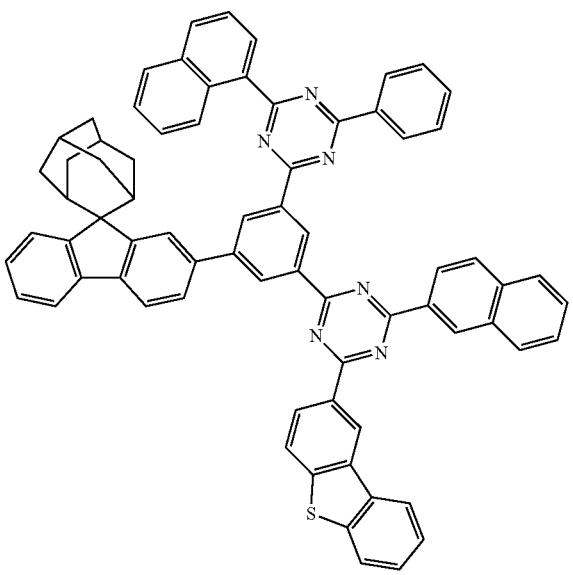
Compound M-29
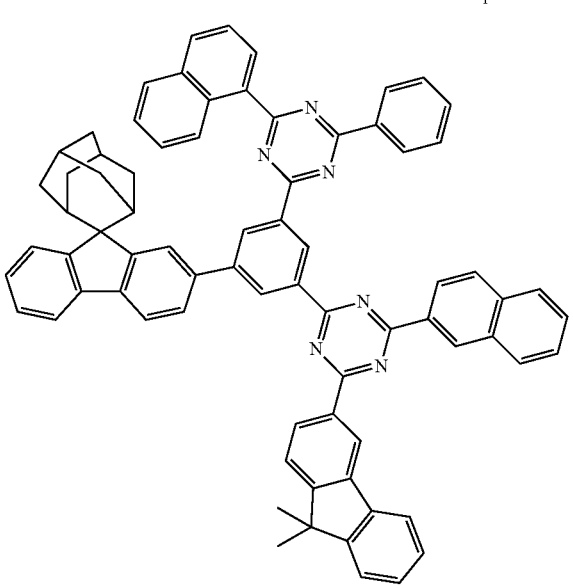
Compound M-30
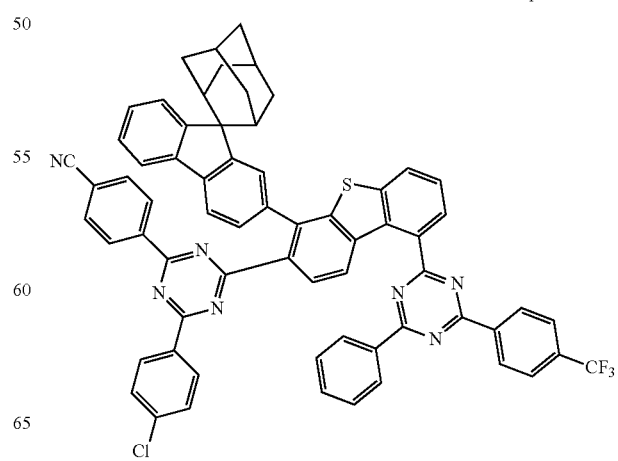

-continued
Compound M-31
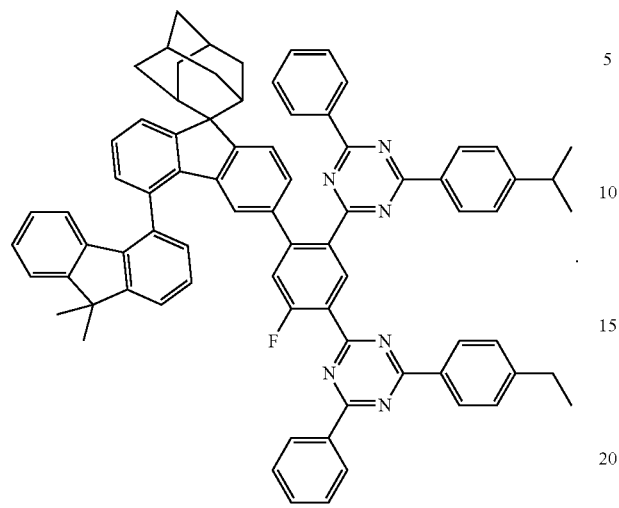
* * * * *